US007632922B1

(12) United States Patent
Boyle et al.

(10) Patent No.: US 7,632,922 B1
(45) Date of Patent: Dec. 15, 2009

(54) OSTEOPROTEGERIN

(75) Inventors: William J. Boyle, Moorpark, CA (US); David L. Lacey, Thousand Oaks, CA (US); Frank J. Calzone, Westlake Village, CA (US); Ming-Shi Chang, Newbury Park, CA (US)

(73) Assignee: Amgen, Inc., Thousand Oaks, CA (US)

( * ) Notice: Subject to any disclaimer, the term of this patent is extended or adjusted under 35 U.S.C. 154(b) by 1275 days.

(21) Appl. No.: 09/718,725

(22) Filed: Nov. 22, 2000

Related U.S. Application Data

(63) Continuation of application No. 09/132,985, filed on Aug. 12, 1998, now abandoned, which is a continuation of application No. 08/771,777, filed on Dec. 20, 1996, now abandoned, and a continuation-in-part of application No. 08/706,945, filed on Sep. 3, 1996, now Pat. No. 6,369,027, which is a continuation-in-part of application No. 08/577,788, filed on Dec. 22, 1995, now Pat. No. 6,613,544.

(51) Int. Cl.
*C07K 16/00* (2006.01)
*C07K 17/00* (2006.01)
*G01N 33/53* (2006.01)

(52) U.S. Cl. .............. 530/387.1; 530/387.3; 530/387.9; 530/388.1; 530/391.1; 435/7.1

(58) Field of Classification Search .............. 424/134.1; 435/7.1; 530/350
See application file for complete search history.

(56) References Cited

U.S. PATENT DOCUMENTS

| | | | | |
|---|---|---|---|---|
| 4,179,337 | A | 12/1979 | Davis et al. | 435/181 |
| 4,710,473 | A | 12/1987 | Morris | 435/320 |
| 5,447,851 | A | 9/1995 | Beutler et al. | 435/69.7 |

FOREIGN PATENT DOCUMENTS

| | | | |
|---|---|---|---|
| EP | 0 401 384 | | 12/1990 |
| EP | 0816380 | A1 | 7/1998 |
| JP | 7-207508 | | 2/1995 |
| JP | 7-054977 | | 7/1995 |
| WO | WO 90/14363 | | 11/1990 |
| WO | WO 94/21670 | | 9/1994 |
| WO | WO95/11308 | | 4/1995 |
| WO | 9605309 | A2 | 2/1996 |
| WO | WO96/26217 | | 8/1996 |
| WO | WO 96/28546 | | 9/1996 |
| WO | WO96/28546 | | 9/1996 |
| WO | WO98/12344 | | 3/1998 |

OTHER PUBLICATIONS

Well, J. Additivity of Mutational Effects in Proteins. Biochemistry 29:8509-8517 (1990).*
Daniel et al. Mapping of Linear Antigenic Sites on the S Glycoprotein of a Neurotropic Murine Coronavirus with Synthetic Peptides: Virology 202 pp. 540-549 (1994).*
Alexander et al. Altering the antigenicity of proteins. Proc. Natl. Acad. Sci. USA vol. 89, pp. 3352-3356 (Apr. 1992).*
Wells, Additivity of Mutational Effects in Proteins: Biochemistry vol. 29/37, pp. 8509-8517 (1990).*
Ngo et al. Computational complexity, protein structure prediction, and the levinthal paradox. The protein folding problem and tertiary structure prediction, pp. 433-440 and 492-495. Merz and Le Grand, Editors, (Birkhauser Boston 1994).*
Abbas et al. Cellular and Molecular Immunology, pp. 47-48. Second Edition. W.B. Saunders Company, Philadelphia (1994).*
Banner et al. Cell 73, 431-445 (1993).
Beutler and van Huffel Science 264, 667-663 (1994).
Beutler et al. Ann. Rev., Biochem. 57, 505-518 (1988).
Brinster et al., Proc. Natl. Acad. Sci. USA 82, 4338 (1985).
Capon et al. Nature 337, 525-531 (1989).
Chen et al., Chemistry 270, 2874-2878 (1995).
Chomczynski and Sacchi Anal. Biochem. 162, 156-159, (1987).
Chou and Fasman Adv. Enz. 47, 45-147 (1948).
DeClerck et. atl. J. Biol. Chem. 266, 3893 (1991).
Eisenberg et al. Proc. Natl. Acad. Sci. USA 81, 140-144 (1984).
Lewis et al., Proc. Natl. Acad. Sci. USA 88, 2830-2834 (1991).
Ellison et al. (Nuc. Acids Res. 10, 4071-4079 (1982).
Fisher et al. Cell 81, 935-946 (1995).
Gennaro A.R., *Remington's Pharmaceutical Sciences*, 18th ed. Mack, Easton, PA (1980).
Goeddel et al. Cold Spring Harbor Symp. Quart. Biol. 51, 597-609 (1986).
Goeddel, D.V., *Methods of Enzymology* v. 185, ed. Academic Press (1990).
Goldman et al. Ann. Rev. Biophys. Biophys. Chem. 15, 321-353 (1986).
Gribskov et al. (Proc. Natl. Acad. Sci. USA 83, 4355-4359 (1987).
Harlow and Lane, *Antibodies: A Laboratory Manual* Cold Spring Harbor Laboratory Press, Cold Spring Harbor N.Y. (1988).
Heldin, Cell 80, 213-223 (1995).
Kohno et al. PNAS USA 87, 8331-8335 (1990).
Kraulis, J. Appl. Cryst. 24, 946-950, 1991).
Kyte and Doolittle (J. Mol. Biol. 157, 105-132 (1982).
Loetscher et al. Cancer Cells 3(6), 221-226 (1991).
Luethy et al. (Protein Science 3, 139-146 (1994).
Malik et al., Exp. Hematol. 20: 1028-1035 (1992).
Matsudaira et al. J. Biol. Chem. 262, 10-35 (1987).
McDonald et al. Meth. Enzymol. 152, 219 (1987).
Nagata et al. Science 267, 1449-1456 (1995).
Ogden et al. Meth. Enzymol 152, 61 (1987).
Pearson et al. Meth. Enzymol. 183, (1990).

(Continued)

*Primary Examiner*—Marianne P Allen
*Assistant Examiner*—Regina M DeBerry
(74) *Attorney, Agent, or Firm*—Robert B. Winter

(57) ABSTRACT

The present invention discloses a novel secreted polypeptide, termed osteoprotegerin, which is a member of the tumor necrosis factor receptor superfamily and is involved in the regulation of bone metabolism. Also disclosed are nucleic acids encoding osteoprotegerin, polypeptides, recombinant vectors and host cells for expression, antibodies which bind OPG, and pharmaceutical compositions. The polypeptides are used to treat bone diseases characterized by increased resorption such as osteoporosis.

11 Claims, 46 Drawing Sheets

OTHER PUBLICATIONS

Sambrook et al. *Molecular Cloning: A Laboratory Manual*, 2nd ed. Cold Spring Harbor Laboratory Press, Cold Spring Harbor, New York (1989).
Simonet et al. J. Clin, Invest. 94, 1310-1319 (1994).
Smith, et al. Cell 76, 953-962 (1994).
Suda et al. Cell 75, 1169-1178 (1993).
Wigler et al. Cell 11, 233 (1977).
Presentation at Joint Annual Conference Japanase Biochemical Society & Japanese Microbiological Society, Aug. 26, 1996-Aug. 30, 1996 Abstracts 1-P-0538 and 1-P-0544.
Abbas et al., Cellular and Molecular Immunology, pp. 47-48, Second Edition. W.B. Saunders Company, Philadelphia (1994).
Alexander et al., "Altering the Antigenicity of Proteins", *:Pro. Natl. Acad. Sci.*, 89, 3352-3356 (1992).
Garcia et al., "Transgenic Mice Expressing High Levels of Soluble TNF-R1 Fusion Protein are Protected from Lethal Septic Shock and Cerebral Malaria, and are Highly Sensitive to Listeria Monocytogenes and Leishmania Major Infections", *Eur. J. Immunol*, 2401-2407 (1995).
Himmler et al., "Molecular Cloning and Expression of Human and Rat Tumor Necrosis Factor Receptor Chain (p60) and Its Soluble Derivative, Tumor Necrosis Factor-Binding Protein", *DNA and Cell Biology*, 9(10), 705-715 (1990).
Ngo et al., Computational Complexity Protein Structure Prediction, and the Levinthal Paradox, The Protein Folding Problem and Tertiary Structure Prediction, pp. 433-440 and 492-495. Merz and Le Grand, Editors, (Birkhauser Boston 1994).
Wells, James A., "Additivity of Mutational Effects in Proteins", *Biochemistry*, 29(37) 8509-8517 (1990).
Adams et al., "Complementary DNA sequencing: expressed sequence tags and human genome project", Science, 252: 1651-1656 (1991).
Anderson W. F., "Prospects for Human Gene Therapy", Science, 226: 401-409 (1984).
Baylink et al., "The diagnosis and treatment of osteoporosis: future prospects", Mol. Med. Today, pp. 133-140 (1999).
Bork et al., "Go hunting in sequence databases but watch out for the traps", Trends in Genetics, 12: 425-427 (1996).
Bork, P., "Powers and pitfalls in sequence analysis: The 70% hurdle", Genome Research, 10: 398-400 (2000).
Brenner, S., "Errors in genome annotation", Trends in Genetics, 15: 132-133 (1999).
Buckel, "Recombinant proteins for therapy", Trends in Pharmacol. Sciences, 17(12):450-456 (1996).
Crystal, R. G., "Transfer of Genes to Humans: Early Lessons and Obstacles to Success", Science, 270: 404-410 (1995).
Doerks et al., "Protein annotation: detective work for function prediction", Trends in Genetics, 14: 248-250 (1998).
Deonarain, M. P., "Ligand-targeted receptor-mediated vectors for gene delivery", Expert Opin. Ther. Patemts, 8(1): 53-69 (1998).
Eck et al., Gene-based therapy, Chapter 5, pp. 77-101, Goodman & Gilman's The Pharmacological Basis of Therapeutics, 9th Ed., McGraw-Hill (1996).
Anderson, W. French,"The current status of clinical gene therapy", Human Gene Therapy, 13: 1261-1262 (2002).
Miller, N. et al., "Targeted vectors for gene therapy", FASEB J., 9: 190-199 (1995).
Orkin et al., www.nih.gov/news/panelrep.html, pp. 1-36 (Dec. 1995).
Rodan et al., "Therapeutic approaches to bone disease", Science, 289: 1508-1514 (2000).
Robbins et al., "Viral vectors for gene therapy", Pharmacol Ther, 80(1): 35-47 (1998).
Simonet et al., "Osteoprotegrin: A Novel Secreted Protein Involved in the Regulation of Bone Density", Cell, 89:309-319 (1997).
Skolnick et al., "From genes to protein structure and function: novel applications of computational approaches in the genomic era", Trends in Biotech, 18(1): 34-39 (2000).
Smith et al., The challenges of genome sequence annotation or "The devil is in the details", Nature Biotechnology, 15: 1222-1223 (1997).

* cited by examiner

FIG.1A

```
                148         178         208         238         268         298
FRI-1           ALLVFLDIIEWTTQETFPPKYLHYDPETGRQLLCDKCAPGTYLKQHCTVRRKTLCVPCPD
                                                 |:  | ||:||    |  ||   |:| :| |
SW:TNR2_HUMAN   HALPAQVAFTPYAPEPGSTCRLREYYDQTAQMCCSKCSPGQHAKVFCTKTSDTVCDSCED
                         30        40        50        60        70        80

                328
FRI-1           YSYTDSWHTS
                 :||: |:
SW:TNR2_HUMAN   STYTQLWNWVPECLSCGSRCSSDQVETQACTREQNRICTCRPGWYCALSKQEGCRLCAPL
                         90        100       110       120       130       140
```

FIG.1B

```
FRI-1          69  YLHYDPETGRQLLCDKCAPGTYLKQHC.TVRRKTLCV.PCPDY.SYTDSW
                   |  |.  ...   | .| || :|  .|    : | |  || :   |.| .
TNFR profile    6  YHYYDQNGRMCEECHMCQPGHFLVKHCKQPKRDTVCHKPCEPGVTYTDDW

FRI-1         116  H
                   |
TNFR profile   56  H                                  Z Score = 8.29
```

FIG.2A

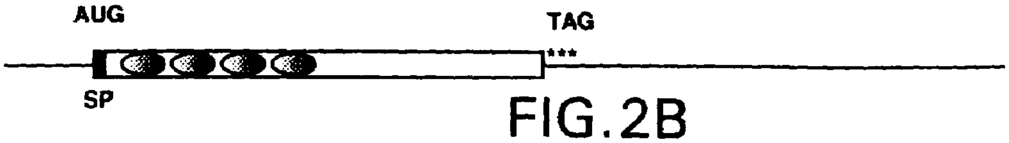

FIG.2B

```
       10                          30                          50
ATCAAAGGCAGGGCATACTTCCTGTTGCCCAGACCTTATATAAAACGTCATGTTCGCCTG
       70                          90                         110
GGCAGCAGAGAAGCACCTAGCACTGGCCCAGCGGCTGCCGCCTGAGGTTTCCAGAGGACC
      130                         150                         170
ACAATGAACAAGTGGCTGTGCTGTGCACTCCTGGTGTTCTTGGACATCATTGAATGGACA
    M  N  K  W  L  C  C  A  L  L  V  F  L  D  I  I  E  W  T
      190                         210                         230
ACCCAGGAAACCTTTCCTCCAAAATACTTGCATTATGACCCAGAAACCGGACGTCAGCTC
 T  Q  E  T  F  P  P  K  Y  L  H  Y  D  P  E  T  G  R  Q  L
      250                         270                         290
TTGTGTGACAAATGTGCTCCTGGCACCTACCTAAAACAGCACTGCACAGTCAGGAGGAAG
 L  C  D  K  C  A  P  G  T  Y  L  K  Q  H  C  T  V  R  R  K
      310                         330                         350
ACACTGTGTGTCCCTTGCCCTGACTACTCTTATACAGACAGCTGGCACACGAGTGATGAA
 T  L  C  V  P  C  P  D  Y  S  Y  T  D  S  W  H  T  S  D  E
      370                         390                         410
TGCGTGTACTGCAGCCCCGTGTGCAAGGAACTGCAGACCGTGAAACAGGAGTGCAACCGC
 C  V  Y  C  S  P  V  C  K  E  L  Q  T  V  K  Q  E  C  N  R
      430                         450                         470
ACCCACAACCGAGTGTGCGAATGTGAGGAAGGGCGCTACCTGGAGCTCGAATTCTGCTTG
 T  H  N  R  V  C  E  C  E  E  G  R  Y  L  E  L  E  F  C  L
      490                         510                         530
AAGCACCGGAGCTGTCCCCCAGGCTTGGGTGTGCTGCAGGCTGGGACCCCAGAGCGAAAC
 K  H  R  S  C  P  P  G  L  G  V  L  Q  A  G  T  P  E  R  N
      550                         570                         590
ACGGTTTGCAAAAGATGTCCGGATGGGTTCTTCTCAGGTGAGACGTCATCGAAAGCACCC
 T  V  C  K  R  C  P  D  G  F  F  S  G  E  T  S  S  K  A  P
      610                         630                         650
TGTAGGAAACACACCAACTGCAGCTCACTTGGCCTCCTGCTAATTCAGAAAGGAAATGCA
 C  R  K  H  T  N  C  S  S  L  G  L  L  L  I  Q  K  G  N  A
      670                         690                         710
ACACATGACAATGTATGTTCCGGAAACAGAGAAGCAACTCAAAATTGTGGAATAGATGTC
 T  H  D  N  V  C  S  G  N  R  E  A  T  Q  N  C  G  I  D  V
      730                         750                         770
ACCCTGTGCGAAGAGGCATTCTTCAGGTTTGCTGTGCCTACCAAGATTATACCGAATTGG
 T  L  C  E  E  A  F  F  R  F  A  V  P  T  K  I  I  P  N  W
      790                         810                         830
CTGAGTGTTCTGGTGGACAGTTTGCCTGGGACCAAAGTGAATGCAGAGAGTGTAGAGAGG
 L  S  V  L  V  D  S  L  P  G  T  K  V  N  A  E  S  V  E  R
      850                         870                         890
ATAAAACGGAGACACAGCTCGCAAGAGCAAACTTTCCAGCTACTTAAGCTGTGGAAGCAT
 I  K  R  R  H  S  S  Q  E  Q  T  F  Q  L  L  K  L  W  K  H
      910                         930                         950
CAAAACAGAGACCAGGAAATGGTGAAGAAGATCATCCAAGACATTGACCTCTGTGAAAGC
 Q  N  R  D  Q  E  M  V  K  K  I  I  Q  D  I  D  L  C  E  S
      970                         990                        1010
AGTGTGCAACGGCATATCGGCCACGCGAACCTCACCACAGAGCAGCTCCGCATCTTGATG
 S  V  Q  R  H  I  G  H  A  N  L  T  T  E  Q  L  R  I  L  M
```

FIG.2C

```
        1030                    1050                    1070
GAGAGCTTGCCTGGGAAGAAGATCAGCCCAGACGAGATTGAGAGAACGAGAAAGACCTGC
E  S  L  P  G  K  K  I  S  P  D  E  I  E  R  T  R  K  T  C
        1090                    1110                    1130
AAACCCAGCGAGCAGCTCCTGAAGCTACTGAGCTTGTGGAGGATCAAAAATGGAGACCAA
K  P  S  E  Q  L  L  K  L  L  S  L  W  R  I  K  N  G  D  Q
        1150                    1170                    1190
GACACCTTGAAGGGCCTGATGTACGCACTCAAGCACTTGAAAGCATACCACTTTCCCAAA
D  T  L  K  G  L  M  Y  A  L  K  H  L  K  A  Y  H  F  P  K
        1210                    1230                    1250
ACCGTCACCCACAGTCTGAGGAAGACCATCAGGTTCTTGCACAGCTTCACCATGTACCGA
T  V  T  H  S  L  R  K  T  I  R  F  L  H  S  F  T  M  Y  R
        1270                    1290                    1310
TTGTATCAGAAACTCTTTCTAGAAATGATAGGGAATCAGGTTCAATCAGTGAAGATAAGC
L  Y  Q  K  L  F  L  E  M  I  G  N  Q  V  Q  S  V  K  I  S
        1330                    1350                    1370
TGCTTATAGTTAGGAATGGTCACTGGGCTGTTTCTTCAGGATGGGCCAACACTGATGGAG
C  L
        1390                    1410                    1430
CAGATGGCTGCTTCTCCGGCTCTTGAAATGGCAGTTGATTCCTTTCTCATCAGTTGGTGG
        1450                    1470                    1490
GAATGAAGATCCTCCAGCCCAACACACACACTGGGGAGTCTGAGTCAGGAGAGTGAGGCA
        1510                    1530                    1550
GGCTATTTGATAATTGTGCAAAGCTGCCAGGTGTACACCTAGAAAGTCAAGCACCCTGAG
        1570                    1590                    1610
AAAGAGGATATTTTTATAACCTCAAACATAGGCCCTTTCCTTCCTCTCCTTATGGATGAG
        1630                    1650                    1670
TACTCAGAAGGCTTCTACTATCTTCTGTGTCATCCCTAGATGAAGGCCTCTTTTATTTAT
        1690                    1710                    1730
TTTTTTATTCTTTTTTTCGGAGCTGGGGACCGAACCCAGGGCCTTGCGCTTGCGAGGCAA
        1750                    1770                    1790
GTGCTCTACCACTGAGCTAAATCTCCAACCCCTGAAGGCCTCTTTCTTTCTGCCTCTGAT
        1810                    1830                    1850
AGTCTATGACATTCTTTTTTCTACAATTCGTATCAGGTGCACGAGCCTTATCCCATTTGT
        1870                    1890                    1910
AGGTTTCTAGGCAAGTTGACCGTTAGCTATTTTTCCCTCTGAAGATTTGATTCGAGTTGC
        1930                    1950                    1970
AGACTTGGCTAGACAAGCAGGGGTAGGTTATGGTAGTTTATTTAACAGACTGCCACCAGG
        1990                    2010                    2030
AGTCCAGTGTTTCTTGTTCCTCTGTAGTTGTACCTAAGCTGACTCCAAGTACATTTAGTA
        2050                    2070                    2090
TGAAAAATAATCAACAAATTTTATTCCTTCTATCAACATTGGCTAGCTTTGTTTCAGGGC
        2110                    2130                    2150
ACTAAAAGAAACTACTATATGGAGAAAGAATTGATATTGCCCCCAACGTTCAACAACCCA
        2170                    2190                    2210
ATAGTTTATCCAGCTGTCATGCCTGGTTCAGTGTCTACTGACTATGCGCCCTCTTATTAC
        2230                    2250                    2270
TGCATGCAGTAATTCAACTGGAAATAGTAATAATAATAATAGAAATAAAATCTAGACTCC
        2290                    2310                    2330
ATTGGATCTCTCTGAATATGGGAATATCTAACTTAAGAAGCTTTGAGATTTCAGTTGTGT
        2350                    2370                    2390
TAAAGGCTTTTATTAAAAAGCTGATGCTCTTCTGTAAAAGTTACTAATATATCTGTAAGA
        2410                    2430
CTATTACAGTATTGCTATTTATATCCATCCAG
```

FIG.2E

```
fas.frg     - C R L C D E G H G L E V E I N C T R T Q N T K C R C K P N F F C N S T V C E H C D P C T K C E H G   152
tnfr1.frg   N C S L C L N G - - - T V H L S C Q E K Q N T V C T C H A G F F L R E N E C V S C S N C K K S L E C   191
sfv-t2.frg  - - - - - P C T G H L S E S Q P C D R T H D R V C N C S T G N Y C L L K G Q N G C R I C A P Q T K C   129
tnfr2.frg   - - - - - R C S S D Q V E T Q A C T R E Q N R I C T C R P G W Y C A L S K Q E G C R L C A P L R K C   143
cd40.frg    - - - - - - - - N Q G L R V K K E G T A E S D T V C T C K E G Q H C T S K D C E - - - A C A Q H T P C   125
osteo.frg   - - - - - V C K E L Q T V K Q E C N R T H N R V C E C E E G R Y - - - L E L E - - - F C L K H R S C   124
ngfr.frg    - - - - - V G L Q S M - - S A P C V E A D D A V C R C A Y G Y Y - - - - Q D E T T G R C E A C R V C   128
ox40.frg    - - - - - R S G S E L - - K Q N C T P T E D T V C Q C - - - - - - - - - - R P G T Q P R Q D S S H - -   116
41bb.frg    - - - - - V C A G Y F R F K K F C S S T H N A E C E C I E G F H C L G P Q C T R C - - - - - - E K D C   105

fas.frg     - - - - - I I K E C T L T S N T K C K E - - - - - - - E G S R S N L - - - - G W L C L L L L P I P L I   187
tnfr1.frg   - - - - - T K L C L P Q I E N V K G T E - - - - - - - D S G T T V L L P L V I F F G L C L L S L L F I   230
sfv-t2.frg  P A G Y G V S - G H T R A G D T L C E K C P P H T Y S D S L S P T E R C G T S F N Y I S V G F N L Y   178
tnfr2.frg   R P G F G V A R P G T E T S D V V C K P C A P G T F S N T T S S T D I C R P H Q I C N V V A I P G N   193
cd40.frg    I P G F G V M E M A T E T T D T V C H P C P V G F F S N Q S S L F E K C Y P W T S C E D K N L E V L   175
osteo.frg   P P G L G V L Q A G T P E R N T V C K R C P D G F F S G E T S S K A P C R K H T N C S S L G L L I   174
ngfr.frg    E A G S G L V F S C Q D K Q N T V C E E C P D G T Y S D E A N H V D P C L P C T V C E D T E R Q L R   178
ox40.frg    - - - - - - - - - - - K L G V D C V P C P P G H F S P G S N - - Q A C K P W T N C T L S G K Q I R   152
41bb.frg    R P G Q E L T K Q G - - - - - - - - C K T C S L G T F N D Q - N G T G V C R P W T N C S L D G R S V L   147

fas.frg     V W V - - - - - - K R K E V Q K T C R K H R K E N Q G S H E S P T L N P E - - - - - - - - - - - - - T   219
tnfr1.frg   G L M Y R Y Q R W K S K L Y S I V C G K S T P E K E G E L E G T T T K P L A P N P S F S P T P G F T   280
sfv-t2.frg  P V N - - - - - - - - - - - - - - - - E T S C T T T A - - - - - G H N E V I K T K E F T V T L N Y T   207
tnfr2.frg   A S R - - - - - - - - - - - - - - - - D A V C T S T S P T R S M A P G A V H L P Q P V S T R S Q H T   227
cd40.frg    Q K G - - - - - - - - - - - - - - - - T S Q T N V I C G L K S R M R - - - - - - - - - - - - A L L V   197
osteo.frg   Q K G - - - - - - - - - - - - - - - - N A T H D N V C S G N R E A T Q N C G I D V T L C E E A F F R   208
ngfr.frg    E C T R W A D A E C E E I P G R - - W I T R S T - - P P E G S D S T A P S T Q E P E A P P E Q D L I   224
ox40.frg    H P A S N S V C E D R S L L A T L L W E T Q R T T F R P T T V P S T T V W P R T S Q L P S T P T L V   202
41bb.frg    K T G T T E K D V V C G P P V V S F S P S T T I S V T P E G G P G - - - - - - G H S L Q V L T L F L   191
```

FIG.9A

```
          10                         30                         50
CCTTATATAARACGTCATGATTGCCTGGGCTGCAGAGACGCACCTAGCACTGACCCAGCG
          70                         90                        110
GCTGCCTCCTGAGGTTTCCCGAGGACCACAATGAACAAGTGGCTGTGCTGCGCACTCCTG
                                     M  N  K  W  L  C  C  A  L  L
         130                        150                        170
GTGCTCCTGGACATCATTGAATGGACAACCCAGGAAACCCTTCCTCCAAAGTACTTGCAT
V  L  L  D  I  I  E  W  T  T  Q  E  T  L  P  P  K  Y  L  H
         190                        210                        230
TATGACCCAGAAACTGGTCATCAGCTCCTGTGTGACAAATGTGCTCCTGGCACCTACCTA
Y  D  P  E  T  G  H  Q  L  L  C  D  K  C  A  P  G  T  Y  L
         250                        270                        290
AAACAGCACTGCACAGTGAGGAGGAAGACATTGTGTGTCCCTTGCCCTGACCACTCTTAT
K  Q  H  C  T  V  R  R  K  T  L  C  V  P  C  P  D  H  S  Y
         310                        330                        350
ACGGACAGCTGGCACACCAGTGATGAGTGTGTGTATTGCAGCCCAGTGTGCAAGGAACTG
T  D  S  W  H  T  S  D  E  C  V  Y  C  S  P  V  C  K  E  L
         370                        390                        410
CAGTCCGTGAAGCAGGAGTGCAACCGCACCCACAACCGAGTGTGTGAGTGTGAGGAAGGG
Q  S  V  K  Q  E  C  N  R  T  H  N  R  V  C  E  C  E  E  G
         430                        450                        470
CGTTACCTGGAGATCGAATTCTGCTTGAAGCACCGGAGCTGTCCCCCGGGCTCCGGCGTG
R  Y  L  E  I  E  F  C  L  K  H  R  S  C  P  P  G  S  G  V
         490                        510                        530
GTGCAAGCTGGAACCCCAGAGCGAAACACAGTTTGCAAAAAATGTCCAGATGGGTTCTTC
V  Q  A  G  T  P  E  R  N  T  V  C  K  K  C  P  D  G  F  F
         550                        570                        590
TCAGGTGAGACTTCATCGAAAGCACCCTGTATAAAACACACGAACTGCAGCACATTTGGC
S  G  E  T  S  S  K  A  P  C  I  K  H  T  N  C  S  T  F  G
         610                        630                        650
CTCCTGCTAATTCAGAAAGGAAATGCAACACATGACAACGTGTGTTCCGGAAACAGAGAA
L  L  L  I  Q  K  G  N  A  T  H  D  N  V  C  S  G  N  R  E
         670                        690                        710
GCCACGCAAAAGTGTGGAATAGATGTCACCCTGTGTGAAGAGGCCTTCTTCAGGTTTGCT
A  T  Q  K  C  G  I  D  V  T  L  C  E  E  A  F  F  R  F  A
         730                        750                        770
GTTCCTACCAAGATTATACCAAATTGGCTGAGTGTTTTGGTGGACAGTTTGCCTGGGACC
V  P  T  K  I  I  P  N  W  L  S  V  L  V  D  S  L  P  G  T
```

FIG.9B

```
        790                           810                           830
AAAGTGAATGCCGAGAGTGTAGAGAGGATAAAACGGAGACACAGCTCACAAGAGCAAACC
K   V   N   A   E   S   V   E   R   I   K   R   R   H   S   S   Q   E   Q   T
        850                           870                           890
TTCCAGCTGCTGAAGCTGTGGAAACATCAAAACAGAGACCAGGAAATGGTGAAGAAGATC
F   Q   L   L   K   L   W   K   H   Q   N   R   D   Q   E   M   V   K   K   I
        910                           930                           950
ATCCAAGACATTGACCTCTGTGAAAGCAGCGTGCAGCGGCATCTCGGCCACTCGAACCTC
I   Q   D   I   D   L   C   E   S   S   V   Q   R   H   L   G   H   S   N   L
        970                           990                          1010
ACCACAGAGCAGCTTCTTGCCTTGATGGAGAGCCTGCCTGGGAAGAAGATCAGCCCAGAA
T   T   E   Q   L   L   A   L   M   E   S   L   P   G   K   K   I   S   P   E
       1030                          1050                          1070
GAGATTGAGAGAACGAGAAAGACCTGCAAATCGAGCGAGCAGCTCCTGAAGCTACTCAGT
E   I   E   R   T   R   K   T   C   K   S   S   E   Q   L   L   K   L   L   S
       1090                          1110                          1130
TTATGGAGGATCAAAAATGGTGACCAAGACACCTTGAAGGGCCTGATGTATGCCCTCAAG
L   W   R   I   K   N   G   D   Q   D   T   L   K   G   L   M   Y   A   L   K
       1150                          1170                          1190
CACTTGAAAACATCCCACTTTCCCAAAACTGTCACCCACAGTCTGAGGAAGACCATGAGG
H   L   K   T   S   H   F   P   K   T   V   T   H   S   L   R   K   T   M   R
       1210                          1230                          1250
TTCCTGCACAGCTTCACAATGTACAGACTGTATCAGAAGCTCTTTTTAGAAATGATAGGG
F   L   H   S   F   T   M   Y   R   L   Y   Q   K   L   F   L   E   M   I   G
       1270                          1290                          1310
AATCAGGTTCAATCCGTGAAAATAAGCTGCTTATAACTAGGAATGGTCACTGGGCTGTTT
N   Q   V   Q   S   V   K   I   S   C   L

CTTCA
```

FIG.9C

```
        10                               30                               50
GTATATATAACGTGATGAGCGTACGGGTGCGGAGACGCACCGGAGCGCTCGCCCAGCCGC
        70                               90                              110
CGYCTCCAAGCCCCTGAGGTTTCCGGGGACCACAATGAACAAGTTGCTGTGCTGCGCGCT
                                    M  N  K  L  L  C  C  A  L
       130                              150                              170
CGTGTTTCTGGACATCTCCATTAAGTGGACCACCCAGGAAACGTTTCCTCCAAAGTACCT
 V  F  L  D  I  S  I  K  W  T  T  Q  E  T  F  P  P  K  Y  L
       190                              210                              230
TCATTATGACGAAGAAACCTCTCATCAGCTGTTGTGTGACAAATGTCCTCCTGGTACCTA
 H  Y  D  E  E  T  S  H  Q  L  L  C  D  K  C  P  P  G  T  Y
       250                              270                              290
CCTAAAACAACACTGTACAGCAAAGTGGAAGACCGTGTGCGCCCCTTGCCCTGACCACTA
 L  K  Q  H  C  T  A  K  W  K  T  V  C  A  P  C  P  D  H  Y
       310                              330                              350
CTACACAGACAGCTGGCACACCAGTGACGAGTGTCTATACTGCAGCCCCGTGTGCAAGGA
 Y  T  D  S  W  H  T  S  D  E  C  L  Y  C  S  P  V  C  K  E
       370                              390                              410
GCTGCAGTACGTCAAGCAGGAGTGCAATCGCACCCACAACCGCGTGTGCGAATGCAAGGA
 L  Q  Y  V  K  Q  E  C  N  R  T  H  N  R  V  C  E  C  K  E
       430                              450                              470
AGGGCGCTACCTTGAGATAGAGTTCTGCTTGAAACATAGGAGCTGCCCTCCTGGATTTGG
 G  R  Y  L  E  I  E  F  C  L  K  H  R  S  C  P  P  G  F  G
       490                              510                              530
AGTGGTGCAAGCTGGAACCCCAGAGCGAAATACAGTTTGCAAAAGATGTCCAGATGGGTT
 V  V  Q  A  G  T  P  E  R  N  T  V  C  K  R  C  P  D  G  F
       550                              570                              590
CTTCTCAAATGAGACGTCATCTAAAGCACCCTGTAGAAAACACACAAATTGCAGTGTCTT
 F  S  N  E  T  S  S  K  A  P  C  R  K  H  T  N  C  S  V  F
       610                              630                              650
TGGTCTCCTGCTAACTCAGAAAGGAAATGCAACACACGACAACATATGTTCCGGAAACAG
 G  L  L  L  T  Q  K  G  N  A  T  H  D  N  I  C  S  G  N  S
       670                              690                              710
TGAATCAACTCAAAAATGTGGAATAGATGTTACCCTGTGTGAGGAGGCATTCTTCAGGTT
 E  S  T  Q  K  C  G  I  D  V  T  L  C  E  E  A  F  F  R  F
       730                              750                              770
TGCTGTTCCTACAAAGTTTACGCCTAACTGGCTTAGTGTCTTGGTAGACAATTTGCCTGG
 A  V  P  T  K  F  T  P  N  W  L  S  V  L  V  D  N  L  P  G
```

FIG.9D

```
        790                          810                          830
CACCAAAGTAAACGCAGAGAGTGTAGAGAGGATAAAACGGCAACACAGCTCACAAGAACA
 T   K   V   N   A   E   S   V   E   R   I   K   R   Q   H   S   S   Q   E   Q
        850                          870                          890
GACTTTCCAGCTGCTGAAGTTATGGAAACATCAAAACAAAGACCAAGATATAGTCAAGAA
 T   F   Q   L   L   K   L   W   K   H   Q   N   K   D   Q   D   I   V   K   K
        910                          930                          950
GATCATCCAAGATATTGACCTCTGTGAAAACAGCGTGCAGCGGCACATTGGACATGCTAA
 I   I   Q   D   I   D   L   C   E   N   S   V   Q   R   H   I   G   H   A   N
        970                          990                          1010
CCTCACCTTCGAGCAGCTTCGTAGCTTGATGGAAAGCTTACCGGGAAAGAAAGTGGGAGC
 L   T   F   E   Q   L   R   S   L   M   E   S   L   P   G   K   K   V   G   A
       1030                         1050                         1070
AGAAGACATTGAAAAAACAATAAAGGCATGCAAACCCAGTGACCAGATCCTGAAGCTGCT
 E   D   I   E   K   T   I   K   A   C   K   P   S   D   Q   I   L   K   L   L
       1090                         1110                         1130
CAGTTTGTGGCGAATAAAAAATGGCGACCAAGACACCTTGAAGGGCCTAATGCACGCACT
 S   L   W   R   I   K   N   G   D   Q   D   T   L   K   G   L   M   H   A   L
       1150                         1170                         1190
AAAGCACTCAAAGACGTACCACTTTCCCAAAACTGTCACTCAGAGTCTAAAGAAGACCAT
 K   H   S   K   T   Y   H   F   P   K   T   V   T   Q   S   L   K   K   T   I
       1210                         1230                         1250
CAGGTTCCTTCACAGCTTCACAATGTACAAATTGTATCAGAAGTTATTTTTAGAAATGAT
 R   F   L   H   S   F   T   M   Y   K   L   Y   Q   K   L   F   L   E   M   I
       1270                         1290                         1310
AGGTAACCAGGTCCAATCAGTAAAAATAAGCTGCTTATAACTGGAAATGGCCATTGAGCT
 G   N   Q   V   Q   S   V   K   I   S   C   L
       1330                         1350
GTTTCCTCACAATTGGCGAGATCCCATGGATGATAA
```

FIG.9E

```
muosteo.frg   MNKWLCCALLVLLDIIEWTTQETLPPKYLHYDPETGHQLLCDKCAPGTYL   50
ratosteo.frg  MNKWLCCALLVFLDIIEWTTQETFPPKYLHYDPETGRQLLCDKCAPGTYL   50
huosteo.frg   MNKLLCCALVFLDISIKWTTQETFPPKYLHYDEETSHQLLCDKCPPGTYL   50

muosteo.frg   KQHCTVRRKTLCVPCPDHSYTDSWHTSDECVYCSPVCKELQSVKQECNRT   100
ratosteo.frg  KQHCTVRRKTLCVPCPDYSYTDSWHTSDECVYCSPVCKELQTVKQECNRT   100
huosteo.frg   KQHCTAKWKTVCAPCPDHYYTDSWHTSDECLYCSPVCKELQYVKQECNRT   100

muosteo.frg   HNRVCECEEGRYLEIEFCLKHRSCPPGSGVVQAGTPERNTVCKKCPDGFF   150
ratosteo.frg  HNRVCECEEGRYLELEFCLKHRSCPPGLGVLQAGTPERNTVCKRCPDGFF   150
huosteo.frg   HNRVCECKEGRYLEIEFCLKHRSCPPGFGVVQAGTPERNTVCKRCPDGFF   150

muosteo.frg   SGETSSKAPCIKHTNCSTFGLLLIQKGNATHDNVCSGNREATQKCGIDVT   200
ratosteo.frg  SGETSSKAPCRKHTNCSSLGLLLIQKGNATHDNVCSGNREATQNCGIDVT   200
huosteo.frg   SNETSSKAPCRKHTNCSVFGLLLTQKGNATHDNICSGNSESTQKCGIDVT   200
```

FIG.9F

```
muosteo.frg   LCEEAFFRFAVPTKIIPNWLSVLVDSLPGTKVNAESVERIKRRHSSQEQT  250
ratosteo.frg  LCEEAFFRFAVPTKIIPNWLSVLVDSLPGTKVNAESVERIKRRHSSQEQT  250
huosteo.frg   LCEEAFFRFAVPTKFTPNWLSVLVDNLPGTKVNAESVERIKRQHSSQEQT  250

muosteo.frg   FQLLKLWKHQNRDQEMVKKIIQDIDLCESSVQRHLGHSNLTTEQLLALME  300
ratosteo.frg  FQLLKLWKHQNRDQEMVKKIIQDIDLCESSVQRHIGHANLTTEQLRILME  300
huosteo.frg   FQLLKLWKHQNKDQDIVKKIIQDIDLCENSVQRHIGHANLTFEQLRSLME  300

muosteo.frg   SLPGKKISPEEIERTRKTCKSSEQLLKLLSLWRIKNGDQDTLKGLMYALK  350
ratosteo.frg  SLPGKKISPDEIERTRKTCKPSEQLLKLLSLWRIKNGDQDTLKGLMYALK  350
huosteo.frg   SLPGKKVGAEDIEKTIKACKPSDQILKLLSLWRIKNGDQDTLKGLMHALK  350

muosteo.frg   HLKTSHFPKTVTHSLRKTMRFLHSFTMYRLYQKLFLEMIGNQVQSVKISC  400
ratosteo.frg  HLKAYHFPKTVTHSLRKTIRFLHSFTMYRLYQKLFLEMIGNQVQSVKISC  400
huosteo.frg   HSKTYHFPKTVTQSLKKTIRFLHSFTMYKLYQKLFLEMIGNQVQSVKISC  400

muosteo.frg   L  401
ratosteo.frg  L  401
huosteo.frg   L  401
```

FIG. 10

```
ltnrr    C P Q - G K Y I H P Q N N S I C C T K C H K G T Y L Y N D C P G P G Q D T D C R E C E S G S F T A S   49
humoste  P P K Y L H Y D E E T S H Q L L C D K C P P G T Y L K Q H C T A K - W K T V C A P C P D H Y Y T D S   49

ltnrr    E N H L R H C L S C S - K C R K E M G Q V E I S S C T V D R D T V C G C R K N Q Y R H Y W S E N L F   98
humoste  W H T S D E C L Y C S P V C - K E L Q Y V K - Q E C N R T H N R V C E C K E G R Y L E I - - - E - F   93

ltnrr    Q C F N C S L C L N G - T V H L S C Q E K Q N T V C T - C H A G F F L R E - - - - N E C V S C     139
humoste  - C L K H R S C P P G F G V V Q A G T P E R N T V C K R C P D G F F S N E T S S K A P C R K H     139
```

FIG. 12B

195-CGIDVTLCEEAFFRFAVPTKFTPNWLSVLVDNLPGTKVNAESVERIKRQHSS-246
195-CGIDVTLCEEAFFRFAVPTKIIPNWLSVLVDSLPGTKVNAESVERIKRRHSS-246

247-QEQTFQLLKLWKHQNKDQDIVKKIIQDIDLCENSVQRHIGHANLTFEQLRSL-298
247-QEQTFQLLKLWKHQNRDQEMVKKIIQDIDLCESSVQRHLGHSNLTTEQLLAL-298

299-MESLPGKKVGAEDIEKTIKACKPSDQILKLLSLWRIKNGDQDTLKGLMHALK-350
299-MESLPGKKISPEEIERTRKTCKSSEQLLKLLSLWRIKNGDQDTLKGLMYALK-350

351-HSKTYHFPKTVTQSLKKTIRFLHSFTMYKLYQKLFLEMIGNQVQSVKISCL-401
351-HLKTSHFPKTVTHSLRKTMRFLHSFTMYRLYQKLFLEMIGNQVQSVKISCL-401

C TERMINAL

OPG - 100 ng/ml

OPG - 10 ng/ml

OPG - 1 ng/ml

OPG - 0.1 ng/ml

FIG.19F
FIG.19E
FIG.19G
OPG - 0.001 ng/ml
OPG - 0.01 ng/ml
Control

Legend

| Growth | Intermediate | Terminal |
|---|---|---|
| Bone marrow cells CSF -1 | PGE2 + CSF-1 | ST2 cells 1,25 (OH)2 D3 Dexamethasone |
| 4 days | 2 days | 8 - 10 days |

| Groups | OPG | OPG |
|---|---|---|
| CTL - CTL | — — — | — — — |
| OPG - CTL | 100 ng/ml | — — — |
| OPG - OPG | — — — | 100 ng/ml |
| OPG - OPG | 100 ng/ml | 100 ng/ml |

* Different to PBS, $p < 0.05$
Different to OPG + IL1, $p < 0.05$

PBS/PBS

PBS/OPG

* Different to control $p < 0.01$

FIG.26A
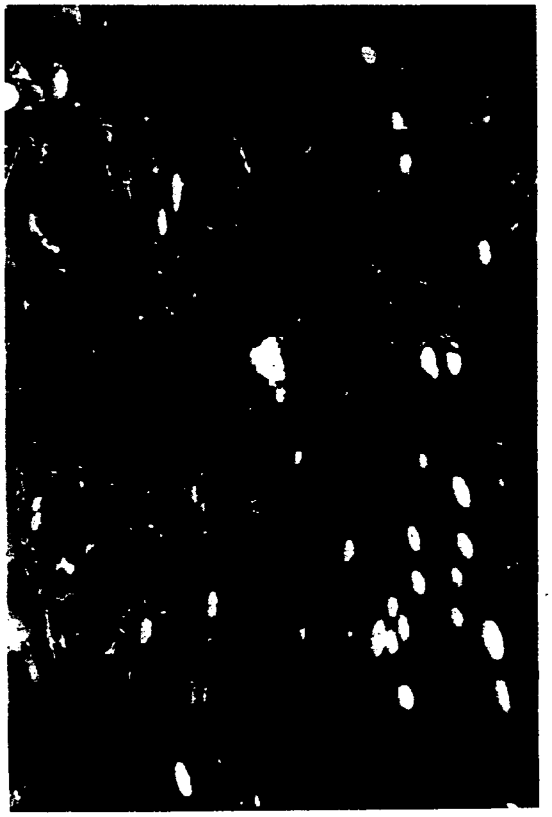
FIG.26.B

* Different to OVX $p < 0.05$

SEQUENCE LISTING

```
<160> NUMBER OF SEQ ID NOS: 179

<210> SEQ ID NO 1
<211> LENGTH: 36
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (28)..(35)
<223> OTHER INFORMATION: n could be any one of A, G, C or T

<400> SEQUENCE: 1

aaaggaagga aaaaagcggc cgctacannn nnnnnt                               36


<210> SEQ ID NO 2
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2

tcgacccacg cgtccg                                                     16


<210> SEQ ID NO 3
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 3

gggtgcgcag gc                                                         12


<210> SEQ ID NO 4
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 4

tgtaaaacga cggccagt                                                   18
```

-continued

<210> SEQ ID NO 5
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 5
caggaaacag ctatgacc 18

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
caattaaccc tcactaaagg 20

<210> SEQ ID NO 7
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 7
gcattatgac ccagaaaccg gac 23

<210> SEQ ID NO 8
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 8
aggtagcgcc cttcctcaca ttc 23

<210> SEQ ID NO 9
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 9
gactagtccc acaatgaaca agtggctgtg 30

<210> SEQ ID NO 10
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 10
ataagaatgc ggccgctaaa ctatgaaaca gcccagtgac cattc 45

<210> SEQ ID NO 11
<211> LENGTH: 21
<212> TYPE: DNA
<213> ORGANISM: Artificial sequence
<220> FEATURE:
<223> OTHER INFORMATION: Synthetic oligonucleotide -continued

<400> SEQUENCE: 11
gcctctagaa agagctggga c 21

<210> SEQ ID NO 12
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 12
cgccgtgttc catttatgag c 21

<210> SEQ ID NO 13
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 13
atcaaaggca gggcatactt cctg 24

<210> SEQ ID NO 14
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 14
gttgcactcc tgtttcacgg tctg 24

<210> SEQ ID NO 15
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 15
caagacacct tgaagggcct gatg 24

<210> SEQ ID NO 16
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 16
taacttttac agaagagcat cagc 24

<210> SEQ ID NO 17
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 17
agcgcggccg catgaacaag tggctgtgct gcg 33

<210> SEQ ID NO 18

-continued

<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 18
agctctagag aaacagccca gtgaccattc c 31

<210> SEQ ID NO 19
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 19
gtgaagctgt gcaagaacct gatg 24

<210> SEQ ID NO 20
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 20
atcaaaggca gggcatactt cctg 24

<210> SEQ ID NO 21
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 21
cagatcctga agctgctcag tttg 24

<210> SEQ ID NO 22
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 22
agcgcggccg cggggaccac aatgaacaag ttg 33

<210> SEQ ID NO 23
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 23
agctctagaa ttgtgaggaa acagctcaat ggc 33

<210> SEQ ID NO 24
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 24

-continued atagcggccg ctgagcccaa atcttgtgac aaaactcac 39

<210> SEQ ID NO 25
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 25
tctagagtcg acttatcatt tacccggaga cagggagagg ctctt 45

<210> SEQ ID NO 26
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 26
cctctgagct caagcttccg aggaccacaa tgaacaag 38

<210> SEQ ID NO 27
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 27
cctctgcggc cgctaagcag cttattttca cggattgaac ctg 43

<210> SEQ ID NO 28
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 28
cctctgagct caagcttccg aggaccacaa tgaacaag 38

<210> SEQ ID NO 29
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 29
tccgtaagaa acagcccagt gacc 24

<210> SEQ ID NO 30
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 30
cctctgcggc cgctgttgca tttcctttct g 31

<210> SEQ ID NO 31
<211> LENGTH: 19
<212> TYPE: PRT

-continued

<213> ORGANISM: Artificial sequence
<220> FEATURE:
<223> OTHER INFORMATION: Synthetic

<400> SEQUENCE: 31

Glu Thr Leu Pro Pro Lys Tyr Leu His Tyr Asp Pro Glu Thr Gly His
1 5 10 15

Gln Leu Leu

<210> SEQ ID NO 32
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 32
tcccttgccc tgaccactct t 21

<210> SEQ ID NO 33
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 33
cctctgcggc cgcacacacg ttgtcatgtg ttgc 34

<210> SEQ ID NO 34
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 34
tcccttgccc tgaccactct t 21

<210> SEQ ID NO 35
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 35
cctctgcggc cgccttttgc gtggcttctc tgtt 34

<210> SEQ ID NO 36
<211> LENGTH: 37
<212> TYPE: DNA
<213> ORGANISM: Artificial sequence
<220> FEATURE:
<223> OTHER INFORMATION: Synthetic oligonucleotide

<400> SEQUENCE: 36
cctctgagct caagcttggt ttccggggac cacaatg 37

<210> SEQ ID NO 37
<211> LENGTH: 38
<212> TYPE: DNA
<213> ORGANISM: Artificial sequence
<220> FEATURE:
<223> OTHER INFORMATION: Synthetic oligonucleotide -continued

<400> SEQUENCE: 37
cctctgcggc cgctaagcag cttattttta ctgaatgg 38

<210> SEQ ID NO 38
<211> LENGTH: 37
<212> TYPE: DNA
<213> ORGANISM: Artificial sequence
<220> FEATURE:
<223> OTHER INFORMATION: Synthetic oligonucleotide

<400> SEQUENCE: 38
cctctgagct caagcttggt ttccggggac cacaatg 37

<210> SEQ ID NO 39
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 39
cctctgcggc cgccagggta acatctattc cac 33

<210> SEQ ID NO 40
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 40
ccgaagcttc caccatgaac aagtggctgt gctgc 35

<210> SEQ ID NO 41
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 41
cctctgtcga ctattataag cagcttattt tcacggattg 40

<210> SEQ ID NO 42
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 42
tcccttgccc tgaccactct t 21

<210> SEQ ID NO 43
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 43
cctctgtcga cttaacacac gttgtcatgt gttgc 35

<210> SEQ ID NO 44
<211> LENGTH: 21

-continued

<212> TYPE: DNA
<213> ORGANISM: Artificial sequence
<220> FEATURE:
<223> OTHER INFORMATION: Synthetic oligonucleotide

<400> SEQUENCE: 44
tcccttgccc tgaccactct t 21

<210> SEQ ID NO 45
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 45
cctctgtcga cttacttttg cgtggcttct ctgtt 35

<210> SEQ ID NO 46
<211> LENGTH: 1537
<212> TYPE: DNA
<213> ORGANISM: Escherichia coli

<400> SEQUENCE: 46
gtgaagagcg tgaagagcgg ttcctccttt cagcaaaaaa cccctcaaga cccgtttaga 60
ggccccaagg ggttatgcta gttattgctc agcggtggca gcagccaact cagcttcctt 120
tcgggctttc ttcttcttct tcttctttcc gcggatcctc gagtaagctt ccatggtacc 180
ctgcaggtcg acactagtga gctcgaattc caacgcgtta accatatgtt attcctcctt 240
taattagtta aaacaaatct agaatcaaat cgattaatcg actataacaa accattttct 300
tgcgtaaacc tgtacgatcc tacaggtact tatgttaaac aattgtattt caagcgatat 360
aatagtgtga caaaaatcca atttattaga atcaaatgtc aatctattac cgttttaatg 420
atatataaca cgcaaaactt gcgacaaaca ataggtaagg ataaagagat gggtatgaaa 480
gacataaatg ccgacgacac ttacagaata attaataaaa ttaaagcctg tagaagcaat 540
aatgatatta atcaatgctt atctgatatg actaaaatgg tacattgtga atattattta 600
ctcgcgatca tttatcctca ttctatggtt aaatctgata tttcaattct ggataattac 660
cctaaaaaat ggaggcaata ttatgatgac gctaatttaa taaaatatga tcctatagta 720
gattattcta actccaatca ttcaccgatt aattggaata tatttgaaaa caatgctgta 780
aataaaaaat ctccaaatgt aattaaagaa gcgaaatcat caggtcttat cactgggttt 840
agtttcccta ttcatactgc taataatggc ttcggaatgc ttagttttgc acattcagag 900
aaagacaact atatagatag tttatttttta catgcgtgta tgaacatacc attaattgtt 960
ccttctctag ttgataatta tcgaaaaata aatatagcaa ataataaatc aaacaacgat 1020
ttaaccaaaa gagaaaaaga atgtttagcg tgggcatgcg aaggaaaaag ctcttgggat 1080
atttcaaaaa tattaggctg tagtaagcgc acggtcactt tccatttaac caatgcgcaa 1140
atgaaactca atacaacaaa ccgctgccaa agtatttcta aagcaatttt aacaggagca 1200
attgattgcc catactttaa aagttaagta cgacgtccat atttgaatgt atttagaaaa 1260
ataaacaaaa gagtttgtag aaacgcaaaa aggccatccg tcaggatggc cttctgctta 1320
atttgatgcc tggcagttta tggcgggcgt cctgcccgcc accctccggg ccgttgcttc 1380
gcaacgttca aatccgctcc cggcggattt gtcctactca ggagagcgtt caccgacaaa 1440
caacagataa aacgaaaggc ccagtctttc gactgagcct ttcgttttat ttgatgcctg 1500

-continued

```
gcagttccct actctcgcat ggggagacca tgcatac                          1537


<210> SEQ ID NO 47
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 47

ccggcggaca tttatcacac agcagctgat gagaagtttc ttcatcca                48


<210> SEQ ID NO 48
<211> LENGTH: 55
<212> TYPE: DNA
<213> ORGANISM: Artificial sequence
<220> FEATURE:
<223> OTHER INFORMATION: Synthetic oligonucleotide

<400> SEQUENCE: 48

cgatttgatt ctagaaggag gaataacata tggttaacgc gttggaattc ggtac         55


<210> SEQ ID NO 49
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 49

cgaattccaa cgcgttaacc atatgttatt cctccttcta gaatcaaat               49


<210> SEQ ID NO 50
<211> LENGTH: 1546
<212> TYPE: DNA
<213> ORGANISM: Escherichia coli

<400> SEQUENCE: 50

gcgtaacgta tgcatggtct ccccatgcga gagtagggaa ctgccaggca tcaaataaaa     60

cgaaaggctc agtcgaaaga ctgggccttt cgttttatct gttgtttgtc ggtgaacgct    120

ctcctgagta ggacaaatcc gccgggagcg gatttgaacg ttgcgaagca acggcccgga    180

gggtggcggg caggacgccc gccataaact gccaggcatc aaattaagca gaaggccatc    240

ctgacggatg gcctttttgc gtttctacaa actcttttgt ttattttttct aaatacattc    300

aaatatggac gtcgtactta acttttaaag tatgggcaat caattgctcc tgttaaaatt    360

gctttagaaa tactttggca gcggtttgtt gtattgagtt tcatttgcgc attggttaaa    420

tggaaagtga ccgtgcgctt actacagcct aatatttttg aaatatccca agagcttttt    480

ccttcgcatg cccacgctaa acattctttt tctcttttgg ttaaatcgtt gtttgattta    540

ttatttgcta tatttatttt tcgataatta tcaactagag aaggaacaat taatggtatg    600

ttcatacacg catgtaaaaa taaactatct atatagttgt ctttctctga atgtgcaaaa    660

ctaagcattc cgaagccatt attagcagta tgaataggga aactaaaccc agtgataaga    720

cctgatgatt tcgcttcttt aattacattt ggagattttt tatttacagc attgttttca    780

aatatattcc aattaatcgg tgaatgattg gagttagaat aatctactat aggatcatat    840

tttattaaat tagcgtcatc ataatattgc ctccattttt tagggtaatt atccagaatt    900

gaaatatcag atttaaccat agaatgagga taaatgatcg cgagtaaata atattcacaa    960

tgtaccattt tagtcatatc agataagcat tgattaatat cattattgct tctacaggct   1020
```

-continued ttaattttat taattattct gtaagtgtcg tcggcattta tgtctttcat acccatctct 1080
ttatccttac ctattgtttg tcgcaagttt tgcgtgttat atatcattaa aacggtaata 1140
gattgacatt tgattctaat aaattggatt tttgtcacac tattatatcg cttgaaatac 1200
aattgtttaa cataagtacc tgtaggatcg tacaggttta cgcaagaaaa tggtttgtta 1260
tagtcgatta atcgatttga ttctagattt gttttaacta attaaaggag gaataacata 1320
tggttaacgc gttggaattc gagctcacta gtgtcgacct gcagggtacc atggaagctt 1380
actcgaggat ccgcggaaag aagaagaaga agaagaaagc ccgaaaggaa gctgagttgg 1440
ctgctgccac cgctgagcaa taactagcat aaccccttgg ggcctctaaa cgggtcttga 1500
ggggtttttt gctgaaagga ggaaccgctc ttcacgctct tcacgc 1546

<210> SEQ ID NO 51
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 51
tatgaaacat catcaccatc accatcatgc tagcgttaac gcgttgg 47

<210> SEQ ID NO 52
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 52
aattccaacg cgttaacgct agcatgatgg tgatggtgat gatgtttca 49

<210> SEQ ID NO 53
<211> LENGTH: 141
<212> TYPE: DNA
<213> ORGANISM: Artificial sequence
<220> FEATURE:
<223> OTHER INFORMATION: Synthetic oligonucleotide

<400> SEQUENCE: 53
ctaattccgc tctcacctac caaacaatgc ccccctgcaa aaaataaatt catataaaaa 60
acatacagat aaccatctgc ggtgataaat tatctctggc ggtgttgaca taaataccac 120
tggcggtgat actgagcaca t 141

<210> SEQ ID NO 54
<211> LENGTH: 147
<212> TYPE: DNA
<213> ORGANISM: Artificial sequence
<220> FEATURE:
<223> OTHER INFORMATION: Synthetic oligonucleotide

<400> SEQUENCE: 54
cgatgtgctc agtatcaccg ccagtggtat ttatgtcaac accgccagag ataatttatc 60
accgcagatg gttatctgta tgttttttat atgaatttat tttttgcagg ggggcattgt 120
ttggtaggtg agagcggaat tagacgt 147

<210> SEQ ID NO 55
<211> LENGTH: 55
<212> TYPE: DNA

-continued

<213> ORGANISM: Artificial sequence
<220> FEATURE:
<223> OTHER INFORMATION: Synthetic oligonucleotide

<400> SEQUENCE: 55
cgatttgatt ctagaaggag gaataacata tggttaacgc gttggaattc ggtac 55

<210> SEQ ID NO 56
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 56
cgaattccaa cgcgttaacc atatgttatt cctccttcta gaatcaaat 49

<210> SEQ ID NO 57
<211> LENGTH: 668
<212> TYPE: DNA
<213> ORGANISM: Escherichia coli

<400> SEQUENCE: 57
gtgaagagcg tgaagagcgg ttcctccttt cagcaaaaaa cccctcaaga cccgtttaga 60
ggccccaagg ggttatgcta gttattgctc agcggtggca gcagccaact cagcttcctt 120
tcgggctttc ttcttcttct tcttctttcc gcggatcctc gagtaagctt ccatggtacc 180
ctgcaggtcg acactagtga gctcgaattc caacgcgtta accatatgtt attcctcctt 240
taattagtta actcaaatct agaatcaaat cgataaattg tgagcgctca caattgagaa 300
tattaatcaa gaattttagc atttgtcaaa tgaatttttt aaaaattatg agacgtccat 360
atttgaatgt atttagaaaa ataaacaaaa gagtttgtag aaacgcaaaa aggccatccg 420
tcaggatggc cttctgctta atttgatgcc tggcagttta tggcgggcgt cctgcccgcc 480
accctccggg ccgttgcttc gcaacgttca aatccgctcc cggcggattt gtcctactca 540
ggagagcgtt caccgacaaa caacagataa aacgaaaggc ccagtctttc gactgagcct 600
ttcgttttat ttgatgcctg gcagttccct actctcgcat ggggagacca tgcatacgtt 660
acgcacgt 668

<210> SEQ ID NO 58
<211> LENGTH: 726
<212> TYPE: DNA
<213> ORGANISM: Escherichia coli

<400> SEQUENCE: 58
gcgtaacgta tgcatggtct ccccatgcga gagtagggaa ctgccaggca tcaaataaaa 60
cgaaaggctc agtcgaaaga ctgggccttt cgttttatct gttgtttgtc ggtgaacgct 120
ctcctgagta ggacaaatcc gccgggagcg gatttgaacg ttgcgaagca acggcccgga 180
gggtggcggg caggacgccc gccataaact gccaggcatc aaattaagca gaaggggcct 240
cccaccgccc gtcctgcggg cggtatttga cggtccgtag tttaattcgt cttcgccatc 300
ctgacggatg gcctttttgc gtttctacaa actcttttgt ttatttttct aaatacattc 360
aaatatggac gtctcataat ttttaaaaaa ttcatttgac aaatgctaaa attcttgatt 420
aatattctca attgtgagcg ctcacaattt atcgatttga ttctagattt gttttaacta 480
attaaaggag gaataacata tggttaacgc gttggaattc gagctcacta gtgtcgacct 540
gcagggtacc atggaagctt actcgaggat ccgcggaaag aagaagaaga agaagaaagc 600

-continued

```
ccgaaaggaa gctgagttgg ctgctgccac cgctgagcaa taactagcat aaccccttgg    660

ggcctctaaa cgggtcttga ggggtttttt gctgaaagga ggaaccgctc ttcacgctct    720

tcacgc                                                               726


<210> SEQ ID NO 59
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 59

tacgcactgg atccttataa gcagcttatt tttactgatt ggac                      44


<210> SEQ ID NO 60
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 60

gtcctcctgg tacctaccta aaacaac                                         27


<210> SEQ ID NO 61
<211> LENGTH: 102
<212> TYPE: DNA
<213> ORGANISM: Artificial sequence
<220> FEATURE:
<223> OTHER INFORMATION: Synthetic oligonucleotide

<400> SEQUENCE: 61

tatggatgaa gaaacttctc atcagctgct gtgtgataaa tgtccgccgg gtacccggcg     60

gacatttatc acacagcagc tgatgagaag tttcttcatc ca                       102


<210> SEQ ID NO 62
<211> LENGTH: 19
<212> TYPE: PRT
<213> ORGANISM: Artificial sequence
<220> FEATURE:
<223> OTHER INFORMATION: Synthetic

<400> SEQUENCE: 62

Met Asp Glu Glu Thr Ser His Gln Leu Leu Cys Asp Lys Cys Pro Pro
1               5                   10                  15

Gly Thr Tyr


<210> SEQ ID NO 63
<211> LENGTH: 84
<212> TYPE: DNA
<213> ORGANISM: Artificial sequence
<220> FEATURE:
<223> OTHER INFORMATION: Synthetic oligonucleotide

<400> SEQUENCE: 63

tatggaaact tttcctccaa aatatcttca ttatgatgaa gaaacttctc atcagctgct     60

gtgtgataaa tgtccgccgg gtac                                            84


<210> SEQ ID NO 64
<211> LENGTH: 78
<212> TYPE: DNA
<213> ORGANISM: Artificial sequence
```

-continued

<220> FEATURE:
<223> OTHER INFORMATION: Synthetic oligonucleotide

<400> SEQUENCE: 64
ccggcggaca tttatcacac agcagctgat gagaagtttc ttcatcataa tgaagatatt 60
ttggaggaaa agtttcca 78

<210> SEQ ID NO 65
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 65
tacgcactgg atccttataa gcagcttatt ttcacggatt gaac 44

<210> SEQ ID NO 66
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 66
gtgctcctgg tacctaccta aaacagcact gcacagtg 38

<210> SEQ ID NO 67
<211> LENGTH: 84
<212> TYPE: DNA
<213> ORGANISM: Artificial sequence
<220> FEATURE:
<223> OTHER INFORMATION: Synthetic oligonucleotide

<400> SEQUENCE: 67
tatggaaact ctgcctccaa aatacctgca ttacgatccg gaaactggtc atcagctgct 60
gtgtgataaa tgtgctccgg gtac 84

<210> SEQ ID NO 68
<211> LENGTH: 78
<212> TYPE: DNA
<213> ORGANISM: Artificial sequence
<220> FEATURE:
<223> OTHER INFORMATION: Synthetic oligonucleotide

<400> SEQUENCE: 68
ccggagcaca tttatcacac agcagctgat gaccagtttc cggatcgtaa tgcaggtatt 60
ttggaggcag agtttcca 78

<210> SEQ ID NO 69
<211> LENGTH: 54
<212> TYPE: DNA
<213> ORGANISM: Artificial sequence
<220> FEATURE:
<223> OTHER INFORMATION: Synthetic oligonucleotide

<400> SEQUENCE: 69
tatggaccca gaaactggtc atcagctgct gtgtgataaa tgtgctccgg gtac 54

<210> SEQ ID NO 70
<211> LENGTH: 48
<212> TYPE: DNA
<213> ORGANISM: Artificial sequence
<220> FEATURE:

-continued

<223> OTHER INFORMATION: Synthetic oligonucleotide

<400> SEQUENCE: 70
ccggagcaca tttatcacac agcagctgat gaccagtttc tgggtcca 48

<210> SEQ ID NO 71
<211> LENGTH: 87
<212> TYPE: DNA
<213> ORGANISM: Artificial sequence
<220> FEATURE:
<223> OTHER INFORMATION: Synthetic oligonucleotide

<400> SEQUENCE: 71
tatgaaagaa actctgcctc caaaatacct gcattacgat ccggaaactg gtcatcagct 60
gctgtgtgat aaatgtgctc cgggtac 87

<210> SEQ ID NO 72
<211> LENGTH: 81
<212> TYPE: DNA
<213> ORGANISM: Artificial sequence
<220> FEATURE:
<223> OTHER INFORMATION: Synthetic oligonucleotide

<400> SEQUENCE: 72
ccggagcaca tttatcacac agcagctgat gaccagtttc cggatcgtaa tgcaggtatt 60
ttggaggcag agtttctttc a 81

<210> SEQ ID NO 73
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 73
gttctcctca tatgaaacat catcaccatc accatcatga aactctgcct ccaaaatacc 60
tgcattacga t 71

<210> SEQ ID NO 74
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 74
gttctcctca tatgaaagaa actctgcctc caaaatacct gca 43

<210> SEQ ID NO 75
<211> LENGTH: 76
<212> TYPE: DNA
<213> ORGANISM: Artificial sequence
<220> FEATURE:
<223> OTHER INFORMATION: Synthetic oligonucleotide

<400> SEQUENCE: 75
tacgcactgg atccttaatg atggtgatgg tgatgatgta agcagcttat tttcacggat 60
tgaacctgat tcccta 76

<210> SEQ ID NO 76
<211> LENGTH: 47
<212> TYPE: DNA
<213> ORGANISM: Artificial sequence -continued
<220> FEATURE:
<223> OTHER INFORMATION: Synthetic oligonucleotide

<400> SEQUENCE: 76
gttctcctca tatgaaatac ctgcattacg atccggaaac tggtcat 47

<210> SEQ ID NO 77
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 77
gttctcctat taatgaaata tcttcattat gatgaagaaa ctt 43

<210> SEQ ID NO 78
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 78
tacgcactgg atccttataa gcagcttatt tttactgatt 40

<210> SEQ ID NO 79
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 79
gttctcctca tatggaaact ctgcctccaa aatacctgca 40

<210> SEQ ID NO 80
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 80
tacgcactgg atccttatgt tgcatttcct ttctgaatta gca 43

<210> SEQ ID NO 81
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 81
ccggaaacag ataatgag 18

<210> SEQ ID NO 82
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 82
gatcctcatt atctgttt 18

-continued

<210> SEQ ID NO 83
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 83
ccggaaacag agaagccacg caaaagtaag 30

<210> SEQ ID NO 84
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 84
gatccttact tttgcgtggc ttctctgttt 30

<210> SEQ ID NO 85
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 85
tatgttaatg ag 12

<210> SEQ ID NO 86
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 86
gatcctcatt aaca 14

<210> SEQ ID NO 87
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 87
tatgttccgg aaacagttaa g 21

<210> SEQ ID NO 88
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 88
gatccttaac tgtttccgga aca 23

<210> SEQ ID NO 89
<211> LENGTH: 36
<212> TYPE: DNA
<213> ORGANISM: Artificial sequence
<220> FEATURE:
<223> OTHER INFORMATION: Synthetic oligonucleotide -continued

<400> SEQUENCE: 89
tatgttccgg aaacagtgaa tcaactcaaa aataag 36

<210> SEQ ID NO 90
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 90
gatccttatt tttgagttga ttcactgttt ccggaaca 38

<210> SEQ ID NO 91
<211> LENGTH: 100
<212> TYPE: DNA
<213> ORGANISM: Artificial sequence
<220> FEATURE:
<223> OTHER INFORMATION: Synthetic oligonucleotide

<400> SEQUENCE: 91
ctagcgacga cgacgacaaa gaaactctgc ctccaaaata cctgcattac gatccggaaa 60
ctggtcatca gctgctgtgt gataaatgtg ctccgggtac 100

<210> SEQ ID NO 92
<211> LENGTH: 92
<212> TYPE: DNA
<213> ORGANISM: Artificial sequence
<220> FEATURE:
<223> OTHER INFORMATION: Synthetic oligonucleotide

<400> SEQUENCE: 92
ccggagcaca tttatcacac agcagctgat gaccagtttc cggatcgtaa tgcaggtatt 60
ttggaggcag agtttctttg tcgtcgtcgt cg 92

<210> SEQ ID NO 93
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 93
acaaacacaa tcgatttgat actaga 26

<210> SEQ ID NO 94
<211> LENGTH: 50
<212> TYPE: DNA
<213> ORGANISM: Artificial sequence
<220> FEATURE:
<223> OTHER INFORMATION: Synthetic oligonucleotide

<400> SEQUENCE: 94
tttgttttaa ctaattaaag gaggaataaa atatgagagg atcgcatcac 50

<210> SEQ ID NO 95
<211> LENGTH: 50
<212> TYPE: DNA
<213> ORGANISM: Artificial sequence
<220> FEATURE:
<223> OTHER INFORMATION: Synthetic oligonucleotide

<400> SEQUENCE: 95

-continued catcaccatc acgaaacctt cccgccgaaa tacctgcact acgacgaaga 50

<210> SEQ ID NO 96
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 96
aacctcccac cagctgctgt gcgacaaatg cccgccgggt acccaaaca 49

<210> SEQ ID NO 97
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 97
tgtttgggta cccggcgggc atttgt 26

<210> SEQ ID NO 98
<211> LENGTH: 50
<212> TYPE: DNA
<213> ORGANISM: Artificial sequence
<220> FEATURE:
<223> OTHER INFORMATION: Synthetic oligonucleotide

<400> SEQUENCE: 98
cgcacagcag ctggtgggag gtttcttcgt cgtagtgcag gtatttcggc 50

<210> SEQ ID NO 99
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 99
gggaaggttt cgtgatggtg atggtgatgc gatcctctca tattttatt 49

<210> SEQ ID NO 100
<211> LENGTH: 50
<212> TYPE: DNA
<213> ORGANISM: Artificial sequence
<220> FEATURE:
<223> OTHER INFORMATION: Synthetic oligonucleotide

<400> SEQUENCE: 100
cctcctttaa ttagttaaaa caaatctagt atcaaatcga ttgtgtttgt 50

<210> SEQ ID NO 101
<211> LENGTH: 59
<212> TYPE: DNA
<213> ORGANISM: Artificial sequence
<220> FEATURE:
<223> OTHER INFORMATION: Synthetic oligonucleotide

<400> SEQUENCE: 101
acaaacacaa tcgatttgat actagatttg ttttaactaa ttaaaggagg aataaaatg 59

<210> SEQ ID NO 102
<211> LENGTH: 48
<212> TYPE: DNA
<213> ORGANISM: Artificial sequence -continued
<220> FEATURE:
<223> OTHER INFORMATION: Synthetic oligonucleotide

<400> SEQUENCE: 102
ctaattaaag gaggaataaa atgaaagaaa cttttcctcc aaaatatc 48

<210> SEQ ID NO 103
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 103
tgtttgggta cccggcggac atttatcaca c 31

<210> SEQ ID NO 104
<211> LENGTH: 59
<212> TYPE: DNA
<213> ORGANISM: Artificial sequence
<220> FEATURE:
<223> OTHER INFORMATION: Synthetic oligonucleotide

<400> SEQUENCE: 104
acaaacacaa tcgatttgat actagatttg ttttaactaa ttaaaggagg aataaaatg 59

<210> SEQ ID NO 105
<211> LENGTH: 54
<212> TYPE: DNA
<213> ORGANISM: Artificial sequence
<220> FEATURE:
<223> OTHER INFORMATION: Synthetic oligonucleotide

<400> SEQUENCE: 105
ctaattaaag gaggaataaa atgaaaaaaa aagaaacttt tcctccaaaa tatc 54

<210> SEQ ID NO 106
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 106
tgtttgggta cccggcggac atttatcaca c 31

<210> SEQ ID NO 107
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 107
cagcccgggt aaaatggaaa cgtttcctcc aaaatatctt catt 44

<210> SEQ ID NO 108
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 108
cgtttccatt ttacccgggc tgagcgagag gctcttctgc gtgt 44

-continued

<210> SEQ ID NO 109
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 109
cgctcagccc gggtaaaatg gaaacgttgc ctccaaaata cctgc 45

<210> SEQ ID NO 110
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 110
ccattttacc cgggctgagc gagaggctct tctgcgtgt 39

<210> SEQ ID NO 111
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 111
gaaaataagc tgcttagctg cagctgaacc aaaatc 36

<210> SEQ ID NO 112
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 112
cagctgcagc taagcagctt attttcacgg attg 34

<210> SEQ ID NO 113
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 113
aaaaataagc tgcttagctg cagctgaacc aaaatc 36

<210> SEQ ID NO 114
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 114
cagctgcagc taagcagctt atttttactg attgg 35

<210> SEQ ID NO 115
<211> LENGTH: 102
<212> TYPE: DNA
<213> ORGANISM: Artificial sequence
<220> FEATURE:
<223> OTHER INFORMATION: Synthetic oligonucleotide -continued

<400> SEQUENCE: 115
ctagaaggag gaataacata tggaaacttt tgctccaaaa tatcttcatt atgatgaaga 60
aactagtcat cagctgctgt gtgataaatg tccgccgggt ac 102

<210> SEQ ID NO 116
<211> LENGTH: 94
<212> TYPE: DNA
<213> ORGANISM: Artificial sequence
<220> FEATURE:
<223> OTHER INFORMATION: Synthetic oligonucleotide

<400> SEQUENCE: 116
ccggcggaca tttatcacac agcagctgat gactagtttc ttcatcataa tgaagatatt 60
ttggagcaaa agtttccata tgttattcct cctt 94

<210> SEQ ID NO 117
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 117
ctagaaggag gaataacata tggaaacttt tcctgctaaa tatcttcatt atgatgaaga 60
aa 62

<210> SEQ ID NO 118
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 118
ctagtttctt catcataatg aagatattta gcaggaaaag tttccatatg ttattcctcc 60
tt 62

<210> SEQ ID NO 119
<211> LENGTH: 51
<212> TYPE: PRT
<213> ORGANISM: Artificial sequence
<220> FEATURE:
<223> OTHER INFORMATION: Synthetic

<400> SEQUENCE: 119

```
Tyr His Tyr Tyr Asp Gln Asn Gly Arg Met Cys Glu Glu Cys His Met
1               5                   10                  15

Cys Gln Pro Gly His Phe Leu Val Lys His Cys Lys Gln Pro Lys Arg
            20                  25                  30

Asp Thr Val Cys His Lys Pro Cys Glu Pro Gly Val Thr Tyr Thr Asp
        35                  40                  45

Asp Trp His
    50
```

<210> SEQ ID NO 120
<211> LENGTH: 2432
<212> TYPE: DNA
<213> ORGANISM: Rattus rattus
<220> FEATURE:
<221> NAME/KEY: CDS
<222> LOCATION: (124)..(1326)

-continued

```
<223> OTHER INFORMATION:

<400> SEQUENCE: 120

atcaaaggca gggcatactt cctgttgccc agaccttata taaaacgtca tgttcgcctg      60

ggcagcagag aagcacctag cactggccca gcggctgccg cctgaggttt ccagaggacc     120

aca atg aac aag tgg ctg tgc tgt gca ctc ctg gtg ttc ttg gac atc       168
    Met Asn Lys Trp Leu Cys Cys Ala Leu Leu Val Phe Leu Asp Ile
    1               5                   10                  15

att gaa tgg aca acc cag gaa acc ttt cct cca aaa tac ttg cat tat       216
Ile Glu Trp Thr Thr Gln Glu Thr Phe Pro Pro Lys Tyr Leu His Tyr
                20                  25                  30

gac cca gaa acc gga cgt cag ctc ttg tgt gac aaa tgt gct cct ggc       264
Asp Pro Glu Thr Gly Arg Gln Leu Leu Cys Asp Lys Cys Ala Pro Gly
            35                  40                  45

acc tac cta aaa cag cac tgc aca gtc agg agg aag aca ctg tgt gtc       312
Thr Tyr Leu Lys Gln His Cys Thr Val Arg Arg Lys Thr Leu Cys Val
        50                  55                  60

cct tgc cct gac tac tct tat aca gac agc tgg cac acg agt gat gaa       360
Pro Cys Pro Asp Tyr Ser Tyr Thr Asp Ser Trp His Thr Ser Asp Glu
    65                  70                  75

tgc gtg tac tgc agc ccc gtg tgc aag gaa ctg cag acc gtg aaa cag       408
Cys Val Tyr Cys Ser Pro Val Cys Lys Glu Leu Gln Thr Val Lys Gln
80                  85                  90                  95

gag tgc aac cgc acc cac aac cga gtg tgc gaa tgt gag gaa ggg cgc       456
Glu Cys Asn Arg Thr His Asn Arg Val Cys Glu Cys Glu Glu Gly Arg
                100                 105                 110

tac ctg gag ctc gaa ttc tgc ttg aag cac cgg agc tgt ccc cca ggc       504
Tyr Leu Glu Leu Glu Phe Cys Leu Lys His Arg Ser Cys Pro Pro Gly
            115                 120                 125

ttg ggt gtg ctg cag gct ggg acc cca gag cga aac acg gtt tgc aaa       552
Leu Gly Val Leu Gln Ala Gly Thr Pro Glu Arg Asn Thr Val Cys Lys
        130                 135                 140

aga tgt ccg gat ggg ttc ttc tca ggt gag acg tca tcg aaa gca ccc       600
Arg Cys Pro Asp Gly Phe Phe Ser Gly Glu Thr Ser Ser Lys Ala Pro
    145                 150                 155

tgt agg aaa cac acc aac tgc agc tca ctt ggc ctc ctg cta att cag       648
Cys Arg Lys His Thr Asn Cys Ser Ser Leu Gly Leu Leu Leu Ile Gln
160                 165                 170                 175

aaa gga aat gca aca cat gac aat gta tgt tcc gga aac aga gaa gca       696
Lys Gly Asn Ala Thr His Asp Asn Val Cys Ser Gly Asn Arg Glu Ala
                180                 185                 190

act caa aat tgt gga ata gat gtc acc ctg tgc gaa gag gca ttc ttc       744
Thr Gln Asn Cys Gly Ile Asp Val Thr Leu Cys Glu Glu Ala Phe Phe
            195                 200                 205

agg ttt gct gtg cct acc aag att ata ccg aat tgg ctg agt gtt ctg       792
Arg Phe Ala Val Pro Thr Lys Ile Ile Pro Asn Trp Leu Ser Val Leu
        210                 215                 220

gtg gac agt ttg cct ggg acc aaa gtg aat gca gag agt gta gag agg       840
Val Asp Ser Leu Pro Gly Thr Lys Val Asn Ala Glu Ser Val Glu Arg
    225                 230                 235

ata aaa cgg aga cac agc tcg caa gag caa act ttc cag cta ctt aag       888
Ile Lys Arg Arg His Ser Ser Gln Glu Gln Thr Phe Gln Leu Leu Lys
240                 245                 250                 255

ctg tgg aag cat caa aac aga gac cag gaa atg gtg aag aag atc atc       936
Leu Trp Lys His Gln Asn Arg Asp Gln Glu Met Val Lys Lys Ile Ile
                260                 265                 270

caa gac att gac ctc tgt gaa agc agt gtg caa cgg cat atc ggc cac       984
Gln Asp Ile Asp Leu Cys Glu Ser Ser Val Gln Arg His Ile Gly His
            275                 280                 285
```

-continued

```
gcg aac ctc acc aca gag cag ctc cgc atc ttg atg gag agc ttg cct     1032
Ala Asn Leu Thr Thr Glu Gln Leu Arg Ile Leu Met Glu Ser Leu Pro
        290                 295                 300

ggg aag aag atc agc cca gac gag att gag aga acg aga aag acc tgc     1080
Gly Lys Lys Ile Ser Pro Asp Glu Ile Glu Arg Thr Arg Lys Thr Cys
    305                 310                 315

aaa ccc agc gag cag ctc ctg aag cta ctg agc ttg tgg agg atc aaa     1128
Lys Pro Ser Glu Gln Leu Leu Lys Leu Leu Ser Leu Trp Arg Ile Lys
320                 325                 330                 335

aat gga gac caa gac acc ttg aag ggc ctg atg tac gca ctc aag cac     1176
Asn Gly Asp Gln Asp Thr Leu Lys Gly Leu Met Tyr Ala Leu Lys His
                340                 345                 350

ttg aaa gca tac cac ttt ccc aaa acc gtc acc cac agt ctg agg aag     1224
Leu Lys Ala Tyr His Phe Pro Lys Thr Val Thr His Ser Leu Arg Lys
            355                 360                 365

acc atc agg ttc ttg cac agc ttc acc atg tac cga ttg tat cag aaa     1272
Thr Ile Arg Phe Leu His Ser Phe Thr Met Tyr Arg Leu Tyr Gln Lys
        370                 375                 380

ctc ttt cta gaa atg ata ggg aat cag gtt caa tca gtg aag ata agc     1320
Leu Phe Leu Glu Met Ile Gly Asn Gln Val Gln Ser Val Lys Ile Ser
    385                 390                 395

tgc tta tagttaggaa tggtcactgg gctgtttctt caggatgggc caacactgat      1376
Cys Leu
400

ggagcagatg gctgcttctc cggctcttga aatggcagtt gattcctttc tcatcagttg   1436

gtgggaatga agatcctcca gcccaacaca cacactgggg agtctgagtc aggagagtga   1496

ggcaggctat ttgataattg tgcaaagctg ccaggtgtac acctagaaag tcaagcaccc   1556

tgagaaagag gatattttta taacctcaaa cataggccct ttccttcctc tccttatgga   1616

tgagtactca gaaggcttct actatcttct gtgtcatccc tagatgaagg cctcttttat   1676

ttattttttt attctttttt tcggagctgg ggaccgaacc cagggccttg cgcttgcgag   1736

gcaagtgctc taccactgag ctaaatctcc aacccctgaa ggcctctttc tttctgcctc   1796

tgatagtcta tgacattctt ttttctacaa ttcgtatcag gtgcacgagc cttatcccat   1856

ttgtaggttt ctaggcaagt tgaccgttag ctattttttcc ctctgaagat ttgattcgag  1916

ttgcagactt ggctagacaa gcaggggtag gttatggtag tttatttaac agactgccac   1976

caggagtcca gtgtttcttg ttcctctgta gttgtaccta agctgactcc aagtacattt   2036

agtatgaaaa ataatcaaca aattttattc cttctatcaa cattggctag ctttgtttca   2096

gggcactaaa agaaactact atatggagaa agaattgata ttgcccccaa cgttcaacaa   2156

cccaatagtt tatccagctg tcatgcctgg ttcagtgtct actgactatg cgccctctta   2216

ttactgcatg cagtaattca actggaaata gtaataataa taatagaaat aaaatctaga   2276

ctccattgga tctctctgaa tatgggaata tctaacttaa gaagctttga gatttcagtt   2336

gtgttaaagg cttttattaa aaagctgatg ctcttctgta aaagttacta atatatctgt   2396

aagactatta cagtattgct atttatatcc atccag                             2432


<210> SEQ ID NO 121
<211> LENGTH: 401
<212> TYPE: PRT
<213> ORGANISM: Rattus rattus

<400> SEQUENCE: 121

Met Asn Lys Trp Leu Cys Cys Ala Leu Leu Val Phe Leu Asp Ile Ile
1               5                   10                  15
```

-continued

```
Glu Trp Thr Thr Gln Glu Thr Phe Pro Pro Lys Tyr Leu His Tyr Asp
            20                  25                  30

Pro Glu Thr Gly Arg Gln Leu Leu Cys Asp Lys Cys Ala Pro Gly Thr
        35                  40                  45

Tyr Leu Lys Gln His Cys Thr Val Arg Arg Lys Thr Leu Cys Val Pro
    50                  55                  60

Cys Pro Asp Tyr Ser Tyr Thr Asp Ser Trp His Thr Ser Asp Glu Cys
65                  70                  75                  80

Val Tyr Cys Ser Pro Val Cys Lys Glu Leu Gln Thr Val Lys Gln Glu
                85                  90                  95

Cys Asn Arg Thr His Asn Arg Val Cys Glu Cys Glu Glu Gly Arg Tyr
            100                 105                 110

Leu Glu Leu Glu Phe Cys Leu Lys His Arg Ser Cys Pro Pro Gly Leu
        115                 120                 125

Gly Val Leu Gln Ala Gly Thr Pro Glu Arg Asn Thr Val Cys Lys Arg
    130                 135                 140

Cys Pro Asp Gly Phe Phe Ser Gly Glu Thr Ser Ser Lys Ala Pro Cys
145                 150                 155                 160

Arg Lys His Thr Asn Cys Ser Ser Leu Gly Leu Leu Leu Ile Gln Lys
                165                 170                 175

Gly Asn Ala Thr His Asp Asn Val Cys Ser Gly Asn Arg Glu Ala Thr
            180                 185                 190

Gln Asn Cys Gly Ile Asp Val Thr Leu Cys Glu Glu Ala Phe Phe Arg
        195                 200                 205

Phe Ala Val Pro Thr Lys Ile Ile Pro Asn Trp Leu Ser Val Leu Val
    210                 215                 220

Asp Ser Leu Pro Gly Thr Lys Val Asn Ala Glu Ser Val Glu Arg Ile
225                 230                 235                 240

Lys Arg Arg His Ser Ser Gln Glu Gln Thr Phe Gln Leu Leu Lys Leu
                245                 250                 255

Trp Lys His Gln Asn Arg Asp Gln Glu Met Val Lys Lys Ile Ile Gln
            260                 265                 270

Asp Ile Asp Leu Cys Glu Ser Ser Val Gln Arg His Ile Gly His Ala
        275                 280                 285

Asn Leu Thr Thr Glu Gln Leu Arg Ile Leu Met Glu Ser Leu Pro Gly
    290                 295                 300

Lys Lys Ile Ser Pro Asp Glu Ile Glu Arg Thr Arg Lys Thr Cys Lys
305                 310                 315                 320

Pro Ser Glu Gln Leu Leu Lys Leu Leu Ser Leu Trp Arg Ile Lys Asn
                325                 330                 335

Gly Asp Gln Asp Thr Leu Lys Gly Leu Met Tyr Ala Leu Lys His Leu
            340                 345                 350

Lys Ala Tyr His Phe Pro Lys Thr Val Thr His Ser Leu Arg Lys Thr
        355                 360                 365

Ile Arg Phe Leu His Ser Phe Thr Met Tyr Arg Leu Tyr Gln Lys Leu
    370                 375                 380

Phe Leu Glu Met Ile Gly Asn Gln Val Gln Ser Val Lys Ile Ser Cys
385                 390                 395                 400

Leu
```

<210> SEQ ID NO 122
<211> LENGTH: 1324
<212> TYPE: DNA

-continued

```
<213> ORGANISM: Mus musculus
<220> FEATURE:
<221> NAME/KEY: CDS
<222> LOCATION: (90)..(1292)
<223> OTHER INFORMATION:

<400> SEQUENCE: 122

ccttatataa acgtcatgat tgcctgggct gcagagacgc acctagcact gacccagcgg      60

ctgcctcctg aggtttcccg aggaccaca atg aac aag tgg ctg tgc tgc gca      113
                                Met Asn Lys Trp Leu Cys Cys Ala
                                1               5

ctc ctg gtg ctc ctg gac atc att gaa tgg aca acc cag gaa acc ctt      161
Leu Leu Val Leu Leu Asp Ile Ile Glu Trp Thr Thr Gln Glu Thr Leu
    10                  15                  20

cct cca aag tac ttg cat tat gac cca gaa act ggt cat cag ctc ctg      209
Pro Pro Lys Tyr Leu His Tyr Asp Pro Glu Thr Gly His Gln Leu Leu
25                  30                  35                  40

tgt gac aaa tgt gct cct ggc acc tac cta aaa cag cac tgc aca gtg      257
Cys Asp Lys Cys Ala Pro Gly Thr Tyr Leu Lys Gln His Cys Thr Val
                45                  50                  55

agg agg aag aca ttg tgt gtc cct tgc cct gac cac tct tat acg gac      305
Arg Arg Lys Thr Leu Cys Val Pro Cys Pro Asp His Ser Tyr Thr Asp
            60                  65                  70

agc tgg cac acc agt gat gag tgt gtg tat tgc agc cca gtg tgc aag      353
Ser Trp His Thr Ser Asp Glu Cys Val Tyr Cys Ser Pro Val Cys Lys
        75                  80                  85

gaa ctg cag tcc gtg aag cag gag tgc aac cgc acc cac aac cga gtg      401
Glu Leu Gln Ser Val Lys Gln Glu Cys Asn Arg Thr His Asn Arg Val
    90                  95                  100

tgt gag tgt gag gaa ggg cgt tac ctg gag atc gaa ttc tgc ttg aag      449
Cys Glu Cys Glu Glu Gly Arg Tyr Leu Glu Ile Glu Phe Cys Leu Lys
105                 110                 115                 120

cac cgg agc tgt ccc ccg ggc tcc ggc gtg gtg caa gct gga acc cca      497
His Arg Ser Cys Pro Pro Gly Ser Gly Val Val Gln Ala Gly Thr Pro
                125                 130                 135

gag cga aac aca gtt tgc aaa aaa tgt cca gat ggg ttc ttc tca ggt      545
Glu Arg Asn Thr Val Cys Lys Lys Cys Pro Asp Gly Phe Phe Ser Gly
            140                 145                 150

gag act tca tcg aaa gca ccc tgt ata aaa cac acg aac tgc agc aca      593
Glu Thr Ser Ser Lys Ala Pro Cys Ile Lys His Thr Asn Cys Ser Thr
        155                 160                 165

ttt ggc ctc ctg cta att cag aaa gga aat gca aca cat gac aac gtg      641
Phe Gly Leu Leu Leu Ile Gln Lys Gly Asn Ala Thr His Asp Asn Val
    170                 175                 180

tgt tcc gga aac aga gaa gcc acg caa aag tgt gga ata gat gtc acc      689
Cys Ser Gly Asn Arg Glu Ala Thr Gln Lys Cys Gly Ile Asp Val Thr
185                 190                 195                 200

ctg tgt gaa gag gcc ttc ttc agg ttt gct gtt cct acc aag att ata      737
Leu Cys Glu Glu Ala Phe Phe Arg Phe Ala Val Pro Thr Lys Ile Ile
                205                 210                 215

cca aat tgg ctg agt gtt ttg gtg gac agt ttg cct ggg acc aaa gtg      785
Pro Asn Trp Leu Ser Val Leu Val Asp Ser Leu Pro Gly Thr Lys Val
            220                 225                 230

aat gcc gag agt gta gag agg ata aaa cgg aga cac agc tca caa gag      833
Asn Ala Glu Ser Val Glu Arg Ile Lys Arg Arg His Ser Ser Gln Glu
        235                 240                 245

caa acc ttc cag ctg ctg aag ctg tgg aaa cat caa aac aga gac cag      881
Gln Thr Phe Gln Leu Leu Lys Leu Trp Lys His Gln Asn Arg Asp Gln
    250                 255                 260

gaa atg gtg aag aag atc atc caa gac att gac ctc tgt gaa agc agc      929
```

-continued

```
Glu Met Val Lys Lys Ile Ile Gln Asp Ile Asp Leu Cys Glu Ser Ser
265                 270                 275                 280

gtg cag cgg cat ctc ggc cac tcg aac ctc acc aca gag cag ctt ctt      977
Val Gln Arg His Leu Gly His Ser Asn Leu Thr Thr Glu Gln Leu Leu
                285                 290                 295

gcc ttg atg gag agc ctg cct ggg aag aag atc agc cca gaa gag att     1025
Ala Leu Met Glu Ser Leu Pro Gly Lys Lys Ile Ser Pro Glu Glu Ile
            300                 305                 310

gag aga acg aga aag acc tgc aaa tcg agc gag cag ctc ctg aag cta     1073
Glu Arg Thr Arg Lys Thr Cys Lys Ser Ser Glu Gln Leu Leu Lys Leu
        315                 320                 325

ctc agt tta tgg agg atc aaa aat ggt gac caa gac acc ttg aag ggc     1121
Leu Ser Leu Trp Arg Ile Lys Asn Gly Asp Gln Asp Thr Leu Lys Gly
    330                 335                 340

ctg atg tat gcc ctc aag cac ttg aaa aca tcc cac ttt ccc aaa act     1169
Leu Met Tyr Ala Leu Lys His Leu Lys Thr Ser His Phe Pro Lys Thr
345                 350                 355                 360

gtc acc cac agt ctg agg aag acc atg agg ttc ctg cac agc ttc aca     1217
Val Thr His Ser Leu Arg Lys Thr Met Arg Phe Leu His Ser Phe Thr
                365                 370                 375

atg tac aga ctg tat cag aag ctc ttt tta gaa atg ata ggg aat cag     1265
Met Tyr Arg Leu Tyr Gln Lys Leu Phe Leu Glu Met Ile Gly Asn Gln
            380                 385                 390

gtt caa tcc gtg aaa ata agc tgc tta taactaggaa tggtcactgg           1312
Val Gln Ser Val Lys Ile Ser Cys Leu
        395                 400

gctgtttctt ca                                                       1324


<210> SEQ ID NO 123
<211> LENGTH: 401
<212> TYPE: PRT
<213> ORGANISM: Mus musculus

<400> SEQUENCE: 123

Met Asn Lys Trp Leu Cys Cys Ala Leu Leu Val Leu Leu Asp Ile Ile
1               5                   10                  15

Glu Trp Thr Thr Gln Glu Thr Leu Pro Pro Lys Tyr Leu His Tyr Asp
            20                  25                  30

Pro Glu Thr Gly His Gln Leu Leu Cys Asp Lys Cys Ala Pro Gly Thr
        35                  40                  45

Tyr Leu Lys Gln His Cys Thr Val Arg Arg Lys Thr Leu Cys Val Pro
    50                  55                  60

Cys Pro Asp His Ser Tyr Thr Asp Ser Trp His Thr Ser Asp Glu Cys
65                  70                  75                  80

Val Tyr Cys Ser Pro Val Cys Lys Glu Leu Gln Ser Val Lys Gln Glu
                85                  90                  95

Cys Asn Arg Thr His Asn Arg Val Cys Glu Cys Glu Glu Gly Arg Tyr
            100                 105                 110

Leu Glu Ile Glu Phe Cys Leu Lys His Arg Ser Cys Pro Pro Gly Ser
        115                 120                 125

Gly Val Val Gln Ala Gly Thr Pro Glu Arg Asn Thr Val Cys Lys Lys
    130                 135                 140

Cys Pro Asp Gly Phe Phe Ser Gly Glu Thr Ser Ser Lys Ala Pro Cys
145                 150                 155                 160

Ile Lys His Thr Asn Cys Ser Thr Phe Gly Leu Leu Leu Ile Gln Lys
                165                 170                 175

Gly Asn Ala Thr His Asp Asn Val Cys Ser Gly Asn Arg Glu Ala Thr
```

-continued

```
            180                 185                 190

Gln Lys Cys Gly Ile Asp Val Thr Leu Cys Glu Glu Ala Phe Phe Arg
        195                 200                 205

Phe Ala Val Pro Thr Lys Ile Ile Pro Asn Trp Leu Ser Val Leu Val
    210                 215                 220

Asp Ser Leu Pro Gly Thr Lys Val Asn Ala Glu Ser Val Glu Arg Ile
225                 230                 235                 240

Lys Arg Arg His Ser Ser Gln Glu Gln Thr Phe Gln Leu Leu Lys Leu
                245                 250                 255

Trp Lys His Gln Asn Arg Asp Gln Glu Met Val Lys Lys Ile Ile Gln
            260                 265                 270

Asp Ile Asp Leu Cys Glu Ser Ser Val Gln Arg His Leu Gly His Ser
        275                 280                 285

Asn Leu Thr Thr Glu Gln Leu Leu Ala Leu Met Glu Ser Leu Pro Gly
    290                 295                 300

Lys Lys Ile Ser Pro Glu Glu Ile Glu Arg Thr Arg Lys Thr Cys Lys
305                 310                 315                 320

Ser Ser Glu Gln Leu Leu Lys Leu Leu Ser Leu Trp Arg Ile Lys Asn
                325                 330                 335

Gly Asp Gln Asp Thr Leu Lys Gly Leu Met Tyr Ala Leu Lys His Leu
            340                 345                 350

Lys Thr Ser His Phe Pro Lys Thr Val Thr His Ser Leu Arg Lys Thr
        355                 360                 365

Met Arg Phe Leu His Ser Phe Thr Met Tyr Arg Leu Tyr Gln Lys Leu
    370                 375                 380

Phe Leu Glu Met Ile Gly Asn Gln Val Gln Ser Val Lys Ile Ser Cys
385                 390                 395                 400

Leu


<210> SEQ ID NO 124
<211> LENGTH: 1355
<212> TYPE: DNA
<213> ORGANISM: Homo sapiens
<220> FEATURE:
<221> NAME/KEY: CDS
<222> LOCATION: (94)..(1296)
<223> OTHER INFORMATION:

<400> SEQUENCE: 124

gtatatataa cgtgatgagc gtacgggtgc ggagacgcac cggagcgctc gcccagccgc      60

cgctccaagc ccctgaggtt tccggggacc aca atg aac aag ttg ctg tgc tgc      114
                                     Met Asn Lys Leu Leu Cys Cys
                                     1               5

gcg ctc gtg ttt ctg gac atc tcc att aag tgg acc acc cag gaa acg      162
Ala Leu Val Phe Leu Asp Ile Ser Ile Lys Trp Thr Thr Gln Glu Thr
        10                  15                  20

ttt cct cca aag tac ctt cat tat gac gaa gaa acc tct cat cag ctg      210
Phe Pro Pro Lys Tyr Leu His Tyr Asp Glu Glu Thr Ser His Gln Leu
    25                  30                  35

ttg tgt gac aaa tgt cct cct ggt acc tac cta aaa caa cac tgt aca      258
Leu Cys Asp Lys Cys Pro Pro Gly Thr Tyr Leu Lys Gln His Cys Thr
40                  45                  50                  55

gca aag tgg aag acc gtg tgc gcc cct tgc cct gac cac tac tac aca      306
Ala Lys Trp Lys Thr Val Cys Ala Pro Cys Pro Asp His Tyr Tyr Thr
                60                  65                  70

gac agc tgg cac acc agt gac gag tgt cta tac tgc agc ccc gtg tgc      354
Asp Ser Trp His Thr Ser Asp Glu Cys Leu Tyr Cys Ser Pro Val Cys
```

-continued

```
            75                  80                  85

aag gag ctg cag tac gtc aag cag gag tgc aat cgc acc cac aac cgc      402
Lys Glu Leu Gln Tyr Val Lys Gln Glu Cys Asn Arg Thr His Asn Arg
        90                  95                 100

gtg tgc gaa tgc aag gaa ggg cgc tac ctt gag ata gag ttc tgc ttg      450
Val Cys Glu Cys Lys Glu Gly Arg Tyr Leu Glu Ile Glu Phe Cys Leu
    105                 110                 115

aaa cat agg agc tgc cct cct gga ttt gga gtg gtg caa gct gga acc      498
Lys His Arg Ser Cys Pro Pro Gly Phe Gly Val Val Gln Ala Gly Thr
120                 125                 130                 135

cca gag cga aat aca gtt tgc aaa aga tgt cca gat ggg ttc ttc tca      546
Pro Glu Arg Asn Thr Val Cys Lys Arg Cys Pro Asp Gly Phe Phe Ser
                140                 145                 150

aat gag acg tca tct aaa gca ccc tgt aga aaa cac aca aat tgc agt      594
Asn Glu Thr Ser Ser Lys Ala Pro Cys Arg Lys His Thr Asn Cys Ser
            155                 160                 165

gtc ttt ggt ctc ctg cta act cag aaa gga aat gca aca cac gac aac      642
Val Phe Gly Leu Leu Leu Thr Gln Lys Gly Asn Ala Thr His Asp Asn
        170                 175                 180

ata tgt tcc gga aac agt gaa tca act caa aaa tgt gga ata gat gtt      690
Ile Cys Ser Gly Asn Ser Glu Ser Thr Gln Lys Cys Gly Ile Asp Val
    185                 190                 195

acc ctg tgt gag gag gca ttc ttc agg ttt gct gtt cct aca aag ttt      738
Thr Leu Cys Glu Glu Ala Phe Phe Arg Phe Ala Val Pro Thr Lys Phe
200                 205                 210                 215

acg cct aac tgg ctt agt gtc ttg gta gac aat ttg cct ggc acc aaa      786
Thr Pro Asn Trp Leu Ser Val Leu Val Asp Asn Leu Pro Gly Thr Lys
                220                 225                 230

gta aac gca gag agt gta gag agg ata aaa cgg caa cac agc tca caa      834
Val Asn Ala Glu Ser Val Glu Arg Ile Lys Arg Gln His Ser Ser Gln
            235                 240                 245

gaa cag act ttc cag ctg ctg aag tta tgg aaa cat caa aac aaa gcc      882
Glu Gln Thr Phe Gln Leu Leu Lys Leu Trp Lys His Gln Asn Lys Ala
        250                 255                 260

caa gat ata gtc aag aag atc atc caa gat att gac ctc tgt gaa aac      930
Gln Asp Ile Val Lys Lys Ile Ile Gln Asp Ile Asp Leu Cys Glu Asn
    265                 270                 275

agc gtg cag cgg cac att gga cat gct aac ctc acc ttc gag cag ctt      978
Ser Val Gln Arg His Ile Gly His Ala Asn Leu Thr Phe Glu Gln Leu
280                 285                 290                 295

cgt agc ttg atg gaa agc tta ccg gga aag aaa gtg gga gca gaa gac     1026
Arg Ser Leu Met Glu Ser Leu Pro Gly Lys Lys Val Gly Ala Glu Asp
                300                 305                 310

att gaa aaa aca ata aag gca tgc aaa ccc agt gac cag atc ctg aag     1074
Ile Glu Lys Thr Ile Lys Ala Cys Lys Pro Ser Asp Gln Ile Leu Lys
            315                 320                 325

ctg ctc agt ttg tgg cga ata aaa aat ggc gac caa gac acc ttg aag     1122
Leu Leu Ser Leu Trp Arg Ile Lys Asn Gly Asp Gln Asp Thr Leu Lys
        330                 335                 340

ggc cta atg cac gca cta aag cac tca aag acg tac cac ttt ccc aaa     1170
Gly Leu Met His Ala Leu Lys His Ser Lys Thr Tyr His Phe Pro Lys
    345                 350                 355

act gtc act cag agt cta aag aag acc atc agg ttc ctt cac agc ttc     1218
Thr Val Thr Gln Ser Leu Lys Lys Thr Ile Arg Phe Leu His Ser Phe
360                 365                 370                 375

aca atg tac aaa ttg tat cag aag tta ttt tta gaa atg ata ggt aac     1266
Thr Met Tyr Lys Leu Tyr Gln Lys Leu Phe Leu Glu Met Ile Gly Asn
                380                 385                 390

cag gtc caa tca gta aaa ata agc tgc tta taactggaaa tggccattga       1316
```

-continued

```
Gln Val Gln Ser Val Lys Ile Ser Cys Leu
            395                 400

gctgtttcct cacaattggc gagatcccat ggatgataa                          1355


<210> SEQ ID NO 125
<211> LENGTH: 401
<212> TYPE: PRT
<213> ORGANISM: Homo sapiens

<400> SEQUENCE: 125

Met Asn Lys Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
    210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Ala Gln Asp Ile Val Lys Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
    290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
            340                 345                 350
```

-continued

Lys Thr Tyr His Phe Pro Lys Thr Val Thr Gln Ser Leu Lys Lys Thr
355 360 365

Ile Arg Phe Leu His Ser Phe Thr Met Tyr Lys Leu Tyr Gln Lys Leu
370 375 380

Phe Leu Glu Met Ile Gly Asn Gln Val Gln Ser Val Lys Ile Ser Cys
385 390 395 400

Leu

<210> SEQ ID NO 126
<211> LENGTH: 139
<212> TYPE: PRT
<213> ORGANISM: Homo sapiens

<400> SEQUENCE: 126

Cys Pro Gln Gly Lys Tyr Ile His Pro Gln Asn Asn Ser Ile Cys Cys
1 5 10 15

Thr Lys Cys His Lys Gly Thr Tyr Leu Tyr Asn Asp Cys Pro Gly Pro
20 25 30

Gly Gln Asp Thr Asp Cys Arg Glu Cys Glu Ser Gly Ser Phe Thr Ala
35 40 45

Ser Glu Asn His Leu Arg His Cys Leu Ser Cys Ser Lys Cys Arg Lys
50 55 60

Glu Met Gly Gln Val Glu Ile Ser Ser Cys Thr Val Asp Arg Asp Thr
65 70 75 80

Val Cys Gly Cys Arg Lys Asn Gln Tyr Arg His Tyr Trp Ser Glu Asn
85 90 95

Leu Phe Gln Cys Phe Asn Cys Ser Leu Cys Leu Asn Gly Thr Val His
100 105 110

Leu Ser Cys Gln Glu Lys Gln Asn Thr Val Cys Thr Cys His Ala Gly
115 120 125

Phe Phe Leu Arg Glu Asn Glu Cys Val Ser Cys
130 135

<210> SEQ ID NO 127
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 127
ccggcggaca tttatcacac agcagctgat gagaagtttc ttcatcca 48

<210> SEQ ID NO 128
<211> LENGTH: 219
<212> TYPE: PRT
<213> ORGANISM: Homo sapiens

<400> SEQUENCE: 128

Met Leu Gly Ile Trp Thr Leu Leu Pro Leu Val Leu Thr Ser Val Ala
1 5 10 15

Arg Leu Ser Ser Lys Ser Val Asn Ala Gln Val Thr Asp Ile Asn Ser
20 25 30

Lys Gly Leu Glu Leu Arg Lys Thr Val Thr Thr Val Glu Thr Gln Asn
35 40 45

Leu Glu Gly Leu His His Asp Gly Gln Phe Cys His Lys Pro Cys Pro
50 55 60

Pro Gly Glu Arg Lys Ala Arg Asp Cys Thr Val Asn Gly Asp Glu Pro

-continued 65 70 75 80

Asp Cys Val Pro Cys Gln Glu Gly Lys Glu Tyr Thr Asp Lys Ala His
85 90 95

Phe Ser Ser Lys Cys Arg Arg Cys Arg Leu Cys Asp Glu Gly His Gly
100 105 110

Leu Glu Val Glu Ile Asn Cys Thr Arg Thr Gln Asn Thr Lys Cys Arg
115 120 125

Cys Lys Pro Asn Phe Phe Cys Asn Ser Thr Val Cys Glu His Cys Asp
130 135 140

Pro Cys Thr Lys Cys Glu His Gly Ile Ile Lys Glu Cys Thr Leu Thr
145 150 155 160

Ser Asn Thr Lys Cys Lys Glu Glu Gly Ser Arg Ser Asn Leu Gly Trp
165 170 175

Leu Cys Leu Leu Leu Leu Pro Ile Pro Leu Ile Val Trp Val Lys Arg
180 185 190

Lys Glu Val Gln Lys Thr Cys Arg Lys His Arg Lys Glu Asn Gln Gly
195 200 205

Ser His Glu Ser Pro Thr Leu Asn Pro Glu Thr
210 215

<210> SEQ ID NO 129
<211> LENGTH: 280
<212> TYPE: PRT
<213> ORGANISM: Homo sapiens

<400> SEQUENCE: 129

Met Gly Leu Ser Thr Val Pro Asp Leu Leu Leu Pro Leu Val Leu Leu
1 5 10 15

Glu Leu Leu Val Gly Ile Tyr Pro Ser Gly Val Ile Gly Leu Val Pro
20 25 30

His Leu Gly Asp Arg Glu Lys Arg Asp Ser Val Cys Pro Gln Gly Lys
35 40 45

Tyr Ile His Pro Gln Asn Asn Ser Ile Cys Cys Thr Lys Cys His Lys
50 55 60

Gly Thr Tyr Leu Tyr Asn Asp Cys Pro Gly Pro Gly Gln Asp Thr Asp
65 70 75 80

Cys Arg Glu Cys Glu Ser Gly Ser Phe Thr Ala Ser Glu Asn His Leu
85 90 95

Arg His Cys Leu Ser Cys Ser Lys Cys Arg Lys Glu Met Gly Gln Val
100 105 110

Glu Ile Ser Ser Cys Thr Val Asp Arg Asp Thr Val Cys Gly Cys Arg
115 120 125

Lys Asn Gln Tyr Arg His Tyr Trp Ser Glu Asn Leu Phe Gln Cys Phe
130 135 140

Asn Cys Ser Leu Cys Leu Asn Gly Thr Val His Leu Ser Cys Gln Glu
145 150 155 160

Lys Gln Asn Thr Val Cys Thr Cys His Ala Gly Phe Phe Leu Arg Glu
165 170 175

Asn Glu Cys Val Ser Cys Ser Asn Cys Lys Lys Ser Leu Glu Cys Thr
180 185 190

Lys Leu Cys Leu Pro Gln Ile Glu Asn Val Lys Gly Thr Glu Asp Ser
195 200 205

Gly Thr Thr Val Leu Leu Pro Leu Val Ile Phe Phe Gly Leu Cys Leu
210 215 220

-continued

```
Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr
        275                 280


<210> SEQ ID NO 130
<211> LENGTH: 207
<212> TYPE: PRT
<213> ORGANISM: Shope fibroma virus

<400> SEQUENCE: 130

Met Leu Arg Leu Ile Ala Leu Leu Val Cys Val Val Tyr Val Tyr Gly
1               5                   10                  15

Asp Asp Val Pro Tyr Ser Ser Asn Gln Gly Lys Cys Gly Gly His Asp
            20                  25                  30

Tyr Glu Lys Asp Gly Leu Cys Cys Ala Ser Cys His Pro Gly Phe Tyr
        35                  40                  45

Ala Ser Arg Leu Cys Gly Pro Gly Ser Asn Thr Val Cys Ser Pro Cys
    50                  55                  60

Glu Asp Gly Thr Phe Thr Ala Ser Thr Asn His Ala Pro Ala Cys Val
65                  70                  75                  80

Ser Cys Arg Gly Pro Cys Thr Gly His Leu Ser Glu Ser Gln Pro Cys
                85                  90                  95

Asp Arg Thr His Asp Arg Val Cys Asn Cys Ser Thr Gly Asn Tyr Cys
            100                 105                 110

Leu Leu Lys Gly Gln Asn Gly Cys Arg Ile Cys Ala Pro Gln Thr Lys
        115                 120                 125

Cys Pro Ala Gly Tyr Gly Val Ser Gly His Thr Arg Ala Gly Asp Thr
    130                 135                 140

Leu Cys Glu Lys Cys Pro Pro His Thr Tyr Ser Asp Ser Leu Ser Pro
145                 150                 155                 160

Thr Glu Arg Cys Gly Thr Ser Phe Asn Tyr Ile Ser Val Gly Phe Asn
                165                 170                 175

Leu Tyr Pro Val Asn Glu Thr Ser Cys Thr Thr Thr Ala Gly His Asn
            180                 185                 190

Glu Val Ile Lys Thr Lys Glu Phe Thr Val Thr Leu Asn Tyr Thr
        195                 200                 205


<210> SEQ ID NO 131
<211> LENGTH: 227
<212> TYPE: PRT
<213> ORGANISM: Homo sapiens

<400> SEQUENCE: 131

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60
```

-continued

```
Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Arg Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr
225


<210> SEQ ID NO 132
<211> LENGTH: 197
<212> TYPE: PRT
<213> ORGANISM: Mus musculus

<400> SEQUENCE: 132

Met Val Ser Leu Pro Arg Leu Cys Ala Leu Trp Gly Cys Leu Leu Thr
1               5                   10                  15

Ala Val His Leu Gly Gln Cys Val Thr Cys Ser Asp Lys Gln Tyr Leu
            20                  25                  30

His Asp Gly Gln Cys Cys Asp Leu Cys Gln Pro Gly Ser Arg Leu Thr
        35                  40                  45

Ser His Cys Thr Ala Leu Glu Lys Thr Gln Cys His Pro Cys Asp Ser
    50                  55                  60

Gly Glu Phe Ser Ala Gln Trp Asn Arg Glu Ile Arg Cys His Gln His
65                  70                  75                  80

Arg His Cys Glu Pro Asn Gln Gly Leu Arg Val Lys Lys Glu Gly Thr
                85                  90                  95

Ala Glu Ser Asp Thr Val Cys Thr Cys Lys Glu Gly Gln His Cys Thr
            100                 105                 110

Ser Lys Asp Cys Glu Ala Cys Ala Gln His Thr Pro Cys Ile Pro Gly
        115                 120                 125

Phe Gly Val Met Glu Met Ala Thr Glu Thr Thr Asp Thr Val Cys His
    130                 135                 140

Pro Cys Pro Val Gly Phe Phe Ser Asn Gln Ser Ser Leu Phe Glu Lys
145                 150                 155                 160

Cys Tyr Pro Trp Thr Ser Cys Glu Asp Lys Asn Leu Glu Val Leu Gln
                165                 170                 175

Lys Gly Thr Ser Gln Thr Asn Val Ile Cys Gly Leu Lys Ser Arg Met
            180                 185                 190

Arg Ala Leu Leu Val
        195
```

-continued

<210> SEQ ID NO 133
<211> LENGTH: 208
<212> TYPE: PRT
<213> ORGANISM: Rattus rattus

<400> SEQUENCE: 133

```
Met Asn Lys Trp Leu Cys Cys Ala Leu Leu Val Phe Leu Asp Ile Ile
1               5                   10                  15

Glu Trp Thr Thr Gln Glu Thr Phe Pro Pro Lys Tyr Leu His Tyr Asp
            20                  25                  30

Pro Glu Thr Gly Arg Gln Leu Leu Cys Asp Lys Cys Ala Pro Gly Thr
        35                  40                  45

Tyr Leu Lys Gln His Cys Thr Val Arg Arg Lys Thr Leu Cys Val Pro
    50                  55                  60

Cys Pro Asp Tyr Ser Tyr Thr Asp Ser Trp His Thr Ser Asp Glu Cys
65                  70                  75                  80

Val Tyr Cys Ser Pro Val Cys Lys Glu Leu Gln Thr Val Lys Gln Glu
                85                  90                  95

Cys Asn Arg Thr His Asn Arg Val Cys Glu Cys Glu Glu Gly Arg Tyr
            100                 105                 110

Leu Glu Leu Glu Phe Cys Leu Lys His Arg Ser Cys Pro Pro Gly Leu
        115                 120                 125

Gly Val Leu Gln Ala Gly Thr Pro Glu Arg Asn Thr Val Cys Lys Arg
    130                 135                 140

Cys Pro Asp Gly Phe Phe Ser Gly Glu Thr Ser Ser Lys Ala Pro Cys
145                 150                 155                 160

Arg Lys His Thr Asn Cys Ser Ser Leu Gly Leu Leu Leu Ile Gln Lys
                165                 170                 175

Gly Asn Ala Thr His Asp Asn Val Cys Ser Gly Asn Arg Glu Ala Thr
            180                 185                 190

Gln Asn Cys Gly Ile Asp Val Thr Leu Cys Glu Glu Ala Phe Phe Arg
        195                 200                 205
```

<210> SEQ ID NO 134
<211> LENGTH: 224
<212> TYPE: PRT
<213> ORGANISM: Homo sapiens

<400> SEQUENCE: 134

```
Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125
```

-continued

```
Glu Ala Gly Ser Gly Leu Val Phe Ser Cys Gln Asp Lys Gln Asn Thr
    130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
    210                 215                 220


<210> SEQ ID NO 135
<211> LENGTH: 202
<212> TYPE: PRT
<213> ORGANISM: Rattus rattus

<400> SEQUENCE: 135

Met Tyr Val Trp Val Gln Gln Pro Thr Ala Phe Leu Leu Leu Gly Leu
1               5                   10                  15

Ser Leu Gly Val Thr Val Lys Leu Asn Cys Val Lys Asp Thr Tyr Pro
            20                  25                  30

Ser Gly His Lys Cys Cys Arg Glu Cys Gln Pro Gly His Gly Met Val
        35                  40                  45

Ser Arg Cys Asp His Thr Arg Asp Thr Val Cys His Pro Cys Glu Pro
    50                  55                  60

Gly Phe Tyr Asn Glu Ala Val Asn Tyr Asp Thr Cys Lys Gln Cys Thr
65                  70                  75                  80

Gln Cys Asn His Arg Ser Gly Ser Glu Leu Lys Gln Asn Cys Thr Pro
                85                  90                  95

Thr Glu Asp Thr Val Cys Gln Cys Arg Pro Gly Thr Gln Pro Arg Gln
            100                 105                 110

Asp Ser Ser His Lys Leu Gly Val Asp Cys Val Pro Cys Pro Pro Gly
        115                 120                 125

His Phe Ser Pro Gly Ser Asn Gln Ala Cys Lys Pro Trp Thr Asn Cys
    130                 135                 140

Thr Leu Ser Gly Lys Gln Ile Arg His Pro Ala Ser Asn Ser Val Cys
145                 150                 155                 160

Glu Asp Arg Ser Leu Leu Ala Thr Leu Leu Trp Glu Thr Gln Arg Thr
                165                 170                 175

Thr Phe Arg Pro Thr Thr Val Pro Ser Thr Thr Val Trp Pro Arg Thr
            180                 185                 190

Ser Gln Leu Pro Ser Thr Pro Thr Leu Val
        195                 200


<210> SEQ ID NO 136
<211> LENGTH: 380
<212> TYPE: PRT
<213> ORGANISM: Homo sapiens

<400> SEQUENCE: 136

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
            20                  25                  30
```

-continued

```
Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Ile Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys Cys Gly Ile
                165                 170                 175

Asp Val Thr Leu Cys Glu Glu Ala Phe Phe Arg Phe Ala Val Pro Thr
            180                 185                 190

Lys Phe Thr Pro Asn Trp Leu Ser Val Leu Val Asp Asn Leu Pro Gly
        195                 200                 205

Thr Lys Val Asn Ala Glu Ser Val Glu Arg Ile Lys Arg Gln His Ser
    210                 215                 220

Ser Gln Glu Gln Thr Phe Gln Leu Leu Lys Leu Trp Lys His Gln Asn
225                 230                 235                 240

Lys Asp Gln Asp Ile Val Lys Lys Ile Ile Gln Asp Ile Asp Leu Cys
                245                 250                 255

Glu Asn Ser Val Gln Arg His Ile Gly His Ala Asn Leu Thr Phe Glu
            260                 265                 270

Gln Leu Arg Ser Leu Met Glu Ser Leu Pro Gly Lys Lys Val Gly Ala
        275                 280                 285

Glu Asp Ile Glu Lys Thr Ile Lys Ala Cys Lys Pro Ser Asp Gln Ile
    290                 295                 300

Leu Lys Leu Leu Ser Leu Trp Arg Ile Lys Asn Gly Asp Gln Asp Thr
305                 310                 315                 320

Leu Lys Gly Leu Met His Ala Leu Lys His Ser Lys Thr Tyr His Phe
                325                 330                 335

Pro Lys Thr Val Thr Gln Ser Leu Lys Lys Thr Ile Arg Phe Leu His
            340                 345                 350

Ser Phe Thr Met Tyr Lys Leu Tyr Gln Lys Leu Phe Leu Glu Met Ile
        355                 360                 365

Gly Asn Gln Val Gln Ser Val Lys Ile Ser Cys Leu
    370                 375                 380
```

<210> SEQ ID NO 137
<211> LENGTH: 54
<212> TYPE: DNA
<213> ORGANISM: Artificial sequence
<220> FEATURE:
<223> OTHER INFORMATION: Synthetic oligonucleotide

<400> SEQUENCE: 137
tatggatgaa gaaacttctc atcagctgct gtgtgataaa tgtccgccgg gtac          54

<210> SEQ ID NO 138
<211> LENGTH: 380
<212> TYPE: PRT
<213> ORGANISM: Mus musculus

<400> SEQUENCE: 138

```
Glu Thr Leu Pro Pro Lys Tyr Leu His Tyr Asp Pro Glu Thr Gly His
1               5                   10                  15

Gln Leu Leu Cys Asp Lys Cys Ala Pro Gly Thr Tyr Leu Lys Gln His
            20                  25                  30

Cys Thr Val Arg Arg Lys Thr Leu Cys Val Pro Cys Pro Asp His Ser
        35                  40                  45

Tyr Thr Asp Ser Trp His Thr Ser Asp Glu Cys Val Tyr Cys Ser Pro
    50                  55                  60

Val Cys Lys Glu Leu Gln Ser Val Lys Gln Glu Cys Asn Arg Thr His
65                  70                  75                  80

Asn Arg Val Cys Glu Cys Glu Glu Gly Arg Tyr Leu Glu Ile Glu Phe
                85                  90                  95

Cys Leu Lys His Arg Ser Cys Pro Pro Gly Ser Gly Val Val Gln Ala
            100                 105                 110

Gly Thr Pro Glu Arg Asn Thr Val Cys Lys Lys Cys Pro Asp Gly Phe
        115                 120                 125

Phe Ser Gly Glu Thr Ser Ser Lys Ala Pro Cys Ile Lys His Thr Asn
    130                 135                 140

Cys Ser Thr Phe Gly Leu Leu Leu Ile Gln Lys Gly Asn Ala Thr His
145                 150                 155                 160

Asp Asn Val Cys Ser Gly Asn Arg Glu Ala Thr Gln Lys Cys Gly Ile
                165                 170                 175

Asp Val Thr Leu Cys Glu Glu Ala Phe Phe Arg Phe Ala Val Pro Thr
            180                 185                 190

Lys Ile Ile Pro Asn Trp Leu Ser Val Leu Val Asp Ser Leu Pro Gly
        195                 200                 205

Thr Lys Val Asn Ala Glu Ser Val Glu Arg Ile Lys Arg Arg His Ser
    210                 215                 220

Ser Gln Glu Gln Thr Phe Gln Leu Leu Lys Leu Trp Lys His Gln Asn
225                 230                 235                 240

Arg Asp Gln Glu Met Val Lys Lys Ile Ile Gln Asp Ile Asp Leu Cys
                245                 250                 255

Glu Ser Ser Val Gln Arg His Leu Gly His Ser Asn Leu Thr Thr Glu
            260                 265                 270

Gln Leu Leu Ala Leu Met Glu Ser Leu Pro Gly Lys Lys Ile Ser Pro
        275                 280                 285

Glu Glu Ile Glu Arg Thr Arg Lys Thr Cys Lys Ser Ser Glu Gln Leu
    290                 295                 300

Leu Lys Leu Leu Ser Leu Trp Arg Ile Lys Asn Gly Asp Gln Asp Thr
305                 310                 315                 320

Leu Lys Gly Leu Met Tyr Ala Leu Lys His Leu Lys Thr Ser His Phe
                325                 330                 335

Pro Lys Thr Val Thr His Ser Leu Arg Lys Thr Met Arg Phe Leu His
            340                 345                 350

Ser Phe Thr Met Tyr Arg Leu Tyr Gln Lys Leu Phe Leu Glu Met Ile
        355                 360                 365

Gly Asn Gln Val Gln Ser Val Lys Ile Ser Cys Leu
    370                 375                 380
```

-continued

<210> SEQ ID NO 139
<211> LENGTH: 380
<212> TYPE: PRT
<213> ORGANISM: Homo sapiens

<400> SEQUENCE: 139

```
Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Ile Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys Cys Gly Ile
                165                 170                 175

Asp Val Thr Leu Cys Glu Glu Ala Phe Phe Arg Phe Ala Val Pro Thr
            180                 185                 190

Lys Phe Thr Pro Asn Trp Leu Ser Val Leu Val Asp Asn Leu Pro Gly
        195                 200                 205

Thr Lys Val Asn Ala Glu Ser Val Glu Arg Ile Lys Arg Gln His Ser
    210                 215                 220

Ser Gln Glu Gln Thr Phe Gln Leu Leu Lys Leu Trp Lys His Gln Asn
225                 230                 235                 240

Lys Ala Gln Asp Ile Val Lys Lys Ile Ile Gln Asp Ile Asp Leu Cys
                245                 250                 255

Glu Asn Ser Val Gln Arg His Ile Gly His Ala Asn Leu Thr Phe Glu
            260                 265                 270

Gln Leu Arg Ser Leu Met Glu Ser Leu Pro Gly Lys Lys Val Gly Ala
        275                 280                 285

Glu Asp Ile Glu Lys Thr Ile Lys Ala Cys Lys Pro Ser Asp Gln Ile
    290                 295                 300

Leu Lys Leu Leu Ser Leu Trp Arg Ile Lys Asn Gly Asp Gln Asp Thr
305                 310                 315                 320

Leu Lys Gly Leu Met His Ala Leu Lys His Ser Lys Thr Tyr His Phe
                325                 330                 335

Pro Lys Thr Val Thr Gln Ser Leu Lys Lys Thr Ile Arg Phe Leu His
            340                 345                 350

Ser Phe Thr Met Tyr Lys Leu Tyr Gln Lys Leu Phe Leu Glu Met Ile
        355                 360                 365

Gly Asn Gln Val Gln Ser Val Lys Ile Ser Cys Leu
```

-continued 370 375 380

<210> SEQ ID NO 140
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 140
tggaccaccc agaagtacct tcattatgac 30

<210> SEQ ID NO 141
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 141
gtcataatga aggtacttct gggtggtcca 30

<210> SEQ ID NO 142
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 142
ggaccaccca gcttcattat gacgaagaaa c 31

<210> SEQ ID NO 143
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 143
gtttcttcgt cataatgaag ctgggtggtc c 31

<210> SEQ ID NO 144
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 144
gtggaccacc caggacgaag aaacctctc 29

<210> SEQ ID NO 145
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 145
gagaggtttc ttcgtcctgg gtggtccac 29

<210> SEQ ID NO 146
<211> LENGTH: 29
<212> TYPE: DNA
<213> ORGANISM: Artificial sequence -continued
<220> FEATURE:
<223> OTHER INFORMATION: Synthetic oligonucleotide

<400> SEQUENCE: 146
cgtttcctcc aaagttcctt cattatgac 29

<210> SEQ ID NO 147
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 147
gtcataatga aggaactttg gaggaaacg 29

<210> SEQ ID NO 148
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 148
ggaaacgttt cctgcaaagt accttcatta tg 32

<210> SEQ ID NO 149
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 149
cataatgaag gtactttgca ggaaacgttt cc 32

<210> SEQ ID NO 150
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 150
cacgcaaaag tcgggaatag atgtcac 27

<210> SEQ ID NO 151
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 151
gtgacatcta ttcccgactt ttgcgtg 27

<210> SEQ ID NO 152
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 152
caccctgtcg gaagaggcct tcttc 25

-continued

<210> SEQ ID NO 153
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 153
gaagaaggcc tcttccgaca gggtg 25

<210> SEQ ID NO 154
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 154
tgacctctcg gaaagcagcg tgca 24

<210> SEQ ID NO 155
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 155
tgcacgctgc tttccgagag gtca 24

<210> SEQ ID NO 156
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 156
cctcgaaatc gagcgagcag ctcc 24

<210> SEQ ID NO 157
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 157
cgatttcgag gtctttctcg ttctc 25

<210> SEQ ID NO 158
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 158
ccgtgaaaat aagctcgtta taactaggaa tgg 33

<210> SEQ ID NO 159
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 159
ccattcctag ttataacgag cttattttca cgg 33

<210> SEQ ID NO 160
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 160
cctctgagct caagcttccg aggaccacaa tgaacaag 38

<210> SEQ ID NO 161
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 161
cctctctcga gtcaggtgac atctattcca cacttttgcg tggc 44

<210> SEQ ID NO 162
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 162
cctctgagct caagcttccg aggaccacaa tgaacaag 38

<210> SEQ ID NO 163
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 163
cctctctcga gtcaaggaac agcaaacctg aagaaggc 38

<210> SEQ ID NO 164
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 164
cctctgagct caagcttccg aggaccacaa tgaacaag 38

<210> SEQ ID NO 165
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 165
cctctctcga gtcactctgt ggtgaggttc gagtggcc 38

<210> SEQ ID NO 166

-continued

<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 166
cctctgagct caagcttccg aggaccacaa tgaacaag 38

<210> SEQ ID NO 167
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 167
cctctctcga gtcaggatgt tttcaagtgc ttgagggc 38

<210> SEQ ID NO 168
<211> LENGTH: 16
<212> TYPE: PRT
<213> ORGANISM: Artificial sequence
<220> FEATURE:
<223> OTHER INFORMATION: Synthetic oligonucleotide

<400> SEQUENCE: 168

```
Met Lys His His His His His His His Ala Ser Val Asn Ala Leu Glu
1               5                   10                  15
```

<210> SEQ ID NO 169
<211> LENGTH: 70
<212> TYPE: PRT
<213> ORGANISM: Rattus rattus

<400> SEQUENCE: 169

```
Ala Leu Leu Val Phe Leu Asp Ile Ile Glu Trp Thr Thr Gln Glu Thr
1               5                   10                  15

Phe Pro Pro Lys Tyr Leu His Tyr Asp Pro Glu Thr Gly Arg Gln Leu
            20                  25                  30

Leu Cys Asp Lys Cys Ala Pro Gly Thr Tyr Leu Lys Gln His Cys Thr
        35                  40                  45

Val Arg Arg Lys Thr Leu Cys Val Pro Cys Pro Asp Tyr Ser Tyr Thr
    50                  55                  60

Asp Ser Trp His Thr Ser
65                  70
```

<210> SEQ ID NO 170
<211> LENGTH: 120
<212> TYPE: PRT
<213> ORGANISM: Homo sapiens

<400> SEQUENCE: 170

```
His Ala Leu Pro Ala Gln Val Ala Phe Thr Pro Tyr Ala Pro Glu Pro
1               5                   10                  15

Gly Ser Thr Cys Arg Leu Arg Glu Tyr Tyr Asp Gln Thr Ala Gln Met
            20                  25                  30

Cys Cys Ser Lys Cys Ser Pro Gly Gln His Ala Lys Val Phe Cys Thr
        35                  40                  45

Lys Thr Ser Asp Thr Val Cys Asp Ser Cys Glu Asp Ser Thr Tyr Thr
    50                  55                  60

Gln Leu Trp Asn Trp Val Pro Glu Cys Leu Ser Cys Gly Ser Arg Cys
```

-continued

```
65                  70                  75                  80

Ser Ser Asp Gln Val Glu Thr Gln Ala Cys Thr Arg Glu Gln Asn Arg
                85                  90                  95

Ile Cys Thr Cys Arg Pro Gly Trp Tyr Cys Ala Leu Ser Lys Gln Glu
            100                 105                 110

Gly Cys Arg Leu Cys Ala Pro Leu
        115                 120


<210> SEQ ID NO 171
<211> LENGTH: 48
<212> TYPE: PRT
<213> ORGANISM: Rattus rattus

<400> SEQUENCE: 171

Tyr Leu His Tyr Asp Pro Glu Thr Gly Arg Gln Leu Leu Cys Asp Lys
1               5                   10                  15

Cys Ala Pro Gly Thr Tyr Leu Lys Gln His Cys Thr Val Arg Arg Lys
            20                  25                  30

Thr Leu Cys Val Pro Cys Pro Asp Tyr Ser Tyr Thr Asp Ser Trp His
        35                  40                  45


<210> SEQ ID NO 172
<211> LENGTH: 139
<212> TYPE: PRT
<213> ORGANISM: Homo sapiens

<400> SEQUENCE: 172

Pro Pro Lys Tyr Leu His Tyr Asp Glu Glu Thr Ser His Gln Leu Leu
1               5                   10                  15

Cys Asp Lys Cys Pro Pro Gly Thr Tyr Leu Lys Gln His Cys Thr Ala
            20                  25                  30

Lys Trp Lys Thr Val Cys Ala Pro Cys Pro Asp His Tyr Tyr Thr Asp
        35                  40                  45

Ser Trp His Thr Ser Asp Glu Cys Leu Tyr Cys Ser Pro Val Cys Lys
    50                  55                  60

Glu Leu Gln Tyr Val Lys Gln Glu Cys Asn Arg Thr His Asn Arg Val
65                  70                  75                  80

Cys Glu Cys Lys Glu Gly Arg Tyr Leu Glu Ile Glu Phe Cys Leu Lys
                85                  90                  95

His Arg Ser Cys Pro Pro Gly Phe Gly Val Val Gln Ala Gly Thr Pro
            100                 105                 110

Glu Arg Asn Thr Val Cys Lys Arg Cys Pro Asp Gly Phe Phe Ser Asn
        115                 120                 125

Glu Thr Ser Ser Lys Ala Pro Cys Arg Lys His
    130                 135


<210> SEQ ID NO 173
<211> LENGTH: 51
<212> TYPE: PRT
<213> ORGANISM: Homo sapiens

<400> SEQUENCE: 173

Tyr His Tyr Tyr Asp Gln Asn Gly Arg Met Cys Glu Glu Cys His Met
1               5                   10                  15

Cys Gln Pro Gly His Phe Leu Val Lys His Cys Lys Gln Pro Lys Arg
            20                  25                  30

Asp Thr Val Cys His Lys Pro Cys Glu Pro Gly Val Thr Tyr Thr Asp
        35                  40                  45
```

-continued

```
Asp Trp His
    50


<210> SEQ ID NO 174
<211> LENGTH: 401
<212> TYPE: PRT
<213> ORGANISM: Mus musculus

<400> SEQUENCE: 174

Met Asn Lys Trp Leu Cys Cys Ala Leu Leu Val Leu Leu Asp Ile Ile
1               5                   10                  15

Glu Trp Thr Thr Gln Glu Thr Leu Pro Pro Lys Tyr Leu His Tyr Asp
            20                  25                  30

Pro Glu Thr Gly His Gln Leu Leu Cys Asp Lys Cys Ala Pro Gly Thr
        35                  40                  45

Tyr Leu Lys Gln His Cys Thr Val Arg Arg Lys Thr Leu Cys Val Pro
    50                  55                  60

Cys Pro Asp His Ser Tyr Thr Asp Ser Trp His Thr Ser Asp Glu Cys
65                  70                  75                  80

Val Tyr Cys Ser Pro Val Cys Lys Glu Leu Gln Ser Val Lys Gln Glu
                85                  90                  95

Cys Asn Arg Thr His Asn Arg Val Cys Glu Cys Glu Glu Gly Arg Tyr
            100                 105                 110

Leu Glu Ile Glu Phe Cys Leu Lys His Arg Ser Cys Pro Pro Gly Ser
        115                 120                 125

Gly Val Val Gln Ala Gly Thr Pro Glu Arg Asn Thr Val Cys Lys Lys
    130                 135                 140

Cys Pro Asp Gly Phe Phe Ser Gly Glu Thr Ser Ser Lys Ala Pro Cys
145                 150                 155                 160

Ile Lys His Thr Asn Cys Ser Thr Phe Gly Leu Leu Leu Ile Gln Lys
                165                 170                 175

Gly Asn Ala Thr His Asp Asn Val Cys Ser Gly Asn Arg Glu Ala Thr
            180                 185                 190

Gln Lys Cys Gly Ile Asp Val Thr Leu Cys Glu Glu Ala Phe Phe Arg
        195                 200                 205

Phe Ala Val Pro Thr Lys Ile Ile Pro Asn Trp Leu Ser Val Leu Val
    210                 215                 220

Asp Ser Leu Pro Gly Thr Lys Val Asn Ala Glu Ser Val Glu Arg Ile
225                 230                 235                 240

Lys Arg Arg His Ser Ser Gln Glu Gln Thr Phe Gln Leu Leu Lys Leu
                245                 250                 255

Trp Lys His Gln Asn Arg Asp Gln Glu Met Val Lys Lys Ile Ile Gln
            260                 265                 270

Asp Ile Asp Leu Cys Glu Ser Ser Val Gln Arg His Leu Gly His Ser
        275                 280                 285

Asn Leu Thr Thr Glu Gln Leu Leu Ala Leu Met Glu Ser Leu Pro Gly
    290                 295                 300

Lys Lys Ile Ser Pro Glu Glu Ile Glu Arg Thr Arg Lys Thr Cys Lys
305                 310                 315                 320

Ser Ser Glu Gln Leu Leu Lys Leu Leu Ser Leu Trp Arg Ile Lys Asn
                325                 330                 335

Gly Asp Gln Asp Thr Leu Lys Gly Leu Met Tyr Ala Leu Lys His Leu
            340                 345                 350

Lys Thr Ser His Phe Pro Lys Thr Val Thr His Ser Leu Arg Lys Thr
```

-continued 355 360 365

Met Arg Phe Leu His Ser Phe Thr Met Tyr Arg Leu Tyr Gln Lys Leu
370 375 380

Phe Leu Glu Met Ile Gly Asn Gln Val Gln Ser Val Lys Ile Ser Cys
385 390 395 400

Leu

<210> SEQ ID NO 175
<211> LENGTH: 401
<212> TYPE: PRT
<213> ORGANISM: Rattus rattus

<400> SEQUENCE: 175

Met Asn Lys Trp Leu Cys Cys Ala Leu Leu Val Phe Leu Asp Ile Ile
1 5 10 15

Glu Trp Thr Thr Gln Glu Thr Phe Pro Pro Lys Tyr Leu His Tyr Asp
20 25 30

Pro Glu Thr Gly Arg Gln Leu Leu Cys Asp Lys Cys Ala Pro Gly Thr
35 40 45

Tyr Leu Lys Gln His Cys Thr Val Arg Arg Lys Thr Leu Cys Val Pro
50 55 60

Cys Pro Asp Tyr Ser Tyr Thr Asp Ser Trp His Thr Ser Asp Glu Cys
65 70 75 80

Val Tyr Cys Ser Pro Val Cys Lys Glu Leu Gln Thr Val Lys Gln Glu
85 90 95

Cys Asn Arg Thr His Asn Arg Val Cys Glu Cys Glu Glu Gly Arg Tyr
100 105 110

Leu Glu Leu Glu Phe Cys Leu Lys His Arg Ser Cys Pro Pro Gly Leu
115 120 125

Gly Val Leu Gln Ala Gly Thr Pro Glu Arg Asn Thr Val Cys Lys Arg
130 135 140

Cys Pro Asp Gly Phe Phe Ser Gly Glu Thr Ser Ser Lys Ala Pro Cys
145 150 155 160

Arg Lys His Thr Asn Cys Ser Ser Leu Gly Leu Leu Leu Ile Gln Lys
165 170 175

Gly Asn Ala Thr His Asp Asn Val Cys Ser Gly Asn Arg Glu Ala Thr
180 185 190

Gln Asn Cys Gly Ile Asp Val Thr Leu Cys Glu Glu Ala Phe Phe Arg
195 200 205

Phe Ala Val Pro Thr Lys Ile Ile Pro Asn Trp Leu Ser Val Leu Val
210 215 220

Asp Ser Leu Pro Gly Thr Lys Val Asn Ala Glu Ser Val Glu Arg Ile
225 230 235 240

Lys Arg Arg His Ser Ser Gln Glu Gln Thr Phe Gln Leu Leu Lys Leu
245 250 255

Trp Lys His Gln Asn Arg Asp Gln Glu Met Val Lys Lys Ile Ile Gln
260 265 270

Asp Ile Asp Leu Cys Glu Ser Ser Val Gln Arg His Ile Gly His Ala
275 280 285

Asn Leu Thr Thr Glu Gln Leu Arg Ile Leu Met Glu Ser Leu Pro Gly
290 295 300

Lys Lys Ile Ser Pro Asp Glu Ile Glu Arg Thr Arg Lys Thr Cys Lys
305 310 315 320

Pro Ser Glu Gln Leu Leu Lys Leu Leu Ser Leu Trp Arg Ile Lys Asn

-continued

```
                325                 330                 335

Gly Asp Gln Asp Thr Leu Lys Gly Leu Met Tyr Ala Leu Lys His Leu
            340                 345                 350

Lys Ala Tyr His Phe Pro Lys Thr Val Thr His Ser Leu Arg Lys Thr
        355                 360                 365

Ile Arg Phe Leu His Ser Phe Thr Met Tyr Arg Leu Tyr Gln Lys Leu
    370                 375                 380

Phe Leu Glu Met Ile Gly Asn Gln Val Gln Ser Val Lys Ile Ser Cys
385                 390                 395                 400

Leu


<210> SEQ ID NO 176
<211> LENGTH: 401
<212> TYPE: PRT
<213> ORGANISM: Homo sapiens

<400> SEQUENCE: 176

Met Asn Lys Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Leu
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
    210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Asp Gln Asp Ile Val Lys Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
```

-continued

```
    290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
            340                 345                 350

Lys Thr Tyr His Phe Pro Lys Thr Val Thr Gln Ser Leu Lys Lys Thr
        355                 360                 365

Ile Arg Phe Leu His Ser Phe Thr Met Tyr Lys Leu Tyr Gln Lys Leu
    370                 375                 380

Phe Leu Glu Met Ile Gly Asn Gln Val Gln Ser Val Lys Ile Ser Cys
385                 390                 395                 400

Leu


<210> SEQ ID NO 177
<211> LENGTH: 139
<212> TYPE: PRT
<213> ORGANISM: Homo sapiens

<400> SEQUENCE: 177

Cys Pro Gln Gly Lys Tyr Ile His Pro Gln Asn Asn Ser Ile Cys Cys
1               5                   10                  15

Thr Lys Cys His Lys Gly Thr Tyr Leu Tyr Asn Asp Cys Pro Gly Pro
            20                  25                  30

Gly Gln Asp Thr Asp Cys Arg Glu Cys Glu Ser Gly Ser Phe Thr Ala
        35                  40                  45

Ser Glu Asn His Leu Arg His Cys Leu Ser Cys Ser Lys Cys Arg Lys
    50                  55                  60

Glu Met Gly Gln Val Glu Ile Ser Ser Cys Thr Val Asp Arg Asp Thr
65                  70                  75                  80

Val Cys Gly Cys Arg Lys Asn Gln Tyr Arg His Tyr Trp Ser Glu Asn
                85                  90                  95

Leu Phe Gln Cys Phe Asn Cys Ser Leu Cys Leu Asn Gly Thr Val His
            100                 105                 110

Leu Ser Cys Gln Glu Lys Gln Asn Thr Val Cys Thr Cys His Ala Gly
        115                 120                 125

Phe Phe Leu Arg Glu Asn Glu Cys Val Ser Cys
    130                 135


<210> SEQ ID NO 178
<211> LENGTH: 139
<212> TYPE: PRT
<213> ORGANISM: Homo sapiens

<400> SEQUENCE: 178

Pro Pro Lys Tyr Leu His Tyr Asp Glu Glu Thr Ser His Gln Leu Leu
1               5                   10                  15

Cys Asp Lys Cys Pro Pro Gly Thr Tyr Leu Lys Gln His Cys Thr Ala
            20                  25                  30

Lys Trp Lys Thr Val Cys Ala Pro Cys Pro Asp His Tyr Tyr Thr Asp
        35                  40                  45

Ser Trp His Thr Ser Asp Glu Cys Leu Tyr Cys Ser Pro Val Cys Lys
    50                  55                  60

Glu Leu Gln Tyr Val Lys Gln Glu Cys Asn Arg Thr His Asn Arg Val
65                  70                  75                  80
```

-continued

```
Cys Glu Cys Lys Glu Gly Arg Tyr Leu Glu Ile Glu Phe Cys Leu Lys
                85                  90                  95

His Arg Ser Cys Pro Pro Gly Phe Gly Val Val Gln Ala Gly Thr Pro
            100                 105                 110

Glu Arg Asn Thr Val Cys Lys Arg Cys Pro Asp Gly Phe Phe Ser Asn
        115                 120                 125

Glu Thr Ser Ser Lys Ala Pro Cys Arg Lys His
    130                 135


<210> SEQ ID NO 179
<211> LENGTH: 379
<212> TYPE: PRT
<213> ORGANISM: Mus musculus

<400> SEQUENCE: 179

Glu Thr Leu Pro Pro Lys Tyr Leu His Tyr Asp Pro Glu Thr Gly His
1               5                   10                  15

Gln Leu Leu Cys Asp Lys Cys Ala Pro Gly Thr Tyr Leu Lys Gln His
            20                  25                  30

Cys Thr Val Arg Arg Lys Thr Leu Cys Val Pro Cys Pro Asp His Ser
        35                  40                  45

Tyr Thr Asp Ser Trp His Thr Ser Asp Glu Cys Val Tyr Cys Ser Pro
    50                  55                  60

Val Cys Lys Glu Leu Gln Ser Val Lys Gln Glu Cys Asn Arg Thr His
65                  70                  75                  80

Asn Arg Val Cys Glu Cys Glu Glu Gly Arg Tyr Leu Glu Ile Glu Phe
                85                  90                  95

Cys Leu Lys His Arg Ser Cys Pro Pro Gly Ser Gly Val Val Gln Ala
            100                 105                 110

Gly Thr Pro Glu Arg Asn Thr Val Lys Lys Cys Pro Asp Gly Phe Phe
        115                 120                 125

Ser Gly Glu Thr Ser Ser Lys Ala Pro Cys Ile Lys His Thr Asn Cys
    130                 135                 140

Ser Thr Phe Gly Leu Leu Leu Ile Gln Lys Gly Asn Ala Thr His Asp
145                 150                 155                 160

Asn Val Cys Ser Gly Asn Arg Glu Ala Thr Gln Lys Cys Gly Ile Asp
                165                 170                 175

Val Thr Leu Cys Glu Glu Ala Phe Phe Arg Phe Ala Val Pro Thr Lys
            180                 185                 190

Ile Ile Pro Asn Trp Leu Ser Val Leu Val Asp Ser Leu Pro Gly Thr
        195                 200                 205

Lys Val Asn Ala Glu Ser Val Glu Arg Ile Lys Arg Arg His Ser Ser
    210                 215                 220

Gln Glu Gln Thr Phe Gln Leu Leu Lys Leu Trp Lys His Gln Asn Arg
225                 230                 235                 240

Asp Gln Glu Met Val Lys Lys Ile Ile Gln Asp Ile Asp Leu Cys Glu
                245                 250                 255

Ser Ser Val Gln Arg His Leu Gly His Ser Asn Leu Thr Thr Glu Gln
            260                 265                 270

Leu Leu Ala Leu Met Glu Ser Leu Pro Gly Lys Lys Ile Ser Pro Glu
        275                 280                 285

Glu Ile Glu Arg Thr Arg Lys Thr Cys Lys Ser Ser Glu Gln Leu Leu
    290                 295                 300

Lys Leu Leu Ser Leu Trp Arg Ile Lys Asn Gly Asp Gln Asp Thr Leu
```

-continued

```
305                 310                 315                 320

Lys Gly Leu Met Tyr Ala Leu Lys His Leu Lys Thr Ser His Phe Pro
                325                 330                 335

Lys Thr Val Thr His Ser Leu Arg Lys Thr Met Arg Phe Leu His Ser
            340                 345                 350

Phe Thr Met Tyr Arg Leu Tyr Gln Lys Leu Phe Leu Glu Met Ile Gly
        355                 360                 365

Asn Gln Val Gln Ser Val Lys Ile Ser Cys Leu
    370                 375
```

OSTEOPROTEGERIN

This application is a continuation of Ser. No. 09/132,985 filed Aug. 12, 1998, now abandoned which is a continuation of Ser. No. 08/771,777, filed Dec. 20, 1996, now abandoned which is a continuation in part of Ser. No. 08/706,945, filed Sep. 3, 1996, now U.S. Pat. No. 6,369,027 which is a continuation in part of Ser. No. 08/577,788, filed Dec. 22, 1995 now U.S. Pat. No. 6,613,544 which are hereby incorporated by reference.

FIELD OF THE INVENTION

The invention relates generally to polypeptides involved in the regulation of bone metabolism. More particularly, the invention relates to a novel polypeptide, termed osteoprotegerin, which is a member of the tumor necrosis factor receptor superfamily. The polypeptide is used to treat bone diseases characterized by increased bone loss such as osteoporosis.

BACKGROUND OF THE INVENTION

Polypeptide growth factors and cytokines are secreted factors which signal a wide variety of changes in cell growth, differentiation, and metabolism, by specifically binding to discrete, surface bound receptors. As a class of proteins, receptors vary in their structure and mode of signal transduction. They are characterized by having an extracellular domain that is involved in ligand binding, and cytoplasmic domain which transmits an appropriate intracellular signal. Receptor expression patterns ultimately determine which cells will respond to a given ligand, while the structure of a given receptor dictates the cellular response induced by ligand binding. Receptors have been shown to transmit intracellular signals via their cytoplasmic domains by activating protein tyrosine, or protein serine/threonine phosphorylation (e.g., platelet derived growth factor receptor (PDGFR) or transforming growth factor-β receptor-I (TGFβR-I), by stimulating G-protein activation (e.g., β-adrenergic receptor), and by modulating associations with cytoplasmic signal transducing proteins (e.g., TNFR-1 and Fas/APO) (Heldin, Cell 80, 213-223 (1995)).

The tumor necrosis factor receptor (TNFR) superfamily is a group of type I transmembrane proteins which share a conserved cysteine-rich motif which is repeated three to six times in the extracellular domain (Smith, et al. Cell 76, 953-962 (1994)). Collectively, these repeat units form the ligand binding domains of these receptors (Chen et al., Chemistry 270, 2874-2878 (1995)). The ligands for these receptors are a structurally related group of proteins homologous to TNFα. (Goeddel et al. Cold Spring Harbor Symp. Quart. Biol. 51, 597-609 (1986); Nagata et al. Science 267, 1449-1456 (1995)). TNFα binds to distinct, but closely related receptors, TNFR-1 and TNFR-2. TNFα produces a variety of biological responses in receptor bearing cells, including, proliferation, differentiation, and cytotoxicity and apoptosis (Beutler et al. Ann. Rev. Biochem. 57, 505-518 (1988)).

TNFα is believed to mediate acute and chronic inflammatory responses (Beutler et al. Ann. Rev. Biochem. 57, 505-508 (1988)). Systemic delivery of TNFα induces toxic shock and widespread tissue necrosis. Because of this, TNFα may be responsible for the severe morbidity and mortality associated with a variety of infectious diseases, including sepsis. Mutations in FasL, the ligand for the TNFR-related receptor Fas/APO (Suda et al. Cell 75, 1169-1178 (1993)), is associated with autoimmunity (Fisher et al. Cell 81, 935-946 (1995)), while overproduction of FasL may be implicated in drug-induced hepatitis. Thus, ligands to the various TNFR-related proteins often mediate the serious effects of many disease states, which suggests that agents that neutralize the activity of these ligands would have therapeutic value. Soluble TNFR-1 receptors, and antibodies that bind TNFα, have been tested for their ability to neutralize systemic TNFα (Loetscher et al. Cancer Cells 3(6), 221-226 (1991)). A naturally occurring form of a secreted TNFR-1 mRNA was recently cloned, and its product tested for its ability to neutralize TNFα activity in vitro and in vivo (Kohno et al. PNAS USA 87 8331-8335 (1990)). The ability of this protein to neutralize TNFα suggests that soluble TNF receptors function to bind and clear TNF thereby blocking the cytotoxic effects on TNFR-bearing cells.

An object of the invention to identify new members of the TNFR super family. It is anticipated that new family members may be transmembrane proteins or soluble forms thereof comprising extracellular domains and lacking transmembrane and cytoplasmic domains. We have identified a new member of the TNFR superfamily which encodes a secreted protein that is closely related to TNFR-2. By analogy to soluble TNFR-1, the TNFR-2 related protein may negatively regulate the activity of its ligand, and thus may be useful in the treatment of certain human diseases.

SUMMARY OF THE INVENTION

A novel member of the tumor necrosis factor receptor (TNFR) superfamily has been identified from a fetal rat intestinal cDNA library. A full-length cDNA clone was obtained and sequenced. Expression of the rat cDNA in a transgenic mouse revealed a marked increase in bones density, particularly in long bones, pelvic bone and vertebrae. The polypeptide encoded by the cDNA is termed Osteprotegerin (OPG) and plays a role in promoting bone accumulation.

The invention provides for nucleic acids encoding a polypeptide having at least one of the biological activities of OPG. Nucleic acids which hybridize to nucleic acids encoding mouse, rat or human OPG as shown in FIGS. 2B-2C (SEQ ID NO:120), 9A-9B (SEQ ID NO: 122), and 9C-9D (SEQ ID NO: 124) are also provided. Preferably, OPG is mammalian OPG and more preferably is human OPG. Recombinant vectors and host cells expressing OPG are also encompassed as are methods of producing recombinant OPG. Antibodies or fragments thereof which specifically bind the polypeptide are also disclosed.

Methods of treating bone diseases are also provided by the invention. The polypeptides are useful for preventing bone resorption and may be used to treat any condition resulting in bone loss such as osteoporosis, hypercalcemia, Paget's disease of bone, and bone loss due to rheumatoid arthritis or osteomyelitis, and the like. Bone diseases may also be treated with anti-sense or gene therapy using nucleic acids of the invention. Pharmaceutical compositions comprising OPG nucleic acids and polypeptides are also encompassed.

DESCRIPTION OF THE FIGURES

FIG. 9. Structure and sequence of mouse and human OPG cDNA clones. A, B. Mouse cDNA and protein sequence (SEQ ID NOs. 122 and 123). C, D. Human cDNA and protein sequence (SEQ ID NOs: 124 and 125). The predicted signal peptides are underlined, and potential sites of N-linked glycosylation are indicated in bold. E, F. Sequence alignment and comparison of rat (SEQ ID NO: 174), mouse (SEQ ID NO: 175) and human (SEQ ID NO: 176) OPG amino acid sequences.

FIG. 10. Comparison of conserved sequences in extracellular domain of TNFR-1 and human OPG. PrettyPlot (Wisconsin GCG Package, Version 8.1) of the TNFR1 and OPG alignment described in example 6. Top line, human TNFR1 sequences encoding domains 1-4 (SEQ ID NO: 177). Bottom line, human OPG sequences encoding domains 1-4 (SEQ ID NO: 178). Conserved residues are highlighted by rectangular boxes.

FIG. 26. Histology analysis of bone accumulation in marrow cavity of normal mice. Injection experiments and bone histology performed as described in Example 11C. A. Saline injection B. Injection of muOPG [22-401]-Fc fusion.

DETAILED DESCRIPTION OF THE INVENTION

Figure 2D:
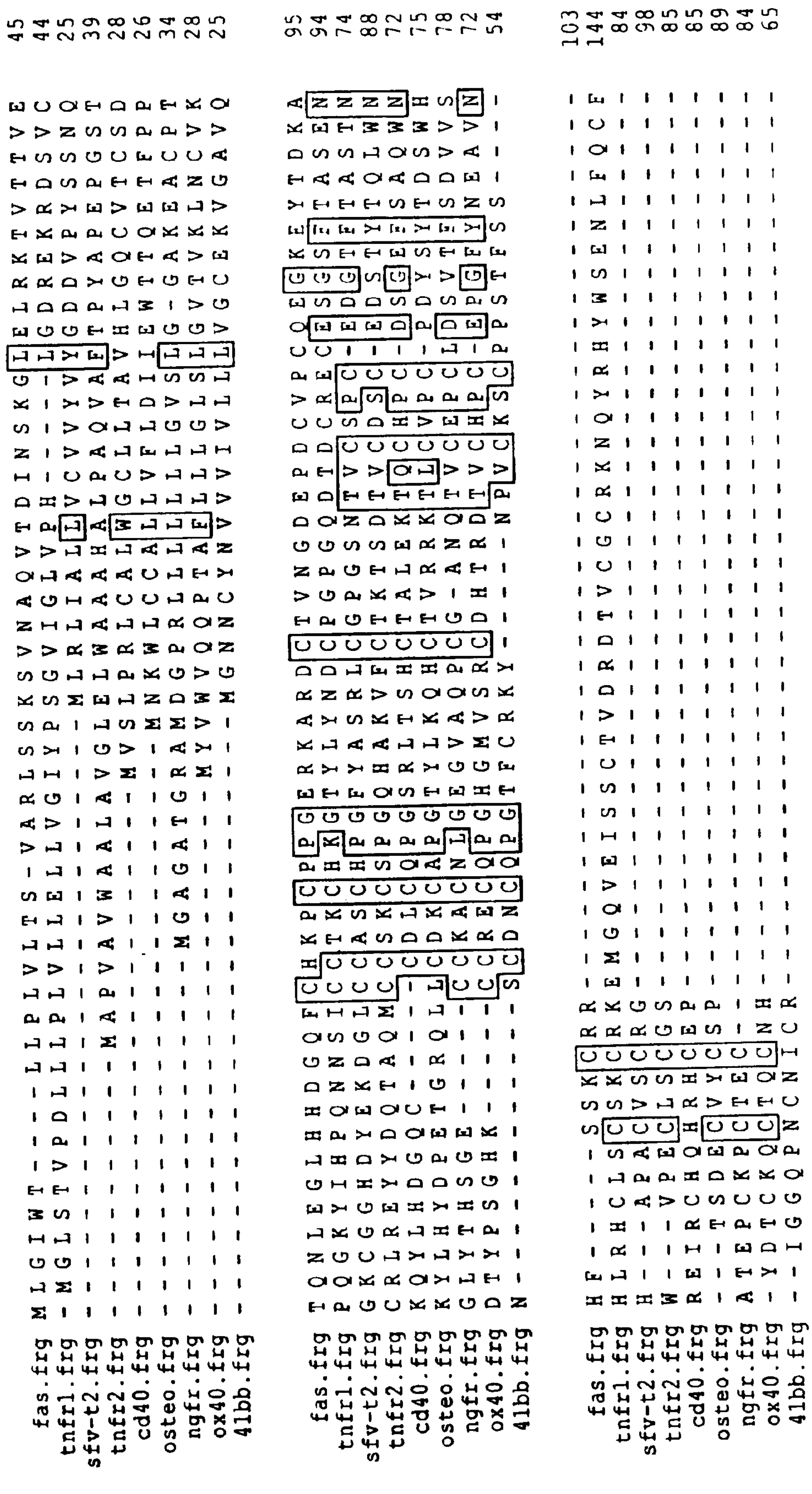
FIG. 2. Structure and sequence of full length rat OPG gene, a novel member of the TNFR superfamily. A. Map of pMOB- B1.1 insert. Box indicates position of LORF within the cDNA sequence (bold line). Black box indicates signal peptide, and gray ellipses indicate position of cysteine-rich repeat sequences. B, C. Nucleic acid and protein sequence of the Rat OPG cDNA. The predicted signal peptide is underlined, and potential sites of N-linked glycosylation are indicated in bold, underlined letters (SEQ ID NO: 120 and 121). D, E. Pileup sequence comparison (Wisconsin GCG Package, Version 8.1) of OPG with other members of the TNFR superfamily, fas (SEQ ID NO:128); tnfr1 (SEQ ID NO: 129); sfu-t2 (SEQ ID NO:130); tnfr2 (SEQ ID NO:131); cd40 (SEQ ID NO:132); osteo (SEQ ID NO:133); ngfr (SEQ ID NO:134); ox40 (SEQ ID NO:135); 41bb (SEQ ID NO:136).
Figures 3A, 3B, 3C, 3D, 3E:
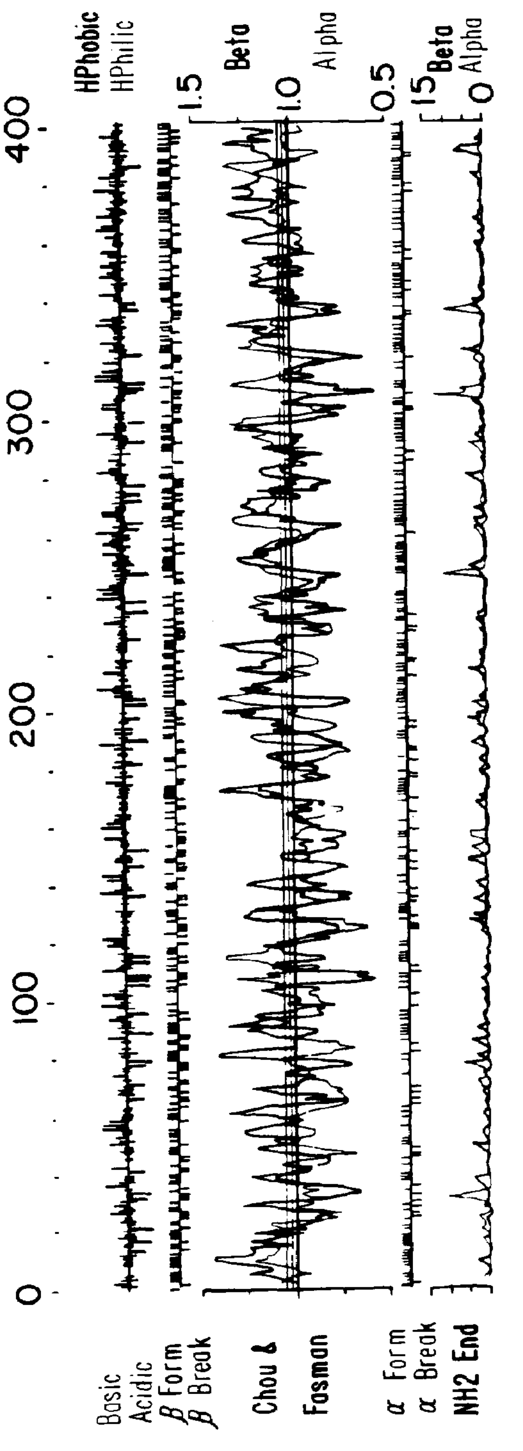
FIG. 3. PepPlot analysis (Wisconsin GCG Package, Version 8.1) of the predicted rat OPG protein sequence. A. Schematic representation of rat OPG showing hydrophobic (up) and hydrophilic (down) amino acids. Also shown are basic (up) and acidic (down) amino acids. B. Display of amino acid residues that are beta-sheet forming (up) and beta-sheet breaking down) as defined by Chou and Fasman (Adv. Enz. 47, 45-147 (1948)). C. Display of propensity measures for alpha-helix and beta-sheet (Chou and Fasman, ibid). Curves above 1.00 show propensity for alpha-helix or beta-sheet structure. Structure may terminate in regions of protein where curves drop below 1.00. D. Display of residues that are alpha-forming (up) or alpha-breaking (down). E. Display of portions of the protein sequence that resemble sequences typically found at the amino end of alpha and beta structures (Chou and Fasman, ibid). F. Display of portions of the protein sequence that resemble sequences typically found at the carboxyl end of alpha and beta structures (Chou and Fasman, ibid). G. Display of portions of the proteins sequence typically found in turns (Chou and Fasman, ibid) H. Display of the helical hydrophobic moment (Eisenberg et al. Proc. Natl. Acad. Sci. USA 81, 140-144 (1984)) at each position in the sequence. I. Display of average hydrophathy based upon Kyte and Doolittle (J. Mol. Biol. 157, 105-132 (1982)) and Goldman et al. (reviewed in Ann. Rev. Biophys. Biophys. Chem. 15, 321-353 (1986)).
Figures 3F, 3G, 3H, 3I:
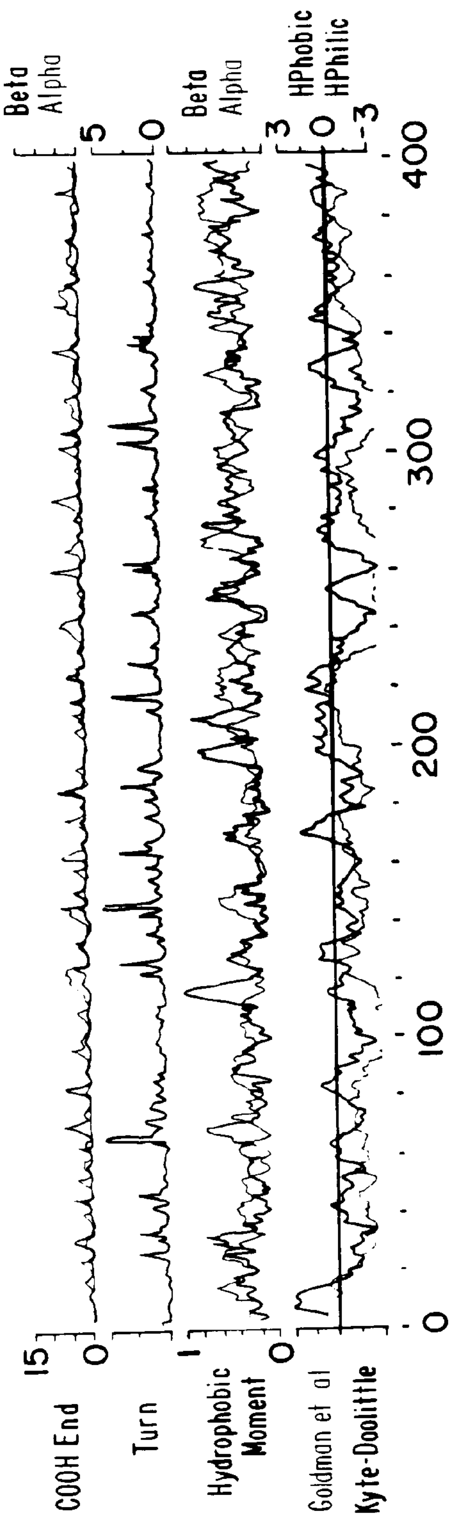
Figure 4A:
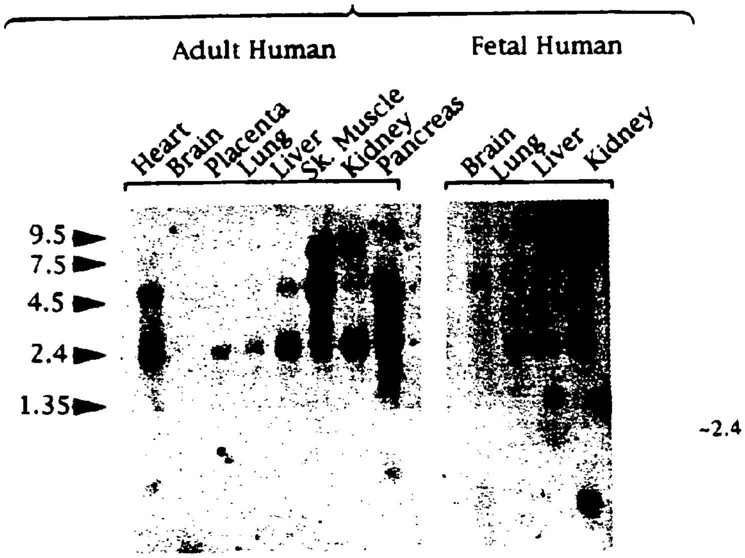
FIG. 4. mRNA expression patterns for the OPG cDNA in human tissues. Northern blots were probed with a 32P-labeled rat cDNA insert (A, left two panels), or with the human cDNA insert (B, right panel).
Figure 4B:
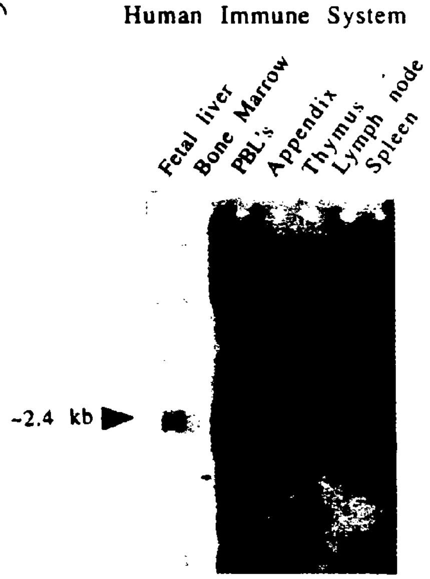
Figure 5:
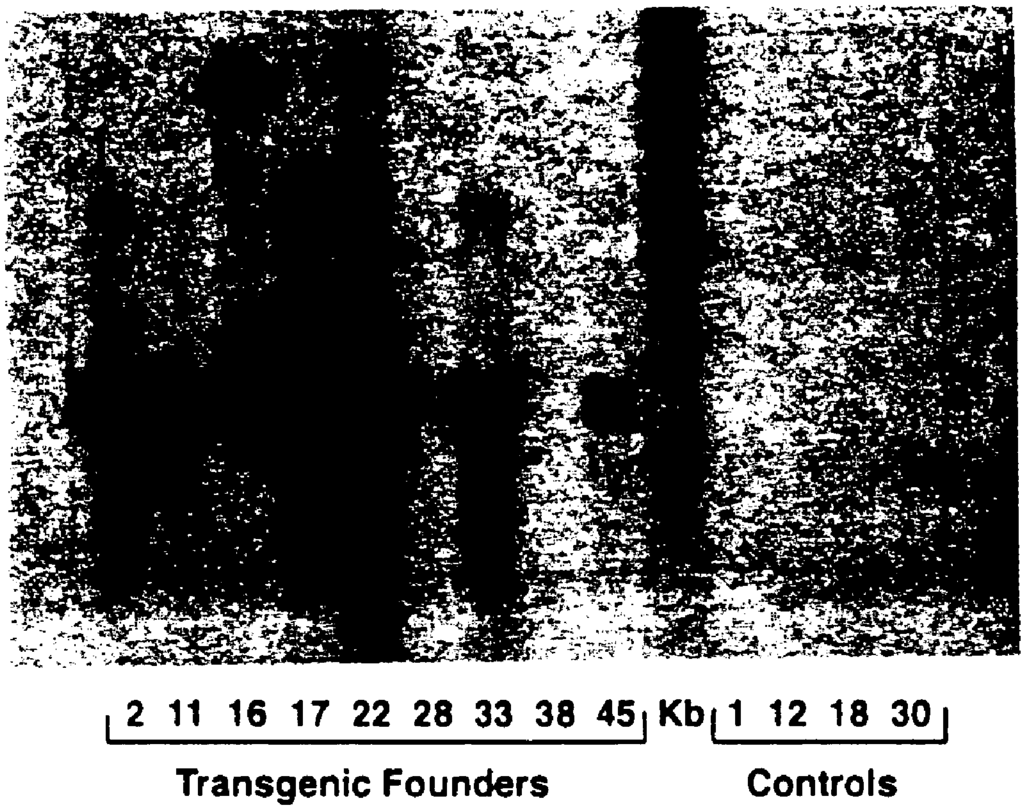
FIG. 5. Creation of transgenic mice expressing the OPG cDNA in hepatocytes. Northern blot expression of HE-OPG transgene in mouse liver.
Figure 6A:
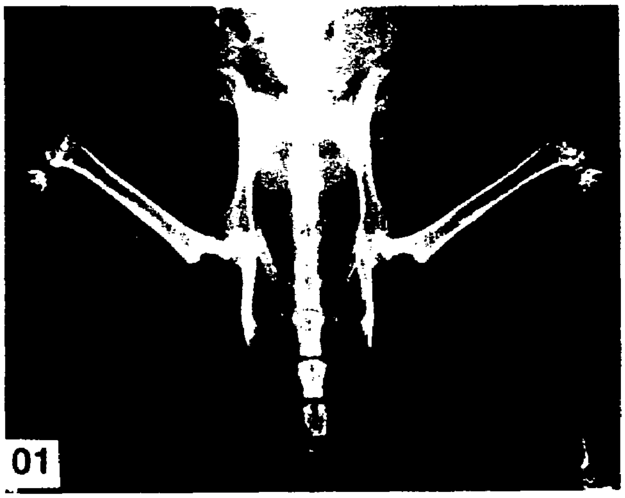
FIG. 6. Increase in bone density in OPG transgenic mice. Panel A-F. Control Mice. G-J, OPG expressing mice. At necropsy, all animals were radiographed and photographs prepared. In A-F, the radiographs of the control animals and the one transgenic non-expressor (#28) are shown. Note that the bones have a clearly defined cortex and a lucent central marrow cavity. In contrast, the OPG (G-J) animals have a poorly defined cortex and increased density in the marrow zone.
Figure 6B:
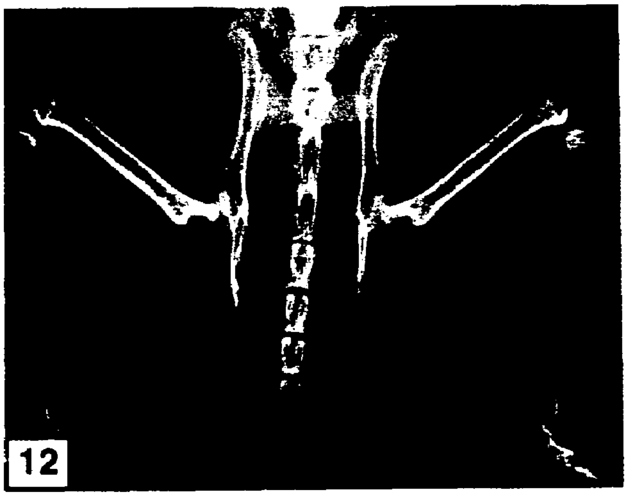
Figure 6C:
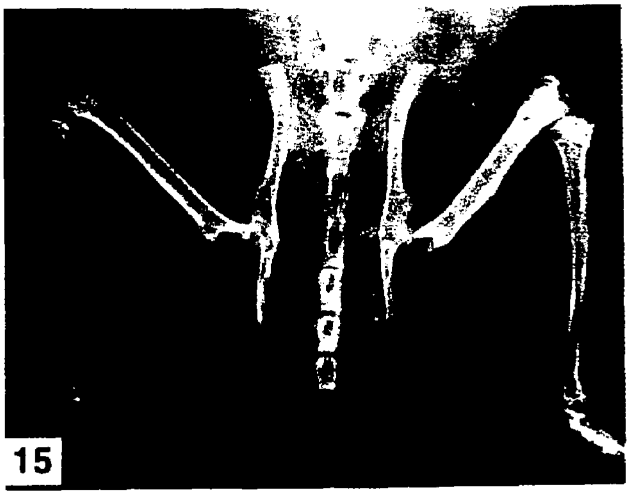
Figure 6D:
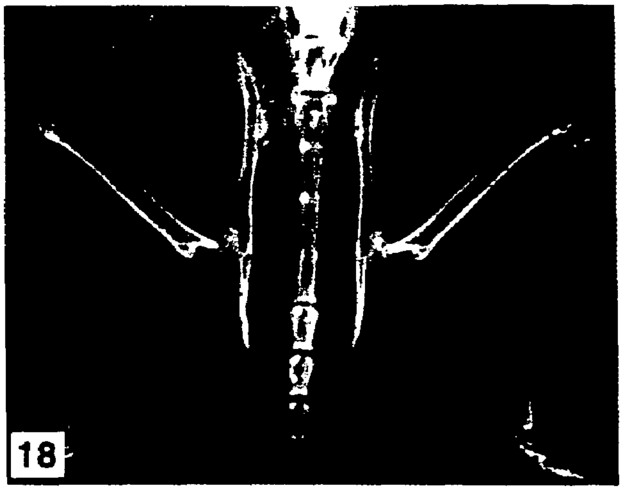
Figure 6E:
Figure 6F:
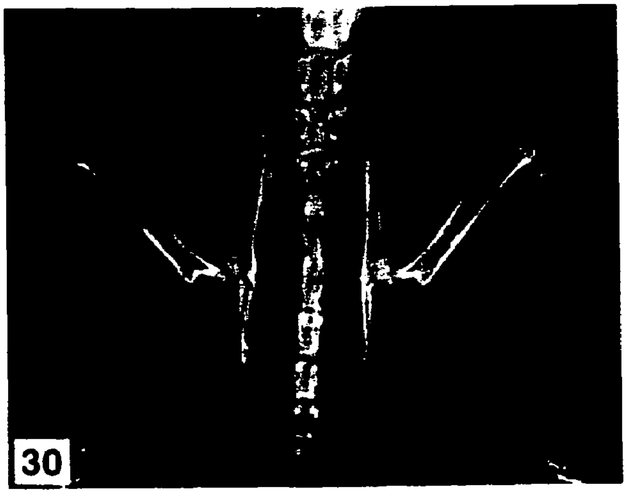
Figure 6G:
Figure 6H:
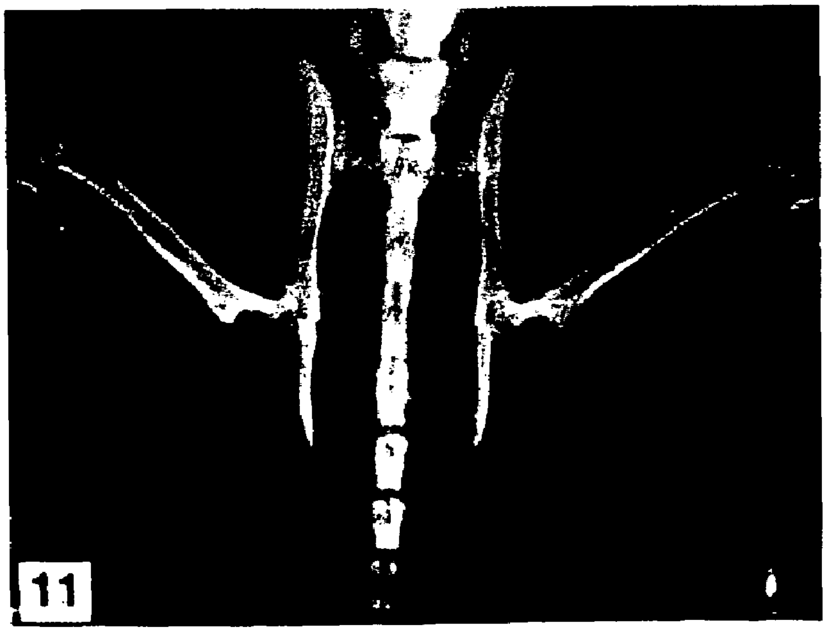
Figure 6I:
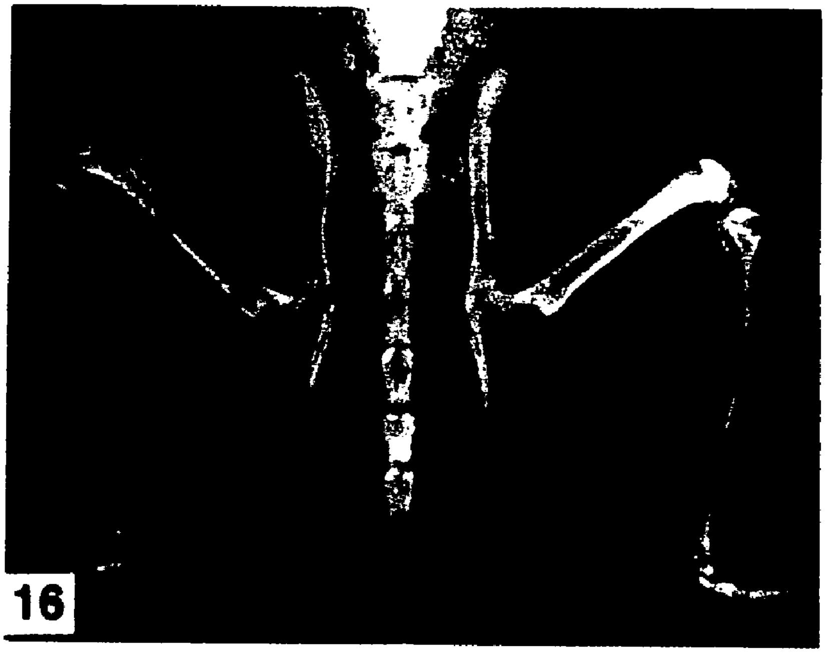
Figure 6J:
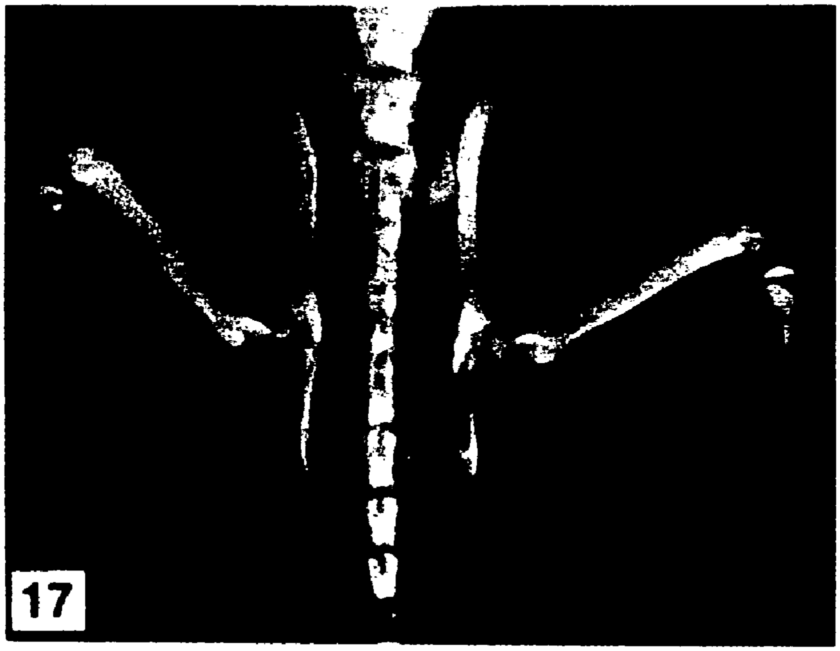
Figure 7A:
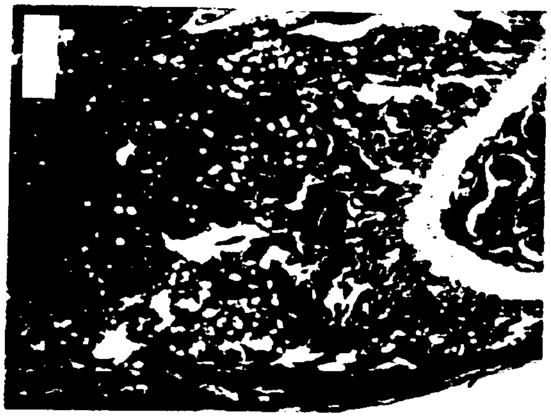
FIG. 7. Increase in trabecular bone in OPG transgenic mice. A-D. Representative photomicrographs of bones from control animals. In A and B, low (4×, 10×) power images of the femurs are shown (Masson Trichrome stain). Stains for tartrate resistant acid phosphatase (TRAP) demonstrate osteoclasts (see arrows) both resorbing cartilage (C) and trabecular bone (D). Note the flattened appearance of osteoclasts on trabecular bone. E-H. Representative photomicrographs of bones from OPG-expressing animals. In E and F, low (4×, 10×) power images of the femurs are shown (Masson Trichrome stain). The clear region is the growth plate cartilage, blue stained area is bone, and the red area is marrow. Note that in contrast to the controls, the trabecular bone has not been resorbed resulting in the absence of the usual marrow cavity. Also, the resulting trabeculae have a variegated appearance with blue and clear areas. The clear areas are remnants of growth plate cartilage that have never been remodelled. Based on TRAP stains, these animals do have osteoclasts (see arrows) at the growth plate (G), which may be reduced in number. However, the surfaces of the trabeculae away from the growth plate are virtually devoid of osteoclasts (H), a finding that stands in direct contrast with the control animals (see D).
Figure 7B:
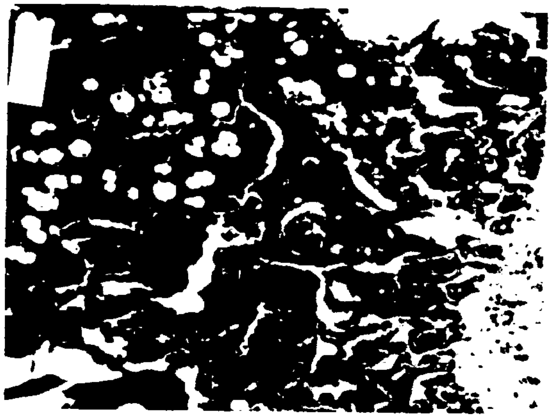
Figure 7C:
Figure 7D:
Figure 7E:
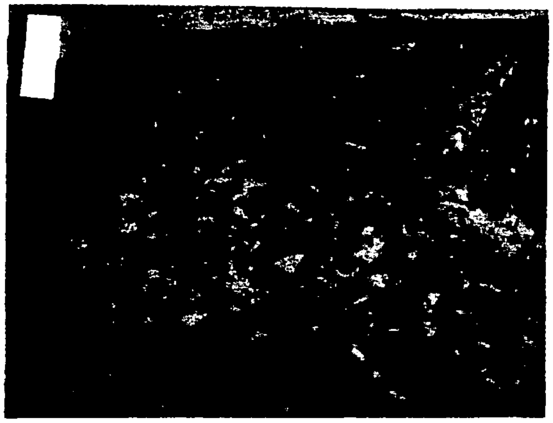
Figure 7F:
Figure 7G:
Figure 7H:
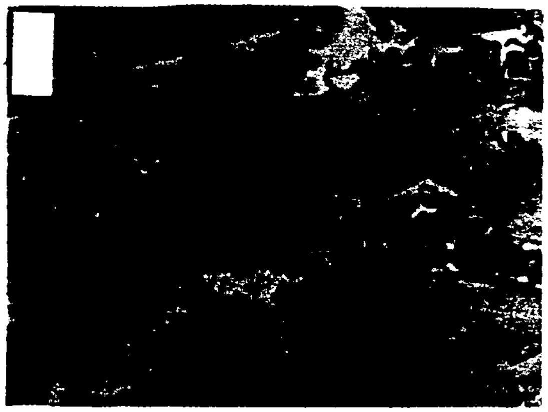
Figure 8A:
FIG. 8. HE-OPG expressors do not have a defect in monocyte-macrophage development. One cause for osteopetrosis in mice is defective M-CSF production due to a point mutation in the M-CSF gene. This results in a marked deficit of circulating and tissue based macrophages. The peripheral blood of OPG expressors contained monocytes as assessed by H1E analysis. To affirm the presence of tissue macrophages, immunohistochemistry was performed using F480 antibodies, which recognize a cell surface antigen on murine macrophages. A and C show low power (4×) photomicrographs of the spleens from normal and CR1 overexpressors. Note that both animals have numerous F480 positive cells. Monocyte-macrophages were also present in the marrow of normal (B) and HE-OPG overexpressors (D) (40×).
Figure 8B:
Figure 8C:
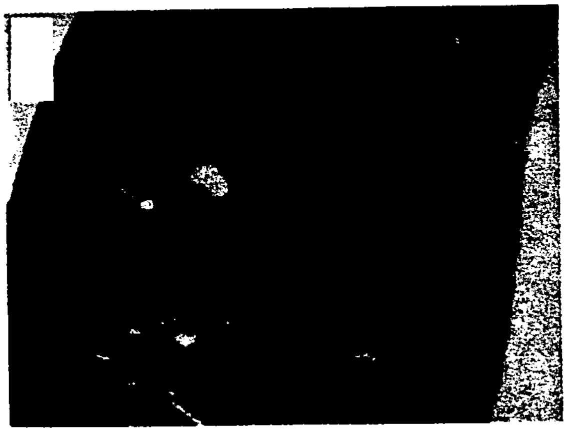
Figure 8D:

A novel member of the tumor necrosis factor receptor (TNFR) superfamily was identified as an expressed sequence tag (EST) isolated from a fetal rat intestinal cDNA library. The structures of the full-length rat cDNA clones and the corresponding mouse and human cDNA clones were determined as described in Examples 1 and 6. The rat, mouse and human genes are shown in FIGS. 2B-2C (SEQ ID NO:120), 9A-9B (SEQ ID NO:122), and 9C-9D (SEQ ID NO:124), respectively. All three sequences showed strong similarity to the extracellular domains of TNFR family members. None of the full-length cDNA clones isolated encoded transmembrane and cytoplasmic domains that would be expected for membrane-bound receptors, suggesting that these cDNAs encode soluble, secreted proteins rather than cell surface receptors. A portion of the human gene spanning nucleotides 1200-1353 shown in FIG. 9D was deposited in the Genebank database on Nov. 22, 1995 under accession no. 17188769.

The tissue distribution of the rat and human mRNA was determined as described in Example 2. In rat, mRNA expression was detected in kidney, liver, placenta and heart with the highest expression in the kidney. Expression in skeletal muscle and pancreas was also detected. In humans, expression was detected in the same tissues along with lymph node, thymus, spleen and appendix.

The rat cDNA was expressed in transgenic mice (Example 3) using the liver-specific ApoE promoter expression system. Analysis of expressors showed a marked increase in bone density, particularly in long bones (femurs), vertebrae and flat bones (pelvis). Histological analysis of stained sections of bone showed severe osteopetrosis (see Example 4) indicating a marked imbalance between bone formation and resorption which has led to a marked accumulation of bone and cartilage. A decrease in the number of trabecular osteoclasts in the bones of OPG expresser animals indicate that a significant portion of the activity of the TNFR-related protein may be to prevent bone resorption, a process mediated by osteoclasts. In view of the activity in transgenic expressors, the TNFR-related proteins described herein are termed OPGs.

Using the rat cDNA sequence, mouse and human cDNA clones were isolated (Example 5). Expression of mouse OPG in 293 cells and human OPG in *E. coli* is described in Examples 7 and 8. Mouse OPG was produced as an Fc fusion which was purified by Protein A affinity chromatography. Also described in Example 7 is the expression of full-length and truncated human and mouse OPG polypeptides in CHO and 293 cells either as fusion polypeptides to the Fc region of human IgG1 or as unfused polypeptides. The expression of full-length and truncated human and mouse OPGs in *E. coli* either as Fc fusion polypeptides or as unfused polypeptides is described in Example 8. Purification of recombinantly produced mammalian and bacterial OPG is described in Example 10.

The biological activity of OPG was determined using an in vitro osteoclast maturation assay, an in vivo model of interleukin-1 (IL-1) induced hypercalcemia, and injection studies of bone density in normal mice (see Example 11). The following OPG recombinant proteins produced in CHO or 293 cells demonstrated activity in the in *E. coli* osteoclast maturation assay: muOPG [22-185]-Fc, muOPG [22-194]-Fc, muOPG [22-401]Fc, muOPG [22-401], huOPG [22-201]-Fc, huOPG [22-401]-Fc. muOPG [22-180]-Fc produced in CHO cells and huOPG met[32-401] produced in *E. coli* did not demonstrate activity in the in vitro assay.

OPG from several sources was produced as a dimer and to some extent as a higher multimer. Rat OPG [22-401] produced in transgenic mice, muOPG [22-401] and huOPG [22-401] produced as a recombinant polypeptide in CHO cells, and OPG expressed as a naturally occurring product from a cytotoxic T cell line were predominantly dimers and trimers when analyzed on nonreducing SDS gels (see Example 9). Truncated OPG polypeptides having deletions in the region of amino acids 186-401 (e.g., OPG [1-185] and OPG [1-194]) were predominantly monomeric suggesting that the region 186-401 may be involved in self-association of OPG polypeptides. However, huOPG met[32-401] produced in *E. coli* was largely monomeric.

OPG may be important in regulating bone resorption. The protein appears to act as a soluble receptor of the TNF family and may prevent a receptor-ligand interaction involved in the osteolytic pathway. One aspect of the regulation appears to be a reduction in the number of osteoclasts.

Nucleic Acids

The invention provides for an isolated nucleic acid encoding a polypeptide having at least one of the biological activities of OPG. As described herein, the biological activities of OPG include, but are not limited to, any activity involving bone metabolism and in particular, include increasing bone density. The nucleic acids of the invention are selected from the following:

a) the nucleic acid sequences as shown in FIGS. 2B-2C (SEQ ID NO:120), 9A-9B (SEQ ID NO:122), and 9C-9D (SEQ ID NO:124) or complementary strands thereof;

b) the nucleic acids which hybridize under stringent conditions with the polypeptide-encoding region in FIGS. 2B-2C (SEQ ID NO:120), 9A-9B (SEQ ID NO:122), and 9C-9D (SEQ ID NO:124); and c) nucleic acids which hybridize under stringent conditions with nucleotides 148 through 337 inclusive as shown in FIG. 1A.

d) the nucleic acid sequences which are degenerate to the sequences in (a) and (b).

The invention provides for nucleic acids which encode rat, mouse and human OPG as well as nucleic acid sequences hybridizing thereto which encode a polypeptide having at least one of the biological activities of OPG. Also provided for are nucleic acids which hybridize to a rat OPG EST encompassing nucleotides 148-337 as shown in FIG. 1A. The conditions for hybridization are generally of high stringency such as 5×SSC, 50% formamide and 42° C. described in Example 1 of the specification. Equivalent stringency to these conditions may be readily obtained by adjusting salt and organic solvent concentrations and temperature. The nucleic acids in (b) encompass sequences encoding OPG-related polypeptides which do not undergo detectable hybridization with other known members of the TNF receptor superfamily. In a preferred embodiment, the nucleic acids are as shown in FIGS. 2B-2C (SEQ ID NO:120), 9A-9B (SEQ ID NO:122), and 9C-9D (SEQ ID NO:124).

The length of hybridizing nucleic acids of the invention may be variable since hybridization may occur in part or all of the polypeptide-encoding regions as shown in FIGS. 2B-2C (SEQ ID NO:120), 9A-9B (SEQ ID NO:122), and 9C-9D (SEQ ID NO:124), and may also occur in adjacent noncoding regions. Therefore, hybridizing nucleic acids may be truncations or extensions of the sequences shown in FIGS. 2B-2C (SEQ ID NO:120), 9A-9B (SEQ ID NO:122), and 9C-9D (SEQ ID NO:124). Truncated or extended nucleic acids are encompassed by the invention provided they retain one or more of the biological properties of OPG. The hybridizing nucleic acids may also include adjacent noncoding regions which are 5' and/or 3' to the OPG coding region. The noncoding regions include regulatory regions involved in OPG expression, such as promoters, enhance, translational initiation sites, transcription termination sites and the like.

Hybridization conditions for nucleic acids are described in Sambrook et al. *Molecular Cloning: A Laboratory Manual,* 2nd ed. Cold Spring Harbor Laboratory Press, Cold Spring Harbor, N.Y. (1989)

DNA encoding rat OPG was provided in plasmid pMO-B1.1 deposited with the American Type Culture Collection, Rockville, Md. on Dec. 27, 1995 under ATCC accession no. 69970. DNA encoding mouse OPG was provided in plasmid pRcCMV-murine OPG deposited with the American Type Culture Collection, Rockville, Md. on Dec. 27, 1995 under accession no. 69971. DNA encoding human OPG was provided in plasmid pRcCMV-human OPG deposited with the American Type Culture Collection, Rockville, Md. on Dec. 27, 1995 under accession no. 69969. The nucleic acids of the invention will hybridize under stringent conditions to the DNA inserts of ATCC accession nos. 69969, 69970, and 69971 and have at least one of the biological activities of OPG.

Also provided by the invention are derivatives of the nucleic acid sequences as shown in FIGS. 2B, 9A and 9B. As used herein, derivatives include nucleic acid sequences having addition, substitution, insertion or deletion of one or more residues such that the resulting sequences encode polypeptides having one or more amino acid residues which have been added, deleted, inserted or substituted and the resulting polypeptide has the activity of OPG. The nucleic acid derivatives may be naturally occurring, such as by splice variation or polymorphism, or may be constructed using site-directed mutagenesis techniques available to the skilled worker. One example of a naturally occurring variant of OPG is a nucleic acid encoding a lys to asn change at residue 3 within the leader sequence (see Example 5). It is anticipated that nucleic acid derivatives will encode amino acid changes in regions of the molecule which are least likely to disrupt biological activity. Other derivatives include a nucleic acid encoding a membrane-bound form of OPG having an extracellular domain as shown in FIGS. 2B-2C (SEQ ID NO:120), 9A-9B (SEQ ID NO:122), and 9C-9D (SEQ ID NO:124) along with transmembrane and cytoplasmic domains.

In one embodiment, derivatives of OPG include nucleic acids encoding truncated forms of OPG having one or more amino acids deleted from the carboxy terminus. Nucleic acids encoding OPG may have from 1 to 216 amino acids deleted from the carboxy terminus. Optionally, an antibody Fc region may extend from the new carboxy terminus to yield a biologically active OPG-Fc fusion polypeptide. (see Example 11). In preferred embodiments, nucleic acids encode OPG having the amino acid sequence from residues 22-185, 22-189, 22-194 or 22-201 (using numbering in FIGS. 9E-F) and optionally, encoding an Fc region of human IgG.

Also included are nucleic acids encoding truncated forms of OPG having one or more amino acids deleted from the amino terminus. Truncated forms include those lacking part or all the 21 amino acids comprising the leader sequence. Additionally, the invention provides for nucleic acids encoding OPG having from 1 to 10 amino acids deleted from the mature amino terminus (at residue 22) and optionally, having from 1 to 216 amino acids deleted from the carboxy terminus (at residue 401). Optionally, the nucleic acids may encode a methionine residue at the amino terminus. Examples of such OPG truncated polypeptides are described in Example 8.

Examples of the nucleic acids of the invention include cDNA, genomic DNA, synthetic DNA and RNA. cDNA is obtained from libraries prepared from mRNA isolated from various tissues expressing OPG. In humans, tissue sources for OPG include kidney, liver, placenta and heart. Genomic DNA encoding OPG is obtained from genomic libraries which are commercially available from a variety of species. Synthetic DNA is obtained by chemical synthesis of overlapping oligonucleotide fragments followed by assembly of the fragments to reconstitute part or all of the coding region and flanking sequences (see U.S. Pat. No. 4,695,623 describing the chemical synthesis of interferon genes). RNA is obtained most easily by procaryotic expression vectors which direct high-level synthesis of mRNA, such as vectors using T7 promoters and RNA polymerase.

Nucleic acid sequences of the invention are used for the detection of OPG sequences in biological samples in order to determine which cells and tissues are expressing OPG mRNA. The sequences may also be used to screen cDNA and genomic libraries for sequences related to OPG. Such screening is well within the capabilities of one skilled in the art using appropriate hybridization conditions to detect homologus sequences. The nucleic acids are also useful for modulating the expression of OPG levels by anti-sense therapy or gene therapy. The nucleic acids are also used for the development of transgenic animals which may be used for the production of the polypeptide and for the study of biological activity (see Example 3).

Vectors and Host Cells

Expression vectors containing nucleic acid sequences encoding OPG, host cells transformed with said vectors and methods for the production of OPG are also provided by the invention. An overview of expression of recombinant proteins is found in *Methods of Enzymology v.* 185, Goeddel, D. V. ed. Academic Press (1990).

Host cells for the production of OPG include procaryotic host cells, such as *E. coli*, yeast, plant, insect and mammalian host cells. *E. coli* strains such as HB101 or JM101 are suitable for expression. Preferred mammalian host cells include COS, CHOd-, 293, CV-1, 3T3, baby hamster kidney (BHK) cells and others. Mammalian host cells are preferred when post-translational modifications, such as glycosylation and polypeptide processing, are important for OPG activity. Mammalian expression allows for the production of secreted polypeptides which may be recovered from the growth medium.

Vectors for the expression of OPG contain at a minimum sequences required for vector propagation and for expression of the cloned insert. These sequences include a replication origin, selection marker, promoter, ribosome binding site, enhancer sequences, RNA splice sites and transcription termination site. Vectors suitable for expression in the aforementioned host cells are readily available and the nucleic acids of the invention are inserted into the vectors using standard recombinant DNA techniques. Vectors for tissue-specific expression of OPG are also included. Such vectors include promoters which function specifically in liver, kidney or other organs for production in mice, and viral vectors for the expression of OPG in targeted human cells.

Using an appropriate host-vector system, OPG is produced recombinantly by culturing a host cell transformed with an expression vector containing nucleic acid sequences encoding OPG under conditions such that OPG is produced, and isolating the product of expression. OPG is produced in the supernatant of transfected mammalian cells or in inclusion bodies of transformed bacterial host cells. OPG so produced may be purified by procedures known to one skilled in the art as described below. The expression of OPG in mammalian and bacterial host systems is described in Examples 7 and 8. Expression vectors for mammalian hosts are exemplified by plasmids such as pDSRα described in PCT Application No. 90/14363. Expression vectors for bacterial host cells are exemplified by plasmids pAMG21 and pAMG22-His described in Example 8. Plasmid pAMG21 was deposited with the American Type Culture Collection, Rockville, Md. on Jul. 24, 1996 under accession no. 98113. Plasmid pAMG22-His was deposited with the American Type Culture Collection, Rockville, Md. on Jul. 24, 1996 under accession no. 98112. It is anticipated that the specific plasmids and host cells described are for illustrative purposes and that other available plasmids and host cells could also be used to express the polypeptides.

The invention also provides for expression of OPG from endogenous nucleic acids by in vivo or ex vivo recombination events to allow modulation of OPG from the host chromosome. Expression of OPG by the introduction of exogenous regulatory sequences (e.g. promoters or enhancers) capable of directing the production of OPG from endogenous OPG coding regions is also encompassed. Stimulation of endogenous regulatory sequences capable of directing OPG production (e.g. by exposure to transcriptional enhancing factors) is also provided by the invention.

Polypeptides

The invention provides for OPG, a novel member of the TNF receptor superfamily, having an activity associated with bone metabolism and in particular having the activity of inhibiting bone resorption thereby increasing bone density. OPG refers to a polypeptide having an amino acid sequence of mouse, rat or human OPG or a derivative thereof having at least one of the biological activities of OPG. The amino acid sequences of rat, mouse and human OPG are shown in FIGS. 2B-2C (SEQ ID NO:121), 9A-9B (SEQ ID NO:123), and 9C-9D (SEQ ID NO:125) respectively. A derivative of OPG refers to a polypeptide having an addition, deletion, insertion or substitution of one or more amino acids such that the resulting polypeptide has at least one of the biological activities of OPG. The biological activities of OPG include, but are not limited to, activities involving bone metabolism. Preferably, the polypeptides will have the amino terminal leader sequence of 21 amino acids removed.

OPG polypeptides encompassed by the invention include rat [1-401], rat [22-180], rat [22-401], rat [22-401]-Fc fusion, rat [1-180]-Fc fusion, mouse [1-401], mouse [1-180], mouse [22-401], human [1-401], mouse [22-180], human [22-401], human [22-180], human [1-180], human [22-180]-Fc fusion and human met-32-401. Amino acid numbering is as shown in SEQ ID NO:121 (rat), SEQ ID NO:123 (mouse) and SEQ ID NO:125 (human). Also encompassed are polypeptide derivatives having deletions or carboxy-terminal truncations of part or all of amino acids residues 180-401 of OPG; one or more amino acid changes in residues 180-401; deletion of part or all of a cysteine-rich domain of OPG, in particular deletion of the distal (carboxy-terminal) cysteine-rich domain; and one or more amino acid changes in a cysteine-rich domain, in particular in the distal (carboxy-terminal) cysteine-rich domain. In one embodiment, OPG has from 1 to about 216 amino acids deleted from the carboxy terminus. In another embodiment, OPG has from 1 to about 10 amino acids deleted from the mature amino terminus (wherein the mature amino terminus is at residue 22) and, optionally, has from 1 to about 216 amino acids deleted from the carboxy terminus.

Additional OPG polypeptides encompassed by the invention include the following: human [22-180]-Fc fusion, human [22-201]-Fc fusion, human [22-401]-Fc fusion, mouse [22-185]-Fc fusion, mouse [22-194]-Fc fusion. These polypeptides are produced in mammalian host cells, such as CHO or 293 cells, Additional OPG polypeptides encompassed by the invention which are expressed in procaryotic host cells include the following: human met[22-401], Fc-human met [22-401] fusion (Fc region is fused at the amino terminus of the full-length OPG coding sequence as described in Example 8), human met[22-401]-Fc fusion (Fc region fused to the full-length OPG sequence), Fc-mouse met[22-401] fusion, mouse met[22-401]-Fc fusion, human met[27-401], human met[22-185], human met[22-189], human met[22-194], human met[22-194] (P25A), human met [22-194] (P26A), human met[27-185], human met[27-189], human met[27-194], human met-arg-gly-ser-$(his)_6$ [22-401], human met-lys [22-401], human met-$(lys)_3$-[22-401], human met [22-401]-Fc (P25A), human met[22-401](P25A), human met [22-401](P26A), human met[22-401] (P26D), mouse met [22-401], mouse met[27-401], mouse met[32-401], mouse met[27-180], mouse met[22-189], mouse met[22-194], mouse met[27-189], mouse met[27-194], mouse met-lys[22-401], mouse HEK[22-401](A45T), mouse met-lys-$(his)_7$[22-401], mouse met-lys[22-401]-$(his)_7$ and mouse met[27-401] (P33E, G36S, A45P). It is understood that the above OPG polypeptides produced in procaryotic host cells have an amino-terminal methionine residue, if such a residue is not indicated. In specific examples, OPG-Fc fusion were produced using a 227 amino acid region of human IgG1-γ1 was used having the sequence as shown in Ellison et al. (Nuc. Acids Res. 10, 4071-4079 (1982)). However, variants of the Fc region of human IgG may also be used.

Analysis of the biological activity of carboxy-terminal OPG truncations fused to the human IgG1 Fc region indicates a portion of OPG of about 164 amino acids which is required for activity. This region encompasses amino acids 22-185, preferably those in FIGS. 9C-9D (SEQ ID NO:125), and comprises four cysteine-rich domains characteristic of the cysteine-rich domains of TNFR extracellular domains.

Figure 11:
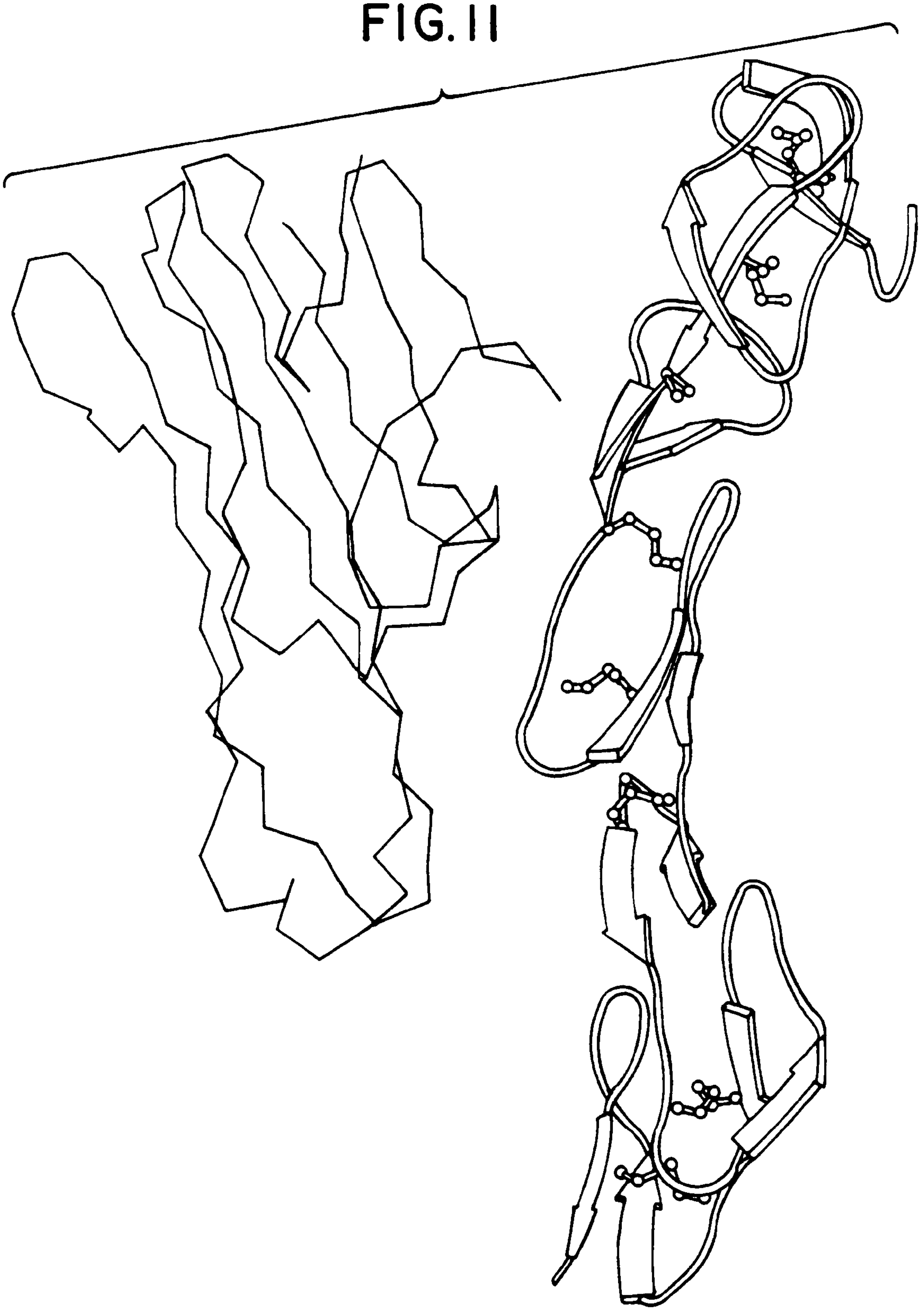
FIG. 11. Three-dimensional representation of human OPG. Side-view of the Molescript display of the predicted 3-dimensional structure of human OPG residues 25 through 163, (wide line), co-crystallized with human TNFβ (thin line). As a reference for orientation, the bold arrows along the OPG polypeptide backbone are pointing in the N-terminal to C-terminal direction. The location of individual cysteine residue side chains are inserted along the polypeptide backbone to help demonstrate the separate cysteine-rich domains. The TNFβ molecule is aligned as described by Banner et al. (1993).
Figure 12A:
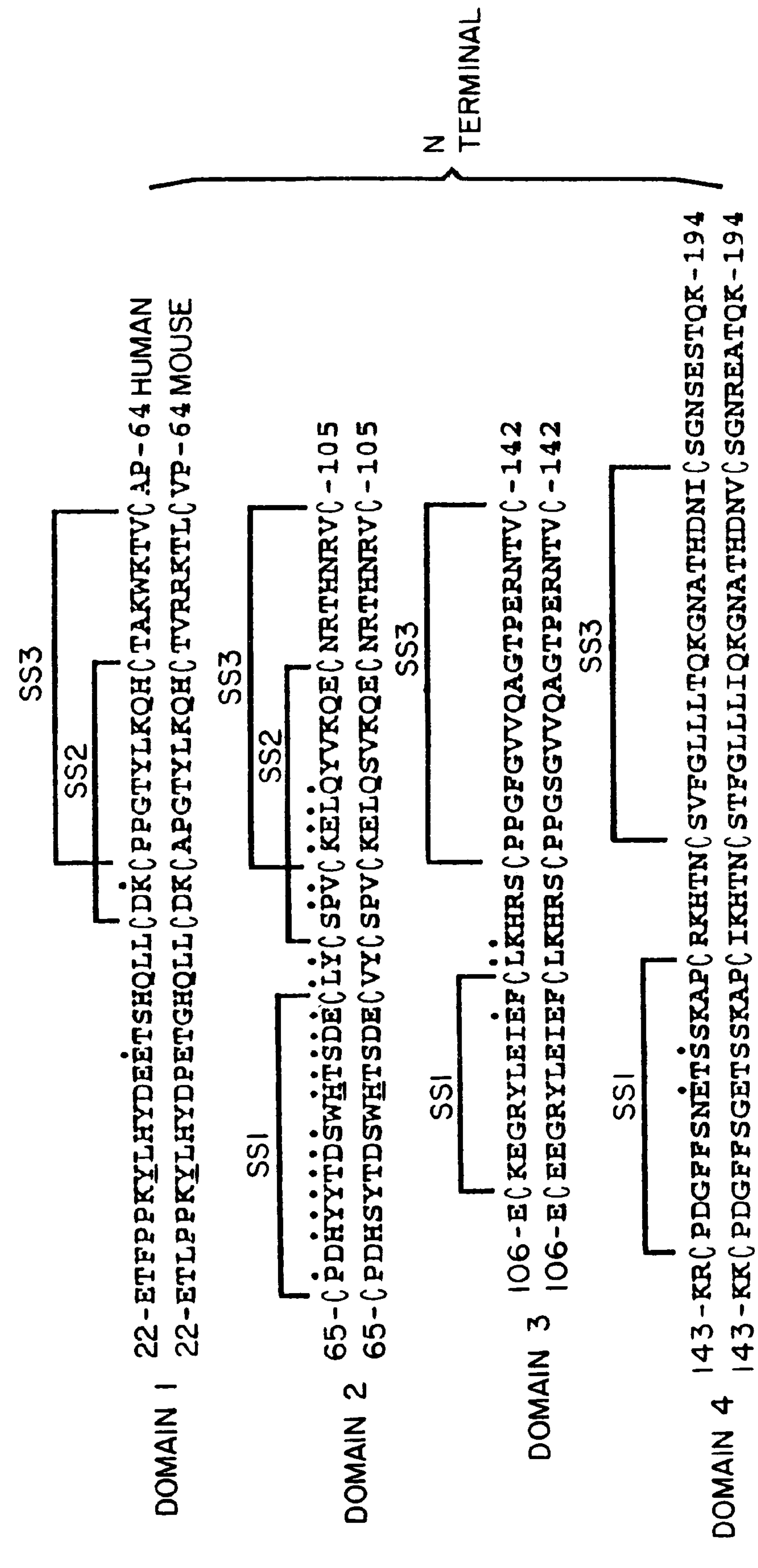
FIG. 12. Structure of OPG cysteine-rich domains. Alignment of the human (top line SEQ ID NO:136) and mouse (bottom line SEQ ID NO: 179) OPG amino acid sequences highlighting the predicted domain structure of OPG. The polypeptide is divided into two halves; the N-terminus (A), and C-terminus (B). The N-terminal half is predicted to contain four cysteine rich domains (labeled 1-4). The predicted intrachain disulfide bonds are indicated by bold lines, labeled “SS1”, “SS2”, or “SS3”. Tyrosine 28 and histidine 75 (underlined) are predicted to form an ionic interaction. Those amino acids predicted to interact with an OPG ligand are indicated by bold dots above the appropriate residue. The cysteine residues located in the C-terminal half of OPG are indicated by rectangular boxes.

Using the homology between OPG and the extracellular ligand binding domains of TNF receptor family members, a three-dimensional model of OPG was generated based upon the known crystal structure of the extracellular domain of TNFR-I (see Example 6). This model was used to identify those residues within OPG which may be important for biological activity. Cysteine residues that are involved in maintaining the structure of the four cysteine-rich domains were identified. The following disulfide bonds were identified in the model: Domain 1: cys41 to cys54, cys44 to cys62, tyr23 and his 66 may act to stabilize the structure of this domain; Domain 2: cys65 to cys80, cys83 to cys98, cys87 to cys105; Domain 3: cys107 to cys118, cys124 to cys142; Domain 4: cys145 to cys160, cys166 to cys185. Residues were also identified which were in close proximity to TNFβ as shown in FIGS. 11 and 12A-12B. In this model, it is assumed that OPG binds to a corresponding ligand; TNFβ was used as a model ligand to simulate the interaction of OPG with its ligand. Based upon this modeling, the following residues in OPG may be important for ligand binding: glu34, lys43, pro66 to gln91 (in particular, pro66, his 68, tyr69, tyr70, thr71, asp72, ser73, his76, ser77, asp78, glu79, leu81, tyr82, pro85, val86, lys88, glu90 and gln91), glu153 and ser155.

Alterations in these amino acid residues, either singly or in combination, may alter the biological activity of OPG. For example, changes in specific cysteine residues may alter the structure of individual cysteine-rich domains, whereas changes in residues important for ligand binding may affect physical interactions of OPG with ligand. Structural models can aid in identifying analogs which have more desirable properties, such as enhanced biological activity, greater stability, or greater ease of formulation.

The invention also provides for an OPG multimer comprising OPG monomers. OPG appears to be active as a multimer (e.g, dimer, trimer of a higher number of monomers). Preferably, OPG multimers are dimers or trimers. OPG multimers may comprise monomers having the amino acid sequence of OPG sufficient to promote multimer formation or may comprise monomers having heterologous sequences such as an antibody Fc region. Analysis of carboxy-terminal deletions of OPG suggest that at least a portion of the region 186-401 is involved in association of OPG polypeptides. Substitution of part or all of the region of OPG amino acids 186-401 with an amino acid sequence capable of self-association is also encompassed by the invention. Alternatively, OPG polypeptides or derivatives thereof may be modified to form dimers or multimers by site directed mutagenesis to create unpaired cysteine residues for interchain disulfide bond romation, by photochemical crosslinking, such as exposure to ultraviolet light, or by chemical crosslinking with bifunctional linker molecules such as bifunctional polyethylene glycol and the like.

Modifications of OPG polypeptides are encompassed by the invention and include post-translational modifications (e.g., N-linked or O-linked carbohydrate chains, processing of N-terminal or C-terminal ends), attachment of chemical moieties to the amino acid backbone, chemical modifications of N-linked or O-linked carbohydrate chains, and addition of an N-terminal methionine residue as a result of procaryotic host cell expression. The polypeptides may also be modified with a detectable label, such as an enzymatic, fluorescent, isotopic or affinity label to allow for detection and isolation of the protein.

Further modifications of OPG include chimeric proteins wherein OPG is fused to a heterologous amino acid sequence. The heterologous sequence may be any sequence which allows the resulting fusion protein to retain the activity of OPG. The heterologous sequences include for example, immunoglobulin fusions, such as Fc fusions, which may aid in purification of the protein. A heterologous sequence which promotes association of OPG monomers to form dimers, trimers and other higher multimeric forms is preferred.

The polypeptides of the invention are isolated and purified from other polypeptides present in tissues, cell lines and transformed host cells expressing OPG, or purified from components in cell cultures containing the secreted protein. In one embodiment, the polypeptide is free from association with other human proteins, such as the expression product of a bacterial host cell.

Also provided by the invention are chemically modified derivatives of OPG which may provide additional advantages such as increasing stability and circulating time of the polypeptide, or decreasing immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g. EP 0 401 384 herein incorporated by reference (coupling PEG to G-CSF), see also Malik et al., Exp. Hematol. 20: 1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydrl groups may also be used as a reactive group for attaching the polyethylene glycol molecule(s). Preferred for therapeutic purposes is attachment at an amino group, such as attachment at the N-terminus or lysine group.

One may specifically desire N-terminally chemically modified protein. Using polyethylene glycol as an illustration of the present compositions, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemically modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

Synthetic OPG dimers may be prepared by various chemical crosslinking procedures. OPG monomers may be chemically linked in any fashion that retains or enhances the biological activity of OPG. A variety of chemical crosslinkers may be used depending upon which properties of the protein dimer are desired. For example, crosslinkers may be short and relatively rigid or longer and more flexible, may be biologically reversible, and may provide reduced immunogenicity or longer pharmacokinetic half-life.

In one example, OPG molecules are linked through the amino terminus by a two step synthesis (see Example 12). In the first step, OPG is chemically modified at the amino terminus to introduce a protected thiol, which after purification is deprotected and used as a point of attachment for site-specific conjugation through a variety of crosslinkers with a second OPG molecule. Amino-terminal crosslinks include, but are not limited to, a disulfide bond, thioether linkages using short-chain, bis-functional aliphatic crosslinkers, and thioether linkages to variable length, bifunctional polyethylene glycol crosslinkers (PEG "dumbbells"). Also encompassed by PEG dumbbell synthesis of OPG dimers is a byproduct of such synthesis, termed a "monobell". An OPG monobell consists of a monomer coupled to a linear bifunctional PEG with a free polymer terminus. Alternatively, OPG may be crosslinked directly through a variety of amine specific homobifunctional crosslinking techniques which include reagents such as: diethylenetriaminepentaacetic dianhydride (DTPA), p-benzoquinone (pBQ) or bis(sulfosuccinimidyl) suberate ($BS^3$) as well as others known in the art. It is also possible to thiolate OPG directly with reagents such as iminothiolane in the presence of a variety of bifunctional, thiol specific crosslinkers, such as PEG bismaleimide, and achieve dimerization and/or dumbbells in a one step process.

A method for the purification of OPG from natural sources and from transfected host cells is also included. The purification process may employ one or more standard protein purification steps in an appropriate order to obtain purified protein. The chromatography steps can include ion exchange, gel filtration, hydrophobic interaction, reverse phase, chromatofocusing, affinity chromatography employing an anti-OPG antibody or biotin-streptavidin affinity complex and the like.

Antibodies

Also encompassed by the invention are antibodies specifically binding to OPG. Antigens for the generation of antibodies may be full-length polypeptides or peptides spanning a portion of the OPG sequence. Immunological procedures for the generation of polyclonal or monoclonal antibodies reactive with OPG are known to one skilled in the art (see, for example, Harlow and Lane, *Antibodies: A Laboratory Manual* Cold Spring Harbor Laboratory Press, Cold Spring Harbor N.Y. (1988)). Antibodies so produced are characterized for binding specificity and epitope recognition using standard enzyme-linked immunosorbent assays. Antibodies also include chimeric antibodies having variable and constant domain regions derived from different species. In one embodiment, the chimeric antibodies are humanized antibodies having murine variable domains and human constant domains. Also encompassed are complementary determining regions grafted to a human framework (so-called CDR-grafted antibodies). Chimeric and CDR-grafted antibodies are made by recombinant methods known to one skilled in the art. Also encompassed are human antibodies made in mice.

Anti-OPG antibodies of the invention may be used as an affinity reagent to purify OPG from biological samples (see Example 10). In one method, the antibody is immobilized on CnBr-activated Sepharose and a column of antibody-Sepharose conjugate is used to remove OPG from liquid samples. Antibodies are also used as diagnostic reagents to detect and quantitate OPG in biological samples by methods described below.

Pharmaceutical Compositions

The invention also provides for pharmaceutical compositions comprising a therapeutically effective amount of the polypeptide of the invention together with a pharmaceutically acceptable diluent, carrier, solubilizer, emulsifier, preservative and/or adjuvant. The term "therapeutically effective amount" means an amount which provides a therapeutic effect for a specified condition and route of administration. The composition may be in a liquid or lyophilized form and comprises a diluent (Tris, acetate or phosphate buffers) having various pH values and ionic strengths, solubilizer such as Tween or Polysorbate, carriers such as human serum albumin or gelatin, preservatives such as thimerosal or benzyl alcohol, and antioxidants such as ascrobic acid or sodium metabisulfite. Also encompassed are compositions comprising OPG modified with water soluble polymers to increase solubility or stability. Compositions may also comprise incorporation of OPG into liposomes, microemulsions, micelles or vesicles for controlled delivery over an extended period of time.

Specifically, OPG compositions may comprise incorporation into polymer matricies such as hydrogels, silicones, polyethylenes, ethylene-vinyl acetate copolymers, or biodegradable polymers. Examples of hydrogels include polyhydroxyalkylmethacrylates (p-HEMA), polyacrylamide, polymethacrylamide, polyvinylpyrrolidone, polyvinyl alcohol and various polyelectrolyte complexes. Examples of biodegradable polymers include polylactic acid (PLA), polyglycolic acid (PGA), copolymers of PLA and PGA, polyamides and copolymers of polyamides and polyesters. Other controlled release formulations include microcapsules, microspheres, macromolecular complexes and polymeric beads which may be administered by injection.

Selection of a particular composition will depend upon a number of factors, including the condition being treated, the route of administration and the pharmacokinetic parameters desired. A more extensive survey of component suitable for pharmaceutical compositions is found in *Remington's Pharmaceutical Sciences,* 18th ed. A. R. Gennaro, ed. Mack, Easton, Pa. (1980).

Compositions of the invention may be administered by injection, either subcutaneous, intravenous or intramuscular, or by oral, nasal, pulmonary or rectal administration. The route of administration eventually chosen will depend upon a number of factors and may be ascertained by one skilled in the art.

The invention also provides for pharmaceutical compositions comprising a therapeutically effective amount of the nucleic acids of the invention together with a pharmaceutically acceptable adjuvant. Nucleic acid compositions will be suitable for the delivery of part or all of the OPG coding region to cells and tissues as part of an anti-sense or gene therapy regimen.

Methods of Treatment

Bone tissue provides support for the body and consists of mineral (largely calcium and phosphorous), a matrix of collagenous and noncollagenous proteins, and cells. Three types of cells found in bone, osteocytes, osteoblasts and osteoclasts, are involved in the dynamic process by which bone is continually formed and resorbed. Osteoblasts promote formation of bone tissue whereas osteoclasts are associated with resorption. Resorption, or the dissolution of bone matrix and mineral, is a fast and efficient process compared to bone formation and can release large amounts of mineral from bone. Osteoclasts are involved in the regulation of the normal remodeling of skeletal tissue and in resorption induced by hormones. For instance, resorption is stimulated by the secretion of parathyroid hormone in response to decreasing concentrations of calcium ion in extracellular fluids. In contrast, inhibition of resorption is the principal function of calcitonin. In addition, metabolites of vitamin D alter the responsiveness of bone to parathyroid hormone and calcitonin.

After skeletal maturity, the amount of bone in the skeleton reflects the balance (or imbalance) of bone formation and bone resorption. Peak bone mass occurs after skeletal maturity prior to the fourth decade. Between the fourth and fifth decades, the equilibrium shifts and bone resorption dominates. The inevitable decrease in bone mass with advancing years starts earlier in females than males and is distinctly accelerated after menopause in some females (principally those of Caucasian and Asian descent).

Osteopenia is a condition relating generally to any decrease in bone mass to below normal levels. Such a condition may arise from a decrease in the rate of bone synthesis or an increase in the rate of bone destruction or both. The most common form of osteopenia is primary osteoporosis, also referred to as postmenopausal and senile osteoporosis. This form of osteoporosis is a consequence of the universal loss of bone with age and is usually a result of increase in bone resorption with a normal rate of bone formation. About 25 to 30 percent of all white females in the United States develop symptomatic osteoporosis. A direct relationship exists between osteoporosis and the incidence of hip, femoral, neck and inter-trochanteric fracture in women 45 years and older. Elderly males develop symptomatic osteoporosis between the ages of 50 and 70, but the disease primarily affects females.

The cause of postmenopausal and senile osteoporosis is unknown. Several factors have been identified which may contribute to the condition. They include alteration in hormone levels accompanying aging and inadequate calcium consumption attributed to decreased intestinal absorption of calcium and other minerals. Treatments have usually included hormone therapy or dietary supplements in an attempt to retard the process. To date, however, an effective treatment for bone loss does not exist.

The invention provides for a method of treating a bone disorder using a therapeutically effective amount of OPG. The bone disorder may be any disorder characterized by a net bone loss (osteopenia or osteolysis). In general, treatment with OPG is anticipated when it is necessary to suppress the rate of bone resorption. Thus treatment may be done to reduce the rate of bone resorption where the resorption rate is above normal or to reduce bone resorption to below normal levels in order to compensate for below normal levels of bone formation.

Conditions which are treatable with OPG include the following:

Osteoporosis, such as primary osteoporosis, endocrine osteoporosis (hyperthyroidism, hyperparathryoidism, Cushing's syndrome, and acromegaly), hereditary and congenital forms of osteoporosis (osteogenesis imperfecta, homocystinuria, Menkes' syndrome, and Riley-Day syndrome) and osteoporosis due to immobilization of extremities.

Paget's disease of bone (osteitis deformans) in adults and juveniles

Osteomyelitis, or an infectious lesion in bone, leading to bone loss.

Hypercalcemia resulting from solid tumors (breast, lung and kidney) and hematologic malignacies (multiple myeloma, lymphoma and leukemia), idiopathic hypercalcemia, and hypercalcemia associated with hyperthryoidism and renal function disorders.

Osteopenia following surgery, induced by steroid administration, and associated with disorders of the small and large intestine and with chronic hepatic and renal diseases.

Osteonecrosis, or bone cell death, associated with traumatic injury or nontraumatic necrosis associated with Gaucher's disease, sickle cell anemia, systemic lupus erythematosus and other conditions.

Bone loss due to rheumatoid arthritis.

Periodontal bone loss.

Osteolytic metastasis

It is understood that OPG may be used alone or in conjunction with other factors for the treatment of bone disorders. In one embodiment, osteoprotegerein is used in conjunction with a therapeutically effective amount of a factor which stimulates bone formation. Such factors include but are not limited to the bone morphogenic factors designated BMP-1 through BMP-12, transforming growth factor-β (TGF-β) and TGF-β family members, interleukin-1 inhibitors, TNFα inhibitors, parathyroid hormone and analogs thereof, parathyroid related protein and analogs thereof, E series prostaglandins, bisphosphonates (such as alendronate and others), and bone-enhancing minerals such as fluoride and calcium.

The following examples are offered to more fully illustrate the invention, but are not construed as limiting the scope thereof.

Example 1

Identification and Isolation of the Rat OPG cDNA

Materials and Methods for cDNA cloning and analysis are described in Maniatis et al, ibid. Polymerase chain reactions (PCR) were performed using a Perkin-Elmer 9600 thermocycler using PCR reaction mixture (Boehringer-Mannheim) and primer concentrations specified by the manufacturer. In general, 25-50 μl reactions were denatured at 94° C., followed by 20-40 cycles of 94° C. for 5 seconds, 50-60° C. for 5 seconds, and 72° C. for 3-5 minutes. Reactions were the treated for 72° C. for 3-5 minutes. Reactions were then analyzed by gel electrophoresis as described in Maniatis et al., ibid.

A cDNA library was constructed using mRNA isolated from embryonic d20 intestine for EST analysis (Adams et al. Science 252, 1651-1656 (1991)). Rat embryos were dissected, and the entire developing small and large intestine removed and washed in PBS. Total cell RNA was purified by acid guanidinium thiocyanate-phenol-chloroform extraction (Chomczynski and Sacchi Anal. Biochem. 162, 156-159, (1987)). The poly (A+) mRNA fraction was obtained from the total RNA preparation by adsorption to, and elution from, Dynabeads Oligo (dT)25 (Dynal Corp) using the manufacturer's recommended procedures. A random primed cDNA library was prepared using the Superscript Plasmid System (Gibco BRL, Gaithersburg, Md.). The random cDNA primer containing an internal Not I restriction site was used to initiate first strand synthesis and had the following sequence:

5'-AAAGGAAGGAAAAAA
<u>GCGGCCGC</u>TACANNNNNNNNT-3' (SEQ ID NO:1)

Not I

For the first strand synthesis three separate reactions were assembled that contained 2.5 μg of poly(A) RNA and 120 ng, 360 ng or 1,080 ng of random primer. After second strand synthesis, the reaction products were separately extracted with a mixture of phenol:choroform:isoamyl alcohol (25:24:1 ratio), and then ethanol precipitated. The double strand (ds) cDNA products of the three reactions were combined and ligated to the following ds oligonucleotide adapter:

5'-TCGACCCACGCGTCCG-3' (SEQ ID NO:2)

3'-GGGTGCGCAGGCp-5' (SEQ ID NO:3)

After ligation the cDNA was digested to completion with Not I, extracted with phenol:chloroform:isoamyl (25:24:1) alcohol and ethanol precipitated. The resuspended cDNA was then size fractionated by gel filtration using premade columns provided with the Superscript Plasmid System (Gibco BRL, Gaithersburg, Md.) as recommended by the manufacturer. The two fractions containing the largest cDNA products were pooled, ethanol precipitated and then directionally ligated into Not I and Sal I digested pMOB vector DNA (Strathmann et al, 1991). The ligated cDNA was introduced into competent ElectroMAX DH10B *E. coli* (Gibco BRL, Gaithersburg, Md.) by electroporation. For automated sequence analysis approximately 10,000 transformants were plated on 20 cm×20 cm agar plates containing ampicillin supplemented LB nutrient media. The colonies that arose were picked and arrayed onto 96 well microtiter plates containing 200 ml of L-broth, 7.5% glycerol, and 50 μg/ml ampicillin. The cultures were grown overnight at 37° C., a duplicate set of microtiter plates were made using a sterile 96 pin replicating tool, then both sets were stored at −80° C. for further analysis. For full-length cDNA cloning approximately one million transformants were plated on 96 bacterial ampicillin plates containing about 10,000 clones each. The plasmid DNA from each pool was separately isolated using the Qiagen Plasmid Maxi Kit (Qiagen Corp., Germany) and arrayed into 96 microtiter plates for PCR analyses.

To sequence random fetal rat intestine cDNA clones, glycerol stocks were thawed, and small aliquots diluted 1:25 in distilled. Approximately 3.0 ul of diluted bacterial cultures were added to PCR reaction mixture (Boehringer-Mannheim) containing the following oligonucleotides:

5'-TGTAAAACGACGGCCAGT-3' (SEQ ID NO:4)

5'-CAGGAAACAGCTATGACC-3' (SEQ ID NO:5)

The reactions were incubated in a thermocycler (Perkin-Elmer 9600) with the following cycle conditions: 94 C for 2 minutes; 30 cycles of 94° C. for 5 seconds, 50° C. for 5 seconds, and 72° C. for 3 minutes. 72° C. for 4 minutes. After incubation in the thermocycler, the reactions were diluted with 2.0 mL of water. The amplified DNA fragments were further purified using Centricon columns (Princeton Separations) using the manufacturer's recommended procedures. The PCR reaction products were sequenced on an Applied Biosystems 373A automated DNA sequencer using T3 primer (oligonucleotide 353-23; 5'-CAATTAACCCTCACTAAAGG-3') (SEQ ID NO:6) Taq dye-terminator reactions (Applied Biosystems) following the manufacturer's recommended procedures.

The resulting 5' nucleotide sequence obtained from randomly picked cDNA clones translated and then compared to the existing database of known protein sequences using a modified version of the FASTA program (Pearson et al. Meth. Enzymol. 183, (1990)). Translated sequences were also analysed for the presence of a specific cysteine-rich protein motif found in all known members of the tumor necrosis factor receptor (TNFR) superfamily (Smith et al. Cell 76, 959-962 (1994)), using the sequence profile method of Gribskov et al. (Proc. Natl. Acad. Sci. USA 83, 4355-4359 (1987)), as modified by Luethy et al. (Protein Science 3, 139-146 (1994)).

Using the FASTA and Profile search data, an EST, FRI-1 (Fetal Rat Intestine-1), was identified as a possible new member of the TNFR superfamily. FRI-1 contained an approximately 600 bp insert with a LORF of about 150 amino acids. The closest match in the database was the human type II TNFR (TNFR-2). The region compared showed an ~43% homology between TNFR-2 and FRI-1 over this 150 aa LORF. Profile analysis using the first and second cysteine-rich repeats of the TNFR superfamily yielded a Z score of ~8, indicating that the FRI-1 gene possibly encodes a new family member.

To deduce the structure of the FRI-1 product, the fetal rat intestine cDNA library was screened for full length clones. The following oligonucleotides were derived from the original FRI-1 sequence:

5'-GCATTATGACCCAGAAACCGGAC-3' (SEQ ID NO:7)

5'-AGGTAGCGCCCTTCCTCACATTC-3' (SEQ ID NO:8)

These primers were used in PCR reactions to screen 96 pools of plasmid DNA, each pool containing plasmid DNA from 10,000 independent cDNA clones. Approximately 1 ug of plasmid pool DNA was amplified in a PCR reaction mixture (Boehringer-Mannheim) using a Perkin-Elmer 96 well thermal cycler with the following cycle conditions: 2 min at 94° C., 1 cycle; 15 sec at 94° C., then 45 sec at 65° C., 30 cycles; 7 min at 65° C., 1 cycle. PCR reaction products were analysed by gel electrophoresis. 13 out of 96 plasmid DNA pools gave rise to amplified DNA products with the expected relative molecular mass.

DNA from one positive pool was used to transform competent ElectroMAX DH10B *E. coli* (Gibco BRL, Gaithersburg, Md.) as described above. Approximately 40,000 transformants were plated onto sterile nitrocellulose filters (BA-85, Schleicher and Schuell), and then screened by colony hybridization using a $^{32}$P-dCTP labelled version of the PCR product obtained above. Filters were prehybridized in 5×SSC, 50% deionized formamide, 5×Denhardt's solution, 0.5% SDS, and 100 ug/ml denatured salmon sperm DNA for 2-4 hours at 42° C. Filters were then hybridized in 5×SSC, 50% deionized formamide, 2×Denhardt's solution, 0.1% SDS, 100 μg/ml denatured salmon sperm DNA, and ~5 ng/ml of labelled probe for ~18 hours at 42° C. The filters were then washed in 2×SSC for 10 min at RT, 1×SSC for 10 min at 55° C., and finally in 0.5×SSC for 10-15 min at 55° C. Hybridizing clones were detected following autoradiography, and then replated onto nitrocellulose filters for secondary screening. Upon secondary screening, a plasmid clone (pB1.1) was isolated, then amplified in L-broth media containing 100 ug/ml ampicillin and the plasmid DNA obtained. Both strands of the 2.4 kb pB1.1 insert were sequenced.

The pB1.1 insert sequence was used for a FASTA search of the public database to detect any existing sequence matches and/or similarities. No matches to any known genes or EST's were found, although there was an approximate 45% similarity to the human and mouse TNFR-2 genes. A methionine start codon is found at bp 124 of the nucleotide sequence, followed by a LORF encoding 401 aa residues that terminates at bp 1327. The 401 aa residue product is predicted to have a hydrophobic signal peptide of approximately 31 residues at its N-terminus, and 4 potential sites of N-linked glycosylation. No hydrophobic transmembrane spanning sequence was identified using the PepPlot program (Wisconsin GCG package, version 8.1). The deduced 401 aa sequence was then used to search the protein database. Again, there were no existing matches, although there appeared to be a strong similarity to many members of the TNFR superfamily, most notably the human and mouse TNFR-2. A sequence alignment of this novel protein with known members of the TNFR-superfamily was prepared using the Pileup program, and then modified by PrettyPlot (Wisconsin GCG package, version 8.1). This alignment shows a clear homology between the full length FRI-1 gene product and all other TNFR family members. The homologus region maps to the extracellular domain of TNFR family members, and corresponds to the three or four cysteine-rich repeats found in the ligand binding domain of these proteins. This suggested that the FRI-1 gene encoded a novel TNFR family member. Since no transmembrane spanning region was detected we predicted that this may be a secreted receptor, similar to TNFR-1 derived soluble receptors (Kohno et al. Proc. Natl. Acad. Sci. USA 87, 8331-8335 (1990)). Due to the apparent biological activity of the FRI-1 gene (vide infra), the product was named Osteoprotegerin (OPG).

Example 2

OPG mRNA Expression Patterns in Tissues

Multiple human tissue northern blots (Clonetech) were probed with a $^{32}P$-dCTP labelled FRI-1 PCR product to detect the size of the human transcript and to determine patterns of expression. Northern blots were prehybridized in 5×SSPE, 50% formamide, 5×Denhardt's solution, 0.5% SDS, and 100 μg/ml denatured salmon sperm DNA for 2-4 hr at 42° C. The blots were then hybridized in 5×SSPE, 50% formamide, 2×Denhardt's solution, 0.1% SDS, 100 μg/ml denatured salmon sperm DNA, and 5 ng/ml labelled probe for 18-24 hr at 42° C. The blots were then washed in 2×SSC for 10 min at RT, 1×SSC for 10 min at 50° C., then in 0.5×SSC for 10-15 min.

Using a probe derived from the rat gene, a predominant mRNA species with a relative molecular mass of about 2.4 kb is detected in several tissues, including kidney, liver, placenta, and heart. Highest levels are detected in the kidney. A large mRNA species of Mr 4.5 and 7.5 kb was detected in skeletal muscle and pancreas. In human fetal tissue, kidney was found to express relatively high levels of the 2.4 kb mRNA. Using a human probe (vide infra), only the 2.4 kb transcript is detected in these same tissues. In addition, relatively high levels of the 2.4 kb transcript was detected in the lymph node, thymus, spleen and appendix. The size of the transcript detected by both the rat and human Osteosprotegerin gene is almost identical to the length of the rat pB1.1 FRI-1 insert, suggesting it was a full length cDNA clone.

Example 3

Systemic Delivery of OPG in Transgenic Mice

The rat OPG clone pB1.1 was used as template to PCR amplify the coding region for subcloning into an ApoE-liver specific expression vector (Simonet et al. J. Clin. Invest. 94, 1310-1319 (1994), and PCT Application No. US94/11675 and co-owned U.S. Ser. No. 08/221,767. The following 5' and 3' oligonucleotide primers were used for PCR amplification, respectively:

5'-GACTAGTCCCACAATGAACAAGTGGCTGTGi-3' (SEQ ID NO:9)

5'-ATAAGAATGCGGCCGCTAAACTATGAAA-CAGCCCAGTGACCATTC-3' (SEQ ID NO:10)

The PCR reaction mixture (Boehringer-Mannheim) was treated as follows: 94° C. for 1 minute, 1 cycle; 94° C. for 20 sec, 62° C. for 30 sec, and 74 C for 1 minute, 25 cycles. Following amplification, the samples were purified over Qiagen PCR columns and digested overnight with SpeI and NotI restriction enzymes. The digested products were extracted and precipitated and subcloned into the ApoE promoter expression vector. Prior to microinjecting the resulting clone, HE-OPG, it was sequenced to ensure it was mutation-free.

The HE-OPG plasmid was purified through two rounds of CsCl density gradient centrifugation. The purified plasmid DNA was digested with XhoI and Ase I, and the 3.6 kb transgene insert was purified by gel electrophoresis. The purified fragment was diluted to a stock injection solution of 1 μg/ml in 5 mM Tris, pH 7.4, 0.2 mM EDTA. Single-cell embryos from BDF1×BDF1-bred mice were injected essentially as described (Brinster et al., Proc. Natl. Acad. Sci. USA 82, 4338 (1985)), except that injection needles were beveled and siliconized before use. Embryos were cultured overnight in a $CO_2$ incubator and 15 to 20 2-cell embryos were transferred to the oviducts of pseudopregnant CD1 female mice.

Following term pregnancy, 49 offspring were obtained from implantation of microinjected embryos. The offspring were screened by PCR amplification of the integrated transgene in genomic DNA samples. The target region for amplification was a 369 bp region of the human Apo E intron which was included in the expression vector. The oligos used for PCR amplification were:

5'-GCC TCT AGA AAG AGC TGG GAC-3' (SEQ ID NO:11)

5'-CGC CGT GTT CCA TTT ATG AGC-3' (SEQ ID NO:12)

The conditions for PCR were: 94° C. for 2 minute, 1 cycle; 94° C. for 1 min, 63° C. for 20 sec, and 72° C. for 30 sec, 30 cycles. Of the 49 original offspring, 9 were identified as PCR positive transgenic founders.

At 8-10 weeks of age, five transgenic founders (2, 11, 16, 17, and 28) and five controls (1, 12, 15, 18, and 30) were sacrificed for necropsy and pathological analysis. Liver was isolated from the remaining 4 founders by partial hepatectomy. For partial hepatectomy, the mice were anesthetized and a lobe of liver was surgically removed. Total cellular RNA was isolated from livers of all transgenic founders, and 5 negative control littermates as described (McDonald et al. Meth. Enzymol. 152, 219 (1987)). Northern blot analysis was performed on these samples to assess the level of transgene expression.

Approximately 10 ug of total RNA from each animal liver was resolved by electrophoresis denaturing gels (Ogden et al. Meth. Enzymol 152, 61 (1987)), then transferred to HYBOND-N nylon membrane (Amersham), and probed with $^{32}P$ dCTP-labelled pB1.1 insert DNA. Hybridization was performed overnight at 42° C. in 50% Formamide, 5×SSPE, 0.5% SDS, 5×Denhardt's solution, 100 μg/ml denatured salmon sperm DNA and $2-4\times10^6$ cpm of labeled probe/ml of hybridization buffer. Following hybridization, blots were washed twice in 2×SSC, 0.1% SDS at room temperature for 5 min each, and then twice in 0.1×SSC, 0.1% SDS at 55° C. for 5-10 min each. Expression of the transgene in founder and control littermates was determined following autoradiography.

The northern blot data indicate that 7 of the transgenic founders express detectable levels of the transgene mRNA (animal #'s 2, 11, 16, 17, 22, 33, and 45). The negative control mice and one of the founders (#28) expressed no transgene-related mRNA. Since OPG is predicted to be a secreted protein, overexpression of transgene mRNA should be a proxy for the level of systemically delivered gene product. Of the PCR and northern blot positive mice, animal 2, 17 and 22 expressed the highest levels of transgene mRNA, and may show more extensive biological effects on host cells and tissues.

Example 4

Biological Activity of OPG

Five of the transgenic mice (animals 2, 11, 16, 17 and 28) and 5 control littermates (animals 1, 12, 15, 18, and 30) were sacrificed for necropsy and pathological analysis using the following procedures: Prior to euthanasia, all animals had their identification numbers verified, then were weighed, anesthetized and blood drawn. The blood was saved as both serum and whole blood for a complete serum chemistry and hematology panel. Radiography was performed just after terminal anesthesia by lethal CO2 inhalation, and prior to the gross dissection. Following this, tissues were removed and fixed in 10% buffered Zn-Formalin for histological examination. The tissues collected included the liver, spleen, pancreas, stomach, duodenum, ileum, colon, kidney, reproductive organs, skin and mammary glands, bone, brain, heart, lung, thymus, trachea, eosphagus, thyroid, jejunem, cecum, rectum, adrenals, urinary bladder, and skeletal muscle. Prior to fixation the whole organ weights were determined for the liver, stomach, kidney, adrenals, spleen, and thymus. After fixation the tissues were processed into paraffin blocks, and 3 um sections were obtained. Bone tissue was decalcified using a formic acid solution, and all sections were stained with hematoxylin and eosin. In addition, staining with Gomori's reticulin and Masson's trichrome were performed on certain tissues. Enzyme histochemistry was performed to determine the expression of tartrate resistant acid phosphatase (TRAP), an enyzme highly expressed by osteoclasts, multinucleated bone-resorbing cells of monocyte-macrophage lineage. Immunohistochemistry for BrdU and F480 monocyte-macrophage surface antigen was also performed to detect replicating cells and cells of the monocyte-macrophage lineage, respectively. To detect F480 surface antigen expression, formalin fixed, paraffin embedded 4 μm sections were deparaffinized and hydrated to deionized water. The sections were quenched with 3% hydrogen peroxide, blocked with Protein Block (Lipshaw, Pittsburgh, Pa.), and incubated in rat monoclonal anti-mouse F480 (Harlan, Indianapolis, Ind.). This antibody was detected by biotinylated rabbit anti-rat immunoglobulins, peroxidase conjugated strepavidin (BioGenex San Ramon, Calif.) with DAB as chromagen (BioTek, Santa Barbara, Calif.). Sections were counterstained with hematoxylin.

Upon gross dissection and observation of visceral tissues, no abnormalities were found in the transgene expressors or control littermates. Analysis of organ weight indicate that spleen size increased by approximately 38% in the transgenic mice relative to controls. There was a slight enlargement of platelet size and increased circulating unstained cells in the transgene expressors. There was a marginal decrease in platelet levels in the transgene expressors. In addition, the serum uric acid, urea nitrogen, and alkaline phosphatase levels all trended lower in the transgene expressors. The expressors were found to have increased radiodensity of the skeleton, including long bones (femurs), vertebrae, and flat bones (pelvis). The relative size of femurs in the expressors were not different from the control mice.

Histological analysis of stained sections of bone from the OPG expressors show severe osteopetrosis with the presence of cartilage remnants from the primary spongiosa seen within bone trabeculae in the diaphysis of the femur. A clearly defined cortex was not identifiable in the sections of femur. In normal animals, the central diaphysis is filled with bone marrow. Sections of vertebra also show osteopetrotic changes implying that the OPG-induced skeletal changes were systemic. The residual bone marrow showed predominantly myeloid elements. Megakaryocytes were present. Reticulin stains showed no evidence for reticulin deposition. Immunohistochemistry for F480, a cell surface antigen expressed by cells of monocyte-macrophage derivation in the mouse, showed the presence of F480 positive cells in the marrow spaces. Focally, flattened F480 positive cells could be seen directly adjacent to trabecular bone surfaces.

The mesenchymal cells lining the bony trabeculae were flattened and appeared inactive. Based on H&E and TRAP stains, osteoclasts were rarely found on the trabecular bone surfaces in the OPG expressors. In contrast, osteoclasts and/or chondroclasts were seen in the region of the growth plate resorbing cartilage, but their numbers may be reduced compared to controls. Also, osteoclasts were present on the cortical surface of the metaphysis where modelling activity is usually robust. The predominant difference between the expressors and controls was the profound decrease in trabecular osteoclasts, both in the vertebrae and femurs. The extent of bone accumulation was directly correlated with the level of OPG transgene mRNA detected by northern blotting of total liver RNA.

The spleens from the OPG expressors had an increased amount of red pulp with the expansion due to increased hematopoiesis. All hematopoietic lineages are represented. F480 positive cells were present in both control and OPG expressors in the red pulp. Two of the expressors (2 and 17) had foci of extramedullary hematopoiesis within the liver and this is likely due to the osteopetrotic marrow.

There were no observable abnormalities in the thymus, lymph nodes, gastrointestinal tract, pancreato-hepatobiliary tract, respiratory tract, reproductive system, genito-urinary system, skin, nervous system, heart and aorta, breast, skeletal muscle and fat.

Example 5

Isolation of Mouse and Human OPG cDNA A cDNA clone corresponding to the 5' end of the mouse OPG mRNA was isolated from a mouse kidney cDNA library (Clontech) by PCR amplification. The oligonucleotides were derived from the rat OPG cDNA sequence and are shown below:

5'-ATCAAAGGCAGGGCATACTTCCTG-3' (SEQ ID NO:13)

5'-GTTGCACTCCTGTTTCACGGTCTG-3' (SEQ ID NO:14)

5'-CAAGACACCTTGAAGGGCCTGATG-3' (SEQ ID NO:15)

5'-TAACTTTTACAGAAGAGCATCAGC-3' (SEQ ID NO:16)

5'-AGCGCGGCCGCATGAACAAGTGGCTGTGCTGCG-3' (SEQ ID NO:17)

5'-AGCTCTAGAGAAACAGCCCAGTGACCATTCC-3' (SEQ ID NO:18)

The partial and full-length cDNA products obtained in this process were sequenced. The full-length product was digested with Not I and Xba I, then directionally cloned into the plasmid vector pRcCMV (Invitrogen). The resulting plasmid was named pRcCMV-Mu-OPG. The nucleotide sequence of the cloned product was compared to the rat OPG cDNA sequence. Over the 1300 bp region spanning the OPG LORF, the rat and mouse DNA sequences are approximately 88% identical. The mouse cDNA sequence contained a 401 aa LORF, which was compared to the rat OPG protein sequence and found to be ~94% identical without gaps. This indicates that the mouse cDNA sequence isolated encodes the murine OPG protein, and that the sequence and structure has been highly conserved throughout evolution. The mouse OPG protein sequence contains an identical putative signal peptide at its N-terminus, and all 4 potential sites of N-linked glycosylation are conserved.

A partial human OPG cDNA was cloned from a human kidney cDNA library using the following rat-specific oligonucleotides:

5'-GTG AAG CTG TGC AAG AAC CTG ATG-3' (SEQ ID NO:19)

5'-ATC AAA GGC AGG GCA TAC TTC CTG-3' (SEQ ID NO:20)

This PCR product was sequenced and used to design primers for amplifying the 3' end of the human cDNA using a human OPG genomic clone in lambda as template:

5'-TCCGTAAGAAACAGCCCAGTGACC-3' (SEQ ID NO:29)

5'-CAGATCCTGAAGCTGCTCAGTTTG-3' (SEQ ID NO:21)

The amplified PCR product was sequenced, and together with the 5' end sequence, was used to design 5' and 3' human-specific primers useful for amplifying the entire human OPG cDNA coding sequences:

5'-AGCGCGGCCGCGGGGACCACAATGAA-CAAGTTG-3' (SEQ ID NO:22)

5'-AGCTCTAGAATTGTGAGGAAACAGCTCAATGGC-3' (SEQ ID NO:23)

The full-length human PCR product was sequenced, then directionally cloned into the plasmid vector pRcCMV (Invitrogen) using Not I and Xba I. The resulting plasmid was named pRcCMV-human OPG. The nucleotide sequence of the cloned product was compared to the rat and mouse OPG cDNA sequences. Over the 1300 bp region spanning the OPG LORF, the rat and mouse DNA sequences are approximately 78-88% identical to the human OPG cDNA. The human OPG cDNA sequence also contained a 401 aa LORF, and it was compared to the rat and mouse protein sequences. The predicted human OPG protein is approximately 85% identical, and ~90% identical to the rat and mouse proteins, respectively. Sequence alignment of rat, mouse and human proteins show that they have been highly conserved during evolution. The human protein is predicted to have a N-terminal signal peptide, and 5 potential sites of N-linked glycosylation, 4 of which are conserved between the rat and mouse OPG proteins.

The DNA and predicted amino acid sequence of mouse OPG is shown in FIGS. 9A and 9B (SEQ ID NO:122). The DNA and predicted amino acid sequence of human OPG is shown in FIG. 9C an 9D (SEQ ID NO:124). A comparison of the rat, mouse and human OPG amino acid sequences is shown in FIGS. 9E and 9F.

Isolation of additional human OPG cDNA clones revealed the presence of a G to C base change at position 103 of the DNA sequence shown in FIG. 9C. This nucleotide change results in substitution of an asparagine for a lysine at position 3 of the amino acid sequence shown in FIG. 9C. The remainder of the sequence in clones having this change was identical to that in FIGS. 9C and 9D.

Example 6

OPG Three-Dimensional Structure Modelling

Figure 1C:
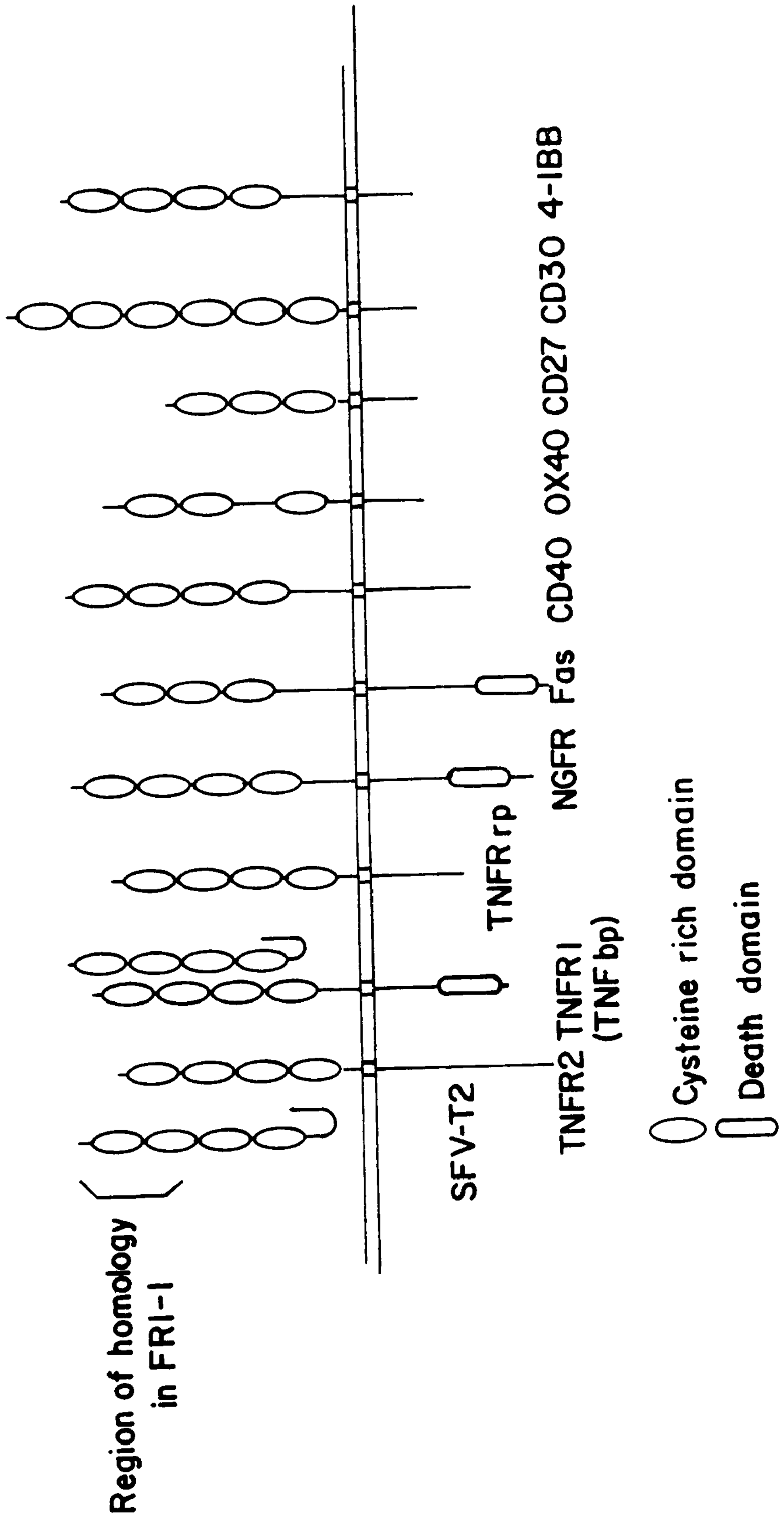
FIG. 1. A. FASTA analysis of novel EST LORF. Shown is the deduced FRI-1 amino acid sequence aligned to the human TNFR-2 sequence (SEQ ID NO: 169 and 170). B. Profile analysis of the novel EST LORF shown is the deduced FRI-1 amino acid sequence aligned to the TNFR-profile (SEQ ID NO: 171 and 173). C. Structural view of TNFR superfamily indicating region which is homologous to the novel FRI-1.

The amino-terminal portion of OPG has homology to the extracellular portion of all known members of the TNFR superfamily (FIG. 1C). The most notable motif in this region of TNFR-related genes is an ~40 amino acid, cysteine-rich repeat sequence which folds into distinct structures (Banner et al. Cell 73, 431-445 (1993)). This motif is usually displayed in four (range 3-6) tandem repeats (see FIG. 1C), and is known to be involved in ligand binding (Beutler and van Huffel Science 264, 667-663 (1994)). Each repeat usually contains six interspaced cysteine residues, which are involved in forming three intradomain disulfide bonds, termed SS1, SS2, and SS3 (Banner et al., ibid). In some receptors, such as TNFR2, CD30 and CD40, some of the repeat domains contain only two intrachain disulfide bonds (SS1 and SS3).

The human OPG protein sequence was aligned to a TNFR1 extracellular domain profile using methods described by Luethy, et al., ibid, and the results were graphically displayed using the PrettyPlot program from the Wisconsin Package, version 8.1 (Genetics Computer Group, Madison, Wis.) (FIG. 10). The alignment indicates a clear conservation of cysteine residues involved in formation of domains 1-4. This alignment was then used to construct a three-dimensional (3-D) model of the human OPG N-terminal domain using the known 3-D structure of the extracellular domain of p55 TNFR1 (Banner et al., ibid) as the template. To do this the atomic coordinates of the peptide backbone and side chains of identical residues were copied from the crystal structure coordinates of TNFR1. Following this, the remaining coordinates for the insertions and different side chains were generated using the LOOK program (Molecular Applications Group, Palo Alto, Calif.). The 3-D model was then refined by minimizing its conformational energy using LOOK.

By analogy with other TNFR family members, it is assumed that OPG binds to a ligand. For the purpose of modelling the interaction of OPG with its ligand, the crystal structure of TNF-β was used to simulate a 3-D representation of an "OPG ligand". This data was graphically displayed (see FIG. 11) using Molscript (Kraulis, J. Appl. Cryst. 24, 946-950, 1991). A model for the OPG/ligand complex with 3 TNFβ and 3 OPG molecules was constructed where the relative positions of OPG are identical to TNFR1 in the crystal structure. This model was then used to find the residues of OPG that could interact with its ligand using the following approach: The solvent accessible area of all residues in the complex and one single OPG model were calculated. The residues that have different accessibility in the complex than in the monomer are likely to interact with the ligand.

The human and mouse OPG amino acid sequences were realigned using this information to highlight sequences comprising each of the cysteine rich domains 1-4 (FIGS. 12A and 12B). Each domain has individual structural characteristics which can be predicted:

Domain 1

Contains 4 cysteines involved in SS2 (C41 to C54) and SS3 (C44 to C62) disulfide bonds. Although no SS1 bond is evident based on disulfide bridges, the conserved tyrosine at position 28 is homologous to Y20 in TNFR1, which is known to be involved in interacting with H66 to aid in domain formation. OPG has a homologous histidine at position 75, suggesting OPG Y28 and H75 stack together in the native protein, as do the homologous residues in TNFR1. Therefore, both of these residues may indeed be important for biological activity, and N-terminal OPG truncations up to and beyond Y28 may have altered activity. In addition, residues E34 and K43 are predicted to interact with a bound ligand based on our 3-dimensional model.

Domain 2

Contains six cysteines and is predicted to contain SS1 (C65 to C80), SS2 (C83 to C98) and SS3 (C87 to C105) disulfide bonds. This region of OPG also contains an region stretching from P66-Q91 which aligns to the portion of TNFR1 domain 2 which forms close contacts with TNFβ (see above), and may interact with an OPG ligand. In particular residues P66, H68, Y69, Y70, T71, D72, S73, H75, T76, S77, D78, E79, L81, Y82, P85, V86, K88, E89, L90, and Q91 are predicted to interact with a bound ligand based on our structural data.

Domain 3

Contains 4 cysteines involved in SS1 (C107 to C 118) and SS3 (C124 to C142) disulfide bonds, but not an SS2 bond. Based on our structural data, residues E115, L118 and K119 are predicted in to interact with an OPG ligand.

Domain 4

Contains 4 cysteines involved in SS1 (C145 to C160) and SS3 (C166 to C185) disulfide bonds, but not an SS2 bond, similar to domain 3. Our structural data predict that E153 and S155 interact with an OPG ligand.

Thus, the predicted structural model for OPG identifies a number of highly conserved residues which are likely to be important for its biological activity.

Example 7

Production of Recombinant Secreted OPG Protein in Mammalian Cells

To determine if OPG is actually a secreted protein, mouse OPG cDNA was fused to the human IgG1 Fc domain as a tag (Capon et al. Nature 337, 525-531 (1989)), and expressed in human 293 fibroblasts. Fc fusions were carried out using the vector pFc-A3. pFc-A3 contains the region encoding the Fc portion of human immunoglobulin IgG-γ1 heavy chain (Ellison et al. ibid) from the first amino acid of the hinge domain (Glu-99) to the carboxyl terminus and is flanked by a 5'-NotI fusion site and 3'-SalI and XbaI sites. The plasmid was constructed by PCR amplification of the human spleen cDNA library (Clontech). PCR reactions were in a final volume of 100 μl and employed 2 units of Vent DNA polymerase (New England Biolabs) in 20 mM Tris-HCl (pH 8.8), 10 mM KCl, 10 μM $(NH_4)2SO_4$, 2 mM $MgSO_4$, 0.1% Triton X-100 with 400 μM each dNTP and 1 ng of the cDNA library to be amplified together with 1 μM of each primer. Reactions were initiated by denaturation at 95° C. for 2 min, followed by 30 cycles of 95° C. for 30 s, 55° C. for 30 s, and 73° C. for 2 min. The 5' primer

5' ATAGCGGCCGCTGAGCCCAAATCTTGTGACAAAACTCAC 3' (SEQ ID NO:24)

incorporated a NotI site immediately 5' to the first residue (Glu-99) of the hinge domain of IgG-γ1. The 3' primer

5'-TCTAGAGTCGACTTATCATTTACCCGGAGACAGGGAGAGGCTCTT-3' (SEQ ID NO:25)

incorporated SalI and XbaI sites. The 717-bp PCR product was digested with NotI and SalI, isolated by electrophoresis through 1% agarose (FMC Corp.), purified by the Geneclean procedure (BIO 101, Inc.) and cloned into NotI, SalI-digested pBluescript II KS vector (Stratagene). The insert in the resulting plasmid, pFc-A3, was sequenced to confirm the fidelity of the PCR reaction.

The cloned mouse cDNA in plasmid pRcCMV-MuOPG was amplified using the following two sets of primer pairs:

Pair 1

5'-CCTCTGAGCTCAAGCTTCCGAGGACCACAATGAACAAG-3' (SEQ ID NO:26)

5'-CCTCTGCGGCCGCTAAGCAGCTTATTTTCACGGATTGAACCTG-3-(SEQ ID NO:27)

Pair 2

5'-CCTCTGAGCTCAAGCTTCCGAGGACCACAATGAACAAG-3' (SEQ ID NO:28)

5'-CCTCTGCGGCCGCTGTTGCATTTCCTTTCTG-3' (SEQ ID NO:30)

The first pair amplifies the entire OPG LORF, and creates a NotI restriction site which is compatible with the in-frame Not I site in Fc fusion vector pFcA3. pFcA3 was prepared by engineering a NotI restriction site 5' to aspartic acid reside 216 of the human IgG1 Fc cDNA. This construct introduces a linker which encodes two irrelevant amino acids which span the junction between the OPG protein and the IgG Fc region. This product, when linked to the Fc portion, would encode all 401 OPG residues directly followed by all 227 amino acid residues of the human IgG1 Fc region (Fl.Fc). The second primer pair amplifies the DNA sequences encoding the first 180 amino acid residues of OPG, which encompasses its putative ligand binding domain. As above, the 3' primer creates an artificial Not I restriction site which fuses the C-terminal truncated OPG LORF at position threonine 180 directly to the IgG1 Fc domain (CT.fc).

The amino acid sequence junction linking OPG residue 401 and aseptic acid residue 221 of the human Fc region can be modified as follows: The DNA encoding residues 216-220 of the human Fc region can be deleted as described below, or the cysteine residue corresponding to C220 of the human Fc region can be mutated to either serine or alanine. OPF-Fc fusion protein encoded by these modified vectors can be transfected into human 293 cells, or CHO cells, and recombinant OPG-Fc fusion protein purified as described below.

Figure 13A:
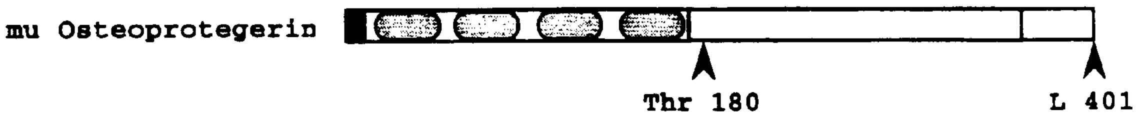
FIG. 13. Expression and secretion of full length and truncated mouse OPG-Fc fusion proteins. A. Map indicating points of fusion to the human IgG1 Fc domain are indicated by arrowheads. B. Silver stain of a SDS-polyacrylamide gel of conditioned media obtained from cells expressing either Fl.Fc (Full length OPG fused to Fc at Leucine 401) or CT.Fc (Carboxy-terminal truncated OPG fused to Fc at threonine 180) fusion protein expression vectors. Lane 1, parent pCEP4 expression vector cell line; Lane 2, Fl.Fc vector cell line; Lane 3, CT.Fc vector cell line. C. Western blot of conditioned media obtained from Fl.Fc and CT.Fc fusion protein expression vectors probed with anti-human IgG1 Fc domain (Pierce). Lane 1, parent pCEP4 expression vector cell line; Lane 2, Fl.Fc vector cell line; Lane 3, CT.Fc vector cell line.
Figure 13B:
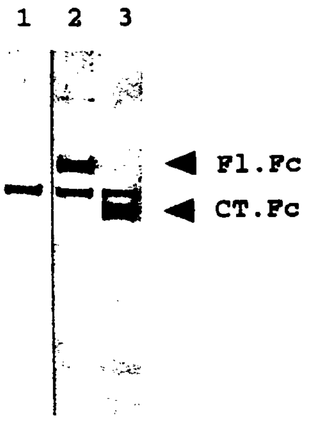
Figure 13C:
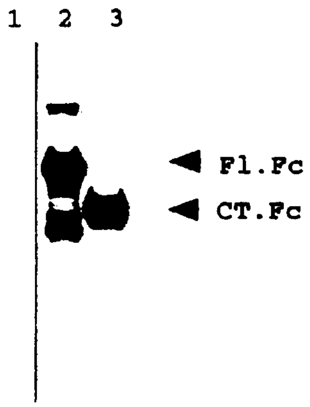

Both products were directionally cloned into the plasmid vector pCEP4 (Invitrogen). pCEP4 contains the Epstein-Barr virus origin of replication, and is capable of episomal replication in 293-EBNA-1 cells. The parent pCEP4, and pCEP4-Fl.Fc and pCEP4-CT.Fc vectors were lipofected into 293-EBNA-1 cells using the manufacturer's recommended methods. The transfected cells were then selected in 100 μg/ml hygromycin to select for vector expression, and the resulting drug-resistant mass cultures were grown to confluence. The cells were then cultured in serum-free media for 72 hr, and the conditioned media removed and analysed by SDS-PAGE. A silver staining of the polyacrylamide gel detects the major conditioned media proteins produced by the drug resistant 293 cultures. In the pCEP4-Fl.Fc and the pCEP4-CT.Fc conditioned media, unique bands of the predicted sizes were abundantly secreted (see FIGS. 13B and 13C). The full-length Fc fusion protein accumulated to a high concentration, indicating that it may be stable. Both Fc fusion proteins were detected by anti-human IgG1 Fc antibodies (Pierce) on western blots, indicating that they are recombinant OPG products.

The full length OPG-Fc fusion protein was purified by Protein-A column chromatography (Pierce) using the manufacturers recommended procedures. The protein was then subjected to N-terminal sequence analysis by automated Edman degradation as essentially described by Matsudaira et al. (J. Biol. Chem. 262, 10-35 (1987)). The following amino acid sequence was read after 19 cycles:

NH2-E T L P P K Y L H Y D P E T G H Q L L-CO2H (SEQ ID NO:31)

This sequence was identical to the predicted mouse OPG amino acid sequence beginning at amino acid residue 22, suggesting that the natural mammalian leader cleavage site is between amino acid residues Q21-E22, not between Y31-D32 as originally predicted. The expression experiments performed in 293-EBNA cells with pCEP4-Fl.Fc and pCEP4-CT.Fc demonstrate that OPG is a secreted protein, and may act systemically to bind its ligand.

Procedures similar to those used to construct and express the muOPG[22-180]-Fc and muOPG[22-401]-Fc fusions were employed for additional mouse and human OPG-Fc fusion proteins.

Murine OPG cDNA encoding amino acids 1-185 fused to the Fc region of human IgG1 [muOPG Ct(185).Fc] was constructed as follows. Murine OPG cDNA from plasmid pRc-CMV Mu Osteoprotegerin (described in Example 5) was amplified using the following primer pair in a polymerase chain reaction as described above:

1333-82:

5'-TCC CTT GCC CTG ACC ACT CTT-3' (SEQ ID NO:32)

1333-80:

5'-CCT CTG CGG CCG CAC ACA CGT TGT CAT GTG TTG C-3' (SEQ ID NO:33)

This primer pair amplifies the murine OPG cDNA region encoding amino acid residues 63-185 (corresponding to bp 278-645) of the OPG reading frame as shown in FIG. 9A. The 3' primer contains a Not I restriction site which is compatible with the in-frame Not I site of the Fc fusion vector pFcA3. The product also spans a unique EcoRI restriction site located at bp 436. The amplified PCR product was purified, cleaved with NotI and EcoRI, and the resulting EcoRI-NotI restriction fragment was purified. The vector pCEP4 having the murine 1-4010PG-Fc fusion insert was cleaved with EcoRI and NotI, purified, and ligated to the PCR product generated above. The resulting pCEP4-based expression vector encodes OPG residues 1-185 directly followed by all 227 amino acid residues of the human IgG1 Fc region. The murine OPG 1-185.Fc fusion vector was transfected into 293 cells, drug selected, and conditioned media was produced as described above. The resulting secreted murine OPG 1-185.Fc fusion product was purified by Protein-A column chromatography (Pierce) using the manufacturers recommended procedures.

Murine OPG DNA encoding amino acid residues 1-194 fused to the Fc region of human IgG1 (muOPG Ct(194).Fc) was constructed as follows. Mouse OPG cDNA from plasmid pRcCMV Mu-Osteoprotegerin was amplified using the following primer pairs:

1333-82:

5'-TCC CTT GCC CTG ACC ACT CTT-3' (SEQ ID NO:34)

1333-81:

5'-CCT CTG CGG CCG CCT TTT GCG TGG CTT CTC TGT T-3' (SEQ ID NO:35)

This primer pair amplifies the murine OPG cDNA region encoding amino acid residues 70-194 (corresponding to bp 298-672) of the OPG reading frame. The 3' primer contains a Not I restriction site which is compatible with the in-frame Not I site of the Fc fusion vector pFcA3. The product also spans a unique EcoRI restriction site located at bp 436. The amplified PCR product was cloned into the murine OPG[1-401] Fc fusion vector as described above. The resulting pCEP4-based expression vector encodes OPG residues 1-194 directly followed by all 227 amino acid residues of the human IgG1 Fc region. The murine OPG 1-194.Fc fusion vector was transfected into 293 cells, drug selected, and conditioned media was produced. The resulting secreted fusion product was purified by Protein-A column chromatography (Pierce) using the manufacturers recommended procedures.

Human OPG DNA encoding amino acids 1-401 fused to the Fc region of human IgG1 was constructed as follows. Human OPG DNA in plasmid pRcCMV-hu osteoprotegerin (described in Example 5) was amplified using the following oligonucleotide primers:

1254-90:

5'CCT CTG AGC TCA AGC TTG GTT TCC GGG GAC CAC AAT G-3' (SEQ ID NO:36)

1254-95:

5'-CCT CTG CGG CCG CTA AGC AGC TTA TTT TTA CTG AAT GG-3' (SEQ ID NO:37)

The resulting PCR product encodes the full-length human OPG protein and creates a Not I restriction site which is compatible with the in-frame Not I site Fc fusion vector FcA3. The PCR product was directionally cloned into the plasmid vector pCEP4 as described above. The resulting expression vector encodes human OPG residues 1-401 directly followed by 227 amino acid residues of the human IgG1 Fc region. Conditioned media from transfected and drug selected cells was produced and the huOPG Fl.Fc fusion product was purified by Protein-A column chromatography (Pierce) using the manufacturers recommended procedures.

Human OPG DNA encoding amino acid residues 1-201 fused to the Fc region of human IgG1 [huOPG Ct(201).Fc] was constructed as follows. The cloned human OPG cDNA from plasmid pRrCMV-hu osteoprotegerin was amplified by PCR using the following oligonucleotide primer pair:

1254-90:

5'-CCT CTG AGC TCA AGC TTG GTT TCC GGG GAC CAC AAT G-3' (SEQ ID NO:38)

1254-92:

5'-CCT CTG CGG CCG CCA GGG TAA CAT CTA TTC CAC-3' (SEQ ID NO:39)

This primer pair amplifies the human OPG cDNA region encoding amino acid residues 1-201 of the OPG reading frame, and creates a Not I restriction site at the 3' end which is compatable with the in-frame Not I site Fc fusion vector FcA3. This product, when linked to the Fc portion, encodes OPG residues 1-201 directly followed by all 221 amino acid residues of the human IgG1 Fc region. The PCR product was directionally cloned into the plasmid vector pCEP4 as described above. Conditioned media from transfected and drug selected cells was produced, and the hu OPG Ct(201).Fc fusion products purified by Protein-A column chromatography (Pierce) using the manufacturer's recommended procedures.

The following procedures were used to construct and express unfused mouse and human OPG.

A plasmid for mammalian expression of full-length murine OPG (residues 1-401) was generated by PCR amplification of the murine OPG cDNA insert from pRcCMV Mu-Osteoprotegerin and subcloned into the expression vector pDSRU (DeClerck et. atl. J. Biol. Chem. 266, 3893 (1991)). The following oligonucleotide primers were used:

1295-26:

5'-CCG AAG CTT CCA CCA TGA ACA AGT GGC TGT GCT GC-3' (SEQ ID NO:40)

1295-27:

5'-CCT CTG TCG ACT ATT ATA AGC AGC TTA TTT TCA CGG ATT G-3' (SEQ ID NO:41)

The murine OPG full length reading frame was amplified by PCR as described above. The PCR product was purified and digested with restriction endonucleases Hind III and Xba I (Boehringer Mannheim, Indianapolis, Ind.) under the manufacturers recommended conditions, then ligated to Hind III and Xba I digested PDSRα. Recombinant clones were detected by restriction endonuclease digestion, then sequenced to ensure no mutations were produced during the PCR amplification steps.

The resulting plasmid, pDSRα-muOPG was introduced into Chinese hamster ovary (CHO) cells by calcium mediated transfection (Wigler et al. Cell 11, 233 (1977)). Individual colonies were selected based upon expression of the dihydrofolate reductase (DHFR) gene in the plasmid vector and several clones were isolated. Expression of the murine OPG recombinant protein was monitored by western blot analysis of CHO cell conditioned media. High expressing cells were selected, and OPG expression was further amplified by treatment with methotrexate as described (DeClerck et al., idid). Conditioned media from CHO cell lines was produced for further purification of recombinant secreted murine OPG protein.

A plasmid for mammalian expression of full-length human OPG (amino acids 1-401) was generated by subcloning the cDNA insert in pRcCMV-hu Osteoprotegerin directly into vector pDSRα (DeClerck et al., ibid). The pRcCMV-OPG plasmid was digested to completion with Not I, blunt ended with Klenow, then digested to completion with Xba I. Vector DNA was digested with Hind III, blunt ended with Klenow, then digested with Xba I, then ligated to the OPG insert. Recombinant plasmids were then sequenced to confirm proper orientation of the human OPG cDNA.

The resulting plasmid pDSRα-huOPG was introduced into Chinese hamster ovary (CHO) cells as described above. Individual colonies were selected based upon expression of the dihydrofolate reductase (DHFR) gene in the plasmid vector and several clones were isolated. Expression of the human OPG recombinant protein was monitored by western blot analysis of CHO cell conditioned media. High expressing clones were selected, and OPG expression was further amplified by treatment with methotrexate. Conditioned media from CHO cell lines expressing human OPG was produced for protein purification.

Expression vectors for murine OPG encoding residues 1-185 were constructed as follows. Murine OPG cDNA from pRcCMV-Mu OPG was amplified using the following oligonucleotide primers:

1333-82:

5'-TCC CTT GCC CTG ACC ACT CTT-3' (SEQ ID NO:42)

1356-12:

5'-CCT CTG TCG ACT TAA CAC ACG TTG TCA TGT GTT GC-3' (SEQ ID NO:43)

This primer pair amplifies the murine OPG cDNA region encoding amino acids 63-185 of the OPG reading frame (bp 278-645) and contains an artificial stop codon directly after the cysteine codon (C185), which is followed by an artificial Sal I restriction endonuclease site. The predicted product contains an internal Eco RI restriction site useful for subcloning into a pre-existing vector. After PCR amplification, the resulting purified product was cleaved with Eco RI and Sal I restriction endonucleases, and the large fragment was gel purified. The purified product was then subcloned into the large restriction fragment of an Eco RI and Sal I digest of pBluescript-muOPG Fl.Fc described above. The resulting plasmid was digested with Hind III and Xho I and the small fragment was gel purified. This fragment, which contains a open reading frame encoding residues 1-185 was then subcloned into a Hind III and Xho I digest of the expression vector pCEP4. The resulting vector, pmuOPG [1-185], encodes a truncated OPG polypeptide which terminates at a cysteine residue located at position 185. Conditioned media from transfected and drug selected cells was produced as described above.

1333-82:

5'-TCC CTT GCC CTG ACC ACT CTT-3' (SEQ ID NO:44)

1356-13:

5'-CCT CTG TCG ACT TAC TTT TGC GTG GCT TCT CTG TT-3' (SEQ ID NO:45)

This primer pair amplifies the murine OPG cDNA region encoding amino acids 70-194 of the OPG reading frame (bp 298-672) and contains an artificial stop codon directly after the lysine codon (K194), which is followed by an artificial Sal I restriction endonuclease site. The predicted product contains an internal Eco RI restriction site useful for subcloning into a pre-existing vector. After PCR amplification, the resulting purified product was cleaved with Eco RI and Sal I restriction endonucleases, and the large fragment was gel purified. The purified product was then subcloned into the large restriction fragment of an Eco RI and Sal I digest of pBluescript-muOPG Fl.Fc described above. The resulting plasmid was digested with Hind III and Xho I and the small fragment was gel purified. This fragment, which contains a open reading frame encoding residues 1-185 was then subcloned into a Hind III and Xho I digest of the expression vector pCEP4. The resulting vector, pmuOPG [1-185], encodes a truncated OPG polypeptide which terminates at a lysine at position 194. Conditioned media from transfected and drug selected cells was produced as described above.

Several mutations were generated at the 5' end of the huOPG [22-401]-Fc gene that introduce either amino acid substitutions, or deletions, of OPG between residues 22 through 32. All mutations were generated with the "QuickChange™ Site-Directed Mutagenesis Kit" (Stratagene, San Diego, Calif.) using the manfacturer's recommended conditions. Briefly, reaction mix containing huOPG [22-401]-Fc plasmid DNA template and mutagenic primers were treated with Pfu polymerase in the presence of deoxynucleotides, then amplified in a thermocycler as described above. An aliqout of the reaction is then transfected into competent *E. coli* XL1-Blue by heatshock, then plated. Plasmid DNA from transformants was then sequenced to verify mutations.

The following primer pairs were used to delete residues 22-26 of the human OPG gene, resulting in the production of a huOPG [27-401]-Fc fusion protein:

1436-11:

5'-TGG ACC ACC CAG AAG TAC CTT CAT TAT GAC-3' (SEQ ID NO:140)

1436-12:

5'-GTC ATA ATG AAG GTA CTT CTG GGT GGT CCA-3' (SEQ ID NO:141)

The following primer pairs were used to delete residues 22-28 of the human OPG gene, resulting in the production of a huOPG [29-401]-Fc fusion protein:

1436-17:

5'-GGA CCA CCC AGC TTC ATT ATG ACG AAG AAA C-3' (SEQ ID NO:142)

1436-18:

5'-GTT TCT TCG TCA TAA TGA AGC TGG GTG GTC C-3' (SEQ ID NO:143)

The following primer pairs were used to delete residues 22-31 of the human OPG gene, resulting in the production of a huOPG [32-401]-Fc fusion protein:

1436-27:

5'-GTG GAC CAC CCA GGA CGA AGA AAC CTC TC-3' (SEQ ID NO:144)

1436-28:

5'-GAG AGG TTT CTT CGT CCT GGG TGG TCC AC-3' (SEQ ID NO:145)

The following primer pairs were used to change the codon for tyrosine residue 28 to phenylalanine of the human OPG gene, resulting in the production of a huOPG [22-401]-Fc Y28F fusion protein:

1436-29:

5'-CGT TTC CTC CAA AGT TCC TTC ATT ATG AC-3' (SEQ ID NO:146)

1436-30:

5'-GTC ATA ATG AAG GAA CTT TGG AGG AAA CG-3' (SEQ ID NO:147)

The following primer pairs were used to change the codon for proline residue 26 to alanine of the human OPG gene, resulting in the production of a huOPG [22-401]-Fc P26A fusion protein:

1429-83:

5'-GGA AAC GTT TCC TGC AAA GTA CCT TCA TTA TG-3 (SEQ ID NO:148)

1429-84:

5'-CAT AAT GAA GGT ACT TTG CAG GAA ACG TTT CC-3' (SEQ ID NO:149)

Each resulting muOPG [22-401]-Fc plasmid containing the appropriate mutation was then transfected into human 293 cells, the mutant OPG-Fc fusion protein purified from conditioned media as described above. The biological activity of each protein was assessed the in vitro osteoclast forming assay described in Example 11.

Example 8

Expression of OPG in *E. coli*

A. Bacterial Expression Vectors pAMG21

The expression plasmid pAMG21 can be derived from the Amgen expression vector pCFM1656 (ATCC #69576) which in turn be derived from the Amgen expression vector system described in U.S. Pat. No. 4,710,473. The pCFM1656 plasmid can be derived from the described pCFM836 plasmid (U.S. Pat. No. 4,710,473) by: (a) destroying the two endogenous NdeI restriction sites by end filling with T4 polymerase enzyme followed by blunt end ligation; (b) replacing the DNA sequence between the unique AatII and ClaI restriction sites containing the synthetic $P_L$ promoter with a similar fragment obtained from pCFM636 (U.S. Pat. No. 4,710,473) containing the $P_L$ promoter AatII

5' CTAATTCCGCTCTCACCTACCAAACAAT-GCCCCCCTGCAAAAAATAAATTCATAT-

3'TGCAGATTAAGGCGAGAGTGGATG-GTTTGTTACGGGGGGACGTTTTTTATTTAAGTATA-

-AAAAAACATACAGATAACCATCTGCGGT-GATAAATTATCTCTGGCGGTGTTGACATAAA-

-TTTTTTGTATGTCTATTGGTAGACGC-CACTATTTAATAGAGACCGCCACAACTGTATTT-

-TACCACTGGCGGTGATACTGAGCACAT 3' (SEQ ID NO:53)

-ATGGTGACCGCCACTATGACTCGTGTAGC5' (SEQ ID NO: 54)

ClaI and then (c) substituting the small DNA sequence between the unique ClaI and KpnI restriction sites with the following oligonucleotide:

5' CGATTTGATTCTAGAAGGAGGAATAA-CATATGGTTAACGCGTTGGAATTCGGTAC3' (SEQ ID NO:48)

3' TAAACTAAGATCTTCCTCCTTATTG-TATACCAATTGCGCAACCTTAAGC 5' (SEQ ID NO:49)

ClaI KpnI

The expression plasmid pAMG21 can then be derived from pCFM1656 by making a series of site directed base changes by PCR overlapping oligo mutagenesis and DNA sequence substitutions. Starting with the BglII site (plasmid bp #180) immediately 5' to the plasmid replication promoter PcopB and proceeding toward the plasmid replication genes, the base pair changes are as follows:

| pAMG21 bp # | bp in pCFM1656 | bp changed to in pAMG21 |
|---|---|---|
| #204 | T/A | C/G |
| #428 | A/T | G/C |
| #509 | G/C | A/T |
| #617 | — | insert two G/C bp |
| #679 | G/C | T/A |
| #980 | T/A | C/G |
| #994 | G/C | A/T |
| #1004 | A/T | C/G |
| #1007 | C/G | T/A |
| #1028 | A/T | T/A |
| #1047 | C/G | T/A |
| #1178 | G/C | T/A |
| #1466 | G/C | T/A |
| #2028 | G/C | bp deletion |
| #2187 | C/G | T/A |
| #2480 | A/T | T/A |
| #2499-2502 | AGTG<br>TCAC | GTCA<br>CAGT |
| #2642 | TCCGAGC<br>AGGCTCG | 7 bp deletion |
| #3435 | G/C | A/T |
| #3446 | G/C | A/T |
| #3643 | A/T | T/A |

The DNA sequence between the unique AatII (position #4364 in pCFM1656) and SacII (position #4585 in pCFM1656) restriction sites is substituted with the following DNA sequence:

```
[AatII sticky end]                5' GCGTAACGTATGCATGGTCTCC-
(position #4358 in pAMG21)     3' TCCACGCATTGCATACGTACCAGAGG-

CCATGCCAGAGTAGGGAACTGCCAGGCATCAAATAAAACGAAAGGCTCAGTCGAAAGACT-
GGTACGCTCTCATCCCTTGACGGTCCGTAGTTTATTTTGCTTTCCGAGTCAGCTTTCTGA-

GGGCCTTTCGTTTTATCTGTTGTTTGTCGGTGAACCCTCTCCTGAGTAGGACAAATCCGC-
CCCGGAAAGCAAAATAGACAACAAACAGCCACTTGCGAGAGGACTCATCCTGTTTAGGCG-

CGGGAGCGGATTTGAACGTTGCGAAGCAACGGCCCGGAGGGTGGCGGGCAGGACGCCCGC-
GCCCTCGCCTAAACTTGCAACGCTTCGTTGCCCGGCCTCCCACCGCCCGTCCTGCGCGCG-
```

-continued

```
CATAAACTGCCAGGCATCAAATTAAGCAGAACCCCATCCTGACGGATGGCCTTTTTGCGT-
GTATTTGACGCTCCCTAGTTTAATTCGTCTTCCGGTAGGACTGCCTACCGGAAAAACGCA-

                                                  AatII
TTCTACAAACTCTTTTGTTTATTTTTCTAAATACATTCAAATATGGACCTCGTACTTAAC-
AAGATGTTTGAGAAAACAAATAAAAAGATTTATGTAAGTTTATACCTGCAGCATGAATTG-

TTTTAAAGTATGGGCAATCAATTGCTCCTCTTAAAATTGCTTTAGAAATACTTTCCCACC-
AAAATTTCATACCCGTTAGTTAACCAGGACAATTTTAACGAAATCTTTATGAAACCGTCG-

GGTTTGTTGTATTGAGTTTCATTTGCGCATTGGTTAAATGGAAAGTCACCGTGCGCTTAC-
CCAAACAACATAACTCAAAGTAAACGCGTAACCAATTTACCTTTCACTGGCACGCGAATG-

TACAGCCTAATATTTTTGAAATATCCCAAGAGCTTTTTCCTTCGCATCCCCACGCTAAAC-
ATGTCGGATTATAAAAACTTTATAGGGTTCTCGAAAAACGAACCGTACGGGTGCGATTTG-

ATTCTTTTTCTCTTTTGGTTAAATCGTTGTTTGATTTATTATTTGCTATATTTATTTTTC-
TAAGAAAAAGAGAAAACCAATTTAGCAACAAACTAAATAATAAACGATATAAATAAAAAG-

GATAATTATCAACTACAGAAGGAACAATTAATGGTATGTTCATACACGCATGTAAAAATA-
CTATTAATAGTTGATCTCTTCCTTGTTAATTACCATACAAGTATGTGCGTACATTTTTAT-

AACTATCTATATAGTTGTCTTTCTCTGAATGTGCAAAACTAAGCATTCCGAAGCCATTAT-
TTGATAGATATATCAACACAAAGACACTTACACGTTTTGATTCGTAAGCCTTCGGTAATA-

TAGCAGTATGAATAGGGAAACTAAACCCACTGATAACACCTGATGATTTCGCTTCTTTAA-
ATCGTCATACTTATCCCTTTGATTTGGGTCACTATTCTGGACTACTAAACCGAAGAAATT-

TTACATTTGGAGATTTTTTATTTACAGCATTGTTTTCAAATATATTCCAATTAATCGCTG-
AATGTAAACCTCTAAAAAATAAATGTCGTAACAAAAGTTTATATAAGCTTAATTAGCCAC-

AATGATTCGAGTTAGAATAATCTACTATAGGATCATATTTTATTAAATTAGCGTCATCAT-
TTACTAACCTCAATCTTATTAGATGATATCCTAGTATAAAATAATTTAATCGCAGTAGTA-

AATATTGCCTCCATTTTTTAGGGTAATTATCCAGAATTGAAATATCAGATTTAACCATAG-
TTATAACGGAGGTAAAAAATCCCATTAATAGGTCTTAACTTTATAGTCTAAATTGGTATC-

AATGAGGATAAATGATCGCGAGTAAATAATATTCACAATGTACCATTTTAGTCATATCAG-
TTACTCCTATTTACTAGCGCTCATTTATTATAAGTGTTACATCGTAAAATCAGTATAGTC-

ATAAGCATTGATTAATATCATTATTCCTTCTACAGGCTTTAATTTTATTAATTATTCTGT-
TATTCGTAACTAATTATAGTAATAACGAACATGTCCCAAATTAAAATAATTAATAAGACA-

AAGTGTCGTCGGCATTTATGTCTTTCATACCCATCTCTTTATCCTTACCTATTGTTTGTC-
TTCACAGCAGCCGTAAATACAGAAAGTATGCGTACAGAAATAGGAATGGATAACAAACAG-

GCAAGTTTTGCGTGTTATATATCATTAAAACGGTAATAGATTGACATTTGATTCTAATAA-
CGTTCAAAACGCACAATATATACTAATTTTGCCATTATCTAACTGTAAACTAAGATTATT-

ATTGGATTTTTGTCACACTATTATATCGCTTGAAATACAATTGTTTAACATAAGTACCTG-
TAACCTAAAAACAGTGTGATAATATAGCGAACTTTATGTTAACAAATTGTATTCATGGAC-

TAGGATCGTACAGGTTTACGCAAGAAAATGGTTTCTTATAGTCGATTAATCGATTTGATT-
ATCCTAGCATGTCCAAATGCGTTCTTTTACCAAACAATATCAGCTAATTAGCTAAACTAA-

CTAGATTTGTTTTAACTAATTAAAGGAGGAATAACATATGGTTAACGCOTTGGAATTCGA-
GATCTAAACAAZATTGATTAATTTCCTCCTTATTGTATACCAATTGCGCAACCTTAAGCT-

                                                      SacII
GCTCACTACTGTCGACCTGCAGGGTACCATGGAAGCTTACTCGAGGATCCGCGGAAAGAA-
CGAGTGATCACACCTGGACGTCCCATGGTACCTTCGAATGAGCTCCTAGGCGCCTTTCTT-

GAAGAAGAACAAGAAAGCCCGAAACGAAGCTGAGTTGGCTGCTGCCACCGCTGAGCAATA-
CTTCTTCTTCTTCTTTCGGGCTTTCCTTCGACTCAACCGACGACGGTGGCGACTCGTTAT-

ACTAGCATAACCCCTTGGGGCCTCTAAACGCGTCTTGAGGGGTTTTTTGCTGAAAGGAGG-
TGATCGTATTGGGGAACCCCGGAGATTTGCCCAGAACTCCCCAAAAAACGACTTTCCTCC-

AACCGCTCTTCACGCTCTTCACGC 3' [SacII sticky end] (SEQ ID NO:50)
TTGGCGAGAAGTGCGAGAAGTG   5' (position #5904 in pAMG21)
(SEQ ID NO: 46)
```

During the ligation of the sticky ends of this substitution DNA sequence, the outside AatII and SacII sites are destroyed. There are unique AatII and SacII sites in the substituted DNA.

pAMG22-His

The expression plasmid pAMG22-His can be derived from the Amgen expression vector pAMG22 by substituting the small DNA sequence between the unique NdeI (#4795) and EcoRI (#4818) restriction sites of pAMG22 with the following oligonucleotide duplex:

```
 NdeI                          NheI            EcoRI
5' TATGAAACATCATCACCATCACCATCATGCTAGCCTTAACGCGTTGG     3'
(SEQ ID NO:51)

3'   ACTTTGTAGTAGTGGTACTGGTAGTACGATCGCAATTGCGCAACCTTAA 5'
(SEQ ID NO:52)

     MetLysHisHisHisHisHisHisHisAlaSerValAsnAlaLeuGlu
(SEQ ID NO:168)
```

pAMG22

The expression plasmid pAMG22 can be derived from the Amgen expression vector pCFM1656 (ATCC #69576) which in turn be derived from the Amgen expression vector system described in U.S. Pat. No. 4,710,473 granted Dec. 1, 1987. The pCFM1656 plasmid can be derived from the described pCFM836 plasmid (U.S. Pat. No. 4,710,473) by: (a) destroying the two endogenous NdeI restriction sites by end filling with T4 polymerase enzyme followed by blunt end ligation; (b) replacing the DNA sequence between the unique AatII and ClaI restriction sites containing the synthetic PL promoter with a similar fragment obtained from pCFM636 (U.S. Pat. No. 4,710,473) containing the PL promoter AatII

5' CTAATTCCGCTCTCACCTACCAAACAATGCCCCCCTGCAAAAAATAAATTCATAT-

3'TGCAGATTAAGGCGAGAGTGGATGGTTTGTTACGGGGGGACGTTTTTTATTTAAGTATA-

-AAAAAACATACAGATAACCATCTGCGGTGATAAATTATCTCTGGCGGTGTTGACATAAA-

-TTTTTTCTATGTCTATTGGTAGACGCCACTATTTAATAGAGACCGCCACAACTGTATTT-

-TACCACTGGCGGTGATACTGAGCACAT 3' (SEQ ID NO:53)

-ATGGTGACCGCCACTATGACTCGTGTAGC5' (SEQ ID NO:54)

ClaI and then (c) substituting the small DNA sequence between the unique ClaI and KpnI restriction sites with the following oligonucleotide:

5' CGATTTGATTCTAGAAGGAGGAATAACATATGGTTAACGCGTTGGAATTCGGTAC 3' (SEQ ID NO:55)

3' TAAACTAAGATCTTCCTCCTTATTGTATACCAATTGCGCAACCTTAAGC 5' (SEQ ID NO:56)

ClaI KpnI

The expression plasmid pAMG22 can then be derived from pCFM1656 by making a series of site directed base changes by PCR overlapping oligo mutagenesis and DNA sequence substitutions. Starting with the BglII site (plasmid bp #180) immediately 5' to the plasmid replication promoter PcopB and proceeding toward the plasmid replication genes, the base pair changes are as follows:

| pAMG22 bp # | bp in pCFM1656 | bp changed to in pAMG22 |
|---|---|---|
| #204 | T/A | C/G |
| #428 | A/T | G/C |
| #509 | G/C | A/T |
| #617 | — | insert two G/C bp |
| #679 | G/C | T/A |
| #980 | T/A | C/G |
| #994 | G/C | A/T |
| #1004 | A/T | C/G |
| #1007 | C/G | T/A |
| #1028 | A/T | T/A |
| #1047 | C/G | T/A |
| #1178 | G/C | T/A |
| #1466 | G/C | T/A |
| #2028 | G/C | bp deletion |
| #2187 | C/G | T/A |
| #2480 | A/T | T/A |
| #2499-2502 | AGTG TCAC | GTCA CAGT |
| #2642 | TCCGAGC AGGCTCG | 7 bp deletion |
| #3435 | G/C | A/T |
| #3446 | G/C | A/T |
| #3643 | A/T | T/A |

The DNA sequence between the unique AatII (position #4364 in pCFM1656) and SacII (position #4585 in pCFM1656) restriction sites is substituted with the following DNA sequence:

```
[AatII sticky end] (position #4358 in pAMG22)
5'     GCCTAACGTATGCATGGTCTCCCCATGCGAGAGTACGGAACTGCCAGGCATCAA-
3' TGCACGCATTGCATACGTACCAGAGGCCTACGCTCTCATCCCTTGACGGTCCGTAGTT-
```

-continued

```
ATAAAACGAAAGGCTCAGTCGAAAGACTGGGCCTTTCGTTTTATCTGTTGTTTGTCGGTG-
TATTTTGCTTTCCGAGTCAGCTTTCTGACCCGGAAAGCAAAATAGACAACAAACAGCCAC-

AACGCTCTCCTGAGTAGGACAAATCCGCCOGGAGCGGATTTGAACGTTGCGAAGCAACGG-
TTGCGAGAGGACTCATCCTGTTTAGGCGGCCCTCGCCTAAACTTGCAACGCTTCCTTGCC-

CCCGGAGGGTCGCGGGCAGGACGCCCGCCATAAACTGCCAGGCATCAAATTAAGCAGAAG-
GGGCCTCCCACCGCCCGTCCTGCGGGCGGTATTTGACGGTCCGTAGTTTAATTCGTCTTC-

GCCATCCTGACGCATGGCCTTTTTGCGTTTCTACAAACTCTTTTGTTTATTTTTCTAAAT-
CGGTAGGACTGCCTACCGGAAAAACGCAAAGATGTTTGAGAAAACAAATAAAAAGATTTA-

              AatII
ACATTCAAATATGGACGTCTCATAATTTTTAAAAAATTCATTTGACAAATGCTAAAATTC-
TGTAAGTTTATACCTGCAGAGTATTAAAAATTTTTTAAGTAAACTGTTTACGATTTTAAG-

TTGATTAATATTCTCAATTGTGAGCGCTCACAATTTATCGATTTCATTCTACATTTGTTT-
AACTAATTATAAGAGTTAACACTCGCGAGTGTTAAATAGCTAAACTAAGATCTAAACTCA-

TAACTAATTAAAGGAGGAATAACATATGGTTAACGCGTTGGAATTCGAGCTCACTAGTGT-
ATTGATTAATTTCCTCCTTATTGTATACCAATTGCGCAACCTTAAGCTCGAGTGATCACA-

                                        SacII
CGACCTGCAGGGTACCATGGAAGCTTACTCGAGGATCCGCGGAAAGAAGAAGAAGAAGAA-
GCTGGACGTCCCATGGTACCTTCGAATGAGCTCCTAGGCGCCTTTCTTCTTCTTCTTCTT-

GAAAGCCCGAAAGGAAGCTGAGTTGGCTCCTGCCACCGCTGAGCAATAACTAGCATAACC-
CTTTCGGGCTTTCCTTCGACTCAACCGACGACGGTCGCGACTCGTTATTGATCGTATPCG-

CCTTGGGGCCTCTAAACGGGTCTTGAGGGGTTTTTTGCTGAAAGCAGGAACCGCTCTTCA-
GGAACCCCGGAGATTTGCCCAGAACTCCCCAAAAAACGACTTTCCTCCTTCGCGAGAAGT-

CGCTCTTCACGC 3' (SEQ ID NO:58)
GCGAGAAGTG   5' (SEQ ID NO:57)
[SacII sticky end] (position #5024 in pAMG22)
```

During the ligation of the sticky ends of this 50 substitution DNA sequence, the outside AatII and SacII sites are destroyed. There are unique AatII and SacII sites in the substituted DNA.

B. Human OPG Met[32-401]

In the example, the expression vector used was pAMG21, a derivative of pCFM1656 (ATCC accession no. 69576) which contains appropriate restriction sites for insertion of genes downstream from the lux PR promoter. (See U.S. Pat. No. 5,169,318 for description of the lux expression system). The host cell used was GM120 (ATCC accession no. 55764). This host has the lacIQ promoter and lacI gene integrated into a second site in the host chromosome of a prototrophic *E. coli* K12 host. Other commonly used *E. coli* expression vectors and host cells are also suitable for expression.

Figure 14A:
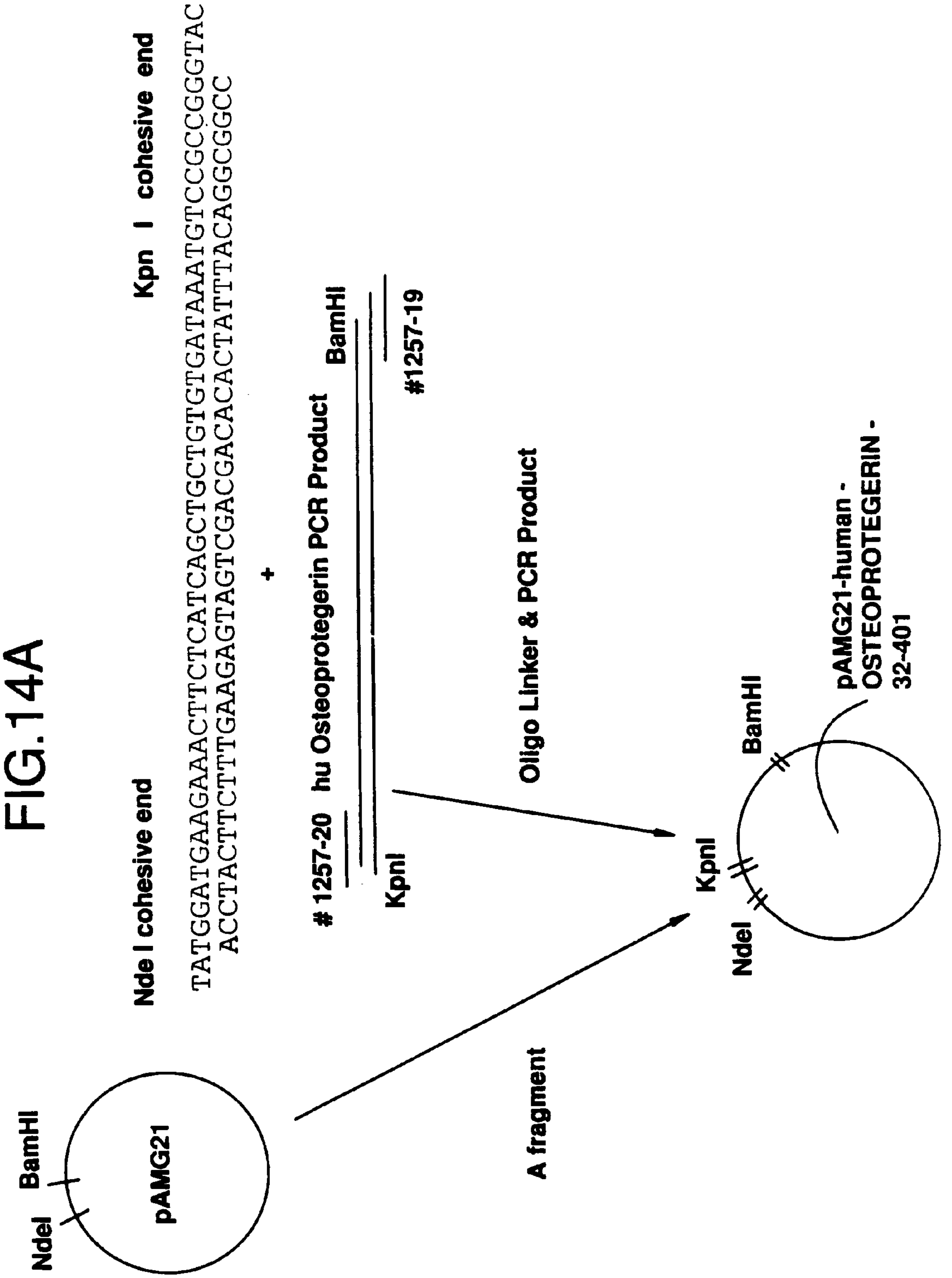
FIG. 14. Expression of human OPG in *E. coli*. A. Construction of a bacterial expression vector. The LORF of the human OPG gene was amplified by PCR, then joined to a oligonucleotide linker fragment (top strand is SEQ ID NO:137; bottom strand is SEQ ID NO:127), and ligated into pAMG21 vector DNA. The resulting vector is capable of expressing OPG residues 32-401 linked to a N-terminal methionine residue. B SDS-PAGE analysis of uninduced and induced bacterial harboring the pAMG21-human OPG-32-401 plasmid. Lane 1, MW standards; lane 2, uninduced bacteria; lane 3, 30° C. induction; lane 4, 37° C. induction; lane 5, whole cell lysate from 37° C. induction; lane 6, soluble fraction of whole cell lysate; lane 7, insoluble fraction of whole cell lysate; lane 8, purified inclusion bodies obtained from whole cell lysate.

A DNA sequence coding for an N-terminal methionine and amino acids 32-401 of the human OPG polypeptide was placed under control of the luxPR promoter in the plasmid expression vector pAMG21 as follows. To accomplish this, PCR using oligonucleotides #1257-20 and #1257-19 as primers was performed using as a template plasmid pRcCMV-Hu OPG DNA containing the human OPG cDNA and thermocycling for 30 cycles with each cycle being: 94° C. for 20 seconds, followed by 37° C. for 30 seconds, followed by 72° C. for 30 seconds. The resulting PCR sample was resolved on an agarose gel, the PCR product was excised, purified, and restricted with KpnI and BamHI restriction endonucleases and purified. Synthetic oligonucleotides #1257-21 and #1257-22 were phosphorylated individually using T4 polynucleotide kinase and ATP, and were then mixed together, heated at 94° C. and allowed to slow cool to room temperature to form an oligonucleotide linker duplex containing NdeI and KpnI sticky ends. The phosphorylated linker duplex formed between oligonucleotides #1257-21 and #1257-22 containing NdeI and KpnI cohesive ends (see FIG. 14A) and the KpnI and BamHI digested and purified PCR product generated using oligo primers #1257-20 and #1257-19 (see above) was directionally inserted between two sites of the plasmid vector pAMG21, namely the NdeI site and BamHI site, using standard recombinant DNA methodology (see FIG. 14A and sequences below). The synthetic linker utilized *E. coli* codons and provided for a N-terminal methionine.

Two clones were selected and plasmid DNA isolated, and the human OPG insert was subsequently DNA sequence confirmed. The resulting pAMG21 plasmid containing amino acids 32-401 of the human OPG polypeptide immediately preceded in frame by a methionine is referred to as pAMG21-huOPG met[32-401] or pAMG21-huOPG met[32-401].

Oligo#1257-19

5'-TACGCACTGGATCCTTATAAGCAGCT-TATTTTTACTGATTGGAC-3' (SEQ ID NO:59)

Oligo#1257-20

5'-GTCCTCCTGGTACCTACCTAAAACAAC-3' (SEQ ID NO:60)

Oligo#1257-21

5'-TATGGATGAAGAAACTTCTCATCAGCT-GCTGTGTGATAAATGTCC GCCGGGTAC-3' (SEQ ID NO:61)

Oligo#1257-22

5'-CCGGCGGACATTTATCACACAGCAGCT-GATGAGAAGTTTCTTCATCCA-3' (SEQ ID NO:47)

Figure 14B:
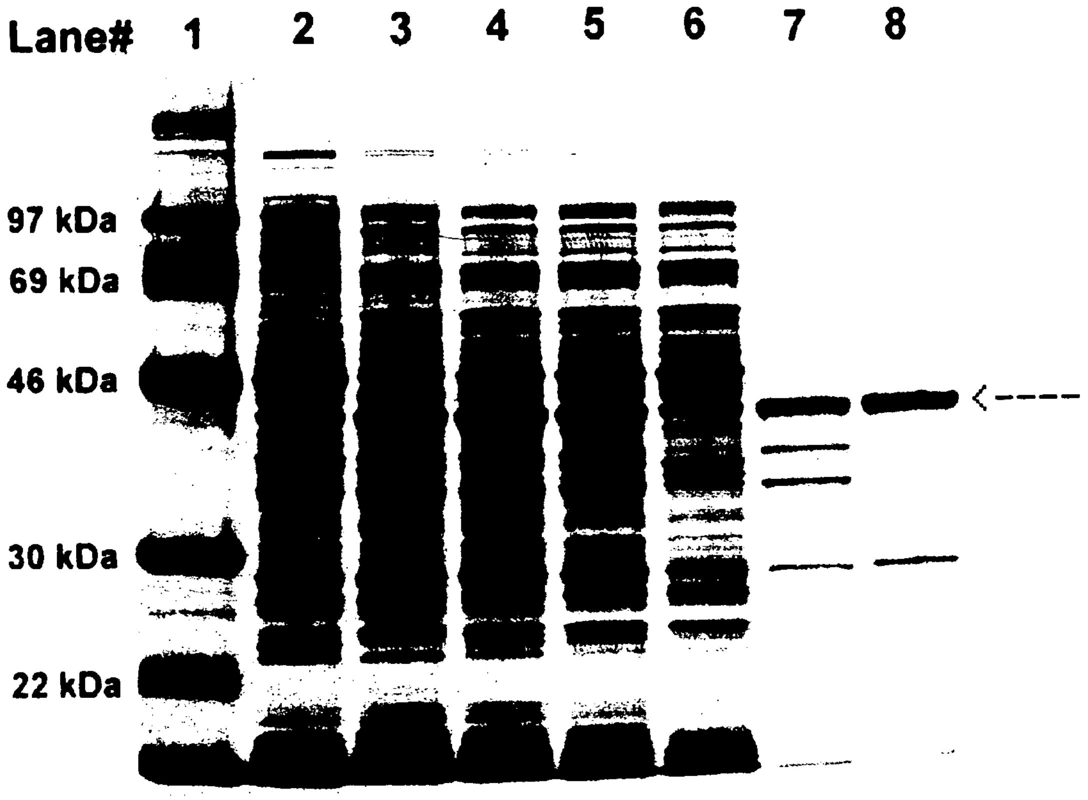

Cultures of pAMG21-huOPG met[32-401] in *E. coli* GM120 in 2XYT media containing 20 μg/ml kanamycin were incubated at 30° C. prior to induction. Induction of huOPG met[32-401] gene product expression from the luxPR promoter was achieved following the addition of the synthetic autoinducer N-(3-oxohexanoyl)-DL-homoserine lactone to the culture media to a final concentration of 30 ng/ml and cultures were incubated at either 30° C. or 37° C. for a further 6 hours. After 6 hours, the bacterial cultures were examined by microscopy for the presence of inclusion bodies and were then pelletted by centrifugation. Refractile inclusion bodies were observed in induced cultures indicating that some of the recombinant huOPG met[32-401] gene product was produced insolubly in *E. coli*. Some bacterial pellets were resuspended in 10 mM Tris-HCl/pH8, 1 mM EDTA and lysed directly by addition of 2× Laemlli sample buffer to 1× final, and β-mercaptoethanol to 5% final concentration, and analyzed by SDS-PAGE. A substantially more intense coomassie stained band of approximately 42 kDa was observed on a SDS-PAGE gel containing total cell lysates of 30° C. and 37° C. induced cultures versus lane 2 which is a total cell lysate of a 30° C. uninduced culture (FIG. 14B). The expected gene product would be 370 amino acids in length and have an expected molecular weight of about 42.2 kDa. Following induction at 37° C. for 6 hours, an additional culture was pelleted and either processed for isolation of inclusion bodies (see below) or processed by microfluidizing. The pellet processed for microfluidizing was resuspended in 25 mM Tris-HCl/pH8, 0.5M NaCl buffer and passed 20 times through a Microfluidizer Model 1108 (Microfluidics Corp.) and collected. An aliquot was removed of the collected sample (microfluidized total lysate), and the remainder was pelleted at 20,000×g for 20 minutes. The supernatant following centrifugation was removed (microfluidized soluble fraction) and the pellet resuspended in a 25 mM Tris-HCl/pH8, 0.5M NaCl, 6M urea solution (microfluidized insoluble fraction). To an aliquot of either the total soluble, or insoluble fraction was added to an equal volume of 2× Laemalli sample buffer and β-mercaptoethanol to 5% final concentration. The samples were then analyzed by SDS-PAGE. A significant amount of recombinant huOPG met[32-401] gene product appeared to be found in the insoluble fraction. To purify the recombinant protein inclusion bodies were purified as follows: Bacterial cells were separated from media by density gradient centrifugation in a Beckman J-6B centrifuge equipped with a JS-4.2 rotor at 4,900×g for 15 minutes at 4° C. The bacterial pellet was resuspended in 5 ml of water and then diluted to a final volume of 10 ml with water. This suspension was transferred to a stainless steel cup cooled in ice and subjected to sonic disruption using a Branson Sonifier equipped with a standard tip (power setting=5, duty cycle=95%, 80 bursts). The sonicated cell suspension was centrifuged in a Beckman Optima TLX ultracentrifuge equipped with a TLA 100.3 rotor at 195,000×g for 5 to 10 minutes at 23° C. The supernatant was discarded and the pellet rinsed with a stream of water from a squirt bottle. The pellets were collected by scraping with a micro spatula and transferred to a glass homogenizer (15 ml capacity). Five ml of Percoll solution (75% liquid Percoll, 0.15 M sodium chloride) was added to the homogenizer and the contents are homogenized until uniformly suspended. The volume was increased to 19.5 ml by the addition of Percoll solution, mixed, and distributed into 3 Beckman Quick-Seal tubes (13×32 mm). Tubes were sealed according to manufacturers instructions. The tubes were spun in a Beckman TLA 100.3 rotor at 23° C., 20,000 rpm (21,600×g), 30 minutes. The tubes were examined for the appropriate banding pattern. To recover the refractile bodies, gradient fractions were recovered and pooled, then diluted with water. The inclusion bodies were pelleted by centrifugation, and the protein concentration estimated following SDS-PAGE.

An aliquot of inclusion bodies isolated as described below was dissolved into 1× Laemlli sample buffer with 5% β-mercaptoethanol and resolved on a SDS-PAGE gel and the isolated inclusion bodies provide a highly purified recombinant huOPG[32-401] gene product. The major ~42 kDa band observed after resolving inclusion bodies on a SDS-polyacrylamide gel was excised from a separate gel and the N-terminal amino acid sequence determined essentially as described (Matsudaira et al. J. Biol. Chem. 262, 10-35 (1987)). The following sequence was determined after 19 cycles:

$NH_2$-MDEETSHQLLCDKCPPGTY-COOH (SEQ ID NO:62)

This sequence was found to be identical to the first 19 amino acids encoded by the pAMG21 Hu-OPG met[32-401] expression vector, produced by a methionine residue provided by the bacterial expression vector.

C. Human OPG met[22-401]

A DNA sequence coding for an N-terminal methionine and amino acids 22 through 401 of human OPG was placed under control of the luxPR promoter in a prokaryotic plasmid expression vector pAMG21 as follows. Isolated plasmid DNA of pAMG21-huOPG met[32-401] (see Section B) was cleaved with KpnI and BamHI restriction endonucleases and the resulting fragments were resolved on an agarose gel. The B fragment (~1064 bp fragment) was isolated from the gel using standard methodology. Synthetic oligonucleotides (oligos) #1267-06 and #1267-07 were phosphorylated individually and allowed to form an oligo linker duplex, which contained NdeI and KpnI cohesive ends, using methods described in Section B. The synthetic linker duplex utilized *E. coli* codons and provided for an N-terminal methionine. The phosphorylated oligo linker containing NdeI and KpnI cohesive ends and the isolated ~1064 bp fragment of pAMG21-huOP met[32-401] digested with KpnI and BamHI restriction endonucleases were directionally inserted between the NdeI and BamHI sites of pAMG21 using standard recombinant DNA methodology. The ligation mixture was transformed into *E. coli* host 393 by electroporation utilizing the manufacturer's protocol. Clones were selected, plasmid DNA was isolated, and DNA sequencing was performed to verify the DNA sequence of the huOPG-met[22-401] gene.

Oligo #1267-06

5'-TAT GGA AAC TTT TCC TCC AAA ATA TCT TCA TTA TGA TGA AGA AAC TTC TCA TCA GCT GCT GTG TGA TAA ATG TCC GCC GGG TAC-3' (SEQ ID NO:63)

Oligo #1267-07

5'-CCG GCG GAC ATT TAT CAC ACA GCA GCT GAT GAG AAG TTT CTT CAT CAT AAT GAA GAT ATT TTG GAG GAA AAG TTT CCA-3' (SEQ ID NO:64)

Cultures of pAMG21-huOPG-met[22-401] in *E. coli* host 393 were placed in 2XYT media containing 20 μg/ml kanamycin and were incubated at 30° C. prior to induction. Induction of recombinant gene product expression from the luxPR promoter of vector pAMG21 was achieved following the addition of the synthetic autoinducer N-(3-oxohexanoyl)-DL-homoserine lactone to the culture media to a final concentration of 30 ng/ml and incubation at either 30° C. or 37° C. for a further 6 hours. After 6 hours, bacterial cultures were pelleted by centrifugation (=30° C. I+6 or 37° C. I+6). Bacterial cultures were also either pelleted just prior to induction (=30° C. PreI) or alternatively no autoinducer was added to a separate culture which was allowed to incubate at 30° C. for a further 6 hours to give an uninduced (UI) culture (=30° C. UI). Bacterial pellets of either 30° C. PreI, 30° C. UI, 30° C. I+6, or 37° C. I+6 cultures were resuspended, lysed, and analyzed by SDS-polyacrylamide gel electrophoresis (PAGE) as described in Section B. Polyacrylamide gels were either stained with coomassie blue and/or Western transferred to nitrocellulose and immunoprobed with rabbit anti-mu OPG-Fc polyclonal antibody as described in Example 10. The level of gene product following induction compared to either an uninduced (30° C. UI) or pre-induction (30° C. PreI) sample.

D. Murine OPG met[22-401]

A DNA sequence coding for an N-terminal methionine and amino acids 22 through 401 of the murine (mu) OPG (OPG) polypeptide was placed under control of the luxPR promoter in a prokaryotic plasmid expression vector pAMG21 as follows. PCR was performed using oligonucleotides #1257-16 and #1257-15 as primers, plasmid pRcCMV-Mu OPG DNA as a template and thermocycling conditions as described in Section B. The PCR product was purified and cleaved with KpnI and BamHI restriction endonucleases as described in Section B. Synthetic oligos #1260-61 and #1260-82 were phosphorylated individually and allowed to form an oligo linker duplex with NdeI and KpnI cohesive ends using methods described in Section B. The synthetic linker duplex utilized *E. coli* codons and provided for an N-terminal methionine. The phosphorylated linker duplex formed between oligos #1260-61 and #1260-82 containing NdeI and KpnI cohesive ends and the KpnI and BamHI digested and purified PCR product generated using oligo primers #1257-16 and #1257-15 were directionally inserted between the NdeI and BamHI sites of pAMG21 using standard methodology. The ligation mixture was transformed into *E. coli* host 393 by electroporation utilizing the manufacturer's protocol. Clones were selected, plasmid DNA was isolated, and DNA sequencing was performed to verify the DNA sequence of the MuOPG met[22-401] gene.

Expression of recombinant muOPG met[22-401] polypeptide from cultures of 393 cells harboring plasmid pAMG21-MuOPG met[22-401] following induction was determined using methods described in Section C.

Oligo #1257-15

5'-TAC GCA CTG GAT CCT TAT AAG CAG CTT ATT TTC ACG GAT TGA AC-3' (SEQ ID NO:65)

Oligo #1257-16

5'-GTG CTC CTG GTA CCT ACC TAA AAC AGC ACT GCA CAG TG-3' (SEQ ID NO:66)

Oligo #1260-61

5'-TAT GGA AAC TCT GCC TCC AAA ATA CCT GCA TTA CGA TCC GGA AAC TGG TCA TCA GCT GCT GTG TGA TAA ATG TGC TCC GGG TAC-3' (SEQ ID NO:67)

Oligo #1260-82

5'-CCG GAG CAC ATT TAT CAC ACA GCA GCT GAT GAC CAG TTT CCG GAT CGT AAT GCA GGT ATT TTG GAG GCA GAG TTT CCA-3' (SEQ ID NO:68)

E. Murine OPG met[32-401]

A DNA sequence coding for an N-terminal methionine and amino acids 32 through 401 of murine OPG was placed under control of the luxPR promoter in a prokaryotic plasmid expression vector pAMG21 as follows. To accomplish this, Synthetic oligos #1267-08 and #1267-09 were phosphorylated individually and allowed to form an oligo linker duplex using methods described in Section B. The synthetic linker duplex utilized *E. coli* codons and provided for an N-terminal methionine. The phosphorylated linker duplex formed between oligos #1267-08 and #1267-09 containing NdeI and KpnI cohesive ends, and the KpnI and BamHI digested and purified PCR product described earlier (see Section D), was directionally inserted between the NdeI and BamHI sites of pAMG21 using standard methodology. The ligation mixture was transformed into *E. coli* host 393 by electroporation utilizing the manufacturer's protocol. Clones were selected, plasmid DNA was isolated, and DNA sequencing was performed to verify the DNA sequence of the muOPG-met[32-401] gene.

Expression of recombinant muOPG-met [32-401] polypeptide from cultures of 393 cells harboring the pAMG21 recombinant plasmid following induction was determined using methods described in Section C.

Oligo #1267-08

5'-TAT GGA CCC AGA AAC TGG TCA TCA GCT GCT GTG TGA TAA ATG TGC TCC GGG TAC-3' (SEQ ID NO:69)

Oligo #1267-09

5'-CCG GAG CAC ATT TAT CAC ACA GCA GCT GAT GAC CAG TTT CTG GGT CCA-3' (SEQ ID NO:70)

F. Murine OPG met-lys[22-401]

A DNA sequence coding for an N-terminal methionine followed by a lysine residue and amino acids 22 through 401 of murine OPG was placed under control of the lux PR promoter in prokaryotic expression vector pAMG21 as follows. Synthetic oligos #1282-95 and #1282-96 were phosphorylated individually and allowed to form an oligo linker duplex using methods described in Section B. The synthetic linker duplex utilized *E. coli* codons and provided for an N-terminal methionine. The phosphorylated linker duplex formed between oligos #1282-95 and #1282-96 containing NdeI and KpnI cohesive ends and the KpnI and BamHI digested and purified PCR product described in Section D was directionally inserted between the NdeI and BamHI sites in pAMG21 using standard methodology. The ligation mixture was transformed into *E. coli* host 393 by electroporation utilizing the manufacturer's protocol. Clones were selected, plasmid DNA was isolated, and DNA sequencing was performed to verify the DNA sequence of the MuOPG-Met-Lys[22-401] gene.

Expression of recombinant MuOPG Met-Lys[22-401] polypeptide from transformed 393 cells harboring the recombinant pAMG21 plasmid following induction was determined using methods described in Section C.

Oligo #1282-95

5'-TAT GAA AGA AAC TCT GCC TCC AAA ATA CCT GCA TTA CGA TCC GGA AAC TGG TCA TCA GCT GCT GTG TGA TAA ATG TGC TCC GGG TAC-3' (SEQ ID NO:71)

Oligo #1282-96

5'-CCG GAG CAC ATT TAT CAC ACA GCA GCT GAT GAC CAG TTT CCG GAT CGT AAT GCA GGT ATT TTG GAG GCA GAG TTT CTT TCA-3' (SEQ ID NO:72)

G. Murine OPG met-lys-$(his)_7$[22-401]

A DNA sequence coding for N-terminal residues Met-Lys-His-His-His-His-His-His-His (=MKH) followed by amino acids 22 through 401 of Murine OPG was placed under control of the lux PR promoter in prokaryotic expression vector pAMG21 as follows. PCR was performed using oligonucleotides #1300-50 and #1257-15 as primers and plasmid pAMG21-muOPG-met[22-401] DNA as template. Thermocycling conditions were as described in Section B. The resulting PCR sample was resolved on an agarose gel, the PCR product was excised, purified, cleaved with NdeI and BamHI restriction endonucleases and purified. The NdeI and BamHI digested and purified PCR product generated using oligo primers #1300-50 and #1257-15 was directionally inserted between the NdeI and BamHI sites of pAMG21 using standard DNA methodology. The ligation mixture was transformed into *E. coli* host 393 by electroporation utilizing the manufacturer's protocol. Clones were selected, plasmid DNA was isolated, and DNA sequencing performed to verify the DNA sequence of the muOPG-MKH[22-401] gene.

Expression of recombinant MuOPG-MKH[22-401] polypeptide from transformed 393 cultures harboring the recombinant pAMG21 plasmid following induction was determined using methods described in Section C.

Oligo #1300-50

5'-GTT CTC CTC ATA TGA AAC ATC ATC ACC ATC ACC ATC ATG AAA CTC TGC CTC CAA AAT ACC TGC ATT ACG AT-3' (SEQ ID NO:73)

Oligo #1257-15

(see Section D)

H. Murine OPG met-lys[22-401] (his)$_7$

A DNA sequence coding for a N-terminal met-lys, amino acids 22 through 401 murine OPG, and seven histidine residues following amino acid 401 (=muOPG MK[22-401]-H$_7$), was placed under control of the lux PR promoter in prokaryotic expression vector pAMG21 as follows. PCR was performed using oligonucleotides #1300-49 and #1300-51 as primers and pAMG21-muOPG met[22-401] DNA as template. Thermocycling conditions were as described in Section B. The resulting PCR sample was resolved on an agarose gel, the PCR product was excised, purified, restricted with NdeI and BamHI restriction endonucleases, and purified. The NdeI and BamHI digested and purified PCR product was directionally inserted between the NdeI and BamHI sites in pAMG21 using standard methodology. The ligation was transformed into *E. coli* host 393 by electroporation utilizing the manufacturer's protocol. Clones were selected, plasmid DNA was isolated, and DNA sequencing was performed to verify the DNA sequence of the muOPG MK[22-401]-H7 gene.

Expression of the recombinant muOPG MK-[22-401]-H$_7$ polypeptide from a transformed 393 cells harboring the recombinant pAMG21 plasmid following induction was determined using methods described in Section C.

Oligo #1300-49

5'-GTT CTC CTC ATA TGA AAG AAA CTC TGC CTC CAA AAT ACC TGC A-3' (SEQ ID NO:74)

Oligo #1300-51

5'-TAC GCA CTG GAT CCT TAA TGA TGG TGA TGG TGA TGA TGT AAG CAG CTT ATT TTC ACG GAT TGA ACC TGA TTC CCT A-3' (SEQ ID NO:75)

I. Murine OPG met[27-401]

A DNA sequence coding for a N-terminal methionine and amino acids 27 through 401 of murine OPG was placed under control of the lux PR promoter of prokaryotic expression vector pAMG21 as follows. PCR was performed with oligonucleotides #1309-74 and #1257-15 as primers and plasmid pAMG21-muOPG-met[22-401] DNA as template. Thermocycling conditions were as described in Section B. The resulting PCR sample was resolved on an agarose gel, the PCR product was excised, purified, cleaved with NdeI and BamHI restriction endonucleases, and purified. The NdeI and BamHI digested and purified PCR product was directionally inserted between the NdeI and BamHI sites of pAMG21 using standard methodology. The ligation mixture was transformed into *E. coli* host 393 by electroporation utilizing the manufacturer's protocol. Clones were selected, plasmid DNA was isolated, and DNA sequencing was performed to verify the DNA sequence of the muOPG-met[27-401] gene.

Expression of recombinant muOPG-met[27-401] polypeptide from a transfected 393 culture harboring the recombinant pAMG21 plasmid following induction was determined using methods described in Section C.

Oligo#1309-74

5'-GTT CTC CTC ATA TGA AAT ACC TGC ATT ACG ATC CGG AAA CTG GTC AT-3' (SEQ ID NO:76)

Oligo#1257-15

(See Section D)

J. Human OPG met[27-401]

A DNA sequence coding for a N-terminal methionine and amino acids 27 through 401 of human OPG was placed under control of the lux PR promoter of prokaryotic expression vector pAMG21 as follows. PCR was performed using oligonucleotides #1309-75 and #1309-76 as primers and plasmid pAMG21-huOPG-met[22-401] DNA as template. Thermocycling conditions were as described in Section B. The resulting PCR sample was resolved on an agarose gel, the PCR product was excised, purified, restricted with AseI and BamHI restriction endonucleases, and purified. The AseI and BamHI digested and purified PCR product above was directionally inserted between the NdeI and BamHI sites of pAMG21 using standard methodology. The ligation mixture was transformed into *E. coli* host 393 by electroporation utilizing the manufacturer's protocol. Clones were selected, plasmid DNA was isolated, and DNA sequencing was performed to verify the DNA sequence of the huOPG-met[27-401] gene.

Expression of the recombinant huOPG-met[27-401] polypeptide following induction of from transfected 393 cells harboring the recombinant pAMG21 plasmid was determined using methods described in Section C.

Oligo #1309-75

5'-GTT CTC CTA TTA ATG AAA TAT CTT CAT TAT GAT GAA GAA ACT T-3' (SEQ ID NO:77)

Oligo #1309-76

5'-TAC GCA CTG GAT CCT TAT AAG CAG CTT ATT TTT ACT GAT T-3' (SEQ ID NO:78)

K. Murine OPG met[22-180]

A DNA sequence coding for a N-terminal methionine and amino acids 22 through 180 of murine OPG was placed under control of the lux PR promoter of prokaryotic expression vector pAMG21 as follows. PCR was performed with oligonucleotides #1309-72 and #1309-73 as primers and plasmid pAMG21-muOPG-met[22-401] DNA as template. Thermocycling conditions were as described in Section B. The resulting PCR sample was resolved on an agarose gel, the PCR product was excised, purified, restricted with NdeI and BamHI restriction endonucleases, and purified. The NdeI and BamHI digested and purified PCR product above was directionally inserted between the NdeI and BamHI sites of pAMG21 using standard methodology. The ligation was transformed into *E. coli* host 393 by electroporation utilizing the manufacturer's protocol. Clones were selected, plasmid DNA was isolated, and DNA sequencing was performed to verify the DNA sequence of the muOPG-met[22-180] gene.

Expression of recombinant muOPG-met[22-180] polypeptide from transformed 393 cultures harboring the recombinant pAMG21 plasmid following induction was determined using methods described in Section C.

Oligo #1309-72

5'-GTT CTC CTC ATA TGG AAA CTC TGC CTC CAA AAT ACC TGC A-3' (SEQ ID NO:79)

Oligo #1309-73

5'-TAC GCA CTG GAT CCT TAT GTT GCA TTT CCT TTC TGA ATT AGC A-3' (SEQ ID NO:80)

L. Murine OPG met[27-180]

A DNA sequence coding for a N-terminal methionine and amino acids 27 through 180 of murine OPG was placed under the control of the lux PR promoter of prokaryotic expression vector pAMG21 as follows. PCR was performed using oligonucleotides #1309-74 (see Section I) and #1309-73 (see Section K) as primers and plasmid pAMG21-muOPG met [22-401] DNA as template. Thermocycling conditions were as described in Section B. The resulting PCR sample was resolved on an agarose gel, the PCR product excised, purified, restricted with NdeI and BamHI restriction endonucleases, and purified. The NdeI and BamHI digested and purified PCR product above was directionally inserted between the NdeI and BamHI sites in pAMG21 using standard methodology. The ligation mixture was transformed into *E. coli* host 393 by electroporation utilizing the manufacturer's protocol. Clones were selected, plasmid DNA was isolated, and DNA sequencing was performed to verify the DNA sequence of the muOPG met[27-180] gene.

Expression of recombinant muOPG met[27-180] polypeptide from cultures of transformed 393 cells harboring the recombinant pAMG21 plasmid following induction was determined using methods described in Section C.

M. Murine OPG met[22-189] and met[22-194]

A DNA sequence coding for a N-terminal methionine and either amino acids 22 through 189, or 22 through 194 of murine OPG was placed under control of the lux PR promoter of prokaryotic expression vector pAMG21 as follows. The pair of synthetic oligonucleotides #1337-92 and #1337-93 (=muOPG-189 linker) or #1333-57 and #1333-58 (=muOPG-194 linker) were phosphorylated individually and allowed to form an oligo linker duplex pair using methods described in Section B. Purified plasmid DNA of pAMG21-muOPG-met[22-401] was cleaved with KpnI and BspEI restriction endonucleases and the resulting DNA fragments were resolved on an agarose gel. The ~413 bp B fragment was isolated using standard recombinant DNA methodology. The phosphorylated oligo linker duplexes formed between either oligos #1337-92 and #1337-93 (muOPG-189 linker) or oligos #1333-57 and #1333-58 (muOPG-194 linker) containing BspEI and BamHI cohesive ends, and the isolated ~413 bp B fragment of plasmid pAMG21-muOPG-met[22-401] digested with KpnI and BspEI restriction endonucleases above, was directionally inserted between the KpnI and BamHI sites of pAMG21-muOPG met[22-401] using standard methodology. Each ligation mixture was transformed into *E. coli* host 393 by electroporation utilizing the manufacturer's protocol. Clones were selected, plasmid DNA was isolated, and DNA sequencing was performed to verify the DNA sequence of either the muOPG-met[22-189] or muOPG-met[22-194] genes.

Expression of recombinant muOPG-met[22-189] and muOPG-met[22-194] polypeptides from recombinant pAMG21 plasmids transformed into 393 cells was determined using methods described in Section C.

Oligo #1337-92

5'-CCG GAA ACA GAT AAT GAG-3' (SEQ ID NO:81)

Oligo #1337-93

5'-GAT CCT CAT TAT CTG TTT-3' (SEQ ID NO:82)

Oligo #1333-57

5'-CCG GAA ACA GAG AAG CCA CGC AAA AGT AAG-3' (SEQ ID NO:83)

Oligo #1333-58

5'-GAT CCT TAC TTT TGC GTG GCT TCT CTG TTT-3' (SEQ ID NO:84)

N. Murine OPG met[27-189] and met[27-194]

A DNA sequence coding for a N-terminal methionine and either amino acids 27 through 189, or 27 through 194 of murine OPG was placed under control of the lux PR promoter of prokaryotic expression vector pAMG21 as follows. Phosphorylated oligo linkers either "muOPG-189 linker" or "muOPG-194 linker" (see Section M) containing BspEI and BamHI cohesive ends, and the isolated ~413 bp B fragment of plasmid pAMG21-muOPG-met[22-401] digested with KpnI and BspEI restriction endonucleases were directionally inserted between the KpnI and BamHI sites of plasmid pAMG21-muOPG-met[27-401] using standard methodology. Each ligation was transformed into *E. coli* host 393 by electroporation utilizing the manufacturer's protocol. Clones were selected, plasmid DNA was isolated, and DNA sequencing was performed to verify the DNA sequence of either the muOPG met[27-189] or muOPG met[27-194] genes.

Expression of recombinant muOPG met[27-189] and muOPG met[27-194] following induction of 393 cells harboring recombinant pAMG21 plasmids was determined using methods described in Section C.

O. Human OPG met[22-185], met[22-189], met[22-194]

A DNA sequence coding for a N-terminal methionine and either amino acids 22 through 185, 22 through 189, or 22 through 194 of the human OPG polypeptide was placed under control of the lux PR promoter of prokaryotic expression vector pAMG21 as follows. The pair of synthetic oligonucleotides #1331-87 and #1331-88 (=huOPG-185 linker), #1331-89 and #1331-90 (=huOPG-189 linker), or #1331-91 & #1331-92 (=huOPG-194 linker) were phosphorylated individually and each allowed to form an oligo linker duplex pair using methods described in Section B. Purified plasmid DNA of pAMG21-huOPG-met[27-401] was restricted with KpnI and NdeI restriction endonucleases and the resulting DNA fragments were resolved on an agarose gel. The ~407 bp B fragment was isolated using standard recombinant DNA methodology. The phosphorylated oligo linker duplexes formed between either oligos #1331-87 and #1331-88 (huOPG-185 linker), oligos #1331-89 and #1331-90 (huOPG-189 linker), or oligos #1331-91 and #1331-92 (huOPG-194 linker), and the isolated ~407 bp B fragment of plasmid pAMG21-huOPG-met[27-401] digested with KpnI and NdeI restriction endonucleases above, was directionally inserted between the KpnI and BamHI sites of plasmid pAMG21-huOPG-met[22-401] using standard methodology. Each ligation was transformed into *E. coli* host 393 by electroporation utilizing the manufacturer's protocol. Clones were selected, plasmid DNA was isolated, and DNA sequencing was performed to verify the DNA sequence of either the huOPG-met[22-185], huOPG-met[22-189], or huOPG-met [22-194] genes.

Expression of recombinant huOPG-met[22-185], huOPG-met[22-189] or huOPG-met[22-194] in transformed 393 cells harboring recombinant pAMG21 plasmids following induction was determined using methods described in Section C.

Oligo #1331-87

5'-TAT GTT AAT GAG-3' (SEQ ID NO:85)

Oligo #1331-88

5'-GAT CCT CAT TAA CA-3' (SEQ ID NO:86)

Oligo #1331-89

5'-TAT GTT CCG GAA ACA GTT AAG-3' (SEQ ID NO:87)

Oligo #1331-90

5'-GAT CCT TAA CTG TTT CCG GAA CA-3' (SEQ ID NO:88)

Oligo #1331-91

5'-TAT GTT CCG GAA ACA GTG AAT CAA CTC AAA AAT AAG-3' (SEQ ID NO:89)

Oligo #1331-92

5'-GAT CCT TAT TTT TGA GTT GAT TCA CTG TTT CCG GAA CA-3' (SEQ ID NO:90)

P. Human OPG met[27-185], met[27-189], met [27-194]

A DNA sequence coding for a N-terminal methionine and either amino acids 27 through 185, 27 through 189, or 27 through 194 of the human OPG polypeptide was placed under control of the lux PR promoter of prokaryotic expression vector pAMG21 as follows. Phosphorylated oligo linkers "huOPG-185 linker", "huOPG-189 linker", or "huOPG-194 linker" (See Section O) each containing NdeI and BamHI cohesive ends, and the isolated ~407 bp B fragment of plasmid pAMG21-huOPG-met[27-401] digested with KpnI and NdeI restriction endonucleases (See Section O) were directionally inserted between the KpnI and BamHI sites of plasmid pAMG21-huOPG-met[27-401] (See Section J) using standard methodology. Each ligation was transformed into *E. coli* host 393 by electroporation utilizing the manufacturer's protocol. Clones were selected, plasmid DNA isolated, and DNA sequencing performed to verify the DNA sequence of either the huOPG-met[27-185], huOPG-met[27-189], or huOPG-met[27-194] genes.

Expression of recombinant huOPG-met[27-185], huOPG-met[27-189], and huOPG-met[27-194] from recombinant pAMG21 plasmids transformed into 393 cells was determined using methods described in Section C.

O. Murine OPG met[27-401] (P33E, G36S, A45P)

A DNA sequence coding for an N-terminal methionine and amino acids 27 through 48 of human OPG followed by amino acid residues 49 through 401 of murine OPG was placed under control of the lux PR promoter of prokaryotic expression vector pAMG21 as follows. Purified plasmid DNA of pAMG21-huOPG-met[27-401] (See Section J) was cleaved with AatII and KpnI restriction endonucleases and a ~1075 bp B fragment isolated from an agarose gel using standard recombinant DNA methodology. Additionally, plasmid pAMG21-muOPG-met[22-401] DNA (See Section D) was digested with KpnI and BamHI restriction endonucleases and the ~1064 bp B fragment isolated as described above. The isolated ~1075 bp pAMG21-huOPG-met[27-401] restriction fragment containing AatII & KpnI cohesive ends (see above), the ~1064 bp pAMG21-muOPG-met[22-401] restriction fragment containing KpnI and BamHI sticky ends and a ~5043 bp restriction fragment containing AatII and BamHI cohesive ends and corresponding to the nucleic acid sequence of pAMG21 between AatII & BamHI were ligated using standard recombinant DNA methodology. The ligation was transformed into *E. coli* host 393 by electroporation utilizing the manufacturer's protocol. Clones were selected, and the presence of the recombinant insert in the plasmid verified using standard DNA methodology. muOPG-27-401 (P33E, G36S, A45P) gene. Amino acid changes in muOPG from proline-33 to glutamic acid-33, glycine-36 to serine-36, and alanine-45 to proline-45, result from replacement of muOPG residues 27 through 48 with huOPG residues 27 through 48.

Expression of recombinant muOPG-met[27-401] (P33E, G36S, A45P) from transformed 393 cells harboring the recombinant pAMG21 plasmid was determined using methods described in Section C.

R. Murine OPG met-lys-(his)$_7$-ala-ser-(asp)$_4$-lys[22-401] (A45T)

A DNA sequence coding for an N-terminal His tag and enterokinase recognition sequence which is ($NH_2$ to COOH terminus): Met-Lys-His-His-His-His-His-His-His-Ala-Ser-Asp-Asp-Asp-Asp-Lys (=HEK), followed by amino acids 22 through 401 of the murine OPG polypeptide was placed under control of the lac repressor regulated Ps4 promoter as follows. pAMG22-His (See Section A) was digested with NheI and BamHI restriction endonucleases, and the large fragment (the A fragment) isolated from an agarose gel using standard recombinant DNA methodology. Oligonucleotides #1282-91 and #1282-92 were phosphorylated individually and allowed to form an oligo linker duplex using methods previously described (See Section B). The phosphorylated linker duplex formed between oligos #1282-91 and #1282-92 containing NheI and KpnI cohesive ends, the KpnI and BamHI digested and purified PCR product described (see Section D), and the A fragment of vector pAMG22-His digested with NheI and BamHI were ligated using standard recombinant DNA methodology. The ligation was transformed into *E. coli* host GM120 by electroporation utilizing the manufacturer's protocol. Clones were selected, plasmid DNA isolated and DNA sequencing performed to verify the DNA sequence of the muOPG-HEK[22-401] gene. DNA sequencing revealed a spurious mutation in the natural muOPG sequence that resulted in a single amino acid change of Alanine-45 of muOPG polypeptide to a Threonine.

Expression of recombinant muOPG-HEK[22-401] (A45T) from GM120 cells harboring the recombinant pAMG21 plasmid was determined using methods similar to those described in Section C, except instead of addition of the synthetic autoinducer, IPTG was added to 0.4 mM final to achieve induction.

Oligo #1282-91

5'-CTA GCG ACG ACG ACG ACA AAG AAA CTC TGC CTC CAA AAT ACC TGC ATT ACG ATC CGG AAA CTG GTC ATC AGC TGC TGT GTG ATA AAT GTG CTC CGG GTA C-3' (SEQ ID NO:91)

Oligo #1282-92

5'-CCG GAG CAC ATT TAT CAC ACA GCA GCT GAT GAC CAG TTT CCG GAT CGT AAT GCA GGT ATT TTG GAG GCA GAG TTT CTT TGT CGT CGT CGT CG-3' (SEQ ID NO:92)

S. Human OPG met-arg-gly-ser-(his)$_6$[22-401]

Eight oligonucleotides (1338-09 to 1338-16 shown below) were designed to produce a 175 base fragment as overlapping, double stranded DNA. The oligos were annealed, ligated, and the 5' and 3' oligos were used as PCR primers to produce large quantities of the 175 base fragment. The final PCR gene products were digested with restriction endonucleases ClaI and KpnI to yield a fragment which replaces the N-terminal 28 codons of human OPG. The ClaI and KpnI digested PCR product was inserted into pAMG21-huOPG [27-401] which had also been cleaved with ClaI and KpnI. Ligated DNA was transformed into competent host cells of *E. coli* strain 393. Clones were screened for the ability to produce the recombinant protein product and to possess the gene fusion having the correct nucleotide sequence. Protein expression levels were determined from 50 ml shaker flask studies. Whole cell lysate and sonic pellet were analyzed for expression of the construct by Coomassie stained PAGE gels and Western analysis with murine anti-OPG antibody. Expression of huOPG Met-Arg-Gly-Ser-(His)$_6$ [22-401] resulting in the formation of large inclusion bodies and the protein was localized to the insoluble (pellet) fraction.

1338-09

ACA AAC ACA ATC GAT TTG ATA CTA GA (SEQ ID NO:93)

1338-10

TTT GTT TTA ACT AAT TAA AGG AGG AAT AAA ATA TGA GAG GAT CGC ATC AC (SEQ ID NO:94)

1338-11

CAT CAC CAT CAC GAA ACC TTC CCG CCG AAA TAC CTG CAC TAC GAC GAA GA (SEQ ID NO:95)

1338-12

AAC CTC CCA CCA GCT GCT GTG CGA CAA ATG CCC GCC GGG TAC CCA AAC A (SEQ ID NO:96)

1338-13

TGT TTG GGT ACC CGG CGG GCA TTT GT (SEQ ID NO:97)

1338-14

CGC ACA GCA GCT GGT GGG AGG TTT CTT CGT CGT AGT GCA GGT ATT TCG GC (SEQ ID NO:98)

1338-15

GGG AAG GTT TCG TGA TGG TGA TGG TGA TGC GAT CCT CTC ATA TTT TAT T (SEQ ID NO:99)

1338-16

CCT CCT TTA ATT AGT TAA AAC AAA TCT AGT ATC AAA TCG ATT GTG TTT GT (SEQ ID NO:100)

T. Human OPG met-lys[22-401] and met(lys)$_3$[22-401]

To construct the met-lys and met-(lys)$_3$ versions of human OPG[22-401], overlapping oligonucleotides were designed to add the appropriate number of lysine residues. The two oligos for each construct were designed to overlap, allowing two rounds of PCR to produce the final product. The template for the first PCR reaction was a plasmid DNA preparation containing the human OPG 22-401 gene. The first PCR added the lysine residue(s). The second PCR used the product of the first round and added sequence back to the first restriction site, ClaI.

The final PCR gene products were digested with restriction endonucleases ClaI and KpnI, which replace the N-terminal 28 codons of hu OPG, and then ligated into plasmid pAMG21-hu OPG [27-401] which had been also digested with the two restriction endonucleases. Ligated DNA was transformed into competent host cells of *E. coli* strain 393. Clones were screened for the ability to produce the recombinant protein product and to possess the gene fusion having the correct nucleotide sequence. Protein expression levels were determined from 50 ml shaker flask studies. Whole cell lysate and sonic pellet were analyzed for expression of the construct by Coomassie stained PAGE gels and Western analysis with murine anti-OPG antibody. Neither construct had a detectable level of protein expression and inclusion bodies were not visible. The DNA sequences were confirmed by DNA sequencing.

Oligonucleotide primers to prepare Met-Lys huOPG[22-401]:

1338-17

ACA AAC ACA ATC GAT TTG ATA CTA GAT TTG TTT TAA CTA ATT AAA GGA GGA ATA AAA TG (SEQ ID NO:101)

1338-18

CTA ATT AAA GGA GGA ATA AAA TGA AAG AAA CTT TTC CTC CAA AAT ATC (SEQ ID NO:102)

1338-20

TGT TTG GGT ACC CGG CGG ACA TTT ATC ACA C (SEQ ID NO:103)

Oligonucleotide primers to prepare Met-(Lys)$_3$-huOPG[22-401]:

1338-17

ACA AAC ACA ATC GAT TTG ATA CTA GAT TTG TTT TAA CTA ATT AAA GGA GGA ATA AAA TG (SEQ ID NO:104)

1338-19

CTA ATT AAA GGA GGA ATA AAA TGA AAA AAA AAG AAA CTT TTC CTC CAA AAT ATC (SEQ ID NO:105)

1338-20

TGT TTG GGT ACC CGG CGG ACA TTT ATC ACA C (SEQ ID NO:106)

U. Human and Murine OPG [22-401]/Fc Fusions

Four OPG-Fc fusions were constructed where the Fc region of human IgG1 was fused at the N-terminus of either human or murine Osteoprotegerin amino acids 22 to 401 (referred to as Fc/OPG [22-401]) or at the C-terminus (referred to as OPG[22-401]/Fc). Fc fusions were constructed using the fusion vector pFc-A3 described in Example 7.

All fusion genes were constructed using standard PCR technology. Template for PCR reactions were plasmid preparations containing the target genes. Overlapping oligos were designed to combine the C-terminal portion of one gene with the N terminal portion of the other gene. This process allows fusing the two genes together in the correct reading frame after the appropriate PCR reactions have been performed. Initially one "fusion" oligo for each gene was put into a PCR reaction with a universal primer for the vector carrying the target gene. The complimentary "fusion" oligo was used with a universal primer to PCR the other gene. At the end of this first PCR reaction, two separate products were obtained, with each individual gene having the fusion site present, creating enough overlap to drive the second round of PCR and create the desired fusion. In the second round of PCR, the first two PCR products were combined along with universal primers and via the overlapping regions, the full length fusion DNA sequence was produced.

The final PCR gene products were digested with restriction endonucleases XbaI and BamHI, and then ligated into the vector pAMG21 having been also digested with the two restriction endonucleases. Ligated DNA was transformed into competent host cells of *E. coli* strain 393. Clones were screened for the ability to produce the recombinant protein product and to possess the gene fusion having the correct nucleotide sequence. Protein expression levels were determined from 50 ml shaker flask studies. Whole cell lysate, sonic pellet, and supernatant were analyzed for expression of the fusion by Coomassie stained PAGE gels and Western analysis with murine anti-OPG antibody.

Fc/huOPG [22-401]

Expression of the Fc/hu OPG [22-401] fusion peptide was detected on a Coomassie stained PAGE gel and on a Western blot. The cells have very large inclusion bodies, and the majority of the product is in the insoluble (pellet) fraction. The following primers were used to construct this OPG-Fc fusion:

1318-48

CAG CCC GGG TAA AAT GGA AAC GTT TCC TCC AAA ATA TCT TCA TT (SEQ ID NO:107)

1318-49

CGT TTC CAT TTT ACC CGG GCT GAG CGA GAG GCT CTT CTG CGT GT (SEQ ID NO:108)

Fc/muOPG [22-401]

Expression of the fusion peptide was detected on a Coomassie stained gel and on a Western blot. The cells have very large inclusion bodies, and the majority of the product is in the insoluble (pellet) fraction. The following primers were used to construct this OPG-Fc fusion:

1318-50

CGC TCA GCC CGG GTA AAA TGG AAA CGT TGC CTC CAA AAT ACC TGC (SEQ ID NO:109)

1318-51

CCA TTT TAC CCG GGC TGA GCG AGA GGC TCT TCT GCG TGT (SEQ ID NO:110)

muOPG [22-401]/Fc

Expression of the fusion peptide was detected on a Coomassie stained gel and on a Western blot. The amount of recombinant product was less than the OPG fusion proteins having the Fc region in the N terminal position. Obvious inclusion bodies were not detected. Most of the product appeared to be in the insoluble (pellet) fraction. The following primers were used to construct this OPG-Fc fusion:

1318-54

GAA AAT AAG CTG CTT AGC TGC AGC TGA ACC AAA ATC (SEQ ID NO:111)

1318-55

CAG CTG CAG CTA AGC AGC TTA TTT TCA CGG ATT G (SEQ ID NO:112)

huOPG [22-401]/Fc

Expression of the fusion peptide was not detected on a Coomassie stained gel, although a faint Western positive signal was present. Obvious inclusion bodies were not detected. The following primers were used to prepare this OPG-Fc fusion:

1318-52

AAA AAT AAG CTG CTT AGC TGC AGC TGA ACC AAA ATC (SEQ ID NO:113)

1318-53

CAG CTG CAG CTA AGC AGC TTA TTT TTA CTG ATT GG (SEQ ID NO:114)

V. Human OPG met[22-401]-Fc fusion (P25A)

This construct combines a proline to alanine amino acid change at position 25 (P25A) with the huOPG met[22-401]-Fc fusion. The plasmid was digested with restriction endonucleases ClaI and KpnI, which removes the N-terminal 28 codons of the gene, and the resulting small (less than 200 base pair) fragment was gel purified. This fragment containing the proline to alanine change was then ligated into plasmid pAMG21-huOPG [22-401]-Fc fusion which had been digested with the two restriction endonucleases. The ligated DNA was transformed into competent host cells of *E. coli* strain 393. Clones were screened for the ability to produce the recombinant protein product and to possess the gene fusion having the correct nucleotide sequence. Protein expression levels were determined from 50 ml shaker flask studies. Whole cell lysate and sonic pellet were analyzed for expression of the construct by Coomassie stained PAGE gels and Western analysis with murine anti-OPG antibody. The expression level of the fusion peptide was detected on a Coomassie stained PAGE gel and on a Western blot. The protein was in the insoluble (pellet) fraction. The cells had large inclusion bodies.

W. Human OPG met[22-401] (P25A)

A DNA sequence coding for an N-terminal methionine and amino acids 22 through 401 of human OPG with the proline at position 25 being substituted by alanine under control of the lux $P_R$ promoter in prokaryotic expression vector pAMG21 was constructed as follows: Synthetic oligos #1289-84 and 1289-85 were annealed to form an oligo linker duplex with XbaI and KpnI cohesive ends. The synthetic linker duplex utilized optimal *E. coli* codons and encoded an N-terminal methionine. The linker also included an SpeI restriction site which was not present in the original sequence. The linker duplex was directionally inserted between the XbaI and KpnI sites in pAMG21-huOPG-22-401 using standard methods. The ligation mixture was introduced into *E. coli* host GM221 by transformation. Clones were initially screened for production of the recombinant protein. Plasmid DNA was isolated from positive clones and DNA sequencing was performed to verify the DNA sequence of the HuOPG-Met[22-401](P25A) gene. The following oligonucleotides were used to generate the XbaI-KpnI linker:

Oligo #1289-84

5'-CTA GAA GGA GGA ATA ACA TAT GGA AAC TTT TGC TCC AAA ATA TCT TCA TTA TGA TGA AGA AAC TAG TCA TCA GCT GCT GTG TGA TAA ATG TCC GCC GGG TAC-3' (SEQ ID NO:115)

Oligo #1289-85

5'-CCG GCG GAC ATT TAT CAC ACA GCA GCT GAT GAC TAG TTT CTT CAT CAT AAT GAA GAT ATT TTG GAG CAA AAG TTT CCA TAT GTT ATT CCT CCT T-3' (SEQ ID NO:116)

X. Human OPG met[22-401] (P26A) and (P26D)

A DNA sequence coding for an N-terminal methionine and amino acids 22 through 401 of human OPG with the proline at position 26 being substituted by alanine under control of the lux $P_R$ promoter in prokaryotic expression vector pAMG21 was constructed as follows: Synthetic oligos #1289-86 and 1289-87 were annealed to form an oligo linker duplex with XbaI and SpeI cohesive ends. The synthetic linker duplex utilized optimal *E. coli* codons and encoded an N-terminal methionine. The linker duplex was directionally inserted between the XbaI and SpeI sites in pAMG21-huOPG [22-401](P25A) using standard methods. The ligation mixture was introduced into *E. coli* host GM221 by transformation. Clones were initially screened for production of the recombinant protein. Plasmid DNA was isolated from positive clones and DNA sequencing was performed to verify the DNA sequence of the huOPG-met[22-401](P26A) gene. One of the clones sequenced was found to have the proline at position 26 substituted by aspartic acid rather than alanine, and this clone was designated huOPG-met[22-401](P26D). The following oligonucleotides were used to generate the XbaI-SpeI linker:

Oligo #1289-86

5'-CTA GAA GGA GGA ATA ACA TAT GGA AAC TTT TCC TGC TAA ATA TCT TCA TTA TGA TGA AGA AA-3' (SEQ ID NO:117)

Oligo #1289-87

5'-CTA GTT TCT TCA TCA TAA TGA AGA TAT TTA GCA GGA AAA GTT TCC ATA TGT TAT TCC TCC TT-3' (SEQ ID NO:118)

Y. Human OPG met[22-194] (P25A)

A DNA sequence coding for an N-terminal methionine and amino acids 22 through 194 of human OPG with the proline at position 25 being substituted by alanine under control of the lux $P_R$ promoter in prokaryotic expression vector pAMG21 was constructed as follows: The plasmids pAMG21-huOPG[27-194] and pAMG21-huOPG[22-401] (P25A) were each digested with KpnI and BamHI endonucleases. The 450 bp fragment was isolated from pAMG21-huOPG[27-194] and the 6.1 kbp fragment was isolated from pAMG21-huOPG[22-401] (P25A). These fragments were ligated together and introduced into *E. coli* host GM221 by transformation. Clones were initially screened for production of the recombinant protein. Plasmid DNA was isolated from positive clones and DNA sequencing was performed to verify the DNA sequence of the huOPG-Met[22-194](P25A) gene.

Example 9

Association of OPG Monomers

Figure 15:
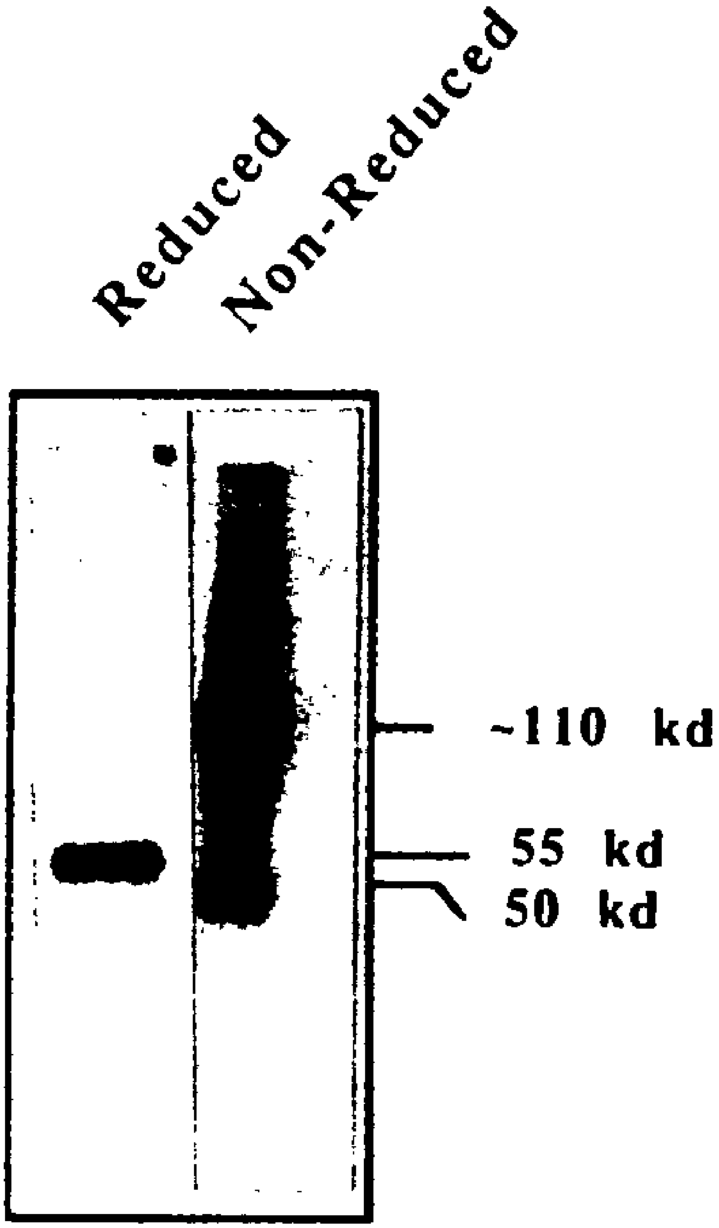
FIG. 15. Analysis of recombinant murine OPG produced in CHO cells by SDS-PAGE and western blotting. An equal amount of CHO conditioned media was applied to each lane shown, and was prepared by treatment with either reducing sample buffer (left lane), or non-reducing sample buffer (right lane). After electrophoresis, the resolved proteins were transferred to a nylon membrane, then probed with anti-OPG antibodies. The relative positions of the 55 kd monomeric and 100 kd dimeric forms of OPG are indicated by arrowheads.

CHO cells engineered to overexpress muOPG [22-401] were used to generate conditioned media for the analysis of secreted recombinant OPG using rabbit polyclonal anti-OPG antibodies. An aliquot of conditioned media was concentrated 20-fold, then analysed by reducing and non-reducing SDS-PAGE (FIG. 15). Under reducing conditions, the protein migrated as a Mr 50-55 kd polypeptide, as would be predicted if the mature product was glycosylated at one or more of its consensus N-linked glycosylation sites. Surprisingly, when the same samples were analysed by non-reducing SDS-PAGE, the majority of the protein migrated as an approximately 100 kd polypeptide, twice the size of the reduced protein. In addition, there was a smaller amount of the Mr 50-55 kd polypeptide. This pattern of migration on SDS-PAGE was consistent with the notion that the OPG product was forming dimers through oxidation of a free sulfhydryl group(s).

The predicted mature OPG polypeptide contains 23 cysteine residues, 18 of which are predicted to be involved in forming intrachain disulfide bridges which comprise the four cysteine-rich domains (FIG. 12A). The five remaining C-terminal cysteine residues are not involved in secondary structure which can be predicted based upon homology with other TNFR family members. Overall there is a net uneven number of cysteine residues, and it is formally possible that at least one residue is free to form an intermolecular disulfide bond between two OPG monomers.

Figure 16A:
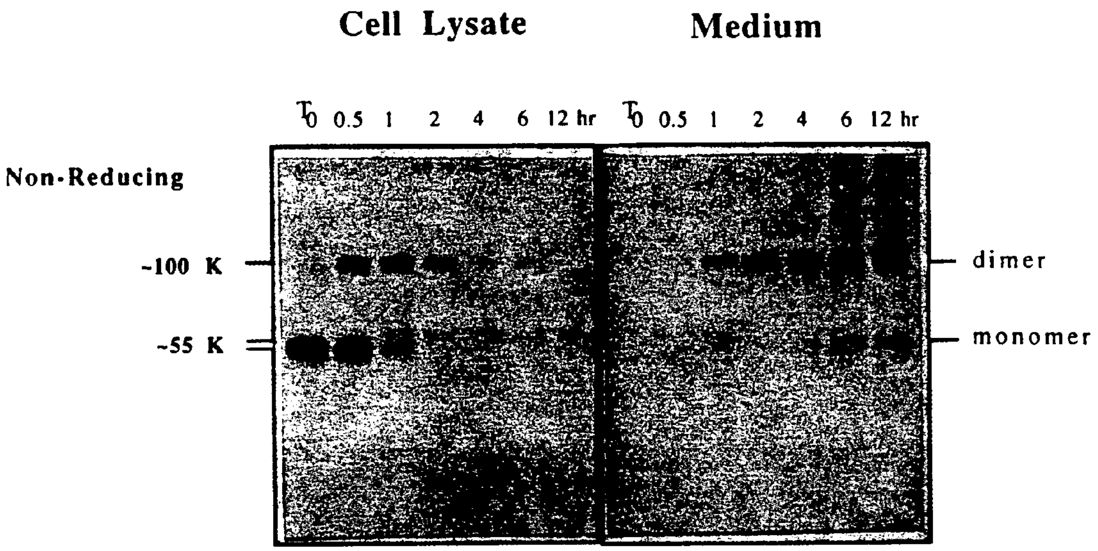
FIG. 16. Pulse-chase analysis of recombinant murine OPG produced in CHO cells. CHO cells were pulse-labeled with $^{35}$S-methionine/cysteine, then chased for the indicated time. Metabolically labeled cultures were separated into both conditioned media and cells, and detergent extracts were prepared from each, clarified, then immunoprecipitated with anti-OPG antibodies. The immunoprecipitates were the resolved by SDS-PAGE, and exposed to film. A. Top left and right panels; samples analyzed under non-reducing conditions. B. Lower left and right panels; samples analyzed under reducing conditions. Top and bottom left panels; Cell extracts. Top and bottom right panels; Conditioned media extracts. The relative mobility of the 55 kd monomeric and 100 kd dimeric forms of OPG are indicated by arrowheads.
Figure 16B:
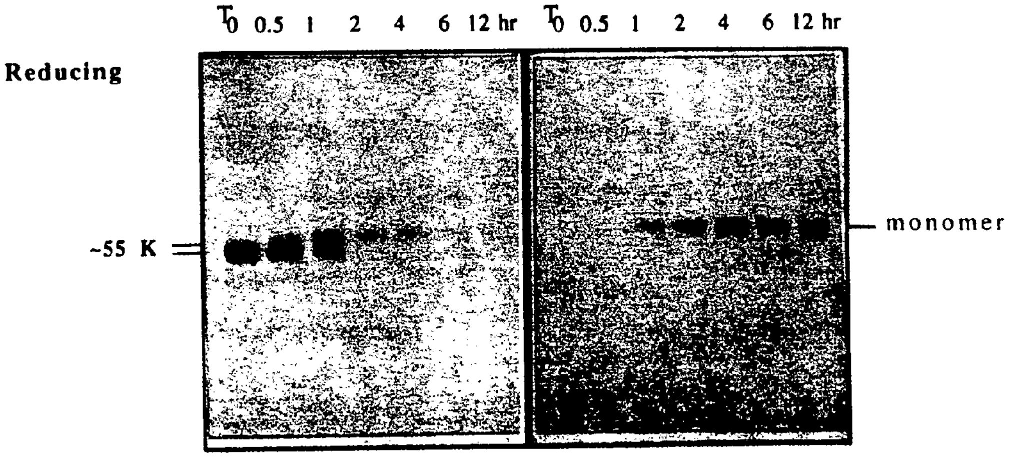

To help elucidate patterns of OPG kinesis and monomer association, a pulse-chase labelling study was performed. CHO cells expressing muOPG [22-401] were metabolically labelled as described above in serum-free medium containing $^{35}S$ methionine and cysteine for 30 min. After this period, the media was removed, and replaced with complete medium containing unlabelled methionine and cysteine at levels approximately 2,000-fold excess to the original concentration of radioactive amino acids. At 30 min, 1 hr, 2 hr, 4 hr, 6 hr and 12 hr post addition, cultures were harvested by the removal of the conditioned media, and lysates of the conditioned media and adherent monolayers were prepared. The culture media and cell lysates were clarified as described above, and then immunoprecipitated using anti-OPG antibodies as described above. After the immunoprecipitates were washed, they were released by boiling in non-reducing SDS-PAGE buffer then split into two equal halves. To one half, the reducing agent β-mercaptothanol was added to 5% (v/v) final concentration, while the other half was maintained in non-reducing conditions. Both sets of immunoprecipitates were analysed by SDS-PAGE as described above, then processed for autoradiography and exposed to film. The results are shown in FIG. 16. The samples analysed by reducing SDS-PAGE are depicted in the bottom two panels. After synthesis, the OPG polypeptide is rapidly processed to a slightly larger polypeptide, which probably represents modification by N-linked glycoslyation. After approximately 1-2 hours, the level of OPG in the cell decreases dramatically, and concomitantly appears in the culture supernatant. This appears to be the result of the vectoral transport of OPG from the cell into the media over time, consistent with the notion that OPG is a naturally secreted protein. Analysis of the same immunoprecipitates under nonreducing conditions reveals the relationship between the formation of OPG dimers and secretion into the conditioned media (FIG. 16, upper panels). In the first 30-60 minutes, OPG monomers are processed in the cell by apparent glycoslylation, followed by dimer formation. Over time, the bulk of OPG monomers are driven into dimers, which subsequently disappear from the cell. Beginning about 60 minutes after synthesis, OPG dimers appear in the conditioned media, and accumulate over the duration of the experiment. Following this period, OPG dimers are formed, which are then secreted into the culture media. OPG monomers persist at a low level inside the cell over time, and small amounts also appear in the media. This does not appear to be the result of breakdown of covalent OPG dimers, but rather the production of sub-stoichiometric amounts of monomers in the cell and subsequent secretion.

Figure 17:
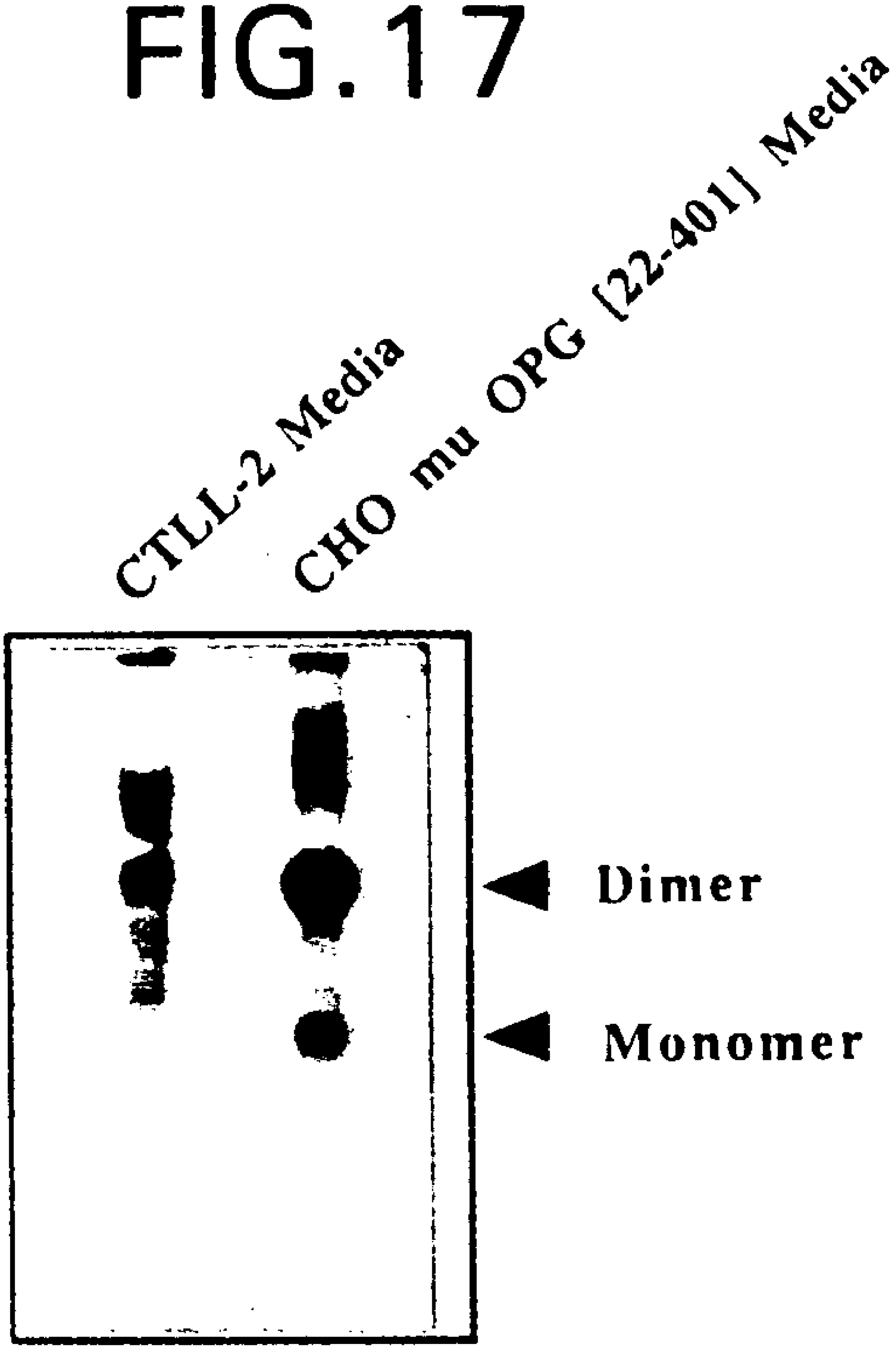
FIG. 17. Expression of OPG in the CTLL-2 cell line. Serum-free conditioned media from CTLL-2 cells and CHO-mu OPG [1-401] transfected cells was prepared, concentrated, then analyzed by non-reducing SDS-PAGE and western blotting. Left lane; CTLL-2 conditioned media. Right lane; CHO-muOPG conditioned media. The relative mobility of the 55 kd monomeric and 100 kd dimeric forms of OPG are indicated by arrowheads.

Recombinantly produced OPG from transfected CHO cells appears to be predominantly a dimer. To determine if dimerization is a natural process in OPG synthesis, we analysed the conditioned media of a cell line found to naturally express OPG. The CTLL-2 cell line, a murine cytotoxic T lymphocytic cell line (ATCC accession no. TIB-214), was found to express OPG mRNA in a screen of tissue and cell line RNA. The OPG transcript was found to be the same as the cloned and sequenced 2.5-3.0 kb RNA identified from kidney and found to encode a secreted molecule. Western blot analysis of conditioned media obtained from CTLL-2 cells shows that most, if not all, of the OPG protein secreted is a dimer (FIG. 17). This suggests that OPG dimerization and secretion is not an artifact of overexpression in a cell line, but is likely to be the main form of the product as it is produced by expressing cells.

Figure 18:
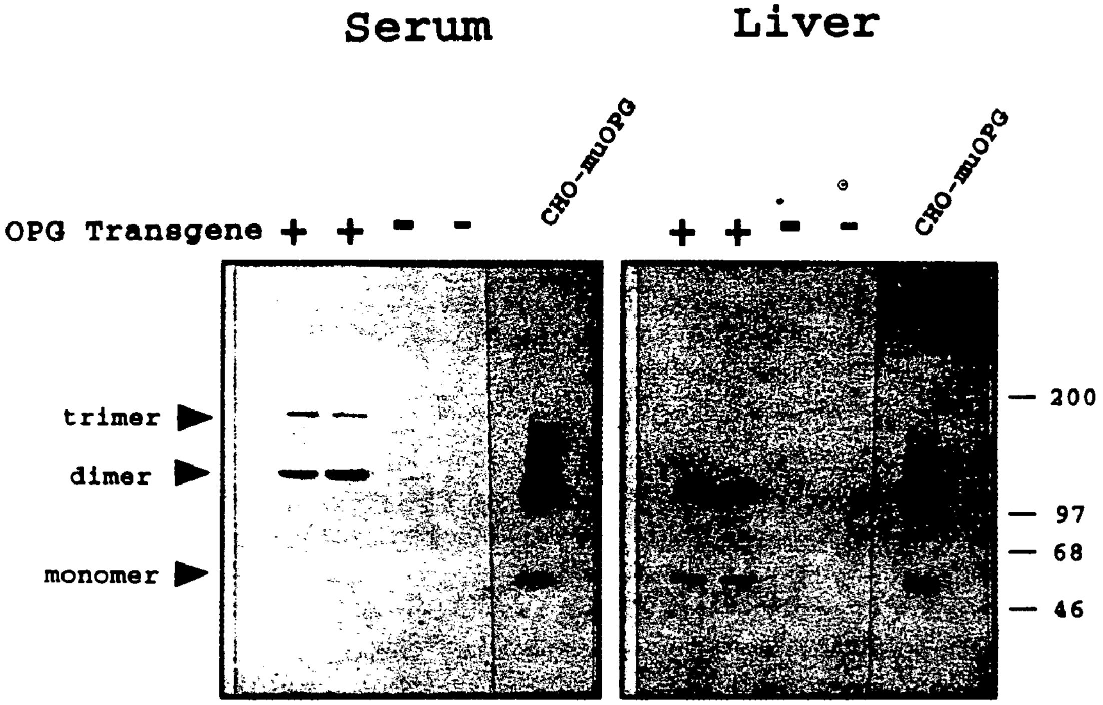
FIG. 18. Detection of OPG expression in serum samples and liver extracts obtained from control and OPG transgenic mice. Transgenic mice were constructed as described in Example 4. OPG expression was visualized after SDS-PAGE followed by Western blotting using anti-OPG antibodies.

Normal and transgenic mouse tissues and serum were analysed to determine the nature of the OPG molecule expressed in OPG transgenic mice. Since the rat OPG cDNA was expressed under the control of a hepatocyte control element, extracts made from the parenchyma of control and transgenic mice under non-reducing conditions were analysed (FIG. 18). In extract from transgenic, but not control mice, OPG dimers are readily detected, along with substoichiometric amounts of monomers. The OPG dimers and monomers appear identical to the recombinant murine protein expressed in the genetically engineered CHO cells. This strongly suggests that OPG dimers are indeed a natural form of the gene product, and are likely to be key active components. Serum samples obtained from control and transgenic mice were similarly analysed by western blot analysis. In control mice, the majority of OPG protein migrates as a dimer, while small amounts of monomer are also detected. In addition, significant amounts of a larger OPG related protein is detected, which migrates with a relative molecular mass consistent with the predicted size of a covalently-linked trimer. Thus, recombinant OPG is expressed predominantly as a dimeric protein in OPG transgenic mice, and the dimer form may be the basis for the osteopetrotic phenotype in OPG mice. OPG recombinant protein may also exist in higher molecular weight "trimeric" forms.

To determine if the five C-terminal cysteine residues of OPG play a role in homodimerization, the murine OPG codons for cytsteine residues 195 (C195), C202, C277, C319, and C400 were changed to serine using the QuickChange Site-Directed Mutagenesis Kit (Stratagene, San Diego, Calif.) as described above. The muOPG gene was subcloned between the Not I and Xba I sites of the pcDNA 3.1 (+) vector (Invitrogen, San Diego, Calif.). The resulting plasmid, pcDNA3.1-muOPG, and mutagenic primers were treated with Pfu polymerase in the presence of deoxynucleotides, then amplified in a thermocycler as described above. An aliqout of the reaction is then transfected into competent *E. coli* XL1-Blue by heatshock, then plated. Plasmid DNA from transformants was then sequenced to verify mutations.

The following primer pairs were used to change the codon for cysteine residue 195 to serine of the murine OPG gene, resulting in the production of a muOPG [22-401] C195S protein:

1389-19:

5'-CAC GCA AAA GTC GGG AAT AGA TGT CAC-3' (SEQ ID NO:150)

1406-38:

5'-GTG ACA TCT ATT CCC GAC TTT TGC GTG-3' (SEQ ID NO:151)

The following primer pairs were used to change the codon for cysteine residue 202 to serine of the murine OPG gene, resulting in the production of a muOPG [22-401] C202S protein:

1389-21:

5'-CAC CCT GTC GGA AGA GGC CTT CTT C-3' (SEQ ID NO:152)

1389-22:

5'-GAA GAA GGC CTC TTC CGA CAG GGT G-3' (1389-22) (SEQ ID NO:153)

The following primer pairs were used to change the codon for cysteine residue 277 to serine of the murine OPG gene, resulting in the production of a muOPG [22-401] C277S protein:

1389-23:

5'-TGA CCT CTC GGA AAG CAG CGT GCA-3' (SEQ ID NO:154)

1389-24:

5'-TGC ACG CTG CTT TCC GAG AGG TCA-3' (SEQ ID NO:155)

The following primer pairs were used to change the codon for cysteine residue 319 to serine of the murine OPG gene, resulting in the production of a muOPG [22-401] C319S protein:

1389-17:

5'-CCT CGA AAT CGA GCG AGC AGC TCC-3' (SEQ ID NO:156)

1389-18:

5'-CGA TTT CGA GGT CTT TCT CGT TCT C-3' (SEQ ID NO:157)

The following primer pairs were used to change the codon for cysteine residue 400 to serine of the murine OPG gene, resulting in the production of a muOPG [22-401] C400S protein:

1406-72:

5'-CCG TGA AAA TAA GCT CGT TAT AAC TAG GAA TGG-3' (SEQ ID NO:158)

1406-75:

5'-CCA TTC CTA GTT ATA ACG AGC TTA TTT TCA CGG-3' (SEQ ID NO:159)

Each resulting muOPG [22-401] plasmid containing the appropriate mutation was then transfected into human 293 cells, the mutant OPG-Fc fusion protein purified from conditioned media as described above. The biological activity of each protein was assessed the in vitro osteoclast forming assay described in example 11. Conditioned media from each transfectant was analysed by non-reducing SDS-PAGE and western blotting with anti-OPG antibodies.

Mutation of any of the five C-terminal cysteine residues results in the production of predominantly (>90%) monomeric 55 kd OPG molecules. This strongly suggests that the C-terminal cysteine residues together play a role in OPG homodimerization.

C-terminal OPG deletion mutants were constructed to map the region(s) of the OPG C-terminal domain which are important for OPG homodimerization. These OPG mutants were constructed by PCR amplification using primers which introduce premature stop translation signals in the C-terminal region of murine OPG. The 5' oligo was designed to the MuOPG start codon (containing a HindIII restriction site) and the 3' oligonucleotides (containing a stop codon and XhoI site) were designed to truncate the C-terminal region of muOPG ending at either threonine residue 200 (CT 200), proline 212 (CT212), glutamic acid 293 (CT-293), or serine 355 (CT-355).

The following primers were used to construct muOPG [22-200]:

1091-39:

5'-CCT CTG AGC TCA AGC TTC CGA GGA CCA CAA TGA ACA AG-3' (SEQ ID NO:160)

1391-91:

5'-CCT CTC TCG AGT CAG GTG ACA TCT ATT CCA CAC TTT TGC GTG GC-3' (1391-91) (SEQ ID NO:161)

The following primers were used to construct muOPG [22-212]:

1091-39:

5'-CCT CTG AGC TCA AGC TTC CGA GGA CCA CAA TGA ACA AG-3' (SEQ ID NO:162)

1391-90:

5'-CCT CTC TCG AGT CAA GGA ACA GCA AAC CTG AAG AAG GC-3' (SEQ ID NO:163)

The following primers were used to construct muOPG [22-293]:

1091-39:

5'-CCT CTG AGC TCA AGC TTC CGA GGA CCA CAA TGA ACA AG-3' (SEQ ID NO:164)

1391-89:

5'-CCT CTC TCG AGT CAC TCT GTG GTG AGG TTC GAG TGG CC-3' (SEQ ID NO:165)

The following primers were used to construct muOPG [22-355]:

1091-39:

5'-CCT CTG AGC TCA AGC TTC CGA GGA CCA CAA TGA ACA AG-3' (SEQ ID NO:166)

1391-88:

5' CCT CTC TCG AGT CAG GAT GTT TTC AAG TGC TTG AGG GC-

3'

(SEQ ID NO:167)

Each resulting muOPG-CT plasmid containing the appropriate truncation was then transfected into human 293 cells, the mutant OPG-Fc fusion protein purified from conditioned media as described above. The biological activity of each protein was assessed the in vitro osteoclast forming assay described in example 11. The conditioned medias were also analysed by non-reducing SDS-PAGE and western blotting using anti-OPG antibodies.

Truncation of the C-terminal region of OPG effects the ability of OPG to form homodimers. CT 355 is predominantly monomeric, although some dimer is formed. CT 293 forms what appears to be equal molar amounts of monomer and dimer, and also high molecular weight aggregates. However, CT 212 and CT 200 are monomeric.

Example 10

Purification of OPG

A. Purification of Mammalian OPG-Fc Fusion Proteins

5 L of conditioned media from 293 cells expressing an OPG-Fc fusion protein were prepared as follows. A frozen sample of cells was thawed into 10 ml of 293S media (DMEM-high glucose, 1×L-glutamine, 10% heat inactivated fetal bovine serum (FBS) and 100 ug/ml hygromycin) and fed with fresh media after one day. After three days, cells were split into two T175 flasks at 1:10 and 1:20 dilutions. Two additional 1:10 splits were done to scale up to 200 T175 flasks. Cells were at 5 days post-thawing at this point. Cells were grown to near confluency (about three days) at which time serum-containing media was aspirated, cells were washed one time with 25 ml PBS per flask and 25 ml of SF media (DMEM-high glucose, 1×L-glutamine) was added to each flask. Cells were maintained at 5% CO2 for three days at which point the media was harvested, centrifuged, and filtered through 0.45 m cellulose nitrate filters (Corning).

OPG-Fc fusion proteins were purified using a Protein G Sepharose column (Pharmacia) equilibrated in PBS. The column size varied depending on volume of starting media. Conditioned media prepared as described above was loaded onto the column, the column washed with PBS, and pure protein eluted using 100 mM glycine pH 2.7. Fractions were collected into tubes containing 1M Tris pH 9.2 in order to neutralize as quickly as possible. Protein containing fractions were pooled, concentrated in either an Amicon Centricon 10 or Centriprep 10 and diafiltered into PBS. The pure protein is stored at −80° C.

Murine [22-401]-Fc, Murine [22-180]-Fc, Murine [22-194]-Fc, human [22-401]-Fc and human [22-201]Fc were purified by this procedure. Murine [22-185]-Fc is purified by this procedure.

B. Preparation of Anti-OPG Antibodies

Three New Zealand White rabbits (5-8 lbs initial wt) were injected subcutaneously with muOPG[22-401]-Fc fusion protein. Each rabbit was immunized on day 1 with 50 μg of antigen emulsified in an equal volume of Freunds complete adjuvant. Further boosts (Days 14 and 28) were performed by the same procedure with the substitution of Freunds incomplete adjuvant. Antibody titers were monitored by EIA. After the second boost, the antisera revealed high antibody titers and 25 ml production bleeds were obtained from each animal. The sera was first passed over an affinity column to which murine OPG-Fc had be immobilized. The anti-OPG antibodies were eluted with Pierce Gentle Elution Buffer containing 1% glacial acetic acid. The eluted protein was then dialyzed into PBS and passed over a Fc column to remove any antibodies specific for the Fc portion of the OPG fusion protein. The run through fractions containing anti-OPG specific antibodies were dialyzed into PBS.

C. Purification of murine OPG[22-401]

Antibody Affinity Chromatography

Affinity purified anti-OPG antibodies were diafiltered into coupling buffer (0.1M sodium carbonate pH 8.3, 0.5M NaCl), and mixed with CNBr-activated sepharose beads (Pharmacia) for two hours at room temperature. The resin was then washed with coupling buffer extensively before blocking unoccupied sited with 1M ethanolamine (pH 8.0) for two hours at room temperature. The resin was then washed with low pH (0.1M sodium acetate pH 4.0, 0.5M NaCl) followed by a high pH wash (0.1M Tris-HCl pH 8.0, 0.5M NaCl). The last washes were repeated three times. The resin was finally equilibrated with PBS before packing into a column. Once packed, the resin was washed with PBS. A blank elution was performed with 0.1M glycine-HCl, pH 2.5), followed by re-equilibration with PBS.

Concentrated conditioned media from CHO cells expressing muOPG[22-410] was applied to the column at a low flow rate. The column was washed with PBS until UV absorbance measured at 280 nm returned to baseline. The protein was eluted from the column first with 0.1M glycine-HCl (pH 2.5), re-equilibrated with PBS, and eluted with a second buffer (0.1M CAPS, pH 10.5), 1M NaCl). The two elution pools were diafiltered separately into PBS and sterile filtered before freezing at −20° C.

Conventional Chromatography

CHO cell conditioned media was concentrated 23× in an Amicon spiral wound cartridge (S10Y10) and diafiltered into 20 mM tris pH 8.0. The diafiltered media was then applied to a Q-sepharose HP (Pharmacia) column which had been equilibrated with 20 mM tris pH 8.0. The column was then washed until absorbence at 280 nm reached baseline. Protein was eluted with a 20 column volume gradient of 0-300 mM NaCl in tris pH 8.0. OPG protein was detected using a western blot of column fractions.

Fractions containing OPG were pooled and brought to a final concentration of 300 mM NaCl, 0.2 mM DTT. A NiNTA superose (Qiagen) column was equilibrated with 20 mM tris pH 8.0, 300 mM NaCl, 0.2 mM DTT after which the pooled fractions were applied. The column was washed with equilibration buffer until baseline absorbence was reached. Proteins were eluted from the column with a 0-30 mM Imidazole gradient in equilibration buffer. Remaining proteins were washed off the column with 1M Imidazole. Again a western blot was used to detect OPG containing fractions.

Pooled fractions from the NiNTA column were dialyzed into 10 mm potassium phosphate pH 7.0, 0.2 mM DTT. The dialyzed pool was then applied to a ceramic hydroxyapatite column (Bio-Rad) which had been equilibrated in 10 mM phosphate buffer. After column washing, the protein was eluted with a 10-100 mM potassium phosphate gradient over 20 column volumes. This was then followed by a 20 column volume gradient of 100-400 mM phosphate.

OPG was detected by coomassie blue staining of SDS-polyacrylamide gels and by western blotting. Fractions were pooled and diafiltered onto PBS and frozen at −80° C. The purified protein runs as a monomer and will remain so after diafiltration into PBS. The monomer is stable when stored frozen or at pH 5 at 4° C. However if stored at 4° C. in PBS, dimers and what appears to be trimers and tetramers will form after one week.

D. Purification of Human OPG met[22-401] from *E. coli*

The bacterial cell paste was suspended into 10 mM EDTA to a concentration of 15% (w/v) using a low shear homogenizer at 5° C. The cells were then disrupted by two homogenizations at 15,000 psi each at 5° C. The resulting homogenate was centrifuged at 5,000×g for one hour at 5° C. The centrifugal pellet was washed by low shear homogenization into water at the original homogenization volume followed by centrifugation as before. The washed pellet was then solubilized to 15% (w/v) by a solution of (final concentration) 6 M guanidine HCl, 10 mM dithiothreitol, 10 mM TrisHCl, pH 8.5 at ambient temperature for 30 minutes. This solution was diluted 30-fold into 2M urea containing 50 mM CAPS, pH 10.5, 1 mM reduced glutathione and then stirred for 72 hours at 5° C. The OPG was purified from this solution at 25° C. by first adjustment to pH 4.5 with acetic acid and then chromatography over a column of SP-HP Sepharose resin equilibrated with 25 mM sodium acetate, pH 4.5. The column elution was carried out with a linear sodium chloride gradient from 50 mM to 550 mM in the same buffer using 20 column volumes at a flow rate of 0.1 column volumes/minute. The peak fractions containing only the desired OPG form were pooled and stored at 5° C. or buffer exchanged into phosphate buffered saline, concentrated by ultrafiltration, and then stored at 5° C. This material was analyzed by reverse phase HPLC, SDS-PAGE, limulus amebocyte lysate assay for the presence of endotoxin, and N-terminal sequencing. In addition, techniques such as mass spectrometry, pH/temperature stability, fluoresence, circular dichroism, differential scanning calorimetry, and protease profiling assays may also be used to examine the folded nature of the protein.

Example 11

Biological Activity of Recombinant OPG

Based on histology and histomorphometry, it appeared that hepatic overexpression of OPG in transgenic mice markedly decreased the numbers of osteoclasts leading to a marked increase in bone tissue (see Example 4). To gain further insight into potential mechanism(s) underlying this in vivo effect, various forms of recombinant OPG have been tested in an in vitro culture model of osteoclast formation (osteoclast forming assay). This culture system was originally devised by Udagawa (Udagawa et al. Endocrinology 125, 1805-1813 (1989), Proc. Natl. Acad. Sci. USA 87, 7260-7264 (1990)) and employs a combination of bone marrow cells and cells from bone marrow stromal cell lines. A description of the modification of this culture system used for these studies has been previously published (Lacey et al. Endocrinology 136, 2367-2376 (1995)). In this method, bone marrow cells, flushed from the femurs and tibiae of mice, are cultured overnight in culture media (alpha MEM with 10% heat inactivated fetal bovine serum) supplemented with 500 U/ml CSF-1 (colony stimulating factor 1, also called M-CSF), a hematopoietic growth factor specific for cells of the monocyte/macrophage family lineage. Following this incubation, the non-adherent cells are collected, subjected to gradient purification, and then cocultured with cells from the bone marrow cell line ST2 ($1\times10^6$ non-adherent cells $1\times10^5$ ST2 cells/ml media). The media is supplemented with dexamethasone (100 nM) and the biologically-active metabolite of vitamin D3 known as 1,25 dihydroxyvitamin D3 (1,25 (OH)2 D3, 10 nM). To enhance osteoclast appearance, prostaglandin E2 (250 nM) is added to some cultures. The coculture period usually ranges from 8-10 days and the media, with all of the supplements freshly added, is renewed every 3-4 days. At various intervals, the cultures are assessed for the presence of tartrate acid phosphatase (TRAP) using either a histochemical stain (Sigma Kit # 387A, Sigma, St. Louis, Mo.) or TRAP solution assay. The TRAP histochemical method allows for the identification of osteoclasts phenotypically which are multinucleated (·3 nuclei) cells that are also TRAP+. The solution assay involves lysing the osteoclast-containing cultures in a citrate buffer (100 mM, pH 5.0) containing 0.1% Triton X-100. Tartrate resistant acid phosphatase activity is then measured based on the conversion of p-nitrophenylphosphate (20 nM) to p-nitrophenol in the presence of 80 mM sodium tartrate which occurs during a 3-5 minute incubation at RT. The reaction is terminated by the addition of NaOH to a final concentration of 0.5 M. The optical density at 405 nm is measured and the results are plotted.

Previous studies (Udagawa et al. ibid) using the osteoclast forming assay have demonstrated that these cells express receptors for $^{125}$I-calcitonin (autoradiography) and can make pits on bone surfaces, which when combined with TRAP positivity confirm that the multinucleated cells have an osteoclast phenotype. Additional evidence in support of the osteoclast phenotype of the multinucleated cells that arise in vitro in the osteoclast forming assay are that the cells express αv and β3 integrins by immunocytochemistry and calcitonin receptor and TRAP mRNA by in situ hybridization (ISH).

Figure 19A:
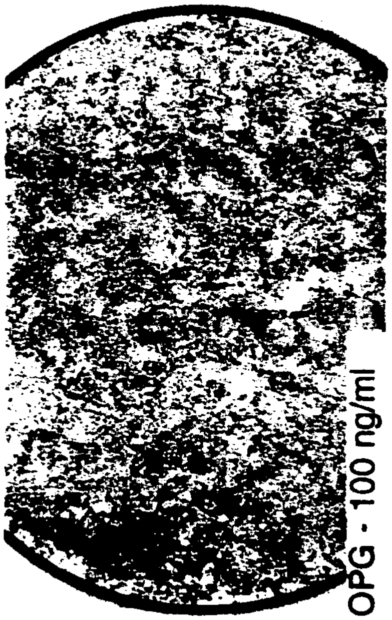
FIG. 19. Effects of huOPG [22-401]-Fc fusion protein on osteoclast formation in vitro. The osteoclast forming assay was performed as described in Example 11A in the absence (control) or presence of the indicated amounts of huOPG [22-401]-Fc fusion. Osteoclast formation was visualized by histochemical staining for tartrate acid phosphatase (TRAP) .). A. OPG added to 100 ng/ml. D. OPG added to 0.1 ng/ml. E. OPG added to 0.01 ng/ml. F. OPG added to 0.001 ng/ml. G. Control. No OPG added.
Figure 19B:
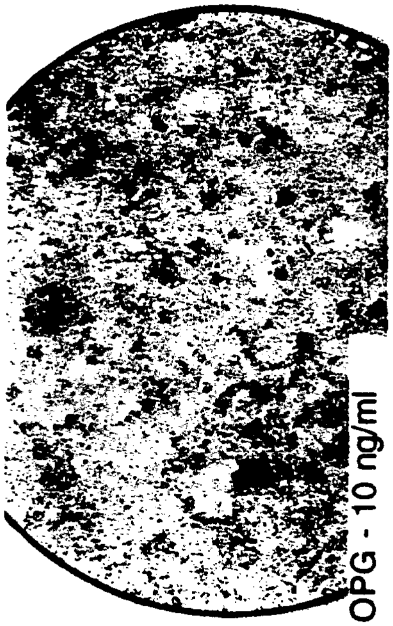
Figure 19C:
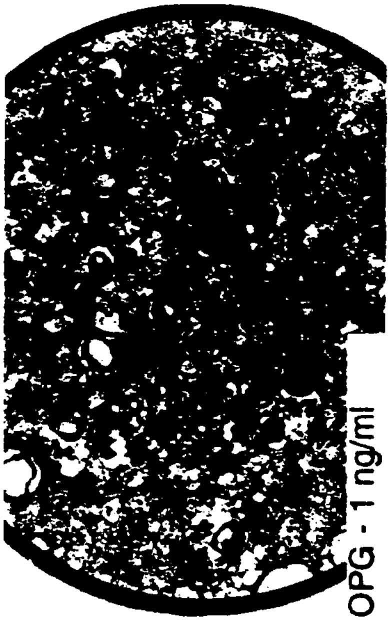
Figure 19D:
Figure 19F:
Figure 19E:
Figure 19G:
Figure 20:
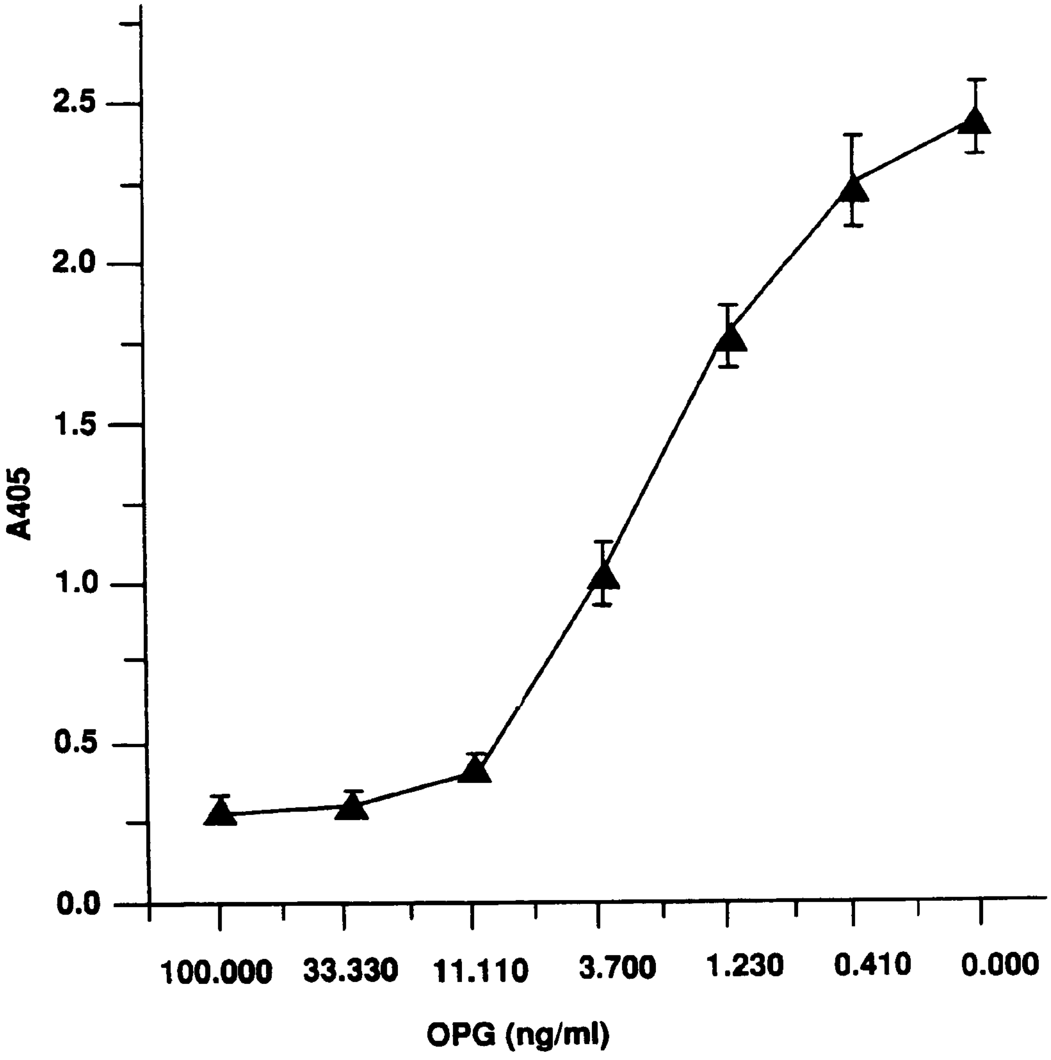
FIG. 20. Decrease in osteoclast culture TRAP activity with increasing amounts of OPG. Indicated concentrations of huOPG [22-401]-Fc fusion protein were added to osteoclast forming assay and TRAP activity quantitated as described in Example 11A.

The huOPG [22-401]-Fc fusion was purified from CHO cell conditioned media and subsequently utilized in the osteoclast forming assay. At 100 ng/ml of huOPG [22-401]-Fc, osteoclast formation was virtually 100% inhibited (FIG. 19A). The levels of TRAP measured in lysed cultures in microtitre plate wells were also inhibited in the presence of OPG with an $ID_{50}$ of approximately 3 ng/ml (FIG. 20). The level of TRAP activity in lysates appeared to correlate with the relative number of osteoclasts seen by TRAP cytochemistry (compare FIGS. 19A-19G and 20). Purified human IgG1 and TNFbp were also tested in this model and were found to have no inhibitory or stimulatory effects suggesting that the inhibitory effects of the huOPG [22-401]-Fc were due to the OPG portion of the fusion protein. Additional forms of the human and murine molecules have been tested and the cumulative data are summarized in Table 1.

TABLE 1

Effects of various OPG forms on in vitro osteoclast formation

| OPG Construct | Relative Bioactivity in vitro |
|---|---|
| muOPG [22-401]-Fc | +++ |
| muOPG [22-194]-Fc | +++ |
| muOPG [22-185]-Fc | ++ |
| muOPG [22-180]-Fc | − |

TABLE 1-continued

| Effects of various OPG forms on in vitro osteoclast formation | |
|---|---|
| OPG Construct | Relative Bioactivity in vitro |
| muOPG [22-401] | +++ |
| muOPG [22-401] C195 | +++ |
| muOPG [22-401] C202 | + |
| muOPG [22-401] C277 | − |
| muOPG [22-401] C319 | + |
| muOPG [22-401] C400 | + |
| muOPG [22-185] | − |
| muOPG [22-194] | ++ |
| muOPG [22-200] | ++ |
| muOPG [22-212] | − |
| muOPG [22-293] | +++ |
| muOPG [22-355] | +++ |
| huOPG [22-401]-Fc | +++ |
| huOPG [22-201]-Fc | +++ |
| huOPG [22-401]-Fc P26A | +++ |
| huOPG [22-401]-Fc Y28F | +++ |
| huOPG [22-401] | +++ |
| huOPG [27-401]-Fc | ++ |
| huOPG [29-401]-Fc | ++ |
| huOPG [32-401]-Fc | +/− |

+++, $ED_{50}$ = 0.4-2 ng/ml
++, $ED_{50}$ = 2-10 ng/ml
+, $ED_{50}$ = 10-100 ng/ml
−, $ED_{50}$ > 100 ng/ml

The cumulative data suggest that murine and human OPG amino acid sequences 22-401 are fully active in vitro, when either fused to the Fc domain, or unfused. They inhibit in a dose-dependent manner and possess half-maximal activities in the 2-10 ng/ml range. Truncation of the murine C-terminus at threonine residue 180 inactivates the molecule, whereas truncations at cysteine 185 and beyond have full activity. The cysteine residue located at position 185 is predicted to form an SS3 bond in the domain 4 region of OPG. Removal of this residue in other TNFR-related proteins has previously been shown to abrogate biological activity (Yan et al. J. Biol. Chem. 266, 12099-12104 (1994)). Our finding that muOPG [22-180]-Fc is inactive while muOPG[22-185]-Fc is active is consistent with these findings. This suggests that amino acid residues 22-185 define a region for OPG activity.

These findings indicate that like transgenically-expressed OPG, recombinant OPG protein also suppressed osteoclast formation as tested in the osteoclast forming assay. Time course experiments examining the appearance of TRAP+ cells, β3+ cells, F480+ cells in cultures continuously exposed to OPG demonstrate that OPG blocks the appearance TRAP+ and P3+ cells, but not F480+ cells. In contrast, TRAP+ and P3+ cells begin to appear as early as day 4 following culture establishment in control cultures. Only F480+ cells can be found in OPG-treated cultures and they appear to be present at qualitatively the same numbers as the control cultures. Thus, the mechanism of OPG effects in vitro appears to involve a blockade in osteoclast differentiation at a step beyond the appearance of monocyte-macrophages but before the appearance of cells expressing either TRAP or β3 integrins. Collectively these findings indicate that OPG does not interfere with the general growth and differentiation of monocyte-macrophage precursors from bone marrow, but rather suggests that OPG specifically blocks the selective differentiation of osteoclasts from monocyte-macrophage precursors.

Figure 21:
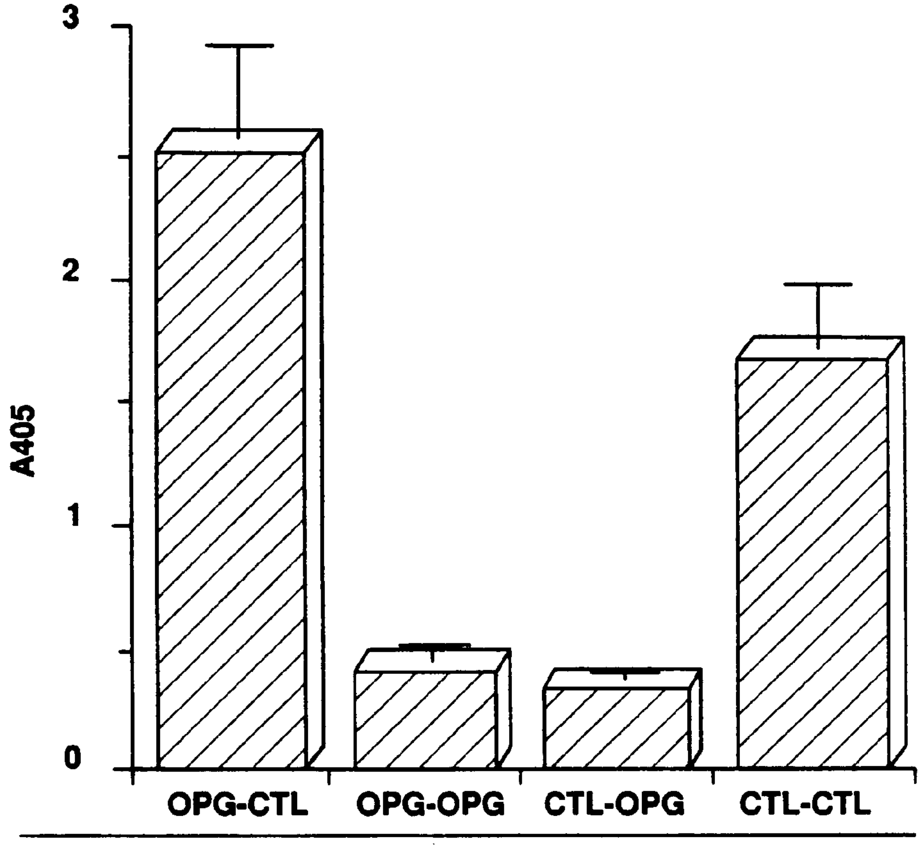
FIG. 21. Effect of OPG on a terminal stage of osteoclast differentiation. huOPG [22-401]-Fc fusion was added to the osteoclast forming assay during the intermediate stage of osteoclast maturation (days 5-6; OPG-CTL) or during the terminal stage of osteoclast maturation (days 7-15; CTL-OPG). TRAP activity was quantitated and compared with the activity observed in the absence of OPG (CTL-CTL) in the presence of OPG throughout (OPG-OPG).

To determine more specifically when in the osteoclast differentiation pathway that OPG was inhibitory, a variation of the in vitro culture method was employed. This variation, described in (Lacey et al. supra), employs bone marrow macrophages as osteoclast precursors. The osteoclast precursors are derived by taking the nonadherent bone marrow cells after an overnight incubation in CSF-1/M-CSF, and culturing the cells for an additional 4 days with 1,000-2,000 U/ml CSF-1. Following 4 days of culture, termed the growth phase, the non-adherent cells are removed. The adherent cells, which are bone marrow macrophages, can then be exposed for up to 2 days to various treatments in the presence of 1,000-2,000 U/ml CSF-1. This 2 day period is called the intermediate differentiation period. Thereafter, the cell layers are again rinsed and then ST-2 cells ($1\times10^5$ cell/ml), dexamethasone (100 nM) and 1,25 (OH)2 D3 (10 nM) are added for the last 8 days for what is termed the terminal differentiation period. Test agents can be added during this terminal period as well. Acquisition of phenotypic markers of osteoclast differentiation are acquired during this terminal period (Lacey et al. ibid).

huOPG [22-401]-Fc (100 ng/ml) was tested for its effects on osteoclast formation in this model by adding it during either the intermediate, terminal or, alternatively, both differentiation periods. Both TRAP cytochemistry and solution assays were performed. The results of the solution assay are shown in FIG. 21. HuOPG [22-401]-Fc inhibited the appearance of TRAP activity when added to both the intermediate and terminal or only the terminal differentiation phases. When added to the intermediate phase and then removed from the cultures by rinsing, huOPG [22-401]-Fc did not block the appearance of TRAP activity in culture lysates. The cytochemistry results parallel the solution assay data. Collectively, these observations indicate that huOPG [22-401]-Fc only needs to be present during the terminal differentiation period for it to exert its all of its suppressive effects on osteoclast formation.

B. In vivo IL1-α and ILL-β challenge experiments

IL1 increases bone resorption both systemically and locally when injected subcutaneously over the calvaria of mice (Boyce et al., Endocrinology 125, 1142-1150 (1989)). The systemic effects can be assessed by the degree of hypercalcemia and the local effects histologically by assessing the relative magnitude of the osteoclast-mediated response. The aim of these experiments was to determine if recombinant muOPG [22-401]-Fc could modify the local and/or systemic actions of IL1 when injected subcutaneously over the same region of the calvaria as IL1.

IL-1 β Experiment

Male mice (ICR Swiss white) aged 4 weeks were divided into the following treatment groups (5 mice per group): Control group: IL1 treated animals (mice received 1 injection/day of 2.5 ug of IL1-β); Low dose muOPG [22-401]-Fc treated animals (mice received 3 injections/day of 1 μg of muOPG [22-401]-Fc); Low dose muopg [22-401]-Fc and IL1-β; High dose muOPG [22-401]-Fc treated animals (mice receive 3 injections/day of 10 μg muOPG [22-401]-Fc); High dose muOPG [22-401]-Fc and IL1-β. All mice received the same total number of injections of either active factor or vehicle (0.1% bovine serum albumin in phosphate buffered saline). All groups are sacrificed on the day after the last injection. The weights and blood ionized calcium levels are measured before the first injections, four hours after the second injection and 24 hours after the third IL1 injection, just before the animals were sacrificed. After sacrifice the calvaria were removed and processed for paraffin sectioning.

IL1-α Experiment

Male mice (ICR Swiss white) aged 4 weeks were divided into the following treatment groups (5 mice per group): Control group; IL1 alpha treated animals (mice received 1 injection/day of 5 ug of IL1-alpha); Low dose muOPG [22-401]-Fc treated animals (mice received 1 injection/day of 10 μg of muOPG [22-401]-Fc; Low dose muopg [22-401]-Fc and IL1-alpha, (dosing as above); High dose muopg [22-401]-Fc treated animals (mice received 3 injections/day of 10 μg muOPG [22-401]-Fc; High dose muOPG [22-401]-Fc and IL1-α. All mice received the same number of injections/day of either active factor or vehicle. All groups were sacrificed on the day after the last injection. The blood ionized calcium levels were measured before the first injection, four hours after the second injection and 24 hours after the third IL1 injection, just before the animals were sacrificed. The animal weights were measured before the first injection, four hours after the second injection and 24 hours after the third IL1 injection, just before the animals were sacrificed. After sacrifice the calvaria were removed and processed for paraffin sectioning.

Histological Methods

Calvarial bone samples were fixed in zinc formalin, decalcified in formic acid, dehydrated through ethanol and mounted in paraffin. Sections (5 μm thick) were cut through the calvaria adjacent to the lambdoid suture and stained with either hematoxylin and eosin or reacted for tartrate resistant acid phosphatase activity (Sigma Kit #387A) and counterstained with hematoxylin. Bone resorption was assessed in the IL1-α treated mice by histomorphometric methods using the Osteomeasure (Osteometrics, Atlanta, Ga.) by tracing histologic features onto a digitizor platen using a microscope-mounted camera lucida attachment. Osteoclast numbers, osteoclast lined surfaces, and eroded surfaces were determined in the marrow spaces of the calvarial bone. The injected and non-injected sides of the calvaria were measured separately.

Results

Figure 22A:
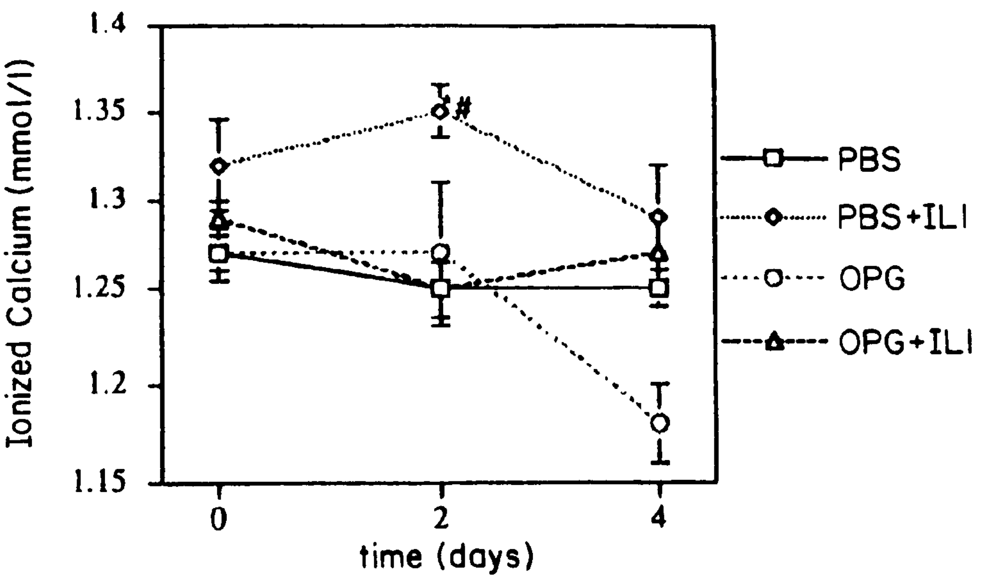
FIG. 22. Effects of IL-1β, IL-1α and OPG on blood ionized calcium in mice. Levels of blood ionized calcium were monitored after injection of IL-1β alone, IL-1α alone, IL-1β plus muOPG [22-401]-Fc, IL-1α plus MuOPG [22-401]-Fc, and muOPG [22-401]-Fc alone. Control mice received injections of phosphate buffered saline (PBS) only. IL-1β experiment shown in A; IL-1α experiment shown in B.
Figure 22B:
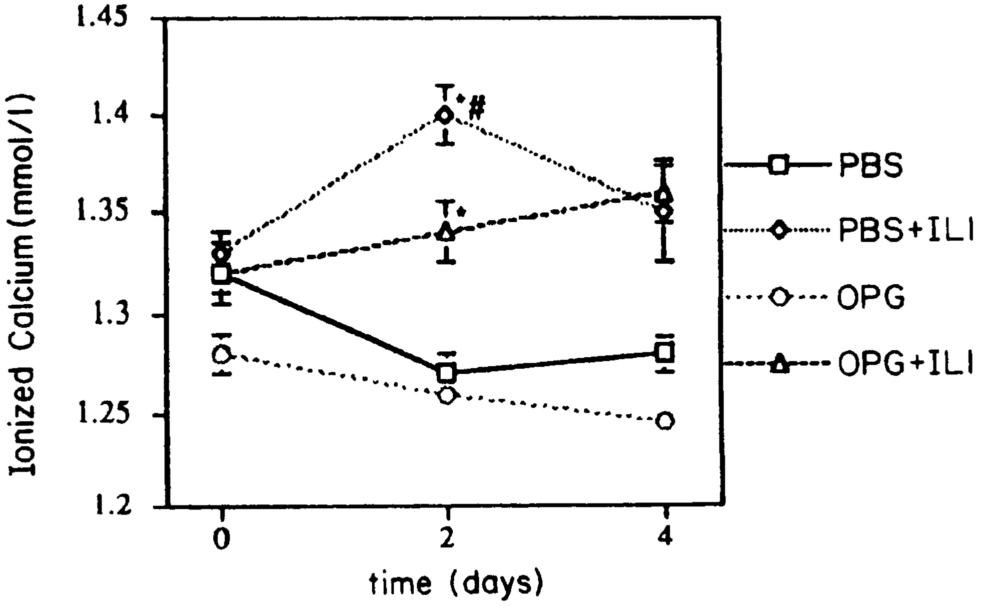

IL1-α and ILL-β produced hypercalcemia at the doses used, particularly on the second day, presumably by the induction of increased bone resorption systemically. The hypercalcemic response was blocked by muOPG [22-401]-Fc in the IL1-beta treated mice and significantly diminished in mice treated with IL1-alpha, an effect most apparent on day 2 (FIG. 22A-22B).

Figure 23A:
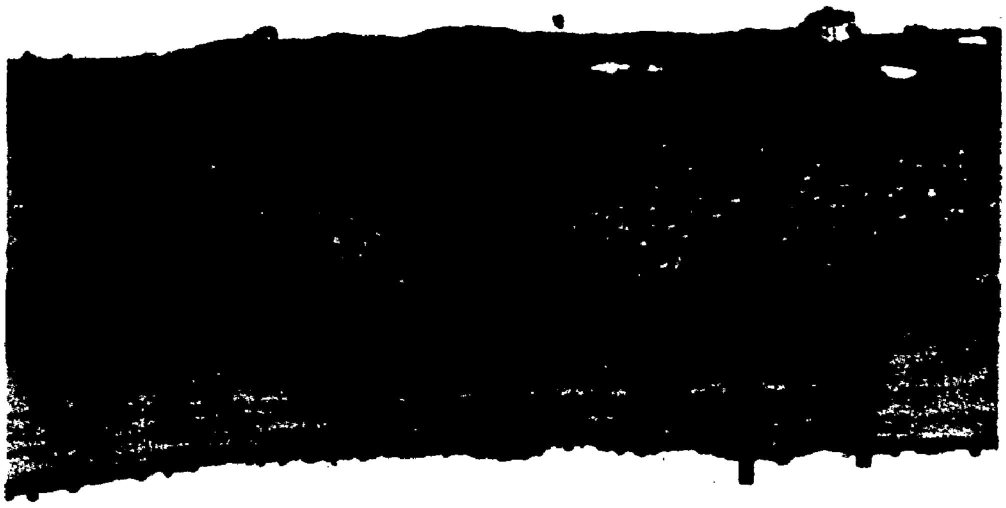
FIG. 23. Effects of OPG on calvarial osteoclasts in control and IL1-treated mice. Histological methods for analyzing mice calvarial bone samples are described in Example 11B. Arrows indicate osteoclasts present in day 2-treated mice. Calvarial samples of mice receiving four PBS injections daily (A), one injection of IL-1 and three injections of PBS daily (B), one injection of PBS and three injections of OPG daily (C), one injection of IL-1 and three injections of OPG daily.
Figure 23B:
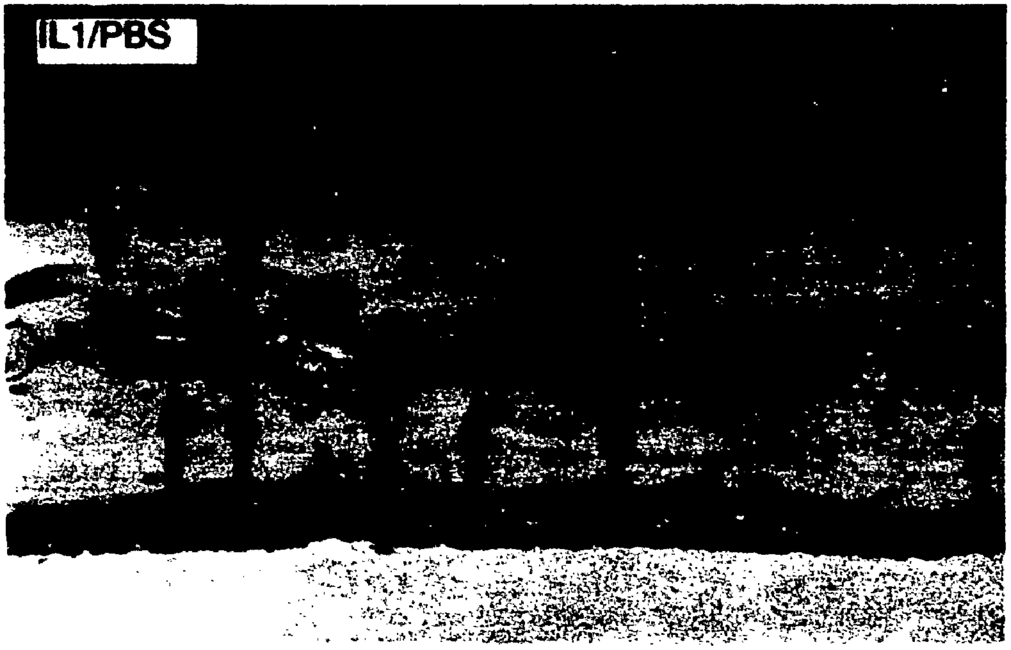
Figure 23C:
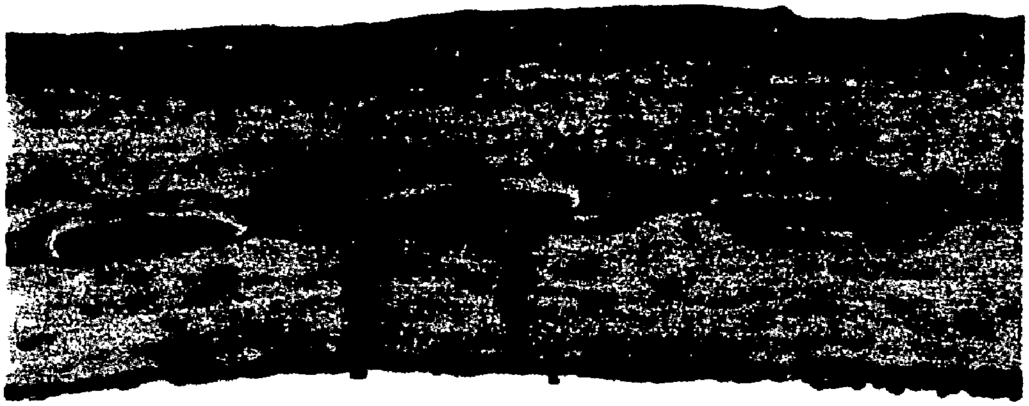
Figure 23D:
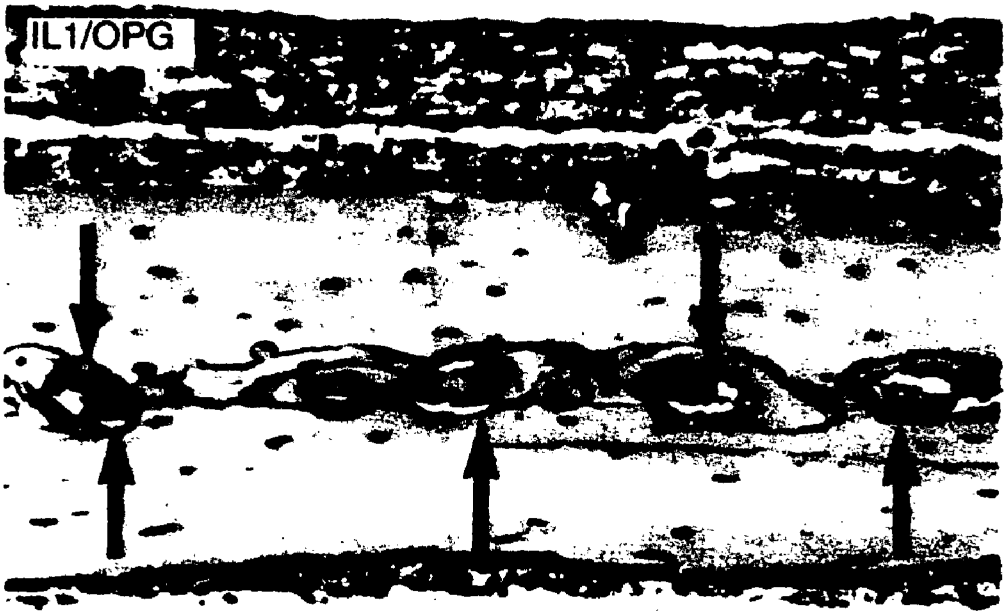

Histologic analysis of the calvariae of mice treated with IL1-alpha and beta shows that IL1 treatments alone produce a marked increase in the indices of bone resorption including: osteoclast number, osteoclast lined surface, and eroded surface (surfaces showing deep scalloping due to osteoclastic action (FIG. 23B, Table 2). In response to IL1-α or ILL-β, the increases in bone resorption were similar on the injected and non-injected sides of the calvaria. Muopg [22-401]-Fc injections reduced bone resorption in both IL1-alpha and beta treated mice and in mice receiving vehicle alone but this reduction was seen only on the muopg [22-401]-Fc injected sides of the calvariae.

The most likely explanation for these observations is that muOPG [22-401]-Fc inhibited bone resorption, a conclusion supported by the reduction of both the total osteoclast number and the percentage of available bone surface undergoing bone resorption, in the region of the calvaria adjacent to the muOPG [22-401]-Fc injection sites. The actions of muOPG [22-401]-Fc appeared to be most marked locally by histology, but the fact that muOPG [22-401]-Fc also blunted IL1-induced hypercalcemia suggests that muOPG [22-401]-Fc has more subtle effects on bone resorption systemically.

Table 2. Effects of OPG on variables of bone resorption in IL-1 injected mice.

C. Systemic Effects of muOPG [22-401]-Fc in Growing Mice

Male BDF1 mice aged 3-4 weeks, weight range 9.2-15.7 g were divided into groups of ten mice per group. These mice were injected subcutaneously with saline or muOPG [22-401]-Fc 2.5 mg/kg bid for 14 days (5 mg/kg/day). The mice were radiographed before treatment, at day 7 and on day 14. The mice were sacrificed 24 hours after the final injection. The right femur was removed, fixed in zinc formalin, decalcified in formic acid and embedded in paraffin. Sections were cut through the mid region of the distal femoral metaphysis and the femoral shaft. Bone density, by histomorphometry, was determined in six adjacent regions extending from the metaphyseal limit of the growth plate, through the primary and secondary spongiosa and into the femoral diaphysis (shaft). Each region was 0.5×0.5 $mm^2$.

Radiographic Chances

Figure 24B:
FIG. 24. Radiographic analysis of bone accumulation in marrow cavity of normal mice. Mice were injected subcutaneously with saline (A) or muOPG [22-401]-Fc fusion (5 mg/kg/d) for 14 days (B) and bone density determined as described in Example 11C.
Figure 24A:
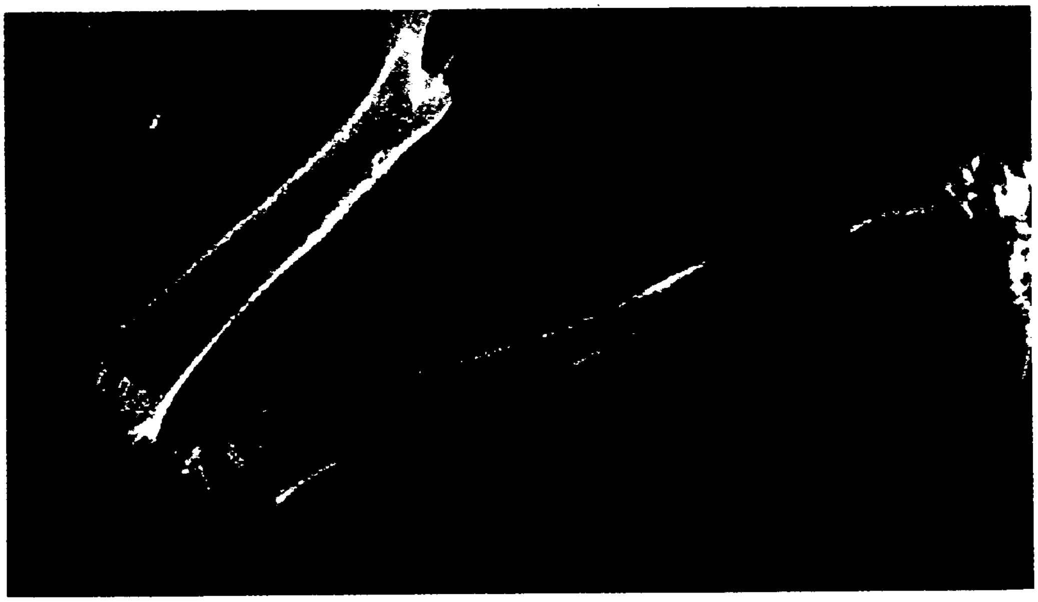

After seven days of treatment there was evidence of a zone of increased bone density in the spongiosa associated with the growth plates in the OPG treated mice relative to that seen in the controls. The effects were particularly striking in the distal femoral and the proximal tibial metaphases (FIG. 24A-24B). However bands of increased density were also apparent in the vertebral bodies, the iliac crest and the distal tibia. At 14 days, the regions of opacity had extended further into the femoral and tibial shafts though the intensity of the radio-opacity was diminished. Additionally, there were no differences in the length of the femurs at the completion of the experiment or in the change in length over the duration of the experiment implying that OPG does not alter bone growth.

Histological Changes

Figure 25:
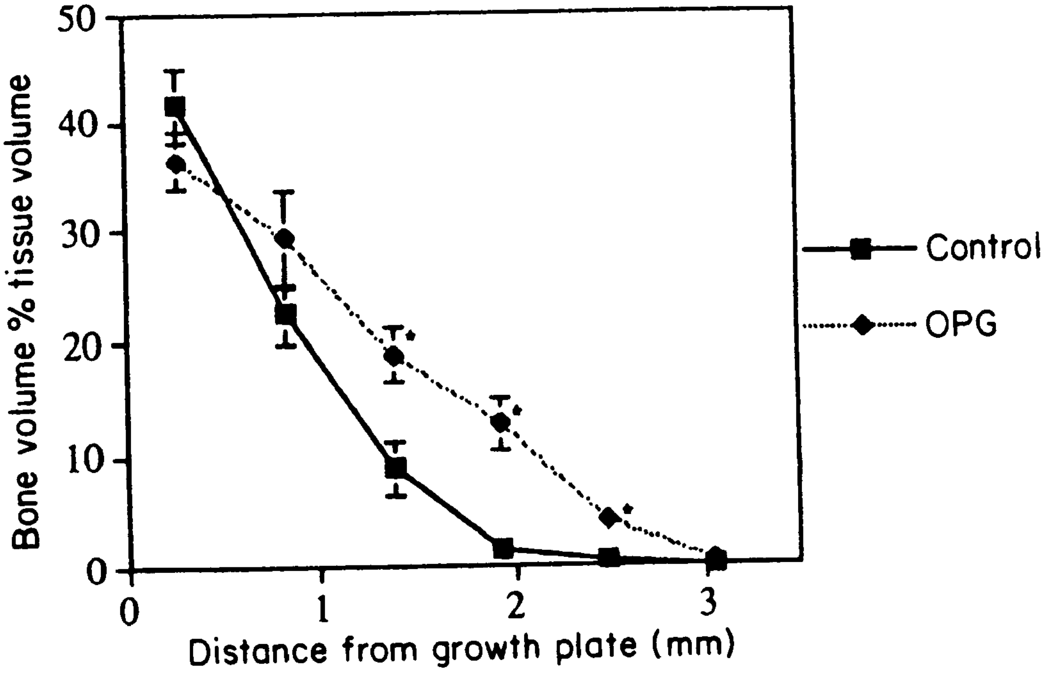
FIG. 25. Histomorphometric analysis of bone accumulation in marrow cavity of normal mice. Injection experiments and bone histology performed as described in Example 11C.

The distal femoral metaphysis showed increased bone density in a regions 1.1 to 2.65 mm in distance from the growth plate (FIGS. 25 and 26A-26B). This is a region where bone is rapidly removed by osteoclast-mediated bone resorption in mice. In these rapidly growing young mice, the increase in bone in this region observed with OPG treatment is consistent with an inhibition of bone resorption.

D. Effects of Osteoprotegerin on Bone Loss Induced by Ovariectomy in the Rat

Twelve week old female Fisher rats were ovariectomized (OVX) or sham operated and dual x-ray absorptiometry (DEXA) measurements made of the bone density in the distal femoral metaphysis. After 3 days recovery period, the animals received daily injections for 14 days as follows: Ten sham operated animals received vehicle (phosphate buffered saline); Ten OVX animals received vehicle (phosphate buffered saline); Six OVX animals received OPG-Fc 5 mg/kg SC; Six OVX animals received pamidronate (PAM) 5 mg/kg SC; Six OVX animals received estrogen (ESTR) 40 ug/kg SC. After 7 and 14 days treatment the animals had bone density measured by DEXA. Two days after the last injection the animals were killed and the right tibia and femur removed for histological evaluation.

Figure 27:
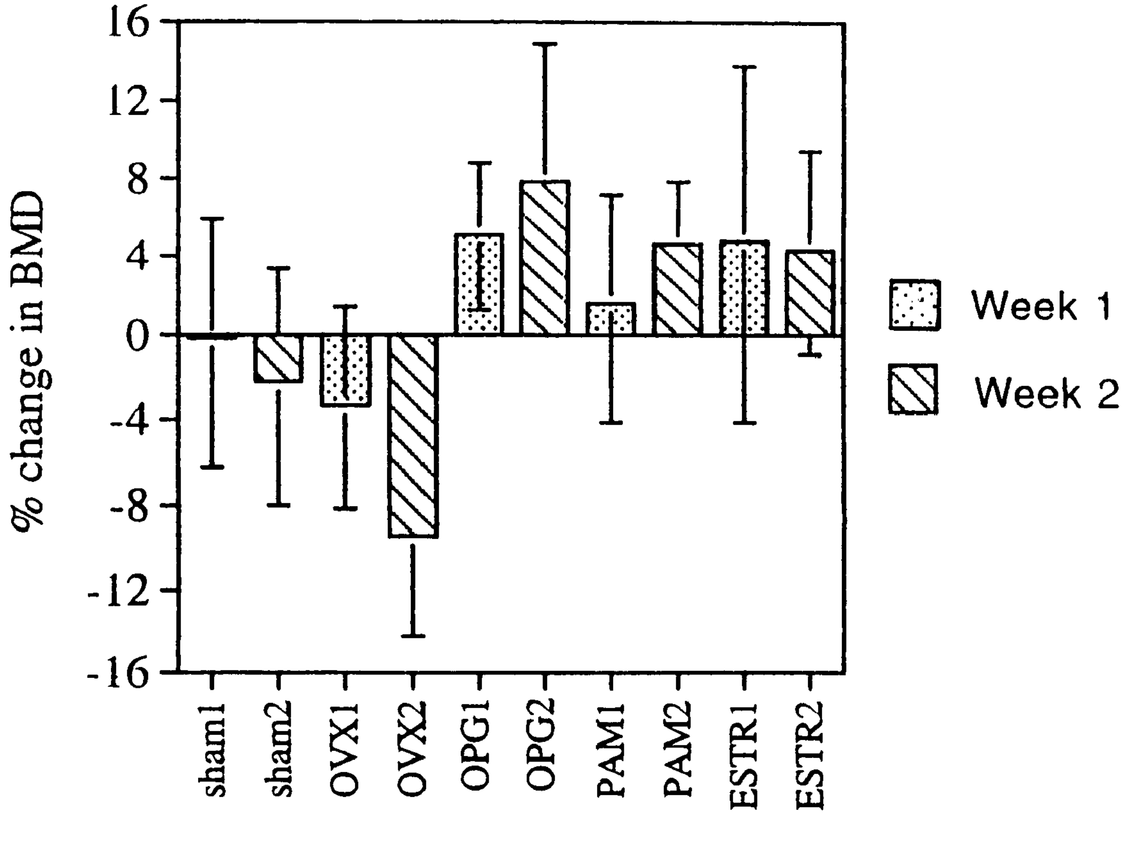
FIG. 27. Activity of OPG administered to ovariectomized rats. In this two week experiment the trend to reduced bone density appears to be blocked by OPG or other anti-resorptive therapies. DEXA measurements were taken at time of ovariectomy and at week 1 and week 2 of treatment. The results are expressed as % change from the initial bone density (Mean+/−SEM).
Figure 28:
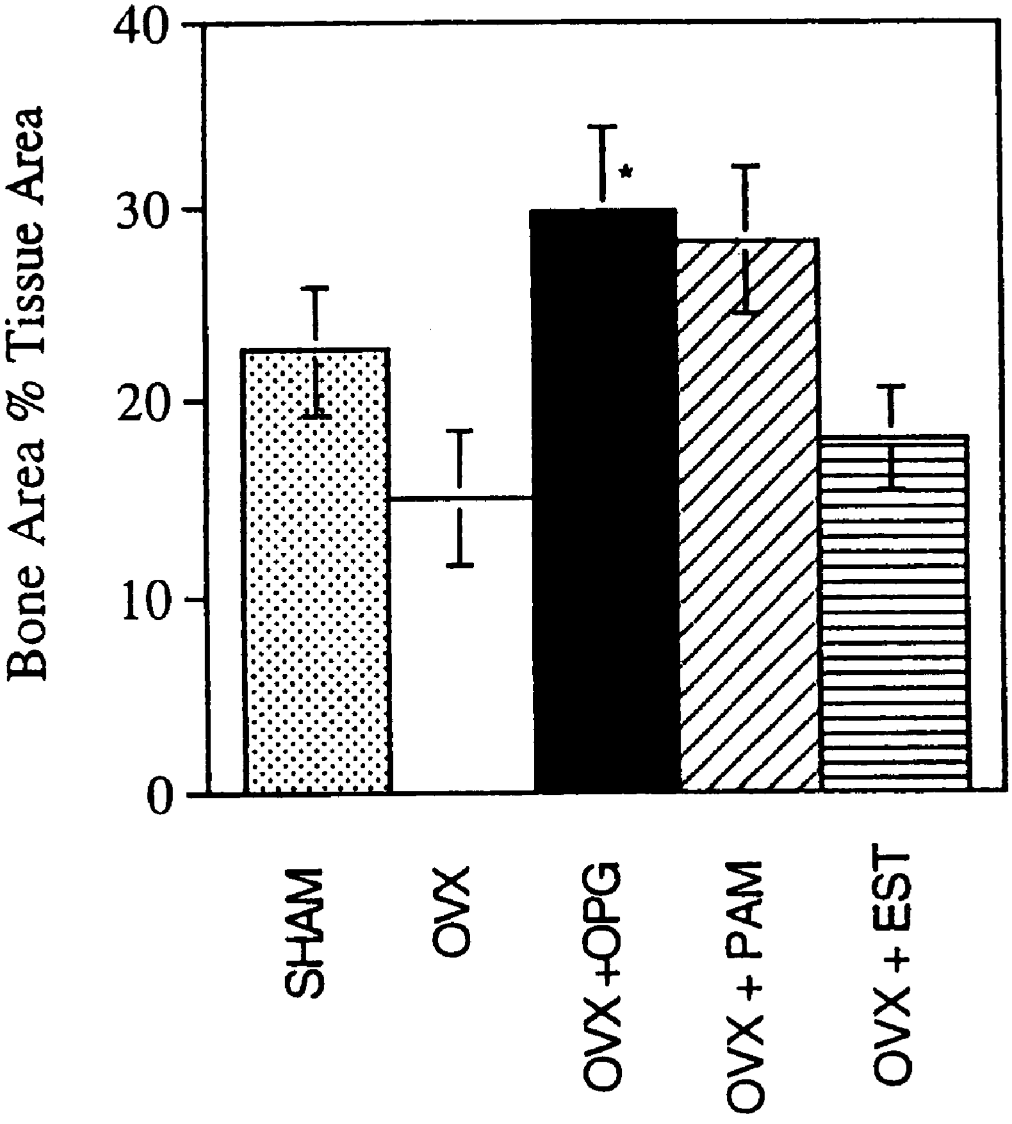
FIG. 28. Bone density in the femoral metaphysis, measured by histomorphometric methods, tends to be lower in ovariectomized rats (OVX) than sham operated animals (SHAM) 17 days following ovariectomy. This effect was blocked by OPG-Fc, with OPG-Fc treated ovariectomized rats (OVX+OPG) having significantly higher bone density than vehicle treated ovariectomized rats (OVX). (Mean+/−SEM).

The DEXA measurements of bone density showed a trend to reduction in the bone density following ovariectomy that was blocked by OPG-Fc. Its effects were similar to the known antiresorptive agents estrogen and pamidronate. (FIG. 27). The histomorphometric analysis confirmed these observations with OPG-Fc treatment producing a bone density that was significantly higher in OVX rats than that seen in untreated OVX rats (FIG. 28). These results confirm the activity of OPG in the bone loss associated with withdrawal of endogenous estrogen following ovariectomy.

In Vivo Summary

The in vivo actions of recombinant OPG parallel the changes seen in OPG transgenic mice. The reduction in osteoclast number seen in the OPG transgenic is reproduced by injecting recombinant OPG locally over the calvaria in both normal mice and in mice treated with IL1-α or IL1β. The OPG transgenic mice develop an osteopetrotic phenotype with progressive filling of the marrow cavity with bone and unremodelled cartilage extending from the growth plates from day 1 onward after birth. In normal three week old (growing) mice, OPG treatments also led to retention of bone and unremodelled cartilage in regions of endochondral bone formation, an effect observed radiographically and confirmed histologically. Thus, recombinant OPG produces phenotypic changes in normal animals similar to those seen in the transgenic animals and the changes are consistent with OPG-induced inhibition of bone resorption. Based on in vitro assays of osteoclast formation, a significant portion of this inhibition is due to impaired osteoclast formation. Consistent with this hypothesis, OPG blocks ovariectomy-induced osteoporosis in rat. Bone loss in this model is known to be mediated by activated osteoclasts, suggesting a role for OPG in treatment of primary osteoporosis.

Example 12

Pegylation Derivatives of OPG

Preparation of N-Terminal Peg-OPG Conjugates by Reductive Alkylation

HuOPG met [22-194] P25A was buffer exchanged into 25-50 mM NaOAc, pH 4.5-4.8 and concentrated to 2-5 mg/ml. This solution was used to conduct OPG reductive alkylation with monofunctional PEG aldehydes at 5-7° C. PEG monofunctional aldehydes, linear or branched, MW=1 to 57 kDa (available from Shearwater Polymers) were added to the OPG solution as solids in amounts constituting 2-4 moles of PEG aldehyde per mole of OPG. After dissolution of polymer into the protein solution, sodium cyanoborohydride was added to give a final concentration of 15 to 20 mM in the reaction mixture from 1-1.6 M freshly prepared stock solution in cold DI water. The progress of the reaction and the extent of OPG PEGylation was monitored by size exclusion HPLC on a G3000SW$_{XL}$ column (Toso Haas) eluting with 100 mM $NaPO_4$, 0.5 M NaCl, 10% ethanol, pH 6.9. Typically the reaction was allowed to proceed for 16-18 hours, after which the reaction mixture was diluted 6-8 times and the pH lowered to 3.5-4. The reaction mixture was fractionated by ion exchange chromatography (HP SP HiLoad 16/10, Pharmacia) eluting with 20 mM NaOAc pH 4 with a linear gradient to 0.75M NaCl over 25 column volumes at a flow rate of 30 cm/h. Fractions of mono-, di- or poly-PEGylated OPG were pooled and characterized by SEC HPLC and SDS-PAGE. By N-terminal sequencing, it was determined that the monoPEG-OPG conjugate, the major reaction product in most cases, was 98% N-terminally PEG-modified OPG.

This procedure was generally used to prepare the following N-terminal PEG-OPG conjugates (where OPG is HuOPG met [22-194] P25A: 5 kD monoPEG, 10 kD mono branched PEG, 12 kD monoPEG, 20 kD monoPEG, 20 kD mono branched PEG, 25 kD monoPEG, 31 kD monoPEG, 57 kD monoPEG, 12 kD diPEG, 25 kD diPEG, 31 kD diPEG, 57 kD diPEG, 25 kD triPEG.

Preparation of Peg-OPG Conjugates by Acylation

HuOPG met [22-194] P25A was buffer exchanged into 50 mM BICINE buffer, pH 8 and concentrated to 2-3 mg/ml. This solution was used to conduct OPG acylation with monofunctional PEG N-hydroxysuccinimidyl esters at room temperature. PEG N-hydroxysuccinimidyl esters, linear or branched, MW=1 to 57 kDa (available from Shearwater Polymers) were added to the OPG solution as solids in amounts constituting 4-8 moles of PEG N-hydroxysuccinimidyl ester per mole of OPG. The progress of the reaction and the extent of OPG PEGylation was monitored by size exclusion HPLC on a G3000SW$_{XL}$ column (Toso Haas) eluting with 100 mM $NaPO_4$, 0.5 M NaCl, 10% ethanol, pH 6.9. Typically the reaction was allowed to proceed for 1 hour, after which the reaction mixture was diluted 6-8 times and the pH lowered to 3.5-4. The reaction mixture was fractionated by ion exchange chromatography (HP SP HiLoad 16/10, Pharmacia) eluting with 20 mM NaOAc pH 4 with a linear gradient to 0.75M NaCl over 25 column volumes at a flow rate of 30 cm/h. Fractions of mono-, di- or poly-PEGylated OPG were pooled and characterized by SEC HPLC and SDS-PAGE.

This procedure was generally used to prepare the following PEG-OPG conjugates: 5 kD polyPEG, 20 kD polyPEG, 40 kD poly branched PEG, 50 kD poly PEG.

Preparation of Dimeric Peg-OPG

HuOPG met [22-194] P25A is prepared for thiolation at 1-3 mg/ml in a phosphate buffer at near neutral pH. S-acetyl mecaptosuccinic anhydride (AMSA) is added in a 3-7 fold molar excess while maintaining pH at 7.0 and the rxn stirred at 4° C. for 2 hrs. The monothiolated-OPG is separated from unmodified and polythiolated OPG by ion exchange chromatography and the protected thiol deprotected by treatment with hydroxylamine. After deprotection, the hydroxylamine is removed by gel filtration and the resultant monothiolated-OPG is subjected to a variety of thiol specific crosslinking chemistries. To generate a disulfide bonded dimer, the thiolated OPG at >1 mg/ml is allowed to undergo air oxidation by dialysis in slightly basic phosphate buffer. The covalent thioether OPG dimer was prepared by reacting the bis-maleimide crosslinker, N,N-bis(3-maleimido propianyl)-2-hydroxy 1,3 propane with the thiolated OPG at >1 mg/ml at a 0.6× molar ratio of crosslinker:OPG in phosphate buffer at pH 6.5. Similarly, the PEG dumbbells are produced by reaction of substoichiometric amounts of bis-maleimide PEG crosslinkers with thiolated OPG at >1 mg/ml in phosphate buffer at pH 6.5. Any of the above dimeric conjugates may be further purified using either ion exchange or size exclusion chromatographies.

Dimeric PEG-OPG conjugates (where OPG is HuOPG met [22-194] P25A prepared using the above procedures include disulfide-bonded OPG dimer, covalent thioether OPG dimer with an aliphatic amine type crosslinker, 3.4 kD and 8 kD PEG dumbbells and monobells.

PEG-OPG conjugates were tested for activity in vitro using the osteoclast maturation assay described in Example 11A and for activity in vivo by measuring increased bone density after injection into mice as described in Example 11C. The in vivo activity is shown below in Table 3.

TABLE 3

In vivo biological activity of Pegylated OPG

| OPG Construct | Increase in Tibial Bone Density |
|---|---|
| muOPG met [22-194] | – |
| muOPG met [22-194] 5k PEG | + |
| muOPG met [22-194] 20k PEG | + |
| huOPG met [22-194] P25A | – |

TABLE 3-continued

In vivo biological activity of Pegylated OPG

| OPG Construct | Increase in Tibial Bone Density |
|---|---|
| huOPG met [22-194] P25A 5k PEG | + |
| huOPG met [22-194] P25A 20k PEG | + |
| huOPG met [22-194] P25A 31k PEG | + |
| huOPG met [22-194] P25A 57k PEG | + |
| huOPG met [22-194] P25A 12k PEG | + |
| huOPG met [22-194] P25A 20k Branched PEG | + |
| huOPG met [22-194] P25A 8k PEG dimer | + |
| huOPG met [22-194] P25A disulfide crosslink | + |

While the invention has been described in what is considered to be its preferred embodiments, it is not to be limited to the disclosed embodiments, but on the contrary, is intended to cover various modifications and equivalents included within the spirit and scope of the appended claims, which scope is to be accorded the broadest interpretation so as to encompass all such modifications and equivalents.

What is claimed is:

1. An isolated antibody or fragment thereof which specifically binds to an OPG polypeptide consisting of residues 22-401 inclusive of SEQ ID NO:121.

2. An isolated antibody or fragment thereof which specifically binds to an OPG polypeptide consisting of residues 22-401 inclusive of SEQ ID NO:123.

3. An isolated antibody or fragment thereof which specifically binds to an OPG polypeptide consisting of residues 22-401 inclusive of SEQ ID NO:125.

4. The antibody or fragment thereof of claim 3 which specifically binds to an OPG polypeptide consisting of residues 22-185, 22-189, 22-194 or 22-201 inclusive as shown in SEQ ID NO:125.

5. The antibody or fragment thereof of claims 1, 2, 3 or 4 which is a monoclonal antibody.

6. The antibody or fragment thereof of claims 1, 2, 3 or 4 which is a chimeric antibody.

7. The antibody or fragment thereof of claims 1, 2, 3 or 4 which is a CDR-grafted antibody.

8. The antibody or fragment thereof of claims 1, 2, 3 or 4 which is a humanized antibody.

9. The antibody or fragment thereof of claims 1, 2, 3 or 4 which is a human antibody.

10. A method for detecting the presence of OPG in a biological sample comprising:

incubating the sample with the antibody or fragment thereof of claims 1, 2, 3 or 4 under conditions that allow binding of the antibody to OPG; and detecting the bound antibody.

11. A method for removing OPG from a biological sample comprising:

contacting the sample with the antibody or fragment thereof of claims 1, 2, 3 or 4 under conditions that allow binding of the antibody to OPG; and removing OPG from the sample.

* * * * *

UNITED STATES PATENT AND TRADEMARK OFFICE

CERTIFICATE OF CORRECTION

PATENT NO. : 7,632,922 B1
APPLICATION NO. : 09/718725
DATED : December 15, 2009
INVENTOR(S) : Boyle et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1490 days.

Signed and Sealed this

Twenty-first Day of December, 2010

David J. Kappos
*Director of the United States Patent and Trademark Office*